(12) United States Patent
Tachibana et al.

(10) Patent No.: US 8,470,829 B2
(45) Date of Patent: Jun. 25, 2013

(54) IMIDAZOLIDINE DERIVATIVE AND USE THEREOF

(75) Inventors: Kazutaka Tachibana, Gotenba (JP); Haruhiko Sato, Gotenba (JP); Masateru Ohta, Gotenba (JP); Mitsuaki Nakamura, Gotenba (JP); Takuya Shiraishi, Gotenba (JP); Hitoshi Yoshino, Gotenba (JP); Takashi Emura, Gotenba (JP); Akie Honma, Gotenba (JP); Etsuro Onuma, Kamakura (JP); Hiromitsu Kawata, Kamakura (JP); Kenji Taniguchi, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1109 days.

(21) Appl. No.: 11/662,289

(22) PCT Filed: Sep. 9, 2005

(86) PCT No.: PCT/JP2005/016664
§ 371 (c)(1),
(2), (4) Date: Nov. 2, 2007

(87) PCT Pub. No.: WO2006/028226
PCT Pub. Date: Mar. 16, 2006

(65) Prior Publication Data
US 2011/0306615 A1  Dec. 15, 2011

(30) Foreign Application Priority Data
Sep. 9, 2004  (JP) .................. 2004-262888

(51) Int. Cl.
| | |
|---|---|
| A61K 31/426 | (2006.01) |
| A61K 31/454 | (2006.01) |
| A61K 31/428 | (2006.01) |
| A61K 31/4166 | (2006.01) |
| C07D 401/12 | (2006.01) |
| C07D 403/12 | (2006.01) |
| C07D 277/82 | (2006.01) |
| C07D 233/72 | (2006.01) |
| C07D 233/70 | (2006.01) |

(52) U.S. Cl.
USPC ...... 514/254.05; 514/326; 514/367; 514/391; 544/370; 546/210; 548/163; 548/319.1; 548/319.5

(58) Field of Classification Search
None
See application file for complete search history.

(56) References Cited

U.S. PATENT DOCUMENTS

| | | | |
|---|---|---|---|
| 3,542,849 A | 11/1970 | Knast et al. | |
| 3,686,271 A | 8/1972 | Lafon | |
| 4,005,056 A | 1/1977 | Dunwald et al. | |
| 4,035,143 A | 7/1977 | Heinrich et al. | |
| 5,411,981 A * | 5/1995 | Gaillard-Kelly et al. ..... 514/386 | |
| 5,434,176 A | 7/1995 | Claussner et al. | |
| 5,627,201 A | 5/1997 | Gaillard-Kelly et al. | |
| 5,741,926 A | 4/1998 | Bierer et al. | |
| 5,750,553 A | 5/1998 | Claussner et al. | |
| 6,087,509 A | 7/2000 | Claussner et al. | |
| 2004/0248884 A1 | 12/2004 | Patek et al. | |
| 2006/0025589 A1 | 2/2006 | Binet et al. | |
| 2007/0004753 A1 * | 1/2007 | Sawyers et al. .......... 514/254.05 | |

FOREIGN PATENT DOCUMENTS

| | | |
|---|---|---|
| AU | 39876/93 B2 | 5/1993 |
| DE | 2308044 | 8/1974 |
| JP | 02-019363 | 1/1990 |
| JP | 06-73017 A | 3/1994 |
| WO | 9518794 A | 7/1995 |

OTHER PUBLICATIONS

Byrn et al., Solid-State Chemistry of Drugs (2nd Ed. 1999) (pp. 233-247).*

(Continued)

*Primary Examiner* — Rebecca Anderson
*Assistant Examiner* — Alicia L Otton
(74) *Attorney, Agent, or Firm* — Browdy and Neimark, PLLC

(57) ABSTRACT

An imidazole derivative represented by formula (I):

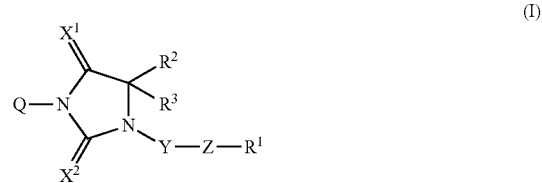

wherein Q is:

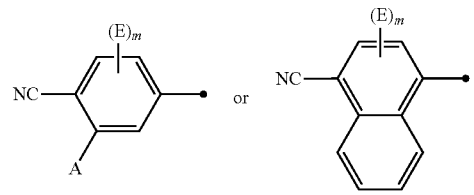

A is hydrogen, halogen, or a substituted or unsubstituted $C_{1-4}$ alkyl group; E is independently selected from a $C_{1-6}$ alkyl group; $R^2$ and $R^3$ are independently selected from $C_{1-6}$ alkyls; $X^1$ and $X^2$ are independently selected from O and S; Y is selected from a substituted or unsubstituted arylene group and a substituted or unsubstituted divalent 5- or 6-membered monocyclic or 8- to 10-membered condensed heterocyclic group; Z is —CON(—Ra)—, —CO—, —OOO—, —NRa—C(=NH)NRb—, —NRa—C(=N—CN)NRb—, —N(—Ra)COO—, —C(=NH)—, —SO$_2$—, —SO$_2$N(—Ra)—, —SO$_2$NR$^1$—, —N(—Ra)CO—, —N(—Ra)CON(—Rb)—, —N(COR$^1$)CO—, —N(—Ra)SO$_2$—, —N(SO$_2$R$^1$)SO$_2$—, —N(—Ra)— or —N(—Ra)SO$_2$N(—Rb)—; $R^1$ is independently a hydrogen atom, a hydroxyl group, or substituted or unsubstituted group selected from $C_{1-6}$ alkyl group, heterocyclic group, aryl group, $C_{3-8}$ cycloalkyl group and $C_{3-8}$ cycloalkenyl group; or salt or prodrug thereof.

29 Claims, No Drawings

OTHER PUBLICATIONS

Fenton et al., Precocious Pseudopuberty, eMedicine, retrieved from Internet on Jan. 18, 2007, URL: <http://emedicine.com/ped/topic1881.htm> p. 1-18.*

Isaacs et al. Androgen receptor outwits prostate cancer drugs, Jan. 2004, Nature Medicine, 10(1), p. 26-27.*

Medical Encyclopedia: Enlarged Prostate, retrieved from internet on Jan. 6, 2007, URL: <http://www.nlm.nih.gov/medlineplus/ency/article/000381.htm>.*

Olsen et al., Evaluation and treatment of male and female pattern hair loss, Nov. 23, 2004, J. Am. Acad. Dermatol. p. 301-311.*

Prostate Cancer Treatment Options, retrieved from Internet on Jan. 6, 2007, URL: <http://familydoctor.org/263.xml?printxml.*

* cited by examiner

IMIDAZOLIDINE DERIVATIVE AND USE THEREOF

FIELD OF THE INVENTION

The present invention relates to an imidazolidine derivative which have a substituted cyclic group in 3-position and a drug containing the imidazolidine derivative as an active ingredient.

BACKGROUND ART

It has been shown that the male hormone androgen plays an important role in prostate cancer, benign prostatic hypertrophy, male pattern baldness, sexual precociousness, acnevulgaris, seborrhea and hypertrichosis. For example, it is known that persons who have been castrated and persons suffering from sexual gland failure almost never develop prostate cancer or benign prostatic hypertrophy.

For example, cyproterone acetate, chlormadinone acetate, flutamide, bicalutamide and the like are already used as anti-androgen agents, i.e., androgen receptor antagonists. These anti-androgen agents show an effect in many cases such as drug therapy in prostate cancer, and are important treatment agents in this area. In addition, it is known that cyproterone acetate suppresses the progression of acne in teenagers and the occurrence of baldness. Furthermore, in females, cyproterone acetate is used in the treatment of androgenization and hair loss. Flutamide and bicalutamide are used as drugs for prostate cancer treatment.

However, as problems encountered in these anti-androgen agents, it is known that even if the anti-androgen agents are effective, the disease recurs in almost all cases in two to five years, and in such cases, androgen resistance appears.

Furthermore, it has been reported that hydroxyflutamide, which is the active form of flutamide, causes an increase in androgen receptor transcription activity at a concentration of 10 μmol/L. Moreover, the hydroxyflutamide concentration in the blood in prostate cancer patients treated with flutamide is several μmol/L. However, it has been reported that this concentration reaches a concentration at which hydroxyflutamide shows an agonist effect (see Non-patent Document 1).

Furthermore, it has been reported that there is an increase in the weight of the prostate gland when cyproterone acetate and chlormadinone acetate are continuously administered to castrated rats for two weeks (see Non-patent Document 2). Moreover, in regard to flutamide and bicalutamide, there are also reports of side effects such as liver toxicity and the like. Accordingly, there is a demand for an anti-androgen agent which has a sufficient antagonistic effect, and in which these problems have been solved.

Meanwhile, the compounds represented by the following formula described in JP 04-308579 A (Patent Document 1) and the corresponding European Patent Application No. 494819 A (Patent Document 2) are known as phenylimidazolidines that show anti-androgen activity.

[Formula 1]

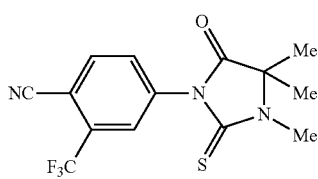

Furthermore, the compounds represented by the following formula described in JP 10-510845 A (Patent Document 3) and the corresponding WO 97/00071 A1 (Patent Document 4) are known as substituted phenylimidazolidines that show an anti-androgen activity.

[Formula 2]

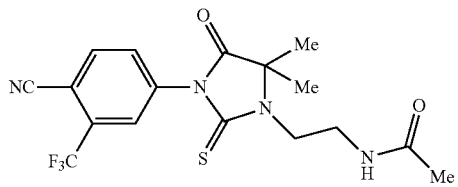

However, the compounds neither constitute means for solving the problems of existing anti-androgen agents.

In the meantime, the compounds described in WO2004/031160 A1 (Patent Document 5) and WO2004/070050 A1 (Patent Document 6) are known as well-known imidazolidine derivatives having a substituent containing a cyclic group in 3-position, but these documents do not mention about an anti-androgen effect.

Patent Document 1: JP 04-308579 A

Patent Document 2: EP 494819 A1

Patent Document 3: JP 10-510845 A

Patent Document 4: WO 97/00071 A1

Patent Document 5: WO2004/031160 A1

Patent Document 6: WO2004/070050 A1

Non-Patent Document 1: J. Biol. Chem., Vol. 270, page 19998-20003, 1995

Non-Patent Document 2: Japanese journal of endocrinology, Vol. 66, page 597-606, 1990

DISCLOSURE OF THE INVENTION

Problems to be Solved

It is one object of the present invention to provide an imidazolidine derivative which has a substituted alkyl group in 3-position, or pharmaceutically acceptable salts, prodrugs or solvates thereof which shows an activity useful as drugs, especially an anti-androgen activity.

It is another object of the present invention to provide a drug containing the abovementioned imidazolidine derivative.

Means for Solving the Problems

The present inventors conducted diligent research with the aim of solving the abovementioned problems. As a result of this research, the inventors have found that an imidazolidine derivative having a cyclic group in 3-position represented by Formula (I) shows anti-androgen activity, and shows no or almost no agonist activity, and then completed the present invention.

That is, according to one aspect of the present invention, a compound represented by formula (I):

[Formula 3]

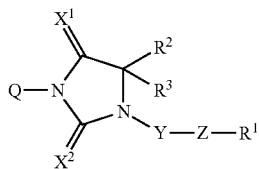

wherein Q is

[Formula 4]

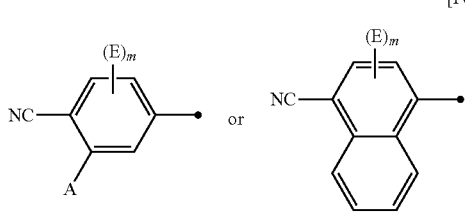

wherein,

A is a hydrogen atom, a halogen atom, —ORa or a $C_{1-4}$ alkyl group which may be substituted by one or more halogen atoms;

E is independently selected from a $C_{1-6}$ alkyl group;

m is selected from integers from 0 to 3;

$R^2$ and $R^3$ are independently selected from a $C_{1-6}$ alkyl group;

$X^1$ and $X^2$ are independently selected from O and S,

Y is selected from an arylene group and a divalent 5- or 6-membered monocyclic or 8- to 10-membered condensed heterocyclic group, wherein the arylene group and the heterocyclic group may be substituted by 1 to 3 substituents independently selected from $E^1$, $E^1$ is independently selected from a hydroxyl group, a halogen atom, a $C_{1-4}$ alkyl group, a cyano group, a $C_{1-4}$ alkoxy group, a carbamoyl group, a $C_{1-4}$ alkylcarbamoyl group, a di($C_{1-4}$ alkyl)carbamoyl group, an amino group, a $C_{1-4}$ alkylamino group, a di($C_{1-4}$ alkyl)amino group, a sulfamoyl group, a $C_{1-4}$ alkylsulfamoyl group and a di($C_{1-4}$ alkyl)sulfamoyl group;

Z is —CON(—Ra)—, —CO—, —COO—, —NRa—C(=NH)N(—Rb)—, —NRa—C(=N—CN)NRb—, —N(—Ra)COO—, —C(=NH)—, —SO$_2$—, —SO$_2$N(—Ra)—, —SO$_2$N(—R$^1$)—, —N(—Ra)CO—, —N(—Ra)CON(—Rb)—, —N(—COR$^1$)CO—, —N(—Ra)SO$_2$—, —N(SO$_2$R$^1$)SO$_2$—, —N(—Ra)— or —N(—Ra)SO$_2$N(—Rb)—;

$R^1$ is independently a hydrogen atom, a hydroxyl group, a $C_{1-6}$ alkyl group which may be substituted by one or more substituents selected from B, a heterocyclic group which may be substituted by one or more substituents selected from B, an aryl group which may be substituted by one or more substituents selected from B, a $C_{3-6}$ cycloalkyl group which may be substituted by one or more substituents selected from B or a $C_{3-6}$ cycloalkenyl group which may be substituted by one or more substituents selected from B;

B is independently selected from a $C_{1-4}$ alkyl group (except in the case where $R^1$ is a $C_{1-6}$ alkyl group or a $C_{1-6}$ alkoxy group), a halogen atom, a hydroxyl group, a cyano group, an oxo group, —CONRa$^1$Rb$^1$, —N(—Ra)CORb, —NRa$^1$Rb$^1$, —N(—Ra)SO$_2$Rb, —SO$_2$NRa$^1$Rb$^1$, —SO$_2$Ra, —COORa, —ORa, an aryl group, a heterocyclic group, a $C_{3-8}$ cycloalkyl group and a $C_{3-8}$ cycloalkenyl group (wherein the aryl group, the heterocyclic group, the heteroaryl group, the cycloalkyl group or the $C_{3-6}$ cycloalkenyl group may be substituted by one or more substituents selected from a $C_{1-4}$ alkyl group or a $C_{1-4}$ alkoxy group, a halogen atom, a hydroxyl group, —COORa.);

Ra and Rb are independently selected from a hydrogen atom, —P(=O)(—OM)$_2$, a $C_{1-6}$ alkyl group and a $C_{1-6}$ alkylcarbonyl group wherein the alkyl group and the alkylcarbonyl group may be substituted by one or more substituents selected from a hydroxyl group, a $C_{1-6}$ alkoxy group, a halogen atom, —NRa$^1$Rb$^1$, —COORa$^1$, an aryl group and a heterocyclic group, and M is a hydrogen atom or a metal ion;

Ra$^1$ and Rb$^1$ are independently selected from a hydrogen atom and a $C_{1-6}$ alkyl group wherein the alkyl group may be substituted by one or more substituents selected from a hydroxyl group, a $C_{1-6}$ alkoxy group, a halogen atom, an aryl group and a heterocyclic group; or Ra$^1$ and Rb$^1$ together with a nitrogen atom to which they bind may form a nitrogen-containing heterocyclic group wherein the heterocyclic group may be substituted by one or more substituents selected from a $C_{1-6}$ alkyl group and a carboxy group;

provided that when Y is a heterocyclic group and $X^1$ and $X^2$ are O, m is not 0;

and that when Y is an arylene group,

Z is not —CON(—Ra)— or —CO—; and

—Z—R$^1$ is not an arylsulphonyl group, an amino group, a $C_{1-6}$ alkylamino group or a di($C_{1-6}$ alkyl)amino group or a salt, prodrug or solvate thereof is provided.

According to another aspect of the present invention, the compound or a salt, prodrug or solvate thereof, wherein, in formula (I), —Y—Z— is selected from the following YZ$^1$ to YZ$^7$:

[Formula 5]

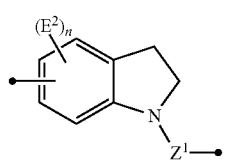
YZ$^1$

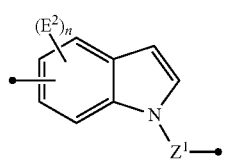
YZ$^2$

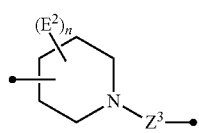
YZ$^3$

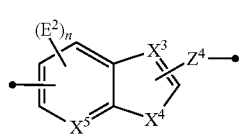
YZ$^4$

-continued

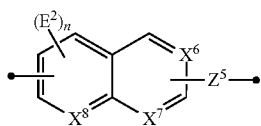
YZ⁵

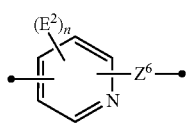
YZ⁶

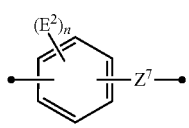
YZ⁷ wherein n is selected from integers from 0 to 3;
$E^2$ is independently selected from a hydroxyl group, a halogen atom, a $C_{1-4}$ alkyl group, a cyano group, a $C_{1-4}$ alkoxy group, a carbamoyl group, a $C_{1-4}$ alkylcarbamoyl group, a di($C_{1-4}$ alkyl)carbamoyl group, an amino group, a $C_{1-4}$ alkylamino group, a di($C_{1-4}$ alkyl)amino group, a sulfamoyl group, a $C_{1-4}$ alkylsulfamoyl group and a di($C_{1-4}$ alkyl)sulfamoyl group;
$X^3$, $X^5$, $X^6$, $X^7$ and $X^8$ are independently selected from CH and N, provided that $X^6$, $X^7$ and $X^8$ are not CH at the same time;
$X^4$ is —$CH_2$—, —S—, —O— or —N(—W)—, provided that $X^4$ is not —$CH_2$— when both $X^3$ and $X^5$ are CH;
W is a hydrogen atom, a $C_{1-6}$ alkyl group, a $C_{1-6}$ alkoxy group, —$SO_2$Ra, —$SO_2$N$Ra^1Rb^1$ or —CORa;
$Z^1$, $Z^2$, $Z^3$, $Z^4$, $Z^5$, $Z^6$ and $Z^7$ are —CON(—Ra)—, —CO—, —COO—, —NRa—C(=NH)NRb—, —NRa—C(=N—CN)NRb—, —N(—Ra)—COO—, —C(=NH)—, —$SO_2$—, —$SO_2$N(—Ra)—, —$SO_2$N$R^1$—, —N(—Ra)CO—, —N(—Ra)CON(—Rb)—, —N(COR$^1$)CO—, —N(—Ra)$SO_2$—, —N($SO_2R^1$)$SO_2$—, —N(—Ra)— or —N(—Ra)$SO_2$N(—Rb)—;
provided that m is not 0 when both of $X^1$ and $X^2$ above are O and —Y—Z— is any of YZ$^1$ to YZ$^6$.

Here, preferable examples of A include a hydrogen atom, a trifluoromethyl group, a methyl group, an ethyl group, a chlorine atom and a methoxy group. In addition, in an embodiment of the present invention, $X^1$ is O and $X^2$ is O or S. In another embodiment of the present invention, $Z^1$, $Z^2$, $Z^3$, $Z^4$, $Z^5$, $Z^6$ and $Z^7$ are selected from —CONH—, —COO—, —NHCO—, —NHCONH—, —NH—COO—, —N(COR$^1$)CO—, —NHC(=NH)NH—, —NHC(=N—CN)NH—, —$SO_2$—, —$SO_2$NH— and —NHSO$_2$—. In another embodiment of the present invention, $Z^1$, $Z^2$ and $Z^3$ are selected from —CON(—Ra)—, —CO—, —COO—, —$SO_2$—, —$SO_2$N(—Ra)— and —$SO_2$N(—R$^1$)—; and $Z^4$ and $Z^5$ are selected from —N(—Ra)CO—, —N(—Ra)CO—O—, —N(—Ra)CON(—Rb)—, —N(—COR$^1$)CO—, —N(—Ra)—$SO_2$— and —$SO_2$—; $Z^6$ is selected from —N(—Ra)CON(—Rb)—, —N(—Ra)CO—, —$SO_2$N(—Ra)—, —$SO_2$N(—R$^1$)—, —N(—Ra)$SO_2$—, —N(—$SO_2R^1$)$SO_2$— and —NRa—; and $Z^7$ is selected from —NRa—C(=NH)NRb—, —NRa—(C=N—CN)—NRb—, —N(—Ra)CO—, —N(—Ra)CON(—Rb)—, —N(COR$^1$)CO—, —$SO_2$—, —$SO_2$N(—Ra)—, —$SO_2$N(—R$^1$)—, —N(—Ra)$SO_2$—, —N(—Ra)$SO_2$N(—Rb)—, —N(—$SO_2R^1$)$SO_2$— and —N(—Ra)—.

In the present invention, examples of metal ion defined by M include ions of alkaline metals such as Li, Na, K.

In addition, Y is a divalent group which binds with a nitrogen atom in imidazolidine through a single bond and with Z through a single bond in the above formula (I), and preferable examples of —Y—Z— include:

(i) YZ$^1$, YZ$^2$ and YZ$^3$ represented by the following formulas:

[Formula 6]

[Structures: YZ$_a^1$, YZ$_b^1$, YZ$_a^2$, YZ$_a^3$]

(ii) YZ$^4$ and YZ$^5$ represented by the following formulas:

[Formula 7]

[Structures: YZ$_a^4$, YZ$_b^4$, YZ$_c^4$, YZ$_d^4$]

-continued

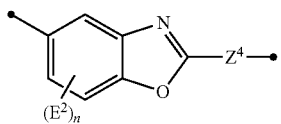

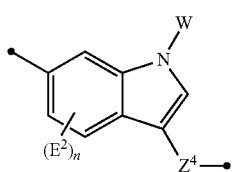

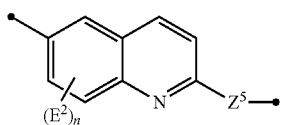

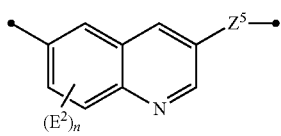

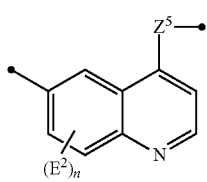

(iv) $YZ^6$ represented by the following formulas:

[Formula 8]

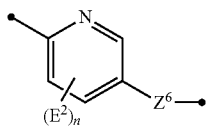

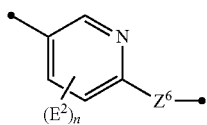

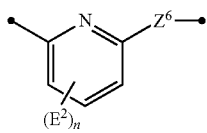

(v) $YZ^7$ represented by the following formulas:

[Formula 9]

$YZ_a^7$
$YZ_b^7$

—Y—Z— is preferably $YZ_a^3$, $YZ_a^4$, $YZ_b^4 YZ_c^4$, $YZ_d^4$, $YZ_a^5$, $YZ_b^6$, $YZ_a^7$ or $YZ_b^7$.

$Z^1$, $Z^2$ and $Z^3$ in the above $YZ^1$, $YZ^2$ and $YZ^3$ are preferably selected from —CON(—Ra)—, —SO$_2$—, —SO$_2$N(—Ra)— and —SO$_2$N(—R$^1$)—; and $Z^4$ and $Z^5$ in $YZ^4$ and $YZ^5$ are preferably selected from —N(—Ra)CO—, —N(—Ra)CON(—Rb)—, —SO$_2$—, —SO$_2$N(—Ra)— and —SO$_2$N(—R$^1$)—. Furthermore, $Z^6$ and $Z^7$ in the above $YZ^6$ are preferably selected from —N(—Ra)CO—, —N(—Ra)CON(—Rb)—, —SO$_2$—, —SO$_2$N(—Ra)—, —SO$_2$N(—R$^1$)— and —N(—Ra)SO$_2$—.

In addition, $E^2$ in the above $YZ^1$ to $YZ^7$ is preferably selected from a hydroxyl group, a halogen atom, a $C_{1-4}$ alkyl group, a $C_{1-4}$ alkoxy group and a carbamoyl group, and more preferably from a hydroxyl group, a chlorine atom, a fluorine atom, a methyl group, an ethyl group, a methoxy group, an ethoxy group and a carbamoyl group.

In an embodiment of the present invention, $E^2$ is preferably a $C_{1-4}$ alkyl group or a halogen atom, and more preferably it is a methyl group, a chlorine atom or a fluorine atom.

In an embodiment of the present invention, n is preferably 0 or 1.

In an embodiment of the present invention, $R^1$ is hydrogen atom, an amino group, a $C_{1-4}$ alkylamino group, a di($C_{1-4}$ alkyl)amino group, a $C_{1-4}$ alkyl group, a hydroxy $C_{1-4}$ alkyl group, a $C_{1-4}$ alkoxy $C_{1-4}$ alkyl group, a piperazinyl group, a piperazinyl $C_{1-4}$ alkyl group, a $C_{1-4}$ alkylpiperazinyl group, a ($C_{1-4}$ alkylpiperidyl)$C_{1-4}$ alkyl group, a ($C_{1-4}$ alkylpiperazinyl)$C_{1-4}$ alkoxy group, a piperidyl group, a $C_{1-4}$ alkylpiperidyl group, a ($C_{1-4}$ alkylpiperazinyl)$C_{1-4}$ alkyl group, an amino $C_{1-4}$ alkyl group, a $C_{1-4}$ alkylamino $C_{1-4}$ alkyl group, a di ($C_{1-4}$ alkyl)amino $C_{1-4}$ alkyl group, a $C_{1-4}$ alkoxy group, a hydroxy $C_{1-4}$ alkoxy group, a $C_{1-4}$ alkoxy $C_{1-4}$ alkoxy group, an aminoalkoxy group, a $C_{1-4}$ alkylamino $C_{1-4}$ alkoxy group, a di($C_{1-4}$ alkyl)amino $C_{1-4}$ alkoxy group, a pyridyl group which may be substituted by a $C_{1-4}$ alkyl, a thienyl group which may be substituted by a $C_{1-4}$ alkyl, an imidazolyl group which may be substituted by a $C_{1-4}$ alkyl, a morpholinyl group that may be substituted by a $C_{1-4}$ alkyl, a morpholinyl $C_{1-4}$ alkyl group, a thienyl $C_{1-4}$ alkyl group, a phenyl group, a phenyl $C_{1-4}$ alkyl group, a halogeno phenyl group, a $C_{1-4}$ alkoxy phenyl group, hydroxy phenyl group, a $C_{3-7}$ cycloalkyl group, a hydroxy cycloalkyl group, a hydroxy $C_{3-7}$ cycloalkyl $C_{1-4}$ alkyl group or a $C_{3-7}$ cycloalkyl $C_{1-4}$ alkyl group.

In another embodiment of the present invention, $R^1$ is a hydrogen atom, an amino group, a $C_{1-4}$ alkylamino group, a di($C_{1-4}$ alkyl)amino group, a $C_{1-4}$ alkyl group, a hydroxy $C_{1-4}$ alkyl group, a dihydroxy $C_{1-4}$ alkyl group, a trihydroxy $C_{1-4}$ alkyl group, a C$_{1-4}$ alkoxy C$_{1-4}$ alkyl group, a piperazinyl group, a piperazinyl C$_{1-4}$ alkyl group, a C$_{1-4}$ alkylpiperazinyl group, a (C$_{1-4}$ alkylpiperidyl)C$_{1-4}$ alkyl group, a piperidyl group, a C$_{1-4}$ alkylpiperidyl group, a (C$_{1-4}$ alkylpiperazinyl) C$_{1-4}$ alkyl group, an amino C$_{1-4}$ alkyl group, a C$_{1-4}$ alkylamino C$_{1-4}$ alkyl group, a di (C$_{1-4}$ alkyl)amino C$_{1-4}$ alkyl group, a piperazinyl group, a piperidyl group, a pyrrolidinyl group, a pyridyl group, a thienyl group, an imidazolyl group, a morpholinyl group, a piperazinyl C1-4 alkyl group, a piperidyl C$_{1-4}$ alkyl group, a pyrrolidinyl C$_{1-4}$ alkyl group, a morpholinyl C$_{1-4}$ alkyl group, a thienyl C$_{1-4}$ alkyl group, a phenyl group, a phenyl C$_{1-4}$ alkyl group, a C$_{3-7}$ cycloalkyl group, a C$_{3-7}$ cycloalkenyl group, a C$_{3-7}$ cycloalkyl C$_{1-4}$ alkyl group or C$_{3-7}$ cycloalkenyl C$_{1-4}$ alkyl groups (wherein the piperazinyl group, the piperidyl group, the pyrrolidinyl group, the pyridyl group, the thienyl group, the imidazolyl group, the morpholinyl group, the phenyl group, the C$_{3-7}$ cycloalkyl group, the C$_{3-7}$ cycloalkenyl group may be substituted by one or more substituents selected from a C$_{1-4}$ alkyl group, a C$_{1-4}$ alkoxy group, a halogen atom, a hydroxyl group or —COORa, and Ra is the same as already defined).

In another embodiment of the present invention, R$^1$ is a hydrogen atom, an amino group, a methyl group, an ethyl group, an n-propyl group, an i-propyl group, an n-butyl group, an i-butyl group, a sec-butyl group, a t-butyl group, a piperazin-1-yl group, a (piperazin-1-yl)methyl group, 4-methylpiperazin-1-yl group, a (4-methylpiperazin-1-yl)methyl group, a (2,5-dimethylpiperazin-1-yl)methyl group, a (4-isopropylpiperazin-1-yl)methyl group, a piperidin-1-yl group, a 4-methylpiperazin-1-yl group, a (piperidin-1-yl)methyl group, a (4-methylpiperazin-1-yl) methyl group, a methoxy group, an ethoxy group, an n-propoxy group, an i-propoxy group, a (3-hydroxy)propoxy group, a (2-dimethylamino) ethoxy group, a (3-dimethylamino)propoxy group, a (4-hydroxy)botoxy group, a 2-aminoethoxy group, a 2-(4-methylpiperidin-1-yl)ethoxy group, a 2-pyridyl group, a 3-pyridyl group, a 4-pyridyl group, a 2-thienyl group, a 2-imidazolyl group, a 1-methyl-2-imidazolyl group, a 2-pyrazinyl group, a 4-morpholinyl group, a (4-morpholinyl)methyl group, a phenyl group, a benzyl group, a cyclopropyl group, a cyclopropyl-methyl group, a cyclopentyl-methyl group or a cyclohexylmethyl group. Preferable, examples of R$^1$ include a hydrogen atom, an amino group, a methyl group, an ethyl group, a (piperazin-1-yl)methyl group, a methoxy group, an ethoxy group, an n-propoxy group, an i-propoxy group, a (3-hydroxy)propoxy group, a 2-(4-methylpiperazin-1-yl) ethoxy group.

Examples of B, which is an arbitrary substituent in R$^1$ can be independently selected from a halogen atom, an oxo group, a carbamoyl group, a C$_{1-4}$ alkylcarbamoyl group, a di(C$_{1-4}$ alkyl)carbamoyl group, a C$_{1-4}$ alkylcarbonylamino group, an amino group, a C$_{1-4}$ alkylamino group, a di(C$_{1-4}$ alkyl)amino group, a C$_{1-4}$ alkylsulfonylamino group, a sulfamoyl group, a C$_{1-4}$ alkylsulfamoyl group, a di(C$_{1-4}$ alkyl) sulfamoyl group, a C$_{1-4}$ alkylsulfonyl group, a carboxyl group, a C$_{1-4}$ alkoxycarbonyl group, a hydroxy group, a C$_{1-4}$ alkoxy group, a piperazinyl group, a piperidyl group, a pyrrolidinyl group, a pyridyl group, an imidazolyl group, a morpholinyl group, a thienyl group and a thiazolyl group (wherein the piperazinyl group, the piperidyl group, the pyrrolidinyl group, the pyridyl group, the imidazolyl group, the morpholinyl group, the thienyl group, the thiazolyl group may be substituted by one or more substituents selected from a C$_{1-4}$ alkyl group, a C$_{1-4}$ alkoxy group, a halogen atom, a hydroxyl group and —COORa, and wherein Ra is the same as already defined here). Preferably B can be selected from a hydroxyl group, a methyl group, an ethyl group, an n-propyl group, an i-propyl group, a methoxy group, an ethoxy group, an n-propoxy group, an i-propoxy group, an amino group, a methylamino group, a dimethylamino group, an ethylamino group, a diethylamino group, a fluorine atom, a chlorine atom, a bromine atom, an iodine atom, a carbamoyl group, a methylcarbamoyl group, a dimethylcarbamoyl group, a carboxyl group, a formamide group, an acetamide group, a methylsulfonylamino group, a sulfamoyl group, a methylsulfamoyl group, a dimethylsulfamoyl group, a methylsulfonyl group, a methoxycarbonyl group, an ethoxycarbonyl group, a piperazinyl group, a piperidyl group, a pyrrolidinyl group, a pyridyl group, an imidazolyl group, a morpholinyl group, a thienyl group or the thiazolyl group (wherein the piperazinyl group, the piperidyl group, the pyrrolidinyl group, the pyridyl group, the imidazolyl group, the morpholinyl group, the thienyl group, the thiazolyl group may be substituted by one or more substituents selected from a hydroxyl group, a methyl group, an ethyl group and a carboxyl group).

Furthermore, in an embodiment of the present invention, both R$^2$ and R$^3$ are a methyl group.

In an embodiment of the present invention, examples of Ra and Rb include a C$_{1-6}$ alkoxy C$_{1-6}$ alkyl group such as a methoxymethyl group, an ethoxy methyl group and a methoxyethyl group; a C$_{7-14}$ aralkyloxy C$_{1-6}$ alkyl group such as a benzyloxymethyl; a C$_7$-C$_{14}$ aralkyl group such as a benzyl group and a 4-methoxybenzyl group, a C$_{7-14}$ aralkyloxy carbonyl group such as a benzyloxycarbonyl group, a C$_{1-6}$ alkylsulfonyl group such as a methanesulphonyl group and an arylsulfonyl group such as p-toluenesulphonyl group.

In addition, it is preferable in the present invention that R$^1$, Ra and Rb in —SO$_2$R$^1$, —SO$_2$Ra and —SO$_2$Rb are not a hydrogen atom.

Preferably Q is a group represented by the following formula:

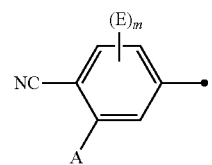

[Formula 10]

wherein A, m and E are the same as defined above] in the present invention. Here, A in the above formula is preferably a trifluoromethyl group, a halogen atom, —OR$^a$ or a C$_{1-4}$ alkyl group, and more preferably a trifluoromethyl group, a halogen atom or —OR$^a$. m is preferably 0 or 1, and more preferably 0. In addition, E is preferably a methyl group.

According to another aspect of the present invention, a compound selected from
4-[3-(1-ethoxycarbonylpiperidine-4-yl)-4,4-dimethyl-5-oxo-2-thioxoimidazolidin-1-yl]-2-trifluoromethylbenzonitrile;
4-[3-(1-ethoxycarbonylpiperidine-4-yl)-4,4-dimethyl-5-oxo-2-thioxoimidazolidin-1-yl]-2-chlorobenzonitrile;
4-[3-(1-ethoxycarbonylpiperidine-4-yl)-4,4-dimethyl-5-oxo-2-thioxoimidazolidin-1-yl]-2-chloro-3-methylbenzonitrile;
4-[3-(1-acetylpiperidin-4-yl)-4,4-dimethyl-5-oxo-2-thioxoimidazolidin-1-yl]-2-trifluoromethylbenzonitrile;
4-[3-(1-ethanesulfonylpiperidin-4-yl)-4,4-dimethyl-5-oxo-2-thioxoimidazolidin-1-yl]-2-trifluoromethylbenzonitrile;
4-[3-(1-acetylpiperidin-4-yl)-4,4-dimethyl-5-oxo-2-thioxoimidazolidin-1-yl]-2-chlorobenzonitrile;

4-[3-(1-propionylpiperidin-4-yl)-4,4-dimethyl-5-oxo-2-thioxoimidazolidin-1-yl]-2-chlorobenzonitrile;
4-[3-(1-propanesulfonylpiperidin-4-yl)-4,4-dimethyl-5-oxo-2-thioxoimidazolidin-1-yl]-2-chlorobenzonitrile;
4-[3-(1-ethanesulfonylpiperidin-4-yl)-4,4-dimethyl-5-oxo-2-thioxoimidazolidin-1-yl]-2-chlorobenzonitrile;
4-[3-(1-ethanesulfonylpiperidin-4-yl)-4,4-dimethyl-2,5-dioxoimidazolidin-1-yl]-2-trifluoromethyl-3-methylbenzonitrile;
4-[3-(1-propanesulfonylpiperidin-4-yl)-4,4-dimethyl-2,5-dioxoimidazolidin-1-yl]-2-chloro-3-methylbenzonitrile;
4-[3-(1-propionylpiperidin-4-yl)-4,4-dimethyl-2,5-dioxoimidazolidin-1-yl]-2-chloro-3-methylbenzonitrile;
{2-chloro-5-[3-(4-cyano-3-trifluoromethylphenyl)-5,5-dimethyl-2,4-dioxoimidazolidin-1-yl]phenyl}carbamic acid ethyl ester;
4-{4,4-dimethyl-3-[1-(3-methylbutyryl)-piperidin-4-yl]-5-oxo-2-thioxoimidazolidin-1-yl}-2-trifluoromethylbenzonitrile;
4-[3-(2-acetylaminobenzothiazol-5-yl)-4,4-dimethyl-5-oxo-2-thioxoimidazolidin-1-yl]-2-trifluoromethylbenzonitrile;
4-[3-(2-acetylaminobenzothiazol-5-yl)-4,4-dimethyl-5-oxo-2-thioxoimidazolidin-1-yl]-2-chlorobenzonitrile;
4-[3-(2-acetylaminobenzothiazol-5-yl)-4,4-dimethyl-5-oxo-2-thioxoimidazolidin-1-yl]-2-methoxybenzonitrile;
{5-[3-(4-cyano-3-trifluoromethylphenyl)-5,5-dimethyl-4-oxo-2-thioxoimidazolidin-1-yl]-benzothiazol-2-yl}urea;
{5-[3-(4-cyano-3-methoxyphenyl)-5,5-dimethyl-4-oxo-2-thioxoimidazolidin-1-yl]-benzothiazol-2-yl}urea;
{5-[3-(4-cyano-3-chlorophenyl)-5,5-dimethyl-4-oxo-2-thioxoimidazolidin-1-yl]-benzothiazol-2-yl}urea;
N-{2-chloro-4-[3-(4-cyano-3-trifluoromethylphenyl)-5,5-dimethyl-2,4-dioxoimidazolidin-1-yl]-phenyl}-2-piperazin-1-ylacetamide;
4-[3-(3-acetylamino-4-chlorophenyl)-4,4-dimethyl-5-oxo-2-thioxoimidazolidin-1-yl]-2-trifluoromethylbenzonitrile;
4-[3-(3-isopropoxycarbonylamino-4-chlorophenyl)-4,4-dimethyl-2,5-dioxoimidazolidin-1-yl]-2-trifluoromethylbenzonitrile;
4-[3-(3-ethoxycarbonylamino-4-chlorophenyl)-4,4-dimethyl-2,5-dioxoimidazolidin-1-yl]-2-methoxybenzonitrile;
4-[3-(3-isopropoxycarbonylamino-4-chlorophenyl)-4,4-dimethyl-2,5-dioxoimidazolidin-1-yl]-2-methoxybenzonitrile;
4-[3-(3-n-propoxycarbonylamino-4-chlorophenyl)-4,4-dimethyl-2,5-dioxoimidazolidin-1-yl]-2-methoxybenzonitrile;
{2-chloro-5-[3-(4-cyano-3-trifluoromethylphenyl)-5,5-dimethyl-2,4-dioxoimidazolidin-1-yl]phenyl}-carbamic acid 3-hydroxypropyl ester;
{2-chloro-5-[3-(4-cyano-3-trifluoromethylphenyl)-5,5-dimethyl-2,4-dioxoimidazolidin-1-yl]phenyl}-carbamic acid 2-dimethylaminoethyl ester;
{2-chloro-5-[3-(4-cyano-3-trifluoromethylphenyl)-5,5-dimethyl-2,4-dioxoimidazolidin-1-yl]phenyl}-carbamic acid 2-(4-methylpiperazin-1-yl)ethyl ester;
{2-chloro-5-[3-(4-cyano-3-methoxyphenyl)-5,5-dimethyl-2,4-dioxoimidazolidin-1-yl]phenyl}-carbamic acid methyl ester;
{2-chloro-5-[3-(4-cyano-3-chlorophenyl)-5,5-dimethyl-2,4-dioxoimidazolidin-1-yl]phenyl}-carbamic acid 2-dimethylaminoethyl ester;
{2-chloro-5-[3-(4-cyano-3-trifluoromethylphenyl)-5,5-dimethyl-2,4-dioxoimidazolidin-1-yl]phenyl}-carbamic acid 3-dimethylaminopropyl ester;
{2-chloro-5-[3-(4-cyano-3-trifluoromethylphenyl)-5,5-dimethyl-2,4-dioxoimidazolidin-1-yl]phenyl}-carbamic acid 4-hydroxybutyl ester;
{2-chloro-5-[3-(4-cyano-3-trifluoromethylphenyl)-5,5-dimethyl-2,4-dioxoimidazolidin-1-yl]phenyl}carbamic acid 2-tert-butoxycarbonylaminoethyl ester;
4-[3-(4-cyano-3-trifluoromethylphenyl)-5,5-dimethyl-4-oxo-2-thioxoimidazolidin-1-yl]piperidine-1-carbamic acid (2-dimethylaminoethyl)amide;
4-[3-(4-cyano-3-trifluoromethylphenyl)-5,5-dimethyl-4-oxo-2-thioxoimidazolidin-1-yl]piperidine-1-carbamic acid 2-dimethylaminoethyl ester;
{2-chloro-5-[3-(4-cyano-3-trifluoromethylphenyl)-5,5-dimethyl-2,4-dioxoimidazolidin-1-yl]phenyl}carbamic acid 2-aminoethyl ester;
4-[3-(1-ethylaminocarbonylpiperidin-4-yl)-4,4-dimethyl-5-oxo-2-thioxoimidazolidin-1-yl]-2-trifluoromethylbenzonitrile;
4-[3-(1-n-propylaminocarbonylpiperidin-4-yl)-4,4-dimethyl-5-oxo-2-thioxoimidazolidin-1-yl]-2-trifluoromethylbenzonitrile;
4-[3-(1-ethylaminocarbonylpiperidin-4-yl)-4,4-dimethyl-5-oxo-2-thioxoimidazolidin-1-yl]-2-chlorobenzonitrile;
4-[3-(1-n-propylaminocarbonylpiperidin-4-yl)-4,4-dimethyl-5-oxo-2-thioxoimidazolidin-1-yl]-2-chlorobenzonitrile;
4-[3-(1-ethylaminosulfonylpiperidin-4-yl)-4,4-dimethyl-5-oxo-2-thioxoimidazolidin-1-yl]-2-trifluoromethylbenzonitrile;
4-{3-[1-(2-dimethylaminoethyl)aminosulfonylpiperidin-4-yl]-4,4-dimethyl-5-oxo-2-thioxoimidazolidin-1-yl}-2-trifluoromethylbenzonitrile;
4-[3-(4-cyano-3-trifluoromethylphenyl)-5,5-dimethyl-4-oxo-2-thioxoimidazolidin-1-yl]piperidine-1-carboxylic acid 2,3-dihydroxypropyl ester;
{2-chloro-5-[3-(4-cyano-3-trifluoromethylphenyl)-5,5-dimethyl-4-oxo-2-thioxoimidazolidin-1-yl]phenyl}carbamic acid 2-hydroxyethyl ester;
{2-chloro-5-[3-(4-cyano-3-chlorophenyl)-5,5-dimethyl-4-oxo-2-thioxoimidazolidin-1-yl]phenyl}carbamic acid 2-hydroxyethyl ester;
{2-chloro-5-[3-(4-cyano-3-methoxyphenyl)-5,5-dimethyl-4-oxo-2-thioxoimidazolidin-1-yl]phenyl}carbamic acid 2-hydroxyethyl ester;
{2-chloro-5-[3-(4-cyano-3-trifluoromethylphenyl)-5,5-dimethyl-4-oxo-2-thioxoimidazolidin-1-yl]phenyl}carbamic acid 2,3-dihydroxypropyl ester;
{2-chloro-5-[3-(4-cyano-3-chlorophenyl)-5,5-dimethyl-4-oxo-2-thioxoimidazolidin-1-yl]phenyl}carbamic acid 2,3-dihydroxypropyl ester;
{2-chloro-5-[3-(4-cyano-3-methoxyphenyl)-5,5-dimethyl-4-oxo-2-thioxoimidazolidin-1-yl]phenyl}carbamic acid 2,3-dihydroxypropyl ester;
{2-chloro-5-[3-(4-cyano-3-trifluoromethylphenyl)-5,5-dimethyl-4-oxo-2-thioxoimidazolidin-1-yl]phenyl}carbamic acid 2-dimethylaminoethyl ester;
{2-chloro-5-[3-(4-cyano-3-chlorophenyl)-5,5-dimethyl-4-oxo-2-thioxoimidazolidin-1-yl]phenyl}carbamic acid 2-dimethylaminoethyl ester;
{2-chloro-5-[3-(4-cyano-3-methoxyphenyl)-5,5-dimethyl-4-oxo-2-thioxoimidazolidin-1-yl]phenyl}carbamic acid 2-dimethylaminoethyl ester;
N-{2-chloro-5-[3-(4-cyano-3-trifluoromethylphenyl)-5,5-dimethyl-4-oxo-2-thioxoimidazolidin-1-yl]phenyl}guanidine;
4-[3-(3-chloro-4-cyanophenyl)-5,5-dimethyl-4-oxo-2-thioxoimidazolidin-1-yl]benzenesulfonamide;

1-{5-[3-(4-cyano-3-trifluoromethylphenyl)-5,5-dimethyl-4-oxo-2-thioxoimidazolidin-1-yl]pyridin-2-yl}-3-(2-dimethylaminoethyl)urea;

{5-[3-(4-cyano-3-trifluoromethylphenyl)-5,5-dimethyl-4-oxo-2-thioxoimidazolidin-1-yl]pyridin-2-yl}carbamic acid 2-dimethylaminoethyl ester;

1-{5-[3-(4-cyano-3-trifluoromethylphenyl)-5,5-dimethyl-4-oxo-2-thioxoimidazolidin-1-yl]pyridin-2-yl}-3-(2-hydroxyethyl)urea;

{5-[3-(4-cyano-3-trifluoromethylphenyl)-5,5-dimethyl-4-oxo-2-thioxoimidazolidin-1-yl]pyridin-2-yl}carbamic acid 2-hydroxyethyl ester;

1-{5-[3-(3-chloro-4-cyanophenyl)-5,5-dimethyl-4-oxo-2-thioxoimidazolidin-1-yl]benzothiazol-2-yl}-3-(2-dimethylaminoethyl)urea;

1-{5-[3-(3-chloro-4-cyanophenyl)-5,5-dimethyl-4-oxo-2-thioxoimidazolidin-1-yl]benzothiazol-2-yl}-3-(2,3-dihydroxypropyl)urea;

1-{5-[3-(3-chloro-4-cyanophenyl)-5,5-dimethyl-4-oxo-2-thioxoimidazolidin-1-yl]benzothiazol-2-yl}-3-(2-hydroxyethyl)urea;

{5-[3-(3-chloro-4-cyanophenyl)-5,5-dimethyl-4-oxo-2-thioxoimidazolidin-1-yl]benzothiazol-2-yl}carbamic acid 2-dimethylaminoethyl ester;

{5-[3-(3-chloro-4-cyanophenyl)-5,5-dimethyl-4-oxo-2-thioxoimidazolidin-1-yl]benzothiazol-2-yl}carbamic acid 2,3-dihydroxypropyl ester;

{5-[3-(3-chloro-4-cyanophenyl)-5,5-dimethyl-4-oxo-2-thioxoimidazolidin-1-yl]benzothiazol-2-yl}carbamic acid 2-hydroxyethyl ester;

N-{2-chloro-5-[3-(4-cyano-3-trifluoromethylphenyl)-5,5-dimethyl-4-oxo-2-thioxoimidazolidin-1-yl]phenyl}succinamide;

3-[3-(3-chloro-4-cyanophenyl)-5,5-dimethyl-4-oxo-2-thioxoimidazolidin-1-yl]benzenesulfonamide;

{5-[3-(3-chloro-4-cyanophenyl)-5,5-dimethyl-4-oxo-2-thioxoimidazolidin-1-yl]pyridin-2-yl}carbamic acid 2-dimethylaminoethyl ester;

{5-[3-(3-chloro-4-cyanophenyl)-5,5-dimethyl-4-oxo-2-thioxoimidazolidin-1-yl]pyridin-2-yl}carbamic acid 2,3-dihydroxypropyl ester;

{5-[3-(4-cyano-3-trifluoromethylphenyl)-5,5-dimethyl-4-oxo-2-thioxoimidazolidin-1-yl]pyridin-2-yl}carbamic acid 2,3-dihydroxypropyl ester;

{2-chloro-5-[3-(3-chloro-4-cyanophenyl)-5,5-dimethyl-4-oxo-2-thioxoimidazolidin-1-yl]phenyl}carbamic acid 2-pyrrolidin-1-ylethyl ester;

{2-chloro-5-[3-(3-chloro-4-cyanophenyl)-5,5-dimethyl-4-oxo-2-thioxoimidazolidin-1-yl]phenyl}carbamic acid 2-diethylaminoethyl ester;

{2-chloro-5-[3-(3-chloro-4-cyanophenyl)-5,5-dimethyl-4-oxo-2-thioxoimidazolidin-1-yl]phenyl}carbamic acid 2-morpholin-4-ylethyl ester;

N-{5-[3-(3-chloro-4-cyanophenyl)-5,5-dimethyl-4-oxo-2-thioxoimidazolidin-1-yl]benzothiazol-2-yl}guanidine;

3-[3-(4-cyano-3-trifluoromethylphenyl)-5,5-dimethyl-4-oxo-2-thioxoimidazolidin-1-yl]benzenesulfonamide;

N-acetyl-3-[3-(4-cyano-3-trifluoromethylphenyl)-5,5-dimethyl-4-oxo-2-thioxoimidazolidin-1-yl]benzenesulfonamide;

{2-chloro-5-[3-(3-chloro-4-cyanophenyl)-5,5-dimethyl-4-oxo-2-thioxoimidazolidin-1-yl]phenyl}carbamic acid (2R,3R)-2,3,4-trihydroxybutyl ester;

{2-chloro-5-[3-(3-chloro-4-cyanophenyl)-5,5-dimethyl-4-oxo-2-thioxoimidazolidin-1-yl]phenyl}-carbamic acid (2S,3S)-2,3,4-trihydroxybutyl ester;

{2-chloro-5-[3-(3-chloro-4-cyanophenyl)-5,5-dimethyl-4-oxo-2-thioxoimidazolidin-1-yl]phenyl}carbamic acid 3-hydroxy-2,2-bishydroxymethylpropyl ester;

{2-chloro-5-[3-(4-cyano-3-trifluoromethylphenyl)-5,5-dimethyl-4-oxo-2-thioxoimidazolidin-1-yl]phenyl}carbamic acid 3-hydroxypropyl ester;

1-{2-chloro-5-[3-(4-cyano-3-trifluoromethylphenyl)-5,5-dimethyl-4-oxo-2-thioxoimidazolidin-1-yl]phenyl}-2-cyanoguanidine;

N-{2-chloro-5-[3-(3-chloro-4-cyanophenyl)-5,5-dimethyl-4-oxo-2-thioxoimidazolidin-1-yl]phenyl}-C,C,C-trifluoromethanesulfonamide;

2-amino-N4-{2-chloro-5-[3-(3-chloro-4-cyanophenyl)-5,5-dimethyl-4-oxo-2-thioxoimidazolidin-1-yl]phenyl}succinamide;

2-amino-N1-{2-chloro-5-[3-(3-chloro-4-cyanophenyl)-5,5-dimethyl-4-oxo-2-thioxoimidazolidin-1-yl]phenyl}succinamide;

N-{5-[3-(3-chloro-4-cyanophenyl)-5,5-dimethyl-4-oxo-2-thioxoimidazolidin-1-yl]benzothiazol-2-yl}succinamide;

4-{2-chloro-5-[3-(3-chloro-4-cyanophenyl)-5,5-dimethyl-4-oxo-2-thioxoimidazolidin-1-yl]phenylcarbamoyl}butyric acid;

4-{2-chloro-5-[3-(3-chloro-4-cyanophenyl)-5,5-dimethyl-4-oxo-2-thioxoimidazolidin-1-yl]phenylcarbamoyl}butyramide;

3-{2-chloro-5-[3-(3-chloro-4-cyanophenyl)-5,5-dimethyl-4-oxo-2-thioxoimidazolidin-1-yl]phenylcarbamoyl}propionic acid;

3-{2-chloro-5-[3-(3-chloro-4-cyanophenyl)-5,5-dimethyl-4-oxo-2-thioxoimidazolidin-1-yl]phenylcarbamoyl}propionamide;

succinic acid mono-(2-{2-chloro-5-[3-(4-cyano-3-trifluoromethylphenyl)-5,5-dimethyl-4-oxo-2-thioxoimidazolidin-1-yl]phenylcarbamoyloxy}ethyl) ester;

dimethylaminoacetic acid 2-{2-chloro-5-[3-(4-cyano-3-trifluoromethylphenyl)-5,5-dimethyl-4-oxo-2-thioxoimidazolidin-1-yl]phenylcarbamoyloxy}ethyl ester;

{2-chloro-5-[3-(3-chloro-4-cyanophenyl)-5,5-dimethyl-4-oxo-2-thioxoimidazolidin-1-yl]phenyl}carbamic acid 3-diethylaminopropyl ester;

L-lysine 2-{2-chloro-5-[3-(4-cyano-3-trifluoromethylphenyl)-5,5-dimethyl-4-oxo-2-thioxoimidazolidin-1-yl]phenylcarbamoyloxy}ethyl ester;

2-chloro-5-[3-(3-chloro-4-cyanophenyl)-5,5-dimethyl-4-oxo-2-thioxoimidazolidin-1-yl]benzenesulfonamide;

N-acetyl-2-chloro-5-[3-(3-chloro-4-cyanophenyl)-5,5-dimethyl-4-oxo-2-thioxoimidazolidin-1-yl]benzenesulfonamide; and N-{5-[3-(3-chloro-4-cyanophenyl)-5,5-dimethyl-4-oxo-2-thioxoimidazolidin-1-yl]benzothiazol-2-yl}-C,C,C-trifluoromethanesulfonamide;

or pharmaceutically acceptable salt, prodrug or the solvate thereof are provided.

According to still another aspect of the present invention, a drug which comprises the compound represented by the above formula (I) or a pharmaceutically acceptable salt, prodrug or solvate thereof as an active ingredient is provided.

According to still another aspect of the present invention, a pharmaceutical composition, an anti-androgen agent, a prophylactic or therapeutic agent for a disease selected from prostate cancer, benign prostatic hypertrophy, male pattern baldness, sexual precociousness, acnevulgaris, seborrhea and hypertrichosis which comprises the compound represented by the above formula (I) or a pharmaceutically acceptable salt, prodrug or solvate thereof as an active ingredient are provided.

Furthermore, according to another aspect of the present invention, use of the compound represented by the above formula (I) or a pharmaceutically acceptable salt, prodrug or solvate thereof in manufacturing a drug used as an androgen receptor antagonist is provided.

According to still another aspect of the present invention, a process for preparing a compound represented by formula (I):

[Formula 11]

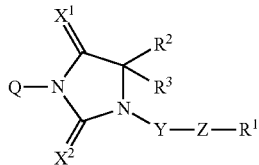

(I)

wherein Q, $X^1$, $X^2$, Y, Z, $R^1$, $R^2$ and $R^3$ are the same as defined in any one of claims 1 to 17, which comprises a step of reacting a compound represented by formula (III):

[Formula 12]

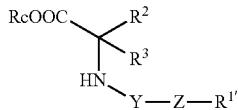

(III)

wherein Y, Z, $R^2$ and $R^3$ are the same as defined above;
$R^{1'}$ is defined similarly as $R^1$ above, and when $R^{1'}$ contains a hydroxyl group, a carboxyl group, an amino group or a $C_{1-4}$ alkylamino group, these groups may be protected by a protecting group;
Rc is a hydrogen atom or a $C_{1-6}$ alkyl group, and the alkyl group may be substituted by one or more substituents selected from a halogen atom, an aryl group, a $C_{1-6}$ alkoxy group with a compound represented by the following formula (IX):

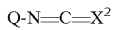 Q-N=C=$X^2$ (IX)

wherein Q and $X^2$ are the same as defined above and which may further comprise a step of removing the protecting group is also provided. Here, removal of the protecting group can be performed by any method known in the art, and, for example, amide or ester protecting groups can be removed by solvolysis (for example, hydrolysis) with an acid or a base, arylalkyl protecting groups such as a benzyl group can be removed by hydrogenation in the presence of a catalyst (for example, palladium catalyst) or by dehydrogenation using dichlorodicyano quinone, etc.

According to still another aspect of the present invention, a compound represented by formula (III):

[Formula 13]

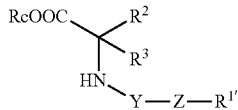

(III)

wherein Rc, Y, Z, $R^{1'}$, $R^2$ and $R^3$ are the same as defined above is also provided.

Here, any group which is used as a protecting group for a hydroxyl group, an amino group, an alkylamino group can be used without particular limitation as a "protecting group" contained in Examples of protecting group for a hydroxyl group include a formyl group, an acetyl group, a methoxycarbonyl group, a trichloroacetyl group, a propionyl group, a pivaloyl group, a benzoyl group, an allyloxycarbonyl group, a trimethylsilyl group, a triethylsilyl group, a triisopropylsilyl group, a t-butyldimethylsilyl group, a t-butyldiphenylsilyl group, an i-propyldimethylsilyl group, a methyl group, a methoxymethyl group, a methylthiomethyl group, a methoxyethoxymethyl group, a bis(2-chloroethoxy)methyl group, a tetrahydropyranyl group, a tetrahydrothiopyranyl group, a 4-methoxytetrahydropyranyl group, a 4-methoxytetrahydrothiopyranyl group, a tetrahydrofuranyl group, a tetrahydrothiofuranyl group, a 1-ethoxyethyl group, a methoxyisopropyl group, a t-butyl group, an allyl group, an ethoxyethyl group, a 1-(2-chloroethoxy)ethyl group, a 1-methyl-1-methoxyethyl group, a 2-(phenylselenenyl)ethyl group, a benzyl group, a p-methoxybenzyl group, an o-nitrobenzyl group, a t-butyloxycarbonyl group, a benzyloxycarbonyl group, a p-toluenesulfonyl group, a t-butylthiomethyl group, a (phenyldimethylsilyl)methoxymethyl group, a benzyloxymethyl group, a p-methoxybenzyloxymethyl group, a p-chlorobenzyloxymethyl group, a (4-methoxyphenoxy)methyl group, a guaicolmethyl group, a t-butoxymethyl group, a 4-pentenyloxymethyl group, a siloxymethyl group, a 2-methoxyethoxymethyl group, a 2,2,2-trichloroethoxymethyl group, a 2-(trimethylsilyl)ethoxymethyl group, a phenylthiomethyl group, a cyclopropylmethyl group, a 3-bromotetrahydropyranyl group, a 1-methoxycyclohexyl group, a 4-methoxytetrahydrothiopyranyl a S,S-dioxide group, a 1-[(2-chloro-4-methyl)phenyl]-4-methoxypiperidin-4-yl group, a 1,4-dioxan-2-yl group, phenacyl group, a p-bromophenacyl group, a 9-anthrylmethyl group, a 1-methyl-benzyloxyethyl group, a 1-methyl-1-benzyloxy-2-fluoroethyl group, a 2,2,2-trichloroethyl group, a 2-trimethylsilylethyl group, a 2,2-dichloro-1,1-difluoroethyl group, an isopropyl group, a cyclohexyl group, a p-chlorophenyl group, a p-methoxyphenyl group, a 2,4-dinitrophenyl group, a heptafluoro-p-toluyl, a tetrafluoro-4-pyridyl, a 3,4-dimethoxybenzyl group, a p-nitrobenzyl group, a p-chlorobenzyl group, a p-bromobenzyl group, a 2,6-dichlorobenzyl group, a 2,6-dimethylbenzyl group, a p-cyanobenzyl group, a p-phenylbenzyl group, a 4-(dimethylaminocarbonyl)benzyl group, a 2-picolyl group, a 4-picolyl group, a 3-methyl-2-picolyl N-oxide group, a diphenylmethyl group, a p,p'-dinitrobenzhydryl group, a 5-dibenzosuberyl group, a triphenylmethyl group, an α-naphthyldiphenylmethyl group, a p-methoxyphenyldiphenylmethyl group, a di(p-methoxyphenyl)phenylmethyl group, a tri(p-methoxyphenyl)methyl group, a 4-(4'-bromophenacyloxy)phenyldiphenylmethyl group, a 4,4',4''-tris (4,5-dichlorophthalimidephenyl)methyl group, a 4,4',4''-tris (levulinoyloxyphenyl)methyl group, a 4,4',4''-tris (benzoyloxyphenyl)methyl group, a 3-(imidazol-1-ylmethyl) bis(4',4''-dimethoxyphenyl)methyl group, a 1,1-bis(4-methoxyphenyl)-1'-pyrenylmethyl group, a 9-anthryl group, a 9-(9-phenyl)xanthenyl group, a 9-(9-phenyl-10-oxo)anthryl group, a 1,3-benzdithiolan-2-yl group, a benzisothiazolyl S,S-dioxide group, a diethylisopropylsilyl group, a dimethylthexylsilyl group, a tribenzylsilyl group, a tri-p-xylylsilyl group, a triphenylsilyl group, a diphenylmethylsilyl group, a t-butylmethoxyphenylsilyl group, a butyryl group, a valeryl group, a levulinyl group, a benzoylformyl group, a chloroacetyl group, a dichloroacetyl group, a trifluoroacetyl group, a methoxyacetyl group, a triphenylmethoxyacetyl group, a phenoxyacetyl group, a p-chlorophenoxyacetyl group, a phenylacetyl group, a 4-methoxyphenylacetyl group, a 2,6-dichloro-4-methylphenoxyacetyl group, a 2,4-bis(1,1-dimethylpropyl)phenoxyacetyl group, a chlorodiphenylacetyl group, propionyl group, a 3-phenylpropionyl group, a butyryl group, an isobutyryl group, a 4-atidobutyryl group, a 4-(methylthiomethoxy)butyryl group, an (E)-2-methyl-2-butenoyl group, a valeryl group, a monosuccinoyl group, a levulinyl(4-oxopentanoyl) group, a 4,4-(ethylenedithio)pentanoyl group, a 4-nitro-methylpentanoyl group, a pivaloyl group, an adamanthyl group, a crotonyl group, a 4-methoxycrotonyl group, a cyclohexanecarbonyl group, a 4-nitrobenzoyl group, a 4-chlorobenzoyl group, a 2-iodobenzoyl group, a 4-methoxybenzoyl group, a p-phenylbenzoyl group, a 2,4,6-triphenylbenzoyl group, an o-(dibromomethyl)benzoyl group, a 2-(methylthiomethoxymethyl)benzoyl group, an o-(methoxycarbonyl)benzoyl group, a naphthoyl group, a toluoyl group, a 9-fluorenecarbonyl group, a 9-fluorenylmethyloxycarbonyl group, an ethoxycarbonyl group, a 2,2,2-trichloroethoxycarbonyl group, a 2-(trimethylsilyl)ethoxycarbonyl group, a 2-(phenylsulfonyl)ethoxycarbonyl group, a 2-(triphenylphosphonio)ethoxycarbonyl group, a 2-(methylthiomethoxy)ethoxycarbonyl group, a propoxycarbonyl group, an isopropoxycarbonyl group, an i-butoxycarbonyl group, a vinyloxycarbonyl group, an allyloxycarbonyl group, a p-nitrophenyloxycarbonyl group, a t-butoxycarbonyl group, a benzyloxycarbonyl group, a 4-methoxybenzyloxycarbonyl group, a 3,4-dimethoxybenzyloxycarbonyl group, an o-nitrobenzyloxycarbonyl group, a p-nitrobenzyloxycarbonyl group, a benzylthiocarbonyl group, a 4-ethoxy-1-naphthyloxycarbonyl group, a (methylthio)thiocarbonyl group, an i-butylaminocarbonyl group, a phenylaminocarbonyl group, a methanesulphonyloxy group, a benzensulphonyloxy group, a 2-formylbenzensulphonyloxy group, a benzylsulfonyloxy group, a tosyl group, a 2,4-dinitrophenylsulfenyloxy group, a dimethylphosphinyl group, and a dimethylthiophosphinyl group.

Of these, preferable protecting group includes a formyl group, an acetyl group, a methoxycarbonyl group, a trichloroacetyl group, a propionyl group, a pivaloyl group, a benzoyl group, an allyloxycarbonyl group, a trimethylsilyl group, a triethylsilyl group, a triisopropylsilyl group, a t-butyldimethylsilyl group, a t-butyldiphenylsilyl group, an i-propyl dimethylsilyl group, a methyl group, a methoxy methyl group, a methylthio methyl group, a methoxyethoxymethyl group, a bis(2-chloroethoxy) methyl group, a tetrahydropyranyl group, a tetrahydrothiopyranyl group, a 4-methoxytetrahydropyranyl group, a 4-methoxytetrahydrothiopyranyl group, a tetrahydrofuranyl group, tetrahydrothiofuranyl group, a 1-ethoxyethyl group, a methoxyisopropyl group, a t-butyl group, an allyl group, an ethoxyethyl group, a 1-(2-chloroethhoxy)ethyl group, a 1-methyl-1-methoxyethyl group, a 2-(phenylselenenyl)ethyl group, a benzyl group, a p-methoxybenzyl group, and an o-nitrobenzyl group.

In addition, examples of suitable protecting group for a carboxy group include $C_{1-6}$ alkyl groups forming $C_{1-6}$ alkyl esters, $C_{7-14}$ aralkyl groups forming $C_{7-14}$ aralkyl esters, and $C_{1-6}$ alkoxy $C_{1-6}$ alkyl groups forming $C_{1-6}$ alkoxy $C_{1-6}$ alkyl esters. Specifically, a methyl group, an ethyl group, an i-propyl group, a pivaloyl group, a t-butyl group, a benzyl group, and a methoxymethyl group are included.

In addition, examples of suitable protecting group for an amino or alkylamino group include a methyloxycarbonyl group, an ethyloxycarbonyl group, a 2,2,2-trichloroethyloxycarbonyl group, a 2-trimethylsilylethyloxycarbonyl group, a 2-chloroethyloxycarbonyl group, a 2,2-dichloroethyloxycarbonyl group, a 1-methyl-1-(4-biphenylyl)ethyloxycarbonyl group, a t-butyloxycarbonyl group, a benzylthiocarbonyl group, a formyl group, an acetyl group, a chloroacetyl group, a trichloroacetyl group, a benzoyl group, an o-nitrophenylacetyl group, a propionyl group, a pivaloyl group, a trimethylsilyl group, a triethylsilyl group, a triisopropylsilyl group, a t-butyldimethylsilyl group, a t-butyldiphenylsilyl group, an i-propyldimethylsilyl group, a 9-fluorenylmethyloxycarbonyl group, a 9-(2-sulfo)fluorenylmethyloxycarbonyl group, a 9-(2,7-dibromo)fluorenylmethyloxycarbonyl group, a 4-methoxyphenacyloxycarbonyl group, a phenethyloxycarbonyl group, a 1-(1-adamantyl)-1-methylethyloxycarbonyl group, a 2-bromoethyloxycarbonyl group, a 2-iodothyloxycarbonyl group, a 2,2-dibromoethyloxycarbonyl group, 2,2,2-trichloroethyloxycarbonyl group, a 2,2,2-tribromoethyloxycarbonyl group, a 1,1-dimethyl-2-chloroethyloxycarbonyl group, a 1,1-dimethyl-2-bromoethyloxycarbonyl group, a 1,1-dimethyl-2,2-dibromoethyloxycarbonyl group, a 1,1-dimethyl-2,2,2-trichloroethyloxycarbonyl group, a 1-(3,5-di-t-butylphenyl)-1-methylethyloxycarbonyl group, a 2-(2'-pyridyl)ethyloxycarbonyl group, a 2-(4'-pyridyl)ethyloxycarbonyl group, a 2-(N,N-dicyclohexylcarboxamide)ethyloxycarbonyl group, a 1-adamantyloxycarbonyl group, a vinyloxycarbonyl group, an allyloxycarbonyl group, a 1-isopropylallyloxycarbonyl group, a cinnamyloxycarbonyl group, a 4-nitrocinnamyloxycarbonyl group, an 8-quinolyloxycarbonyl group, a piperidinyloxycarbonyl group, a benzyloxycarbonyl group, a p-methoxybenzyloxycarbonyl group, a p-nitrobenzyloxycarbonyl group, a p-chlorobenzyloxycarbonyl group, a p-bromobenzyloxycarbonyl group, a p-cyanobenzyloxycarbonyl group, an o-nitrobenzyloxycarbonyl group, a 2,4-dichlorobenzyloxycarbonyl group, a 4-methylsulfinylbenzyloxycarbonyl group, a 9-anthrylmethyloxycarbonyl group, a diphenylmethyloxycarbonyl group, a 2-methylthioethyloxycarbonyl group, a 2-methylsulfonylethyloxycarbonyl group, a 2-(p-toluenesulfonyl)ethyloxycarbonyl group, a [2-(1,3-dithianyl)]methyloxycarbonyl group, a 4-methylthiophenyloxycarbonyl group, a 2,4-dimethylthiophenyloxycarbonyl group, a 2-phosphinoethyloxycarbonyl group, a 2-triphenylphosphonioisopropyloxycarbonyl group, a 1,1-dimethyl-2-cyanoethyloxycarbonyl group, an m-chloro-p-acetylbenzyloxycarbonyl group, a p-(dihydroxyboryl)benzyloxycarbonyl group, a 5-benzisoxazolylmethyloxycarbonyl group, a 2-(trifluoromethyl)-6-chromonylmethyloxycarbonyl group, an m-nitrophenyloxycarbonyl group, a 3,5-dimethoxybenzyloxycarbonyl group, a 3,4-dimethoxy-6-nitrobenzyloxycarbonyl group, a phenyl(o-nitrophenyl)methyloxycarbonyl group, a piperidinylcarbonyl group, a p-toluenesulfonylaminocarbonyl group, a phenylaminothiocarbonyl group, a t-amyloxycarbonyl group, a cyclobutyloxycarbonyl group, a cyclopentyloxycarbonyl group, a cyclohexyloxycarbonyl group, a cyclopropylmethyloxycarbonyl group, a p-decyloxybenzyloxycarbonyl group, a diisopropylmethyloxycarbonyl group, a 2,2-dimethoxycarbonylvinyloxycarbonyl group, an o-(N,N-dimethylcarboxamide)benzyloxycarbonyl group, a 1,1-dimethyl-3-(N,N-dimethylcarboxamide)propyloxycarbonyl group, a 1,1-dimethylpropynyloxycarbonyl group, a di(2-pyridyl)methyloxycarbonyl group, a 2-furanylmethyloxycarbonyl group, an isobornyloxycarbonyl group, an isobutyloxycarbonyl group, an isonicotinyloxycarbonyl group, a p-(p'-methoxyphenylazo)benzyloxycarbonyl group, a 1-methylcyclobutyloxycarbonyl group, a 1-methylcyclohexyloxycarbonyl group, a 1-methyl-1-cyclopropylmethyloxycarbonyl group, a 1-methyl-1-(3,5-dimethoxyphenyl)ethyloxycarbonyl group, a 1-methyl-1-(p-phenylazophenyl)ethyloxycarbonyl group, a 1-methyl-1- phenylethyloxycarbonyl group, a 1-methyl-1-(4-pyridyl)ethyloxycarbonyl group, a p-(phenylazo)benzyloxycarbonyl group, a 2,4,6-tri-t-butylphenyloxycarbonyl group, a 4-(trimethylammonium)benzyloxycarbonyl group, a 2,4,6-trimethylbenzyloxycarbonyl group, a trifluoroacetyl group, a phenylacetyl group, a 3-phenylpropionyl group, a picolinoyl group, a p-phenylbenzoyl group, an o-nitrophenoxyacetyl group, an acetoacetyl group, an (N-dithiobenzyloxycarbonylamino)acetyl group, a 3-(p-hydroxyphenyl)propionyl group, a 3-(o-nitrophenyl)propionyl group, a 2-methyl-2-(o-nitrophenoxy)propionyl group, a 2-methyl-2-(o-phenylazophenoxy)propionyl group, a 4-chlorobutyryl group, a 3-methyl-3-nitrobutyryl group, an o-nitrocinnamoyl group, an o-nitrobenzoyl group, an o-(benzoyloxymethyl)benzoyl group, phthalimide, dithiasuccinimide, 2,3-diphenylmaleimide, 2,5-dimethylpyrrole imide, a methyl group, an allyl group, a [2-(trimethylsilyl)ethoxy]methyl group, a 3-acetoxypropyl group, a benzyl group, a di(4-methoxyphenyl)methyl group, a 5-dibenzosuberyl group, triphenylmethyl group, a (4-methoxyphenyl)diphenylmethyl group, a 9-phenyl fluorenyl group, a ferrocenylmethyl group, 1,1-dimethylthiomethylene, benzylidene, p-methoxybenzylidene, diphenylmethylene, [(2-pyridyl)mesityl]methylene, N,N-dimethylaminomethylene, isopropylidene, p-nitrobenzylidene, salicylidene, 5-chlorosalicylidene, (5-chloro-2-hydroxyphenyl)phenylmethylene, and cyclohexylidene.

Preferable examples include a methyloxycarbonyl group, an ethyloxycarbonyl group, a 2,2,2-trichloroethyloxycarbonyl group, a 2-trimethylsilylethyloxycarbonyl group, a 2-chloroethyloxycarbonyl group, a 2,2-dichloroethyloxycarbonyl group, a 1-methyl-1-(4-biphenylypethyloxycarbonyl group, a t-butyloxycarbonyl group, a benzylthiocarbonyl group, a formyl group, an acetyl group, a chloroacetyl group, a trichloroacetyl group, a benzoyl group, an o-nitrophenylacetyl group, a propionyl group, a pivaloyl group, a trimethylsilyl group, a triethylsilyl group, a triisopropylsilyl group, a t-butyldimethylsilyl group, a t-butyldiphenylsilyl group, and an i-propyldimethylsilyl group.

According to another aspect of the present invention, a compound represented by formula (VII):

[Formula 14]

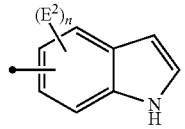

(VII)

wherein Ya is selected from the following formulas:

[Formula 15]

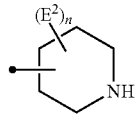

Ya$^1$

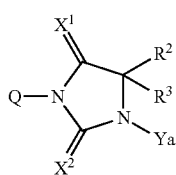

Ya$^2$

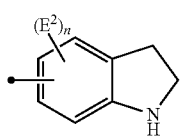

Ya$^3$ and $X^1, X^2, R^2, R^3, Q, E^2$ and n are the same defined above, is provided.

According to a further aspect of the present invention, a compound represented by formula (VII):

[Formula 16]

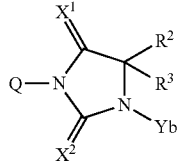

(VIII)

wherein Yb is selected from the following formulas:

[Formula 17]

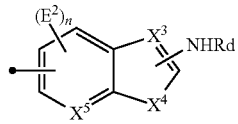

Yb$^4$

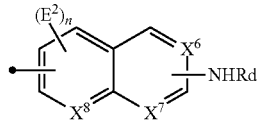

Yb$^5$

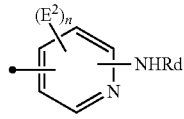

Yb$^6$

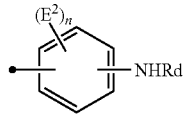

Yb$^7$ and $X^1, X^2, X^3, X^4, X^5, X^6, X^7, X^8, R^2, R^3, Q, E$ and n are the same as defined above, and Rd is a hydrogen atom or a $C_{1-6}$ alkyl group, is provided.

According to a further aspect of the present invention, a compound represented by formula (I'):

[Formula 18]

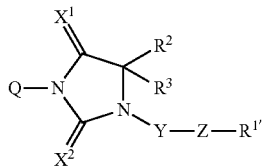

(I')

wherein Q, $X^1$, $X^2$, Y, Z, $R^2$ and $R^3$ are the same as defined above, and $R^{1'}$ is the same as $R^1$ already defined, and when $R^{1'}$ contains a hydroxyl group, an amino group or a $C_{1-4}$ alkylamino group, these groups may be protected by a protecting group, is provided.

According to a further aspect of the present invention, a process for preparing a compound represented by formula (I)

[Formula 19]

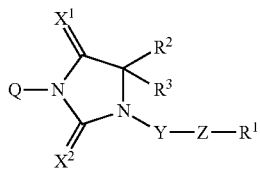

(I)

wherein Q, $X^2$, Y, Z, $R^1$, $R^2$ and $R^3$ are the same as defined in any one of claims 1 to 17 and X' is O, which comprises a step of reacting a compound represented by formula (IV):

[Formula 20]

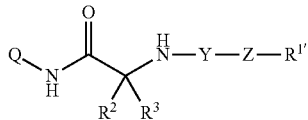

(IV)

wherein Q, Y, Z, $R^2$ and $R^3$ are the same as defined above; $R^{1'}$ is defined the same as above $R^1$, and when $R^{1'}$ contains a hydroxyl group, a carboxyl group, an amino group or a $C_{1-4}$ alkylamino group, these groups may be protected by a protecting group, with a carbonylating agent or a thiocarbonylating agent;
and which may further comprise a step of removing the protecting group is provided. Here, the protecting group which $R^{1'}$ can contain is the same as defined for $R^{1'}$ in the above formula (III). Phenyl chloroformate, phosgene, diphosgene, triphosgene, carbonyldiimidazole are included in the examples of the carbonylation agent which can be used in the production process of the present invention, and phenyl chlorothionoformate, thiophosgene, thiocarbonyldiimidazole are included in the examples of the thiocarbonylation agent which can be used.

In addition, in the production process of the present invention, any suitable inert solvent and base can be used and specifically solvent and base and reaction conditions similar to Step O3 of Production Process O described below can be used.

According to a further aspect of the present invention, a compound represented by formula (IV):

[Formula 18]

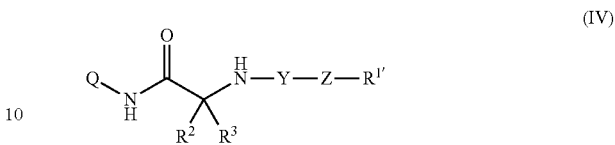

(IV)

wherein Q, Y, Z, $R^{1'}$, $R^2$ and $R^3$ are the same as defined in claim 30, is provided.

In an embodiment of the present invention, when —Y—Z— in formula (I), (I') and (III) is $YZ^1$, $YZ^2$ or $YZ^3$ already defined, $Z^1$, $Z^2$ and $Z^3$ are, for example, —COO—, —CO—, —SO$_2$—, —SO$_2$NH— or —CONH—, and preferably —COO—, —SO$_2$—, —SO$_2$NH— or —CONH—; $R^1$ may be, for example, an amino group, a $C_{1-4}$ alkylamino group, a di($C_{1-4}$ alkyl)amino group, an amino alkyl group, a $C_{1-4}$ alkylamino $C_{1-4}$ alkyl group, a di($C_{1-4}$ alkyl)amino $C_{1-4}$ alkyl group, a $C_{1-4}$ alkyl group, a hydroxy $C_{1-4}$ alkyl group, a hydroxyl group or a $C_{1-4}$ alkoxy group.

In an embodiment of the present invention, when —Y—Z— in formula (I), (I') and (III) is $YZ^4$, $YZ^5$, $YZ^6$ or $YZ^7$ already defined, $Z^4$ and $Z^5$ are, for example, —NHCO—, —NHCONH—, —NH—COO—, —N(COR$^1$)CO—, —NHSO$_2$— or —SO$_2$—, and preferably —NHCONH—, —NH—COO—, —NHSO$_2$— or —SO$_2$—;
$Z^6$ and $Z^7$ are, for example, —NHCO—, —NHCONH—, —NHC(=NH)NH—, NHC(=N—CN)NH—, —NH-COO—, —SO$_2$—, —SO$_2$NH— or —NHSO$_2$—, and preferably —NHCONH—, —NHC(=NH)NH—, NHC(=N—CN)NH—, —NHCOO— or —SO$_2$NH—;
$R^1$ may be, for example, a hydrogen atom, a heterocyclic alkyl group, a $C_{1-4}$ alkyl heterocyclic alkyl group, a hydroxy $C_{1-4}$ alkyl group, an amino group, a alkylamino group, a di($C_{1-4}$ alkyl)amino group, an amino $C_{1-4}$ alkyl group, a $C_{1-4}$ alkylamino $C_{1-4}$ alkyl group, a di($C_{1-4}$ alkyl)amino $C_{1-4}$ alkyl group, a hydroxy $C_{1-4}$ alkyl group, a phenyl group, a hydroxyl group or a $C_{1-4}$ alkyl group.

In this specification, a "$C_{1-4}$ alkyl group" means a linear or branched alkyl group having 1 to 4 carbon atoms and, for example, methyl, ethyl, n-propyl, i-propyl, n-butyl, s-butyl, i-butyl, t-butyl are included. Examples of preferable $C_{1-4}$ alkyl group include a linear or branched alkyl group having 1 to 3 carbon atoms, and methyl and ethyl are particularly preferable.

In this specification, a "$C_{1-6}$ alkyl group" means a linear or branched alkyl group having 1 to 6 carbon atoms and, for example, methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl and 2-ethylbutyl are included. Preferable $C_{1-6}$ alkyl group includes a $C_{1-4}$ alkyl group, for example, a linear or branched alkyl group having 1 to 3 carbon atoms, and methyl and ethyl are particularly preferable.

In this specification, a "$C_{3-8}$ cycloalkyl group", means a cyclic alkyl group having 3 to 8 carbon atoms. The $C_{3-6}$ cycloalkyl group includes, for example, cyclopropyl, cyclobutyl, cyclopentyl, cyclohexyl, cycloheptyl, cyclooctyl, and it is preferably cyclopropyl, cyclopentyl, cyclohexyl.

In this specification, a "$C_{1-6}$ alkoxy group" means an alkyloxy group having a linear or branched alkyl group containing 1 to 6 carbon atoms as an alkyl moiety. The $C_{1-6}$ alkoxy group includes, for example, methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, and it is preferably methoxy, ethoxy, n-propoxy, i-propoxy.

In this specification, a "$C_{3-8}$ cycloalkyloxy group" means a cycloalkyloxy group having a cyclic alkyl group having 3 to 8 carbon atoms and includes, for example, cyclopropyloxy, cyclobutyloxy, cyclopentyloxy, cyclohexyloxy, cycloheptyloxy, cyclooctyloxy.

In this specification, a "$C_{7-14}$ aralkyl" means an arylalkyl group containing an aryl group and having 7 to 14 carbon atoms. The $C_{7-14}$ aralkyl includes, for example, benzyl, 1-phenethyl, 2-phenethyl, 1-naphthylmethyl, 2-naphthylmethyl, and it is preferably benzyl.

In this specification, a "$C_{7-14}$ aralkyloxy" means an aralkyloxy group containing an aralkyl group already defined and having 7 to 14 carbon atoms and means, for example, benzyloxy, 1-phenethyloxy, 2-phenethyloxy, 1-naphthylmethyloxy, 2-naphthylmethyloxy.

In this specification, an "aryl group" means an aryl group having an aromatic hydrocarbon ring having 6 to 10 carbon atoms. The aryl group includes, for example, phenyl, 1-naphthyl and 2-naphthyl, and it is preferably phenyl.

In this specification, an "aryloxy group" means an aryloxy group containing an aromatic hydrocarbon ring having 6 to 10 carbon atoms already defined as an aryl moiety and includes, for example, phenoxy, 1-naphthoxy and 2-naphthoxy.

In this specification, a "heteroaryloxy group" means an heteroaryloxy group containing a 5- to 10-membered aromatic heterocyclic group containing one or more heteroatoms selected from oxygen atom, nitrogen atom and sulfur atom already defined as a heteroaryl moiety and includes, for example, furyloxy, thienyloxy, pyrrolyloxy, imidazolyloxy, pyrazolyloxy, oxazolyloxy, isoxazolyloxy, thiazolyloxy, isothiazolyloxy, oxadiazolyloxy, thiadiazolyloxy, triazolyloxy, tetrazolyloxy, pyridyloxy, pyrimidinyloxy, pyrazinyloxy, pyridazinyloxy, indolyloxy, quinolinyloxy, isoquinolinyloxy. Preferable heteroaryloxy group is 5- to 6-membered heteroaryloxy group.

In this specification, a "$C_{1-4}$ alkylamino group" means an alkylamino group having a linear or branched alkyl group containing 1 to 6 carbon atoms as an alkyl moiety. The $C_{1-4}$ alkylamino group includes, for example, methylamino, ethylamino, n-propylamino, i-propylamino, n-butylamino, s-butylamino, i-butylamino and t-butylamino, and it is preferably methylamino or ethylamino.

In this specification, a "di($C_{1-4}$ alkylamino" means a dialkylamino group having linear or branched alkyl groups containing 1 to 6 carbon atoms as two alkyl moieties and the two alkyl moieties may be the same or different. The di($C_{1-6}$ alkyl)amino includes, for example, dimethylamino, diethylamino, di-n-propylamino, di-i-propylamino, di-n-butylamino, methyl-n-butylamino, methyl-s-butylamino, methyl-i-butylamino, methyl-t-butylamino, ethyl-n-butylamino, ethyl-s-butylamino, ethyl-i-butylamino, ethyl-t-butylamino, and it is preferably dimethylamino or diethylamino.

The $C_{1-4}$ alkoxycarbonyl group includes a methoxycarbonyl group and an ethoxycarbonyl group, and a methoxycarbonyl group is preferable. The $C_{7-14}$ aralkyloxycarbonyl group includes a benzyloxycarbonyl group and a naphthylmethyloxycarbonyl group, and a benzyloxycarbonyl group is preferable.

In this specification, the halogen atom includes for example, a fluorine atom, a chlorine atom, bromine atom and an iodine atom.

In this specification, a nitrogen-containing heterocyclic group means a heterocyclic group which may be completely saturated, or may be partially or completely unsaturated and contains one nitrogen atom, and may contain one or more heteroatoms selected from an oxygen atom, a nitrogen atom and a sulfur atom, and includes, for example, azetidine, pyrrolidine, piperidine, piperazine, morpholine, and piperidine, piperazine and pyrrolidine are particularly preferable.

In this specification, an "arylene group" means a 6- to 10-membered arylene group. The arylene group includes, for example, phenylene group and naphthylene group, and phenylene group is particularly preferable.

In this specification, a "divalent 5- or 6-membered monocyclic heterocyclic group" means a group having two or more valences consisting of a 5- or 6-membered monocyclic heterocyclic group which may be an unsaturated or partially unsaturated or saturated or completely saturated aromatic or non-aromatic group and contains one Or more heteroatoms independently selected from an oxygen atom, a nitrogen atom and a sulfur atom, and the monocyclic heterocyclic group constituting the divalent group includes, for example, unsaturated monocycle heterocyclic groups such as a pyrrole ring, a thiophene ring, a furan ring, a pyridine ring, a thiazole ring, a pyrazole ring, an indazole ring, an oxazole ring, an isoxazole ring, an imidazole ring, a triazole ring, a pyrimidine ring, an uridine ring, a pyrazine ring, a pyridazine ring; dihydro-compounds of these unsaturated monocycle heterocyclic groups (for example, a dihydropyridine ring, a dihydropyrazine ring, a dihydrofuran ring); tetrahydro-compounds of these unsaturated monocycle heterocyclic groups (for example, a tetrahydropyridine ring, a tetrahydropyrazine ring, a tetrahydrofuran ring); and saturated monocycle heterocyclic groups such as a piperidine ring, a pyrrolidine ring, a piperazine ring, a morpholine ring, a thiomorpholine ring, and a piperidine ring and a pyridine ring are particularly preferable.

In this specification, a "divalent 8- to 10-membered condensed heterocyclic group" means a group having two or more valences consisting of an 8- to 10-membered condensed heterocyclic group which may be an unsaturated or partially unsaturated or saturated or completely saturated aromatic or non-aromatic group and contains one or more heteroatoms independently selected from an oxygen atom, a nitrogen atom and a sulfur atom, and the condensed heterocyclic group constituting the divalent group includes, for example, unsaturated condensed heterocyclic groups such as an indole ring, a benzothiophene ring, a benzofuran ring, a quinoline ring, an isoquinoline ring, a benzothiazole ring, an isothiazole ring, a benzisothiazole ring, a benzoxazole ring, a benzisoxazole ring, a benzimidazole ring, a benzotriazole ring, a pyrrolopyridine; dihydro-compounds of these unsaturated condensed heterocyclic groups (for example, a dihydroindole ring, a dihydrobenzothiophene ring, a dihydrobenzofuran ring); tetrahydro-compounds of these unsaturated condensed heterocyclic groups (for example, a tetrahydroquinoline ring); and a benzothiazole ring, an indole ring, a dihydroindole ring are particularly preferable and a benzothiazole ring is more preferable.

In this specification, a "heterocyclic group" means a 4- to 7-membered heterocyclic group which may be a completely saturated or partially or completely unsaturated aromatic or non-aromatic group and contains one or more heteroatoms independently selected from an oxygen atom, a nitrogen atom and a sulfur atom, and includes, for example, azetidinyl, pyrrolidinyl, piperidyl, piperazinyl, pyrrolyl, imidazolyl, imidazolinyl, pyrazolyl, pyrazolinyl, oxazolinyl, morpholinyl, thiomorpholinyl, pyridyl, pyrazinyl, pyrimidinyl, pyridazinyl, hexamethyleneimino, furyl, tetrahydrofuryl, thienyl, tetrahydro thienyl, dioxolanyl, oxathiolanyly, dioxaneyl, and piperidyl, piperazinyl, morpholinyl, pyridyl, pyrazinyl, thienyl are particularly preferable. The binding position of the heterocyclic group is not limited in particular as long as it is a position on a carbon atom or nitrogen atom and it can be substituted.

The pharmaceutically acceptable salts of the compound represented by formula (I) are pharmaceutically acceptable salts which are produced by contacting the above compound with an acid or a base which can be used in the manufacture of drugs. Examples of such salts include hydrochloric acid salts, hydrobromic acid salts, hydroiodic acid salts, sulfuric acid salts, sulfonic acid salts, phosphoric acid salts, phosphonic acid salts; carboxylic acid salts such as acetic acid salts, citric acid salts, malic acid salts, salicylic acid salts; alkali metal salts such as sodium salts, potassium salts; alkaline earth metal salts such as magnesium salts, calcium salts; ammonium salts such as ammonium salts, alkylammonium salts, dialkylammonium salts, trialkylammonium salts, tetraalkylammonium salts, and other such salts.

The "prodrug" in the present invention means a derivative of a compound represented by formula (I) which can be converted into the compound represented by formula (I) or a pharmaceutically acceptable salt by enzymatic or non-enzymatic decomposition under a physiology condition. The prodrug may be inactive when it is administered to a patient, but it is converted into and present as a compound represented by formula (I) in a living body. The compounds of formula (I) may include those which act as a prodrug in themselves but the "prodrug" in the present invention include compounds further derived from the compound so that they may have more preferable properties as a drug.

The "prodrug" of the present invention includes, for example:
1) Compounds in which a hydroxyl group is protected by a protecting group when the compounds of formula (I) has a hydroxyl group in a molecule;
2) Compounds in which an —NH— group or an amino group is protected by a protecting group when the compounds of formula (I) has such a group in a molecule; and
3) Compounds in which a carboxy group is converted into an ester group or an amide group which may be substituted when the compounds of formula (I) has a carboxy group in a molecule.

Examples of protecting group for a hydroxyl group in the prodrug of the present invention include —PO(OR$^{41}$)OR$^{42}$, a $C_{1-6}$ alkylcarbonyl group, a $C_{3-6}$ cycloalkylcarbonyl group (wherein the $C_{1-6}$ alkylcarbonyl group and $C_{3-8}$ cycloalkylcarbonyl group may be substituted by one or more substituents selected from a hydroxyl group, —NR$^{37}$R$^{38}$, an aryl group, a carboxy group, a $C_{1-6}$ alkoxycarbonyl group, a $C_{1-6}$ alkylaminocarbonyl group and di($C_{1-6}$ alkyl)aminocarbonyl group (wherein $C_{1-6}$ alkylaminocarbonyl group and the di($C_{1-6}$ alkyl)aminocarbonyl group may be substituted with one or more substituent selected from amino group, a $C_{1-6}$ alkylamino group and di($C_{1-6}$ alkyl)amino group)), an arylcarbonyl group and a 4- to 7-membered heterocyclic carbonyl group (wherein the arylcarbonyl group and the heterocyclic carbonyl group may be substituted by one or more substituents selected from a carboxy group, a $C_{1-6}$ alkoxycarbonyl group, a $C_{1-6}$ alkylcarbonyl group (wherein the $C_{1-6}$ alkoxycarbonyl group and the $C_{1-6}$ alkylcarbonyl group may be substituted by one or more substituents selected from a hydroxyl group, —NR$^{37}$R$^{38}$, a carboxy group and a hydroxyl group)); Here, R$^{37}$ and R$^{38}$ are each independently selected from a hydrogen atom, a $C_{1-6}$ alkyl group (wherein the alkyl group may be substituted by one or more substituents selected from a halogen atom, a hydroxyl group, a $C_{1-6}$ alkoxy group, an aryl group, an amino group, a $C_{1-6}$ alkylamino group and a di($C_{1-6}$ alkyl)amino group), —S(O)$_n$R$^{39}$ (wherein n is an integer selected from 1 or 2), a $C_{1-6}$ alkylcarbonyl group (wherein the $C_{1-6}$ alkylcarbonyl group may be substituted by one or more substituents selected from an amino group, a $C_{1-6}$ alkylamino group, a di($C_{1-6}$ alkyl)amino group, an aryl group), a $C_{1-6}$ alkylaminocarbonyl group, a $C_{1-6}$ alkoxycarbonyl group, aryl group and heteroaryl group; or R$^{37}$ and R$^{38}$ together with a nitrogen atom to which they bind may form a 4- to 7-membered heterocyclic group containing at least one nitrogen atom (wherein the heterocyclic group may be substituted by a hydroxyl group, a $C_{1-13}$ alkyl group (wherein the alkyl group may be substituted by a hydroxyl group, a $C_{1-8}$ alkoxy group, an aryl group), a $C_{1-8}$ alkoxy group (wherein the alkoxy group may be substituted by a hydroxyl group, a $C_{1-8}$ alkoxy group, an aryl group) or aryl group and heteroaryl group);

R$^{39}$ is selected from a hydrogen atom, a $C_{1-8}$ alkyl group (wherein the alkyl group may be substituted by one or more substituents selected from a hydroxyl group, a $C_{1-6}$ alkoxy group, an aryl $C_{1-6}$ alkoxy group, an aryl group and a heteroaryl group), a $C_{2-8}$ alkenyl group, a $C_{3-6}$ cycloalkyl group, an aryl group and a heteroaryl group;

R$^{41}$ and R$^{42}$ are each independently selected from a hydrogen atom, an aryl $C_{1-6}$ alkyl group, a $C_{1-8}$ alkyl group or a metal ion (for example, alkaline metal ions such as Li$^+$, Na$^+$, K$^+$).

In addition, the protected hydroxyl group may be an ester of natural amino acids (that is, asparagine, aspartic acid, alanine, arginine, isoleucine, glycine, glutamine, glutaminic acid, cysteine, serine, tyrosine, tryptophan, threonine, valine, histidine, phenylalanine, proline, methionine, lysine and leucin) or an ester of a non-natural amino acid, an ester of a dipeptide, an ester of a tripeptide and an ester of a tetrapeptide.

Examples of protecting group for —NH— group or an amino group include a $C_1$-$C_6$ alkylcarbonyl group, arylcarbonyl group, a heteroarylcarbonyl group, a $C_1$-$C_6$ alkoxycarbonyl group, a $C_1$-$C_6$ alkylaminocarbonyl group, a di($C_1$-$C_6$ alkyl)aminocarbonyl group, an aryl $C_1$-$C_6$ alkyl group, a heteroaryl $C_1$-$C_6$ alkyl group, an (aryl $C_1$-$C_6$ alkyl)aminocarbonyl group, —P(=O)(OH)$_2$, —CH$_2$OP(=O)(OH)$_2$, a $C_1$-$C_6$ alkyl group, a $C_1$-$C_6$ alkylsulfonyl group. In addition, the protected —NH— group or amino group may be an amide of a natural or non-natural amino acid, an amide of dipeptide, an ester of tripeptide and an amide of tetrapeptide.

In addition, an amino group may form a saturated or unsaturated heterocyclic group such as a phthalic acid imide group, a succinic acid imide group, a glutaric acid imide group, 1-pyrrolyl group by being protected.

When a carboxy group is converted into an ester group or an amide group which may be substituted, examples of the ester group include $C_1$-$C_6$ alkyl ester, aryl ester, heteroaryl ester, aryl $C_1$-$C_6$ alkyl ester, heteroaryl $C_1$-$C_6$ alkyl ester, $C_1$-$C_6$ alkoxy $C_1$-$C_6$ alkyl ester, aryloxy $C_1$-$C_6$ alkyl ester, aryl $C_1$-$C_6$ alkyloxy $C_1$-$C_6$ alkyl ester, hydroxy $C_1$-$C_6$ alkyl ester, amino $C_1$-$C_6$ alkyl ester, $C_1$-$C_6$ alkylamino $C_1$-$C_6$ alkyl ester, a di($C_1$-$C_6$ alkyl)amino $C_1$-$C_6$ alkyl ester. Preferable ester groups include a methyl ester group, an ethyl ester group, a 2-hydroxyethyl ester or a 2-(dimethylamino)ethyl ester group.

The amide group is, for example, an amide group represented by —C(=O)NR$^{71}$R$^{72}$, and R$^{71}$ and R$^{72}$ can be each independently selected from, for example, a hydrogen atom, a $C_1$-$C_6$ alkyl group, an aryl group, a heteroaryl group, an aryl $C_1$-$C_6$ alkyl group, a heteroaryl $C_1$-$C_6$ alkyl group, a $C_1$-$C_6$ alkoxy $C_1$-$C_6$ alkyl group, an aryloxy $C_1$-$C_6$ alkyl group, an aryl $C_1$-$C_6$ alkyloxy $C_1$-$C_6$ alkyl group, a hydroxy $C_1$-$C_6$ alkyl group, an amino $C_1$-$C_6$ alkyl group, a $C_1$-$C_6$ alkylamino $C_1$-$C_6$ alkyl group, a di($C_1$-$C_6$ alkyl)amino $C_1$-$C_6$ alkyl group, a hydroxyl group, alkoxy group. Preferably $R^{71}$ and $R^{72}$ are a methyl group, an ethyl group, a 2-hydroxyethyl group or a 2-(dimethylamino)ethyl group.

A solvate of a compound represented by formula (I) includes a compound in which molecules of a solvent that can be used in the manufacture of drugs are coordinated with the abovementioned compound. For example, such a solvate include a hydrate.

The compound of the present invention represented by general formula (I) is expected to act as an anti-androgen agent which is not associated with any appearance of androgen resistance due to long-term administration, and/or side effects such as toxicity or the like, and is expected to be useful as a therapeutic agent for the treatment of diseases such as prostate cancer, benign prostatic hypertrophy, male pattern baldness, sexual precociousness, acnevulgaris, seborrhea and hypertrichosis. Furthermore, if the compound of the present invention represented by general formula (I) is administered beforehand, it is expected that the onset of diseases such as prostate cancer, benign prostatic hypertrophy, male pattern baldness, sexual precociousness, acnevulgaris, seborrhea and hypertrichosis will be prevented or delayed. Accordingly, it is expected that the compound will also constitute a prophylactic agent for such diseases.

The pharmaceutical composition of the present invention contains a compound represented by formula (I), or a salt, prodrug or solvate thereof, in an amount effective in treatment, and a pharmaceutically acceptable carrier. If necessary, this composition may contain other chemotherapeutic agents. For example, one or more agents selected from cell division inhibiting agents, alkylating agents, antimetabolic agents, intercalating antibiotics, growth factor inhibiting agents, cell cycle inhibiting agents, enzymes, enzyme inhibitors, aromatase inhibitors, topoisomerase inhibitors, biological response modifiers, anti-hormone agents, anti-estrogen agents and anti-androgen agents.

The compound of the present invention represented by general formula (I) is expected to act as an anti-androgen agent which is not associated with any appearance of androgen resistance due to long-term administration, and/or side effects such as toxicity or the like, and is expected to be useful as a therapeutic agent for the treatment of diseases such as prostate cancer, benign prostatic hypertrophy, male pattern baldness, sexual precociousness, acnevulgaris, seborrhea and hypertrichosis. Furthermore, if the compound of the present invention represented by general formula (I) is administered beforehand, it is expected that the onset of diseases such as prostate cancer, benign prostatic hypertrophy, male pattern baldness, sexual precociousness, acnevulgaris, seborrhea and hypertrichosis will be prevented or delayed. Accordingly, it is expected that the compound will also constitute prophylactic agents for such diseases.

The compound of the present invention represented by general formula (I), as well as a salt, prodrug and solvate thereof, can be administered orally or parenterally in the form of a pharmaceutical composition which also contains pharmaceutically acceptable additive agents such as carriers, excipients, binders, diluents, stabilizing agents, lubricants, flavoring agents, disintegrating agents, coating agents, coloring agents, antioxidants, buffering agents, aqueous solvents, oily solvents, isotonic agents, dispersing agents, preservatives, solubilizing agents, fluidizing agents, analgesic agents, pH adjusting agents, antiseptic agents, base agents and the like. Examples of the above pharmaceutical composition include granules, powder, tablets, hard capsules, soft capsules, syrup, emulsions, suspensions and the like as orally administered agents. Examples of parenteral formulations include injections such as subcutaneous injections, intravenous injections, intramuscular injections, intra-abdominal injections and the like; transdermal administration formulations such as ointments, creams, lotions and the like; suppositories such as rectal suppositories, vaginal suppositories and the like; nasal administration formulations; and other agents. These formulations can be manufactured by universally known methods that are commonly used in formulation processes.

Examples of excipients that can be used in the present invention include sugars such as lactose, white sugar, glucose, D-mannitol, sorbit and the like; cellulose and cellulose derivatives such as crystalline cellulose, hydroxypropylcellulose, hydroxypropylmethyl cellulose, methylcellulose and the like; starch and starch derivatives such as corn starch, potato starch, α-starch, dextrin, β-cyclodextrin, carboxymethylstarch sodium, hydroxypropylstarch and the like; silicates such as synthetic aluminum silicate, magnesium aluminum silicate, calcium silicate, magnesium silicate and the like; phosphates such as calcium phosphate and the like; carbonates such as calcium carbonate and the like; sulfates such as calcium sulfate and the like; tartaric acid, potassium hydrogentartarate, magnesium hydroxide and the like.

Examples of binders that can be used include agar, stearyl alcohol, gelatin, traganth, polyvinyl alcohols, polyvinylpyrrolidones; cellulose and cellulose derivatives such as crystalline cellulose, hydroxypropylcellulose, hydroxypropylmethyl cellulose, methylcellulose and the like; starch and starch derivatives such as corn starch, potato starch, α-starch, dextrin, β-cyclodextrin, carboxymethylstarch sodium, hydroxypropylstarch and the like; sugars such as lactose, white sugar, glucose, D-mannitol, sorbit and the like; and other binders.

Examples of stabilizing agents that can be used include hardened oils, sesame oil, sodium chondroitin sulfate, dibutylhydroxytoluene, adipic acid, ascorbic acid, L-ascorbic acid stearic acid esters, sodium L-ascorbate, L-aspartic acid, sodium L-aspartate, acetyltryptophan sodium, acetanalid, aprotinin liquid, aminoethysulfonic acid, aminoacetic acid, DL-alanine, L-alanine; para-oxybenzoic acid esters such as methylparaben, propylparaben and the like; alcohols such as chlorobutanol, benzyl alcohol, phenyl ethyl alcohol and the like; benzalkonium chloride; phenols such as phenol, cresol and the like; sorbic acid; sulfites such as sodium hydrogensulfite, sodium sulfite and the like; edetates such as sodium edentate, tetrasodium edentate and the like; and other stabilizing agents.

Examples of lubricants that can be used include powdered gum Arabic, cacao butter, carmellose calcium, carmellose sodium, caropeptide, hydrated silicon dioxide, hydrated amorphous silicon oxide, dry aluminum hydroxide gel, glycerol, light liquid paraffin, crystalline cellulose, hardened oils, synthetic aluminum silicate, sesame oil, wheat starch, talc, macrogols, phosphoric acid; stearic acids such as stearic acid, calcium stearate, magnesium stearate and the like; waxes such as bleached beeswax, carnauba wax and the like; sulfates such as sodium sulfate and the like; silicates such as magnesium silicate, light amorphous silicic acid and the like; laurylsulfates such as sodium laurylsulfate and the like; and other lubricants.

Examples of flavoring agents that can be used include ascorbic acid, L-aspartic acid, sodium L-aspartate, magnesium L-aspartate, aspartame, hydrangea tea, hydrangea tea extract, powdered hydrangea tea; aminoethylsulfonic acid, aminoacetic acid, DL-alanine, saccharine sodium, dl-menthol, 1-menthols; sugars such as lactose, white sugar, glucose, D-mannitol and the like; and other taste enhancing agents.

Examples of disintegrating agents that can be used include agar, gelatin, traganth, adipic acid, alginic acid, sodium alginate; cellulose and cellulose derivatives such as crystalline cellulose, hydroxypropylcellulose, hydroxypropylmethyl cellulose, methylcellulose and the like; carbonates such as calcium carbonate, sodium hydrogencarbonate, magnesium carbonate and the like; starch and starch derivatives such as corn starch, potato starch, α-starch, dextrin, β-cyclodextrin, carboxymethylstarch sodium, hydroxypropylstarch and the like; and other agents.

Examples of coating agents that can be used include shellac, polyvinylpyrrolidiones, polyethylene glycols, macrogols, methacrylic acid copolymers, liquid paraffin, Eudragit; cellulose derivatives such as cellulose acetate, hydroxypropylcellulose, cellulose acetophthalate, hydroxypropylmethylcellulose and the like; and other coating agents.

Examples of coloring agents that can be used include indigo carmine, caramel, riboflavin and the like.

Examples of buffering agents that can be used include aminoacetic acid, L-arginine, benzoic acid, sodium benzoate, ammonium chloride, potassium chloride, sodium chloride, dry sodium sulfite, dry sodium carbonate, dilute hydrochloric acid, citric acid, calcium citrate, sodium citrate, disodium citrate, calcium gluconate, L-glutamic acid, sodium L-glutamate, creatinine, chlorobutanol, crystalline sodium dihydrogenphosphate, disodium succinate, acetic acid, potassium acetate, sodium acetate, tartaric acid, sodium hydrogencarbonate, sodium carbonate, triethanolamine, lactic acid, sodium lactate liquid, glacial acetic acid, boric acid, maleic acid, citric anhydride, anhydrous sodium citrate, anhydrous sodium acetate, anhydrous sodium carbonate, anhydrous sodium monohydrogenphosphate, anhydrous trisodium phosphate, anhydrous sodium dihydrogenphosphate, dl-malic acid, phosphoric acid, trisodium phosphate, sodium hydrogenphosphate, dipotassium phosphate, potassium dihydrogenphosphate, sodium dihydrogenphosphate, sodium dihydrogenphosphate monohydrate and the like.

Examples of aqueous solvents that can be used include distilled water, physiological saline, Ringer's solution and the like.

Examples of oily solvents that can be used include propylene glycol; vegetable oils such as olive oil, sesame oil, cottonseed oil, corn oil and the like; and other agents.

Examples of isotonic agents that can be used include potassium chloride, sodium chloride, glycerol, sodium bromide, D-sorbitol, nicotinic acid amide, glucose, boric acid and the like.

Examples of dispersing agents that can be used include gum arabic, alginic acid propylene glycol ester, sorbitan sesquieoleate, D-sorbitol, traganth, methylcellulose, aluminum monostearate, aminoalkyl methacrylate copolymer RS, lactose, concentrated glycerol, propylene glycol, macrogols, sodium laurylsulfate; stearic acid and salts thereof such as calcium stearate, lead stearate, magnesium stearate and the like; and other dispersing agents.

Examples of preservatives that can be used include benzalkonium chloride, benzethonium chloride, dry sodium sulfite, dry sodium sulfate, cresol, chlorocresol, dibutylhydroxytoluene, potassium sorbate, sodium dehydroacetate, phenol, formalin, phosphoric acid, gum benzoin, thymerosal, thymol, sodium dehydroacetate; alcohols such as chlorobutanol, phenethyl alcohol, propylene glycol, benzyl alcohol and the like; para-oxybenzoic acid esters such as isobutyl para-oxybenzoate, ethyl para-oxybenzoate, methyl para-oxybenzoate and the like; and other preservatives.

Examples of solubilizing agents that can be used include sodium benzoate, ethylenediamine, citric acid, sodium citrate, glycerol, sodium acetate, sodium salicylate, sorbitan sesquioleate, nicotinic acid amide, glucose, benzyl alcohol, polyvinylpyrrolidones, acetone, ethanol, isopropanol, D-sorbitol, sodium hydrogencarbonate, sodium carbonate, lactose, urea, white sugar and the like.

Examples of fluidizing agents that can be used include hydrated silicon dioxide, talc, anhydrous ethanol, crystalline cellulose, synthetic aluminum silicate, calcium hydrogenphosphate; stearic acid and salts of the same such as magnesium stearate and the like; and other agents.

Examples of analgesic agents that can be used include benzalkonium chloride, caproin hydrochloride, meprylcaine hydrochloride, lidocaine hydrochloride, lidocaine and the like.

Examples of pH adjusting agents that can be used include hydrochloric acid, citric acid, succinic acid, acetic acid, boric acid, maleic acid, sodium hydroxide and the like.

Examples of antiseptic agents that can be used include benzoic acid, sodium benzoate, cetylpyridinium chloride, salicylic acid, sodium salicylate, sorbic acid, potassium sorbate, thymol, methyl para-oxybenzoate, butyl para-oxybenzoate and the like.

Examples of base agents that can be used include glycerol, stearyl alcohol, polyethylene glycols, propylene glycol, cetanol, lard, white Vaseline, paraffin, bentonite, lanoline fatty acid isopropyl ester, Vaseline, polysorbates, macrogols, lauryl alcohol, sodium laurylsulfate, ethyl linolate, sodium hydrogenphosphate, rosin; vegetable oils such as olive oil, sesame oil, wheat germ oil and the like; and other base agents.

The amount of the compound represented by general formula (I) in the pharmaceutical composition of the present invention varies according to the dosage form, but is preferably approximately 0.1 to 100 wt % based on the total amount of the pharmaceutical composition. The dose of the pharmaceutical composition of the present invention may vary over a wide range depending on the subject of administration (warm-blooded animals such as human), severity of the disease, age, sex, administration method, physician's diagnosis and the like. However, in regard to the dose of the compound represented by formula (I) for adults, it is preferable that the dose be approximately 0.1 to 500 mg/kg per day both in the case of oral administration and in the case of parenteral administration. The above dose is the value per unit weight of the object of administration. Furthermore, in the present invention, depending on the severity of the disease, judgment of the physician and the like, the above dose may be administered as one dose in a period ranging from one day to one month, or may be divided into several doses or more.

<General Production Process>

Compound 54 which is an intermediate for synthesizing a compound of the present invention can be produced by Method A shown below:

Method A

[Formula 22]

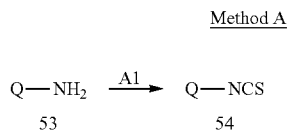

wherein Q is the same as defined above.

Compound 54 can be produced, for example, in accordance with a method of The Journal of Steroid Biochemistry and Molecular Biology, Vol. 48, No. 1, page 111-119, 1994.

Step A1 is achieved by reacting Compound 53 and thiophosgene in an inert solvent. There are no particular restrictions on the inert solvent used, as long as the solvent does not participate in the reaction. Examples of the solvent which can be used include halogen solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, and it is preferably dichloromethane, diethylether, tetrahydrofuran, dioxane, etc. and more preferably tetrahydrofuran, etc.

The reaction temperature varies depending on the type of solvent and the like, but it is ordinarily −30° C. to 100° C., and preferably 0° C. to 50° C. In addition, the reaction time varies depending on the reaction temperature and the like, but it is ordinarily from 10 minutes to 48 hours, and preferably from 30 minutes to 24 hours.

Compound 55 which is an intermediate for synthesizing a compound of the present invention can be produced by Method B shown below:

Method B

[Formula 23]

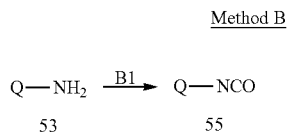

wherein Q is the same as defined above.

Compound 55 can be produced, for example, in accordance with a method of The Journal of Steroid Biochemistry and Molecular Biology, Vol. 48, No. 1, page 55-60, 1994.

Step B1 is achieved by reacting Compound 53 and a reagent such as phosgene, diphosgene, triphosgene or carbonyldiimidazole (preferably, phosgene) in an inert solvent. There are no particular restrictions on the inert solvent used, as long as the solvent does not participate in the reaction. Examples of the solvent which can be used include halogen solvents such as dichloromethane, chloroform and carbon tetrachloride; ether type solvents such as diethyl ether, tetrahydrofuran, dioxane and dimethoxyethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile; ethyl acetate, and it is preferably dichloromethane, diethylether, tetrahydrofuran, dioxane, toluene, ethyl acetate, etc. and more preferably tetrahydrofuran, toluene, ethyl acetate, etc. The reaction temperature varies depending on the type of solvent and the like, but it is ordinarily −30° C. to 150° C., and preferably 0° C. to 120° C. The reaction time varies depending on the reaction temperature and the like, but it is ordinarily from 10 minutes to 48 hours, and preferably from 30 minutes to 24 hours.

Compound 57 which is an intermediate for synthesizing a compound of the present invention can be produced by Method C shown below:

Method C

[Formula 24]

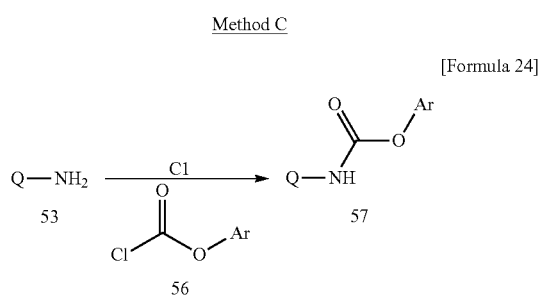

wherein Q is the same as defined above, and Ar represents an aromatic hydrocarbon group, and preferably a phenyl group, a p-nitrophenyl group, etc.

Compound 57 can be produced, for example, in accordance with a method of Synthesis, page 1189-1194, 1997. Step C1 is achieved by reacting Compound 53 and Compound 56 in an inert solvent. There are no particular restrictions on the inert solvent used, as long as the solvent does not participate in the reaction. Examples of the solvent which can be used include ether type solvents such as diethyl ether, tetrahydrofuran, dioxane and dimethoxyethane; halogen solvents such as dichloromethane and carbon tetrachloride; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile; ethyl acetate, and it is preferably dichloromethane, diethylether, tetrahydrofuran, dioxane, toluene, ethyl acetate, etc. and more preferably tetrahydrofuran.

Examples of the base used include amines such as triethylamine, diisopropylethylamine, 1,8-diazabicyclo[5.4.0]-7-undecene, pyridine, dimethylaminopyridine, pyrazine, carbonates such as sodium carbonate, potassium carbonate, cesium carbonate, sodium hydrogen carbonate, potassium hydrogen carbonate, metal alkoxides such as sodium alkoxide, potassium t-butoxide, metal hydrides such as sodium hydride, potassium hydride, calcium hydride, alkyllithium such as methyllithium, ethyllithium, n-butyllithium, t-butyllithium, metal hydroxides such as lithium hydroxide, sodium hydroxide, potassium hydroxide, calcium hydroxide, barium hydroxide, cesium hydroxide, metal amides such as sodium amide, potassium bistrimethylsilylamide, sodium bistrimethylsilylamide, lithium diisopropylamide, and it is preferably amines such as triethylamine, diisopropylethylamine, 1,8-diazabicyclo[5.4.0]-7-undecene; pyridine, dimethylaminopyridine, pyrazine, etc. and more preferably triethylamine, diisopropylethylamine, pyridine, dimethylaminopyridine, etc. The reaction temperature varies depending on the type of solvent and the like, but it is ordinarily −30° C. to 100° C., and preferably 0° C. to 50° C. The reaction time varies depending on the reaction temperature and the like, but it is ordinarily from 10 minutes to 48 hours, and it is preferably from 30 minutes to 24 hours.

Method D is a method for producing Compound 61 in which $X^1$ is O and $X^2$ is S and Compound 62 in which $X^1$ and $X^2$ are O among the compounds represented by general formula (I).

Merhod D

[Formula 25]

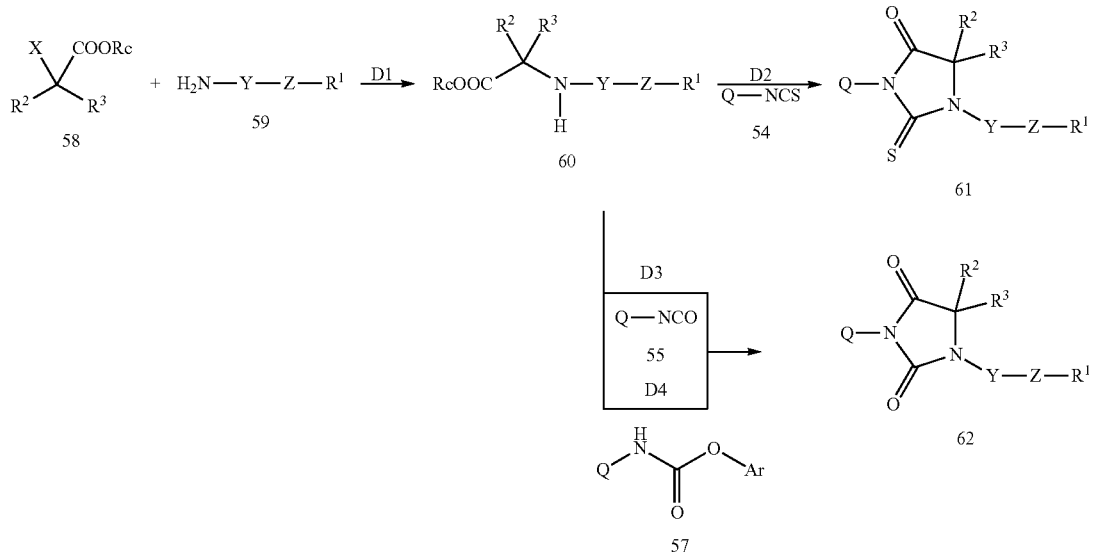

wherein X represents a halogen atom, and Q, Y, Z, $R^1$, $R^2$, $R^3$, Rc and Ar are the same as defined above; preferably Rc is not a hydrogen atom.

Step D1 is a step to produce Compound 60 and it is achieved by reacting Compound 58 and Compound 59 in the presence of a base in an inert solvent. There are no particular restrictions on the inert solvent used, as long as the solvent does not participate in the reaction. Examples of the solvent which can be used include ether type solvents such as diethyl ether, tetrahydrofuran, dioxane and dimethoxyethane; alcohol type solvents such as methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol, 1,5-pentanediol; dimethylsulfoxide; dimethylformamide; dimethylacetamide; N-methylpyrrolidon, and it is preferably methanol, ethanol, n-butanol, dimethylacetamide, N-methylpyrrolidon, etc. and more preferably methanol, ethanol, dimethylacetamide, etc. Examples of the base used include carbonates such as sodium carbonate, potassium carbonate, cesium carbonate, sodium hydrogen carbonate, potassium hydrogen carbonate, amines such as triethylamine, diisopropylethylamine, 1,8-diazabicyclo[5.4.0]-7-undecene, pyridine, dimethylaminopyridine, pyrazine, metal alkoxides such as sodium alkoxide, potassium t-butoxide, metal hydrides such as sodium hydride, potassium hydride, calcium hydride, alkyllithium such as methyllithium, ethyllithium, n-butyllithium, t-butyllithium, metal hydroxides such as lithium hydroxide, sodium hydroxide, potassium hydroxide, calcium hydroxide, barium hydroxide, cesium hydroxide, metal amides such as sodium amide, potassium bistrimethylsilylamide, sodium bistrimethylsilylamide, lithium diisopropylamide, and it is preferably carbonates such as sodium carbonate, potassium carbonate, cesium carbonate, sodium hydrogen carbonate, potassium hydrogen carbonate, amines such as triethylamine, diisopropylethylamine, 1,8-diazabicyclo[5.4.0]-7-undecene, pyridine, dimethylaminopyridine, pyrazine, etc. and more preferably carbonates such as sodium carbonate, potassium carbonate, cesium carbonate, sodium hydrogen carbonate, potassium hydrogen carbonate, etc. The reaction temperature varies depending on the type of solvent and the like, but it is ordinarily 0° C. to 200° C., and it is preferably 10° C. to 150° C. The reaction time varies depending on the reaction temperature and the like, but it is ordinarily from 10 minutes to 96 hours, and preferably from 30 minutes to 48 hours.

Step D2 is a step to produce Compound 61 and it is achieved by reacting Compound 60 and Compound 54 in the presence of a base in an inert solvent.

There are no particular restrictions on the inert solvent used, as long as the solvent does not participate in the reaction. Examples of the solvent which can be used include halogen solvents such as dichloromethane, carbon tetrachloride and 1,2-dichloroethane; ether type solvents such as diethyl ether, tetrahydrofuran, dioxane and dimethoxyethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, and it is preferably halogen solvents such as dichloromethane, carbon tetrachloride and 1,2-dichloroethane; ether type solvents such as diethyl ether, tetrahydrofuran, dioxane and dimethoxyethane; aromatic solvents such as benzene, toluene, xylene, quinoline, chlorobenzene; dimethylacetamide; dimethylformamide; N-methylpyrrolidon, etc., more preferably 1,2-dichloroethane, tetrahydrofuran, toluene, etc.

Examples of the base used include amines such as triethylamine, diisopropylethylamine, 1,8-diazabicyclo[5.4.0]-7-undecene, pyridine, dimethylaminopyridine, pyrazine, and it is preferably triethylamine, dimethylaminopyridine, etc. The reaction temperature varies depending on the type of solvent and the like, but it is ordinarily −30° C. to 200° C., and preferably 20° C. to 120° C. The reaction time varies depending on the reaction temperature and the like, but it is ordinarily from 10 minutes to 48 hours, and preferably from 30 minutes to 24 hours.

Step D3 is a step to produce Compound 62 and it is achieved by reacting Compound 60 and Compound 55 in the presence of a base in an inert solvent, and this step can be performed in the same way as Step D2 of Method D.

Step D4 is another step to produce Compound 62 and it is achieved by reacting Compound 60 and Compound 57 in the presence of a base in an inert solvent. There are no particular restrictions on the inert solvent used, as long as the solvent triethylamine, dimethylaminopyridine, sodium bistrimethylsilylamide, etc. The reaction temperature varies depending on the type of solvent and the like, but it is ordinarily −30° C. to 200° C., and preferably −10° C. to 30° C. The reaction time varies depending on the reaction temperature and the like, but it is ordinarily from 10 minutes to 48 hours, and preferably from 30 minutes to 24 hours.

Method E is a method to produce Compound 67 or Compound 68 in the following formula among the compounds represented by general formula (I):

Method E

[Formula 26]

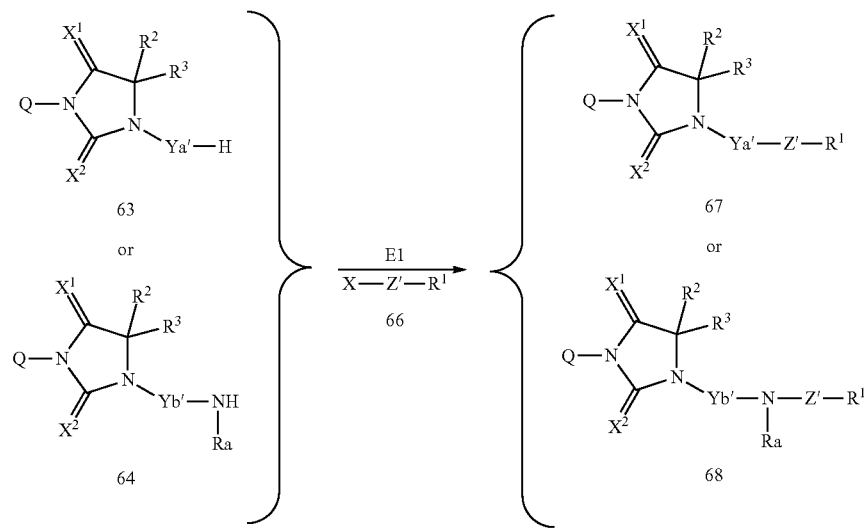

does not participate in the reaction. Examples of the solvent which can be used include halogen solvents such as dichloromethane, carbon tetrachloride and 1,2-dichloroethane; ether type solvents such as diethyl ether, tetrahydrofuran, dioxane and dimethoxyethane; aromatic solvents such as benzene, toluene, xylene, quinoline, chlorobenzene; cyclohexane; dimethylsulfoxide; dimethylacetamide; dimethylformamide; N-methylpyrrolidon; acetonitrile, and it is preferably halogen solvents such as dichloromethane, carbon tetrachloride and 1,2-dichloroethane; ether type solvents such as diethyl ether, tetrahydrofuran, dioxane and dimethoxyethane; aromatic solvents such as benzene, toluene, xylene, quinoline, chlorobenzene; dimethylacetamide; dimethylformamide; N-methylpyrrolidon, etc., and more preferably 1,2-dichloroethane, tetrahydrofuran, toluene, etc.

Examples of the base used include amines such as triethylamine, diisopropylethylamine, 1,8-diazabicyclo[5.4.0]-7-undecene, pyridine, dimethylaminopyridine, pyrazine, carbonates such as sodium carbonate, potassium carbonate, cesium carbonate, sodium hydrogen carbonate, potassium hydrogen carbonate, metal alkoxides such as sodium alkoxide, potassium t-butoxide, metal hydrides such as sodium hydride, potassium hydride, calcium hydride, alkyllithium such as methyllithium, ethyllithium, n-butyllithium, t-butyllithium, metal hydroxides such as lithium hydroxide, sodium hydroxide, potassium hydroxide, calcium hydroxide, barium hydroxide, cesium hydroxide, metal amides such as sodium amide, potassium bistrimethylsilylamide, sodium bistrimethylsilylamide, lithium diisopropylamide, and it is preferably wherein Ya' is selected from the following formulas:

[Formula 27]

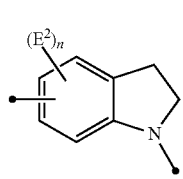

$Ya^{l1}$

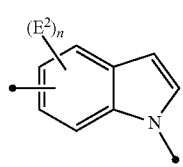

$Ya^{l2}$

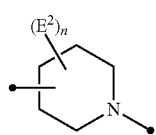

$Ya^{l3}$

Yb' is selected from the following formulas:

[Formula 28]

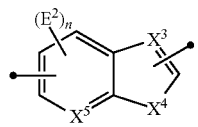
Yb¹⁴

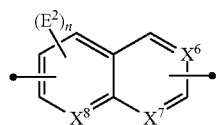
Yb¹⁵

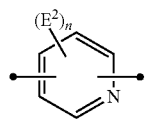
Yb¹⁶

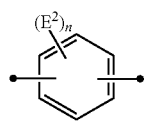
Yb¹⁷

Z' is —CO—, —COO—, —CONH— or —SO$_2$—; $R^1$, $R^2$, $R^3$, Ra, Q, $X^1$, $X^2$, $X^3$, $X^4$, $X^5$, $X^6$, $X^7$, $X^8$, X, n and $E^2$ are the same as defined above provided that $R^1$ is not a hydrogen atom.

Step E1 is a step to produce Compound 67 or Compound 68 and it is achieved by reacting Compound 63 or Compound 64 and Compound 66 in the presence of a base in an inert solvent. There are no particular restrictions on the inert solvent used, as long as the solvent does not participate in the reaction. Examples of the solvent which can be used include halogen solvents such as dichloromethane, carbon tetrachloride and 1,2-dichloroethane; ether type solvents such as diethyl ether, tetrahydrofuran, dioxane and dimethoxyethane; aromatic solvents such as benzene, toluene, xylene, quinoline, chlorobenzene; cyclohexane; dimethylsulfoxide; dimethylacetamide; dimethylformamide; dimethylimidazolidinone; N-methylpyrrolidon; acetonitrile, and it is preferably halogen solvents such as dichloromethane, carbon tetrachloride and 1,2-dichloroethane; ether type solvents such as diethyl ether, tetrahydrofuran, dioxane and dimethoxyethane; dimethylacetamide; dimethylformamide; N-methylpyrrolidon, etc., and more preferably dichloromethane, tetrahydrofuran, etc.

Examples of the base used include amines such as triethylamine, diisopropylethylamine, 1,8-diazabicyclo[5.4.0]-7-undecene, pyridine, dimethylaminopyridine, pyrazine, and it is preferably triethylamine, pyridine, dimethylaminopyridine, etc. The reaction temperature varies depending on the type of solvent and the like, but it is ordinarily −30° C. to 200° C., and preferably −10° C. to 80° C. The reaction time varies depending on the reaction temperature and the like, but it is ordinarily from 10 minutes to 48 hours, and preferably from 30 minutes to 24 hours.

Method F is a method to produce Compound 71 or Compound 72 in the following formula among the compounds represented by general formula (I):

Method F

[Formula 29]

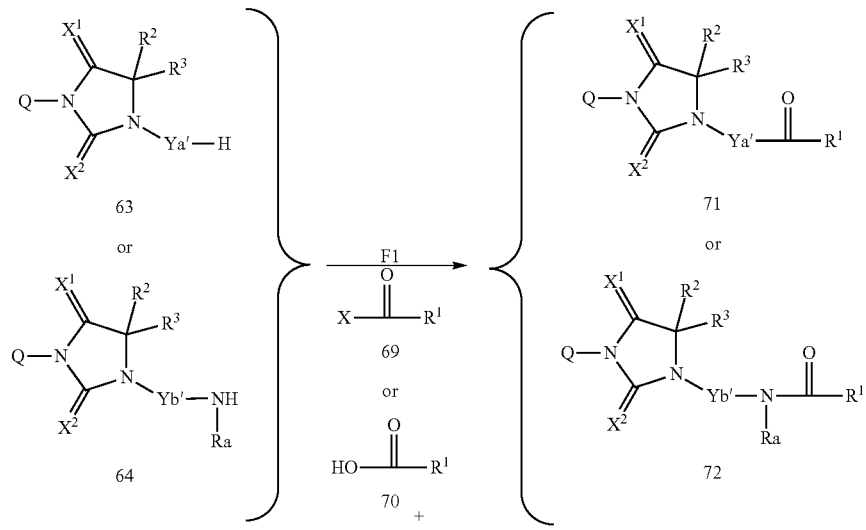

wherein Ya', Yb', R', $R^2$, $R^3$, Ra, Q, X, $X^1$ and $X^2$ are the same as defined above.

Step F1 is a step to produce Compound 71 or Compound 72 and it is achieved by reacting Compound 70 or reactive derivatives thereof (acid halides (for example, Compound 69), mixed acid anhydride or active esters) and Compound 63 or Compound 64 or acid addition salts thereof in an inert solvent.

This reaction is performed, for example, by an acid halide method, mixed anhydride method, active ester method or condensation method. The acid halide method is achieved by reacting Compound 70 with a halogenating agent (for example, thionyl chloride, oxalyl chloride, phosphorous pentachloride, etc.) in an inert solvent to produce an acid halide (for example, acid chloride such as Compound 69), and reacting the acid halide and Compound 63 or Compound 64 or the acid addition salt thereof in an inert solvent in the presence or absence of a base (preferably, in the presence of a base). Examples of the base used can include organic amines such as triethylamine, N-methylmorpholine, pyridine, 4-dimethylaminopyridine, alkali metal bicarbonates such as sodium bicarbonate, potassium bicarbonate, alkali metal carbonates such as sodium carbonate, potassium carbonate and it is preferably an organic amine (particularly preferably, triethylamine). There are no particular restrictions on the inert solvent used, as long as the solvent does not participate in the reaction. Examples of the solvent which can be used include hydrocarbon solvents such as hexane, cyclohexane, benzene, toluene, xylene; halogen solvents such as dichloromethane, 1,2-dichloroethane and carbon tetrachloride; ether type solvents such as ether, tetrahydrofuran, dioxane; ketone solvents such as acetone; amide solvents such as N,N-dimethylacetamide, N,N-dimethylformamide, N-methyl-2-pyrrolidone; sulfoxide solvents such as dimethylsulfoxide, and it is preferably a hydrocarbon solvent, a halogen solvent or an ether type solvent and more preferably an ether type solvent (particularly preferably, tetrahydrofuran). The reaction temperature may vary depending on the type of solvent and the like, but it is ordinarily −20° C. to 150° C. both for the reaction of a halogenating agent with Compound 70 and the reaction of an acid halide with Compound 63 or Compound 64 or the acid addition salt thereof, and it is preferably −10° C. to 50° C. for the reaction of a halogenating agent with Compound 70, and 0° C. to 100° C. for the reaction of an acid halide with Compound 63 or Compound 64 or the acid addition salt thereof. The reaction time varies depending on the reaction temperature and the like, but it is ordinarily from 15 minutes to 24 hours (preferably, from 30 minutes to 15 hours).

The mixed anhydride method is achieved by reacting a $C_{1-6}$ alkyl halogenoformate (here, the $C_{1-6}$ alkyl means a linear or branched alkyl group containing 1 to 6 carbon atoms), a $di(C_{1-6}$ alkyl)cyanophosphoric acid or a diarylphosphoryl azide and Compound 70 to produce a mixed acid anhydride and reacting the mixed acid anhydride and Compound 63 or Compound 64 or the acid addition salt thereof. The reaction to produce a mixed acid anhydride is performed by reacting a $C_{1-6}$ alkyl halogenoformate such as methyl chloroformate, ethyl chloroformate, isobutyl chloroformate, hexyl chloroformate (preferably, ethyl chloroformate or isobutyl chloroformate), a $di(C_{1-6}$ alkyl)cyanophosphoric acid such as dimethylcyanophosphoric acid, diethylcyanophosphoric acid, dihexylcyanophosphoric acid or a diarylphosphoric acid azide such as diphenylphosphoric acid azide, a di(p-nitrophenyl)phosphoric acid azide, dinaphthylphosphoric acid azide (preferably, diphenylphosphoric acid azide) and Compound 70 and it is preferably performed in an inert solvent in the presence of a base.

The base and inert solvent used are similar to those used by the acid halide method of the present process. The reaction temperature varies depending on the type of solvent and the like, but it is ordinarily −20° C. to 50° C. (preferably, 0° C. to 30° C.). The reaction time varies depending on the reaction temperature and the like, but it is ordinarily from 15 minutes to 24 hours (preferably, from 30 minutes to 15 hours).

The reaction between the mixed acid anhydride and Compound 63 or Compound 64 or an acid addition salt is performed in an inert solvent in the presence or in the absence of a base (preferably, in the presence a base) and the base and inert solvent used are similar to those used by the acid halide method mentioned above. The reaction temperature varies depending on the type of solvent and the like, but it is ordinarily −20° C. to 50° C. (preferably, 0° C. to 30° C.). The reaction time varies depending on the reaction temperature and the like, but it is ordinarily from 15 minutes to 24 hours (preferably, from 30 minutes to 15 hours). In addition, when a $di(C_{1-6}$ alkyl)cyano phosphoric acid or a diarylphosphoric acid azide is used in this method, Compound 70 and Compound 63 or Compound 64 or the acid addition salt thereof can be also directly reacted in the presence of a base.

The active esterification method is achieved by reacting Compound 70 with an active esterification agent (for example, N-hydroxy compounds such as N-hydroxysuccinimide, N-hydroxybenzotriazole) in the presence of condensing agent (for example, dicyclohexylcarbodiimide, carbonyldiimidazole) to produce an active ester, and reacting this active ester with Compound 63 or Compound 64 or the acid addition salt thereof. The reaction to produce an active ester is preferably performed in an inert solvent, and the inert solvent used can be, for example, an ether type solvent such as ether, tetrahydrofuran, dioxane, dimethoxyethane, a halogen solvent such as carbon tetrachloride, dichloromethane, dimethylformamide, ethyl acetate, acetonitrile, etc. and it is preferably dichloromethane, acetonitrile, ethyl acetate, etc.

The reaction temperature varies depending on the type of solvent, but it is ordinarily −20° C. to 50° C. (preferably, −10° C. to 30° C.) in the active esterification reaction, and −20° C. to 50° C. (preferably, −10° C. to 30° C.) in the reaction between the active ester compound and Compound 63 or Compound 64 or the acid addition salt thereof. The reaction time varies depending on the reaction temperature, but it is ordinarily from 15 minutes to 24 hours (preferably, from 30 minutes to 15 hours) for the both reaction.

The condensation method is performed by reacting Compound 70 and Compound 63 or Compound 64 or the acid addition salt thereof directly in the presence of a condensing agent [for example, dicyclohexylcarbodiimide, carbonyldiimidazole, 1-(N,N-dimethylaminopropyl)-3-ethyl carbodiimide hydrochloride]. This reaction is performed similarly as the reaction to produce the above active ester.

Method G is a method to produce Compound 74 or Compound 75 in the following formula among the compounds represented by general formula (I):

Method G

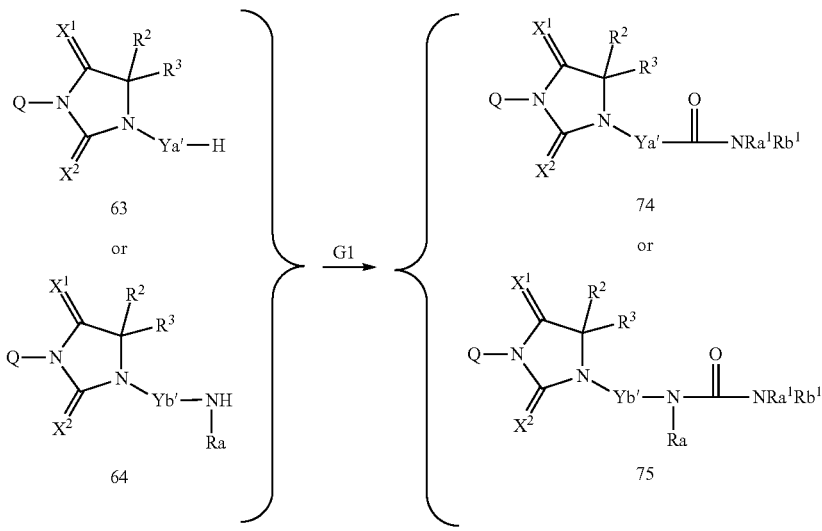

[Formula 30]

wherein Ya', Yb', $R^2$, $R^3$, Ra, $Ra^1$, $Rb^1$, Q, $X^1$ and $X^2$ are the same as defined above.

Step G1 is a process to produce Compound 74 or Compound 75 and is achieved by reacting Compound 63 or Compound 64 with a carbamoylation agent in an inert solvent in the presence of or in the absence of an acid. Examples of carbamoylation agent include a $C_{1-6}$ alkylisocyanate, an aryl isocyanate, an N,N-di($C_{1-6}$ alkyl)carbamoyl chloride. There are no particular restrictions on the inert solvent used, as long as the solvent does not participate in the reaction. Examples of the solvent which can be used include ether type solvents such as dietyl ether, tetrahydrofuran, dioxane, dimethoxyethane; halogen solvents such as dichloromethane, chloroform, carbon tetrachloride and 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, and it is preferably ether type solvents such as diethylether, tetrahydrofuran, dioxane, dimethoxyethane; halogen solvents such as dichloromethane, chloroform, carbon tetrachloride, 1,2-dichloroethane; dimethylacetamide; dimethylformamide; N-methylpyrrolidon; acetonitrile, etc., and more preferably tetrahydrofuran, dichloromethane, acetonitrile, etc. The reaction temperature varies depending on the type of solvent and the like, but it is ordinarily 0° C. to 150° C., and preferably 10° C. to 100° C. The reaction time varies depending on the reaction temperature and the like, but it is ordinarily from 10 minutes to 48 hours, and preferably from 20 minutes to 24 hours.

Compound 74 or Compound 75 can be also produced by reacting Compound 63 or Compound 64 with a carbonylation agent to convert it into a compound to which a chlorocarbonyl group is introduced on a nitrogen atom or an isocyanate and then reacting with an amine ($HNRa^1Rb^1$). The carbonylation agent used here is, for example, phosgene, diphosgene, triphosgene, carbonyldiimidazole, etc. and it is preferably triphosgene. The base used is, for example, an amine such as triethylamine, diisopropylethylamine, 1,8-diazabicyclo[5.4.0]-7-undecene, pyridine, dimethylaminopyridine, pyrazine and it is preferably triethylamine, pyridine, dimethylaminopyridine, etc. There are no particular restrictions on the inert solvent used, as long as the solvent does not participate in the reaction, but, for example, it is ether type solvents such as diethylether, tetrahydrofuran, dioxane, dimethoxyethane; halogen solvents such as dichloromethane, chloroform, carbon tetrachloride, 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidone; acetonitrile, etc. and it is preferably ether type solvents such as diethylether, tetrahydrofuran, dioxane, dimethoxyethane; halogen solvents such as dichloromethane, chloroform, carbon tetrachloride, 1,2-dichloroethane; dimethylacetamide, dimethylformamide, N-methylpyrrolidone, etc. and more preferably dioxane, tetrahydrofuran, dichloromethane. The reaction temperature varies depending on the type of solvent and the like, but it is ordinarily −30° C. to 80° C., and preferably −10° C. to 30° C. The reaction time varies depending on the reaction temperature and the like, but it is ordinarily from 10 minutes to 24 hours, and preferably from 20 minutes to 15 hours.

In particular, the carbamoylation agent which is used for synthesizing Compound 74 or Compound 75 in which $Ra^1$ and $Rb^1$ are hydrogen atoms is, for example, sodium cyanate, potassium cyanate, cyanic acid, nitrourea, N-methyl-N-nitrosourea, urea, carbamoyl phosphate, and it is preferably sodium cyanate, potassium cyanate, nitrourea, etc. There are no particular restrictions on the inert solvent used on this occasion as long as the solvent does not participate in the reaction, but, for example, it is alcohols such as methanol, ethanol, n-propanol, i-propanol, n-butanol, sec-butanol, t-butanol, pentanol, hexanol, cyclopropanol; halogen solvents such as dichloromethane, chloroform, carbon tetrachloride; dimethylsulfoxide; dimethylacetamide; dimethylimidazolidinone; dimethylformamide; N-methylpyrrolidon; ethyl acetate; water; acetonitrile, etc. and it is preferably water, ethanol, chloroform, etc. The acid used is, for example, hydrochloric acid, sulfuric acid, acetic acid, trifluoroacetic acid, etc. and preferably hydrochloric acid, acetic acid, etc. Acid does not need to be used, but it is preferably used when the carbamoylation agent used is, for example, sodium cyanate, potassium cyanate. The reaction temperature varies depending on the type of solvent and the like, but it is ordinarily 0° C. to 200° C., and it is preferably 10° C. to 80° C. The reaction time varies depending on the reaction temperature and the like, but it is ordinarily from 10 minutes to 48 hours, and preferably from 30 minutes to 24 hours.

In addition, it is possible in Step G1 to synthesize Compound 74 or Compound 75 in which $Ra^1$ and $Rb^1$ are hydrogen atoms by reacting Compound 63 or Compound 64 with trichloroacetyl isocyanate in an inert solvent, and by reacting the obtained product with neutral activated alumina and the like. There are no particular restrictions on the inert solvent used in the reaction of Compound 63 or Compound 64 with trichloroacetyl isocyanate as long as the solvent does not participate in the reaction, but, for example, it is aromatic solvents such as benzene, toluene, xylene, quinoline, chlorobenzene; halogen solvents such as dichloromethane, chloroform, carbon tetrachloride; ether type solvents such as diethylether, tetrahydrofuran, dioxane, dimethoxyethane; cyclohexane; dimethylsulfoxide; dimethylacetamide; dimethylimidazolidinone; dimethylformamide; N-methylpyrrolidon; acetonitrile, and it is preferably acetonitrile, toluene, dichloromethane, etc. The reaction temperature varies depending on the type of solvent and the like, but it is ordinarily 0° C. to 200° C., and preferably 10° C. to 80° C. The reaction time varies depending on the reaction temperature and the like, but it is ordinarily from 10 minutes to 48 hours, and preferably from 30 minutes to 24 hours.

There are no particular restrictions on the inert solvent used in the reaction with neutral activated alumina as long as the solvent does not participate in the reaction, but, for example, it is alcohols such as methanol, ethanol, n-propanol, i-propanol, n-butanol, sec-butanol, t-butanol, pentanol, hexanol, cyclopropanol; aromatic solvents such as benzene, toluene, xylene, quinoline, chlorobenzene; halogen solvents such as dichloromethane, chloroform, carbon tetrachloride; ether type solvents such as diethylether, tetrahydrofuran, dioxane, dimethoxyethane; cyclohexane; dimethylsulfoxide; dimethylacetamide; dimethylimidazolidinone; dimethylformamide; N-methylpyrrolidon; acetonitrile; ethyl acetate, etc. and it is preferably methanol, chloroform, ethyl acetate, etc. The reaction temperature varies depending on the type of solvent and the like, but it is ordinarily 0° C. to 200° C., and preferably 10° C. to 80° C. The reaction time varies depending on the reaction temperature and the like, but it is ordinarily from 10 minutes to 48 hours, and preferably from 30 minutes to 24 hours.

Method H is a method to produce Compound 78 or Compound 79 in the following formula among the compounds represented by general formula (I):

Method H

[Formula 31]

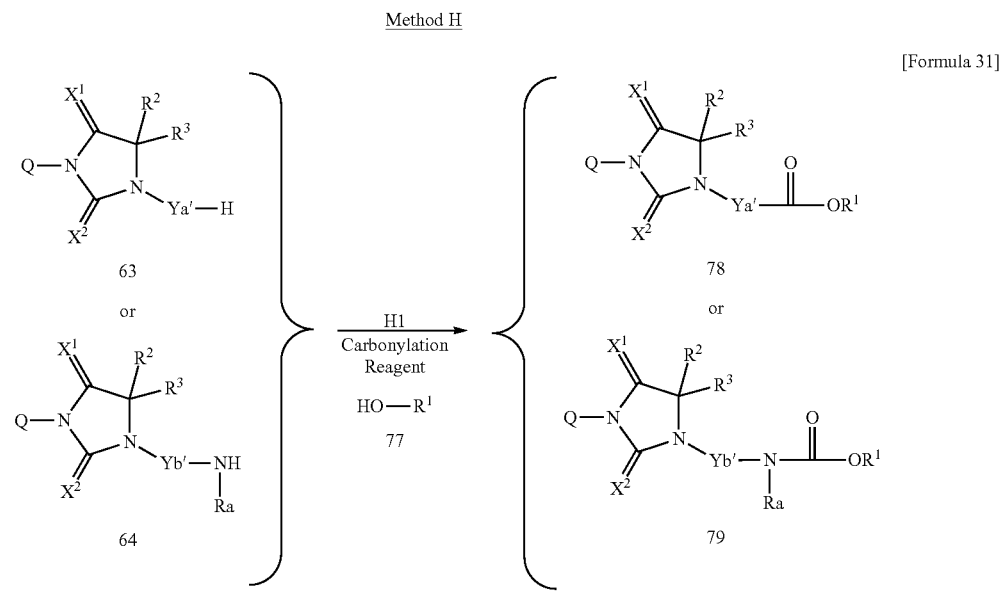

wherein Ya', Yb', $R^1$, $R^2$, $R^3$, Ra, Q, $X^1$ and $X^2$ are the same as defined above. When $R^1$ has a substituent selected from B, it may have a protecting group.

In Step H1, Compound 78 or Compound 79 can be synthesized by reacting Compound 63 or Compound 64 and a carbonylation agent in an inert solvent in the presence of a base and then further reacting with Compound 77.

There are no particular restrictions on the inert solvent used, as long as the solvent does not participate in the reaction, but, for example, it is ether type solvents such as diethylether, tetrahydrofuran, dioxane, dimethoxyethane; halogen solvents such as dichloromethane, carbon tetrachloride, 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc., and it is preferably ether type solvents such as diethylether, tetrahydrofuran, dioxane, dimethoxyethane; halogen solvents such as dichloromethane, carbon tetrachloride, 1,2-dichloroethane; dimethylacetamide; dimethylformamide; N-methylpyrrolidon, and more preferably dioxane, tetrahydrofuran, dichloromethane, etc.

The base used is, for example, amines such as triethylamine, diisopropylethylamine, 1,8-diazabicyclo[5.4.0]-7- undecene, pyridine, dimethylaminopyridine, pyrazine and it is preferably triethylamine, pyridine, dimethylaminopyridine, etc.

The carbonylation agent used is, for example, phosgene, diphosgene, triphosgene, carbonyldiimidazole, phenyl chloroformate or p-nitrophenyl chloroformate, etc. and it is preferably triphosgene, phenyl chloroformate or p-nitrophenyl chloroformate. The reaction temperature varies depending on the type of solvent and the like, but it is ordinarily −30° C. to 80° C., and preferably −10° C. to 30° C. for the both reaction. The reaction time varies depending on the reaction temperature and the like, but it is ordinarily from 10 minutes to 24 hours, and preferably from 20 minutes to 15 hours for the both reactions.

Method J is a method to produce Compound 62 in which $X^1$ and $X^2$ is O among the compounds represented by general formula (I):

Method J

[Formula 32]

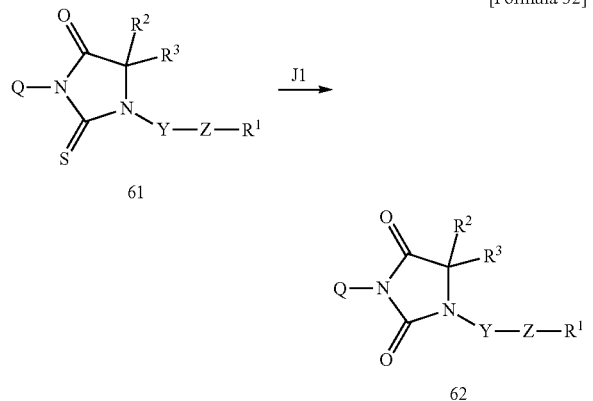

wherein Q, Y, Z, $R^1$, $R^2$ and $R^3$ are the same as defined above.

Step J1 is achieved by reacting Compound 61 with an oxidizing agent in the process to produce Compound 62 in an inert solvent (either single solvent or plurally mixed solvent is used).

There are no particular restrictions on the inert solvent used, as long as the solvent does not participate in the reaction, but, for example, it is halogen solvents such as dichloromethane, chloroform, carbon tetrachloride; ether type solvents such as diethylether, tetrahydrofuran, dioxane, dimethoxyethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile; water, and it is preferably a mixed solvent of carbon tetrachloride, acetonitrile and water, etc.

The oxidizing agent used is not limited in particular, but, for example, it can be halogens such as chlorine, bromine, iodine, hypochlorous acid, sodium hypochlorite, potassium hypochlorite, potassium hypoiodite, sodium chlorate, potassium chlorate, sodium bromate, potassium bromate, sodium iodade, potassium iodate, perchloryl fluoride, orthoperiodic acid, sodium metaperiodate, potassium metaperiodate, N-bromoacetamide, N-bromosuccinimide, N-bromophthalimide, isocyanul chloride, isocyanul bromide, N-bromocaprolactam, 1-chlorobenzotriazole, 1,3-dibromo-5,5-dimethylhydantoin, sodium N-chloro-p-toluene sulfonamide (Chloramine T), sodium N-chlorobenzenesulphonamide (chloramine B), t-butyl hypochlorite, t-butyl hypobromite, t-butyl hypoiodite, acetic acid iodosylbenzene, iodosylbenzene; manganese compounds such as potassium permanganate, manganese dioxide, manganese acetate (III), tris (acetonylacetonite) manganese (III) (MTA), manganese sulfate (III), manganic pyrophosphate (III); chromates such as chromic oxide (IV), Jones reagent, Sarett reagent, Collins reagent, chromic acid t-butyl ester, potassium dichromate, Beckmann mixed solution, sodium dichromate, Kiliani reagent, chromyl chloride, chromyl acetate, pyridinium chlorochromate (PCC), pyridinium dichromate (PDC); lead compounds such as lead tetraacetate, lead tetrabenzoate, diachylon, lead oxide (iV), lead dioxide; mercury compounds such as mercuric acetate (II), mercuric trifluoroacetate (II), anhydrous mercury nitrate (II), mercury oxide (II); organic peroxides such as t-butyl perbenzoate, t-butyl peracetate, t-butylhydroperoxide, t-amyl hydroperoxide, dibenzoylperoxide, di-p-nitrobenzoylperoxide, di-p-chlorobenzoylperoxide; organic peracids such as perbenzoic acid, metachloroperbenzoic acid, p-nitroperbenzoic acid, monoperoxylphthalic acid, peroxyformic acid, peracetic acid, trifluoroperacetic acid, peroxyllauric acid, nitrogen oxide:nitric acid, nitrous acid, nitrosyl chloride, nitrous oxide, nitrogen trioxide, dinitrogen tetraoxide, potassium nitrosodisulfonate (Fremy salt), quinones such as 2,3-dichloro-5,6-dicyano-1,4-benzoquinone (DDQ), tetrachloro-1,2-benzoquinone (o-chloranil), tetrachloro-1,4-benzoquinone (chloranil); alkyl nitrites such as ethyl nitrite, n-butyl nitrite, isoamyl nitrite; silver compounds such as silver oxide (I), silver nitrate, silver carbonate (Fetizon reagent), copper compounds such as copper (I) chloride, copper chloride (II), copper acetate, copper (II) oxide, copper sulfate-pyridine, iron compounds such as iron (III) chloride, potassium ferricyanide, iron (III) sulfate, ruthenium chloride (III)-sodium metaperiodate, hydrogen peroxide, dimethylsulfoxide, oxygen, etc. and it is preferably halogens such as chlorine, bromine, iodine, hypochlorous acid, sodium hypochlorite, potassium hypobromite, potassium hypoiodite, sodium chlorate, potassium chlorate, sodium bromate, potassium bromate, sodium iodate, potassium iodate, perchloryl fluoride, orthoperiodic acid, sodium metaperiodate, potassium metaperiodate, N-bromoacetamide, N-bromosuccinimide, N-bromophthalimide, isocyanul chloride, isocyanul bromide, N-bromocaprolactam, 1-chlorobenzotriazole, 1,3-dibromo-5,5-dimethylhydantoin, sodium N-chloro-p-toluene sulfonamide (Chloramine T), sodium N-chlorobenzenesulphonamide (chloramine B), t-butyl hypochlorite, t-butyl hypobromite, t-butyl hypoiodite, acetic acid iodosylbenzene, iodosylbenzene, manganese compounds such as potassium permanganate, manganese dioxide, manganese acetate (III), tris (acetonylacetonite) manganese (III) (MTA), manganese sulfate (III), manganic pyrophosphate (III), ruthenium chloride (III)-sodium metaperiodate, hydrogen peroxide, dimethylsulfoxide, oxygen, etc. and it is more preferably potassium permanganate, ruthenium chloride (III)-sodium metaperiodate, hydrogen peroxide, dimethylsulfoxide, oxygen, etc.

The reaction temperature varies depending on the type of solvent and the like, but it is ordinarily −30° C. to 100° C., and preferably 0° C. to 50° C. The reaction time varies depending on the reaction temperature and the like, but it is ordinarily from 10 minutes to 48 hours, and preferably from 30 minutes to 24 hours.

Method K is a method to produce Compound 90 or Compound 91 in the following formula among the compounds represented by general formula (I):

Method K

[Formula 33]

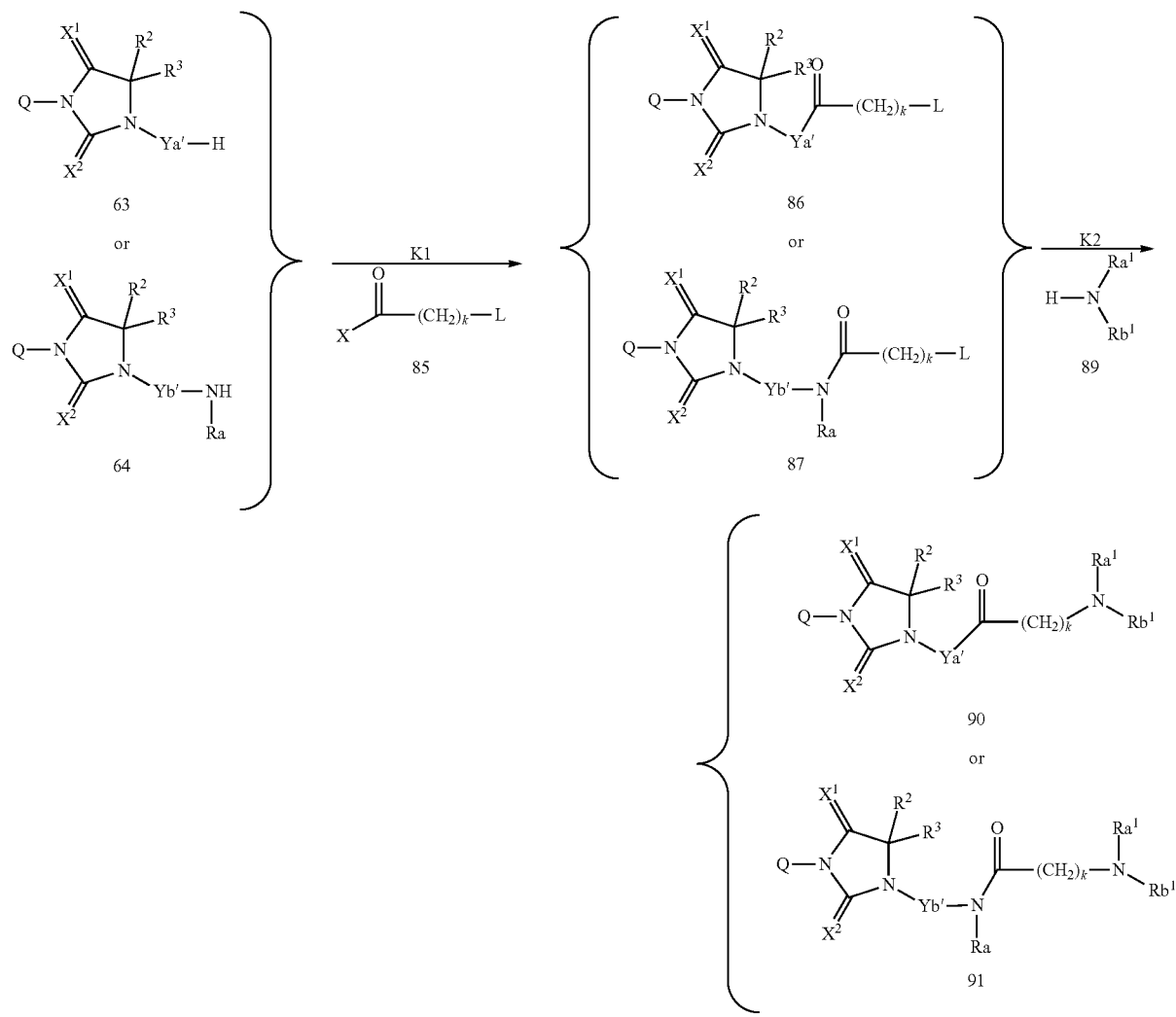

wherein L is a leaving group and includes, for example, halogen atoms such as a bromine atom, a chlorine atom, k is an integer from 1 to 5, and Ya', Yb', $R^2$, $R^3$, Ra, $Ra^1$, $Ra^2$, Q, X, $X^1$ and $X^2$ are the same as defined above, and $Ra^1$ and $Rb^1$, as already defined, together with a nitrogen atom to which they bind form nitrogen-containing heterocyclic groups, for example, of the following formulas:

[Formula 34]

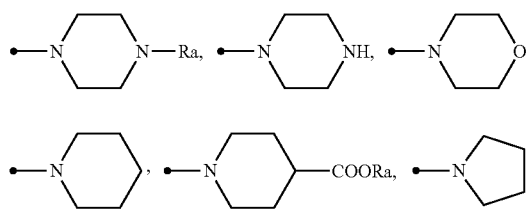

and the like.

In Step K1, Compound 86 or Compound 87 can be prepared by reacting Compound 63 or Compound 64 and Compound 85 in an inert solvent in the presence of a base.

There are no particular restrictions on the inert solvent used, as long as the solvent does not participate in the reaction, but, for example, it is halogen solvents such as dichloromethane, carbon tetrachloride, 1,2-dichloroethane; ether type solvents such as diethylether, tetrahydrofuran, dioxane, dimethoxyethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and it is preferably halogen solvents such as dichloromethane, carbon tetrachloride, 1,2-dichloroethane; ether type solvents such as diethylether, tetrahydrofuran, dioxane, dimethoxyethane; dimethylacetamide; dimethylformamide; N-methylpyrrolidon, etc. and more preferably dichloromethane, tetrahydrofuran, etc.

The base used is, for example, amines such as triethylamine, diisopropylethylamine, 1,8-diazabicyclo[5.4.0]-7-undecene, pyridine, dimethylaminopyridine, pyrazine and it is preferably triethylamine, pyridine, dimethylaminopyridine, etc. The reaction temperature varies depending on the type of solvent and the like, but it is ordinarily −30° C. to 100° C., and preferably −10° C. to 50° C. The reaction time varies depending on the reaction temperature and the like, but it is ordinarily from 10 minutes to 48 hours, and preferably from 30 minutes to 24 hours.

Step K2 is a process to produce Compound 90 and Compound 91 and is achieved by reacting Compound 86, Compound 87 and Compound 88 with Compound 89 in an inert solvent in the presence of or in the absence of a base. There are no particular restrictions on the inert solvent used, as long as the solvent does not participate in the reaction, but, for example, it is halogen solvents such as dichloromethane, chloroform, carbon tetrachloride, 1,2-dichloroethane; ether type solvents such as diethylether, tetrahydrofuran, dioxane, dimethoxyethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and preferably halogen solvents such as dichloromethane, chloroform, carbon tetrachloride, 1,2-dichloroethane; ether type solvents such as diethylether, tetrahydrofuran, dioxane, dimethoxyethane; dimethylacetamide; dimethylformamide; N-methylpyrrolidon, etc. and more preferably dichloromethane, tetrahydrofuran, etc. The base used is, for example, amines such as triethylamine, diisopropylethylamine, 1,8-diazabicyclo[5.4.0]-7-undecene, pyridine, dimethylaminopyridine, pyrazine and it is preferably triethylamine, pyridine, dimethylaminopyridine, etc. The reaction temperature varies depending on the type of solvent and the like, but it is ordinarily −30° C. to 100° C., and preferably −10° C. to 50° C. The reaction time varies depending on the reaction temperature and the like, but it is ordinarily from 10 minutes to 48 hours, and preferably from 30 minutes to 24 hours.

Method L is a method to produce Compound 97 in the following formula among the compounds expressed in a general formula (I):

Method L

[Formula 35]

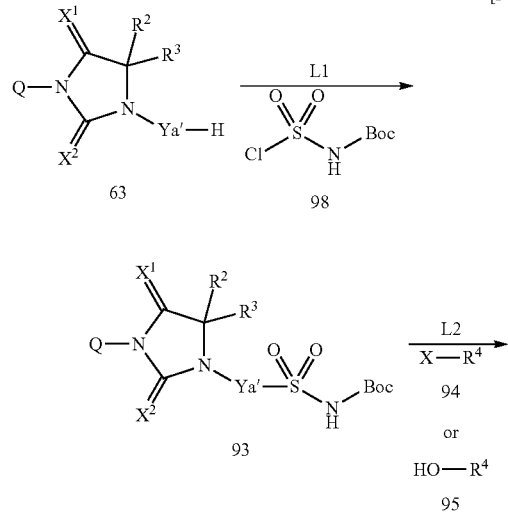

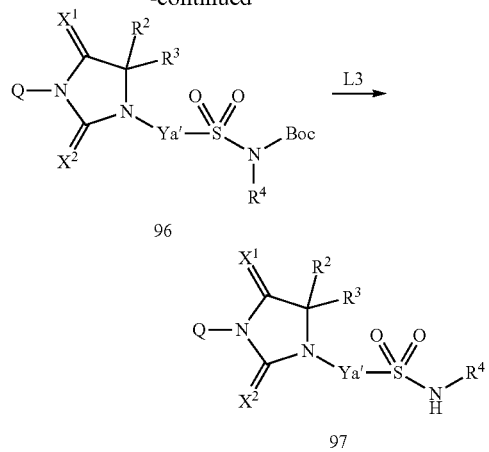

wherein $R^4$ is an alkyl group which may be substituted, an arylalkyl group which may be substituted, a cycloalkyl group which may be substituted, a cycloalkylalkyl group which may be substituted, Ya', $R^2$, $R^3$, Q, $X^1$ and $X^2$ are the same as defined above.

In Step L1, Compound 93 is produced by reacting Compound 98 prepared by reacting chlorosulfonyl isocyanate and t-butanol, and Compound 63 in an inert solvent in the presence of a base.

There are no particular restrictions on the inert solvent used in the reaction to produce Compound 98, as long as the solvent does not participate in the reaction, but, for example, it is halogen solvents such as dichloromethane, carbon tetrachloride, 1,2-dichloroethane; ether type solvents such as diethylether, tetrahydrofuran, dioxane, dimethoxyethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and it is preferably halogen solvents such as dichloromethane, carbon tetrachloride, 1,2-dichloroethane; ether type solvents such as diethylether, tetrahydrofuran, dioxane, dimethoxyethane; dimethylacetamide; dimethylformamide; N-methylpyrrolidon, etc. and more preferably dichloromethane, tetrahydrofuran, etc.

The base used is, for example, amines such as triethylamine, diisopropylethylamine, 1,8-diazabicyclo[5.4.0]-7-undecene, pyridine, dimethylaminopyridine, pyrazine and it is preferably triethylamine, pyridine, dimethylaminopyridine, etc.

The inert solvent and the base used in the reaction of Compound 98 and Compound 63 are similar to those used in the reaction to produce Compound 98. The reaction temperature varies depending on the type of solvent and the like, but it is ordinarily −30° C. to 100° C., and preferably −10° C. to 50° C. for the both reaction. The reaction time varies depending on the reaction temperature, but it is ordinarily from 5 minutes to 24 hours, and preferably from 10 minutes to 12 hours for the both reaction.

Step L2 is a step to produce Compound 96 and, for example, can be performed by utilizing alkylation with an alkyl halide or Mitsunobu reaction using an alkyl alcohol.

Alkylation method is achieved by reacting Compound 93 and Compound 94 in an inert solvent in the presence of a base. There are no particular restrictions on the inert solvent used, as long as the solvent does not participate in the reaction, but, for example, it is ether type solvents such as diethylether, tetrahydrofuran, dioxane, dimethoxyethane; halogen solvents such as dichloromethane, carbon tetrachloride, 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and it is preferably ether type solvents such as diethylether, tetrahydrofuran, dioxane, dimethoxyethane; dimethylacetamide, dimethylformamide; N-methylpyrrolidon, etc. and more preferably tetrahydrofuran, dimethylacetamide, dimethylformamide, etc.

Examples of the base used include carbonates such as potassium carbonate, sodium carbonate, cesium carbonate, potassium hydrogen carbonate, sodium hydrogen carbonate; metal alkoxides such as sodium alkoxide, potassium t-butoxide; metal hydrides such as sodium hydride, potassium hydride, calcium hydride; alkyllithium such as methyllithium, ethyllithium, n-butyllithium, t-butyllithium; metal hydroxides such as lithium hydroxide, sodium hydroxide, potassium hydroxide, calcium hydroxide, barium hydroxide, cesium hydroxide; metal amides such as sodium amide, potassium bistrimethylsilylamide, sodium bistrimethylsilylamide, lithium diisopropylamide, amines such as triethylamine, diisopropylethylamine, 1,8-diazabicyclo[5.4.0]-7-undecene, pyridine, dimethylaminopyridine, and it is preferably carbonates such as potassium carbonate, sodium carbonate, cesium carbonate, potassium hydrogen carbonate, sodium hydrogen carbonate; metal hydrides such as sodium hydride, potassium hydride, calcium hydride, etc. and more preferably potassium carbonate, sodium hydride, etc. The reaction temperature varies depending on the type of solvent and the like, but it is ordinarily −30° C. to 100° C., and preferably 0° C. to 50° C. The reaction time varies depending on the reaction temperature and the like, but it is ordinarily from 10 minutes to 48 hours, and preferably from 30 minutes to 24 hours.

Using Mitsunobu reaction, alkylation can be performed by reacting Compound 93 and Compound 95 in an inert solvent in the presence of Mitsunobu reagent. There are no particular restrictions on the inert solvent used, as long as the solvent does not participate in the reaction, but, for example, it is ether type solvents such as diethylether, tetrahydrofuran, dioxane, dimethoxyethane; aromatic solvents such as benzene, toluene, xylene, quinoline, chlorobenzene; halogen solvents such as dichloromethane, chloroform, carbon tetrachloride, 1,2-dichloroethane; cyclohexane; dimethylsulfoxide; dimethylacetamide; dimethylimidazolidinone; dimethylformamide; N-methylpyrrolidon; acetonitrile, etc. and it is preferably ether type solvents such as diethylether, tetrahydrofuran, dioxane, dimethoxyethane; aromatic solvents such as benzene, toluene, xylene, quinoline, chlorobenzene, etc. and more preferably tetrahydrofuran, dimethoxyethane, benzene, toluene, etc.

Examples of the Mitsunobu reagent include combinations of azodicarboxylic acids such as azodicarboxylic acid diethyl ester, azodicarboxylic acid dibenzyl ester, azodicarboxylic acid diisopropyl ester, azodicarboxylic acid dimethylester, N,N,N',N'-tetraisopropylazodicarboxamide, 1,1'-(azodicarbonyl)dipyridine, N,N,N',N'-tetramethylazodicarboxamide, 1,6-dimethyl-1,5,7-hexahydro-1,4,6,7-tetrazocine-2,5-dione, and phosphines such as triphenylphosphine, tri-n-octylphosphine, tri-n-hexylphosphine, tricyclohexylphosphine, tri-n-butylphosphine, dicyclohexylphenylphosphine, diethylphenylphosphine, 4-(dimethylamino)phenyl diphenylphosphine, diphenyl-2-pyridylphosphine or phosphoranes such as (cyanomethylene)tributylphosphorane, (cyanomethylene)trimethylphosphorane, and preferably, a combination of 1,6-dimethyl-1,5,7-hexahydro-1,4,6,7-tetrazocine-2,5-dione and tri-n-butylphosphine, (cyanomethylene)tributylphosphorane, (cyanomethylene)trimethylphosphorane, etc.

The reaction temperature varies depending on the type of solvent and the like, but it is ordinarily −30° C. to 150° C., and preferably 0° C. to 100° C. The reaction time varies depending on the reaction temperature and the like, but it is ordinarily from 10 minutes to 48 hours, and preferably from 30 minutes to 24 hours.

Step L3 is a step to remove t-butoxycarbonyl group which is a protecting group for deprotection and to produce Compound 97, and it can be performed by methods well-known by those skilled in the art, for example, referring to "Protective Groups in Organic Synthesis 2nd edition", Theodora W. Green, John Wiley & Sons, Inc., 1991, etc.

Method M is a method to produce Compound 74 or Compound 75 in the following formula among the compounds represented by general formula (I):

Method M

[Formula 36]

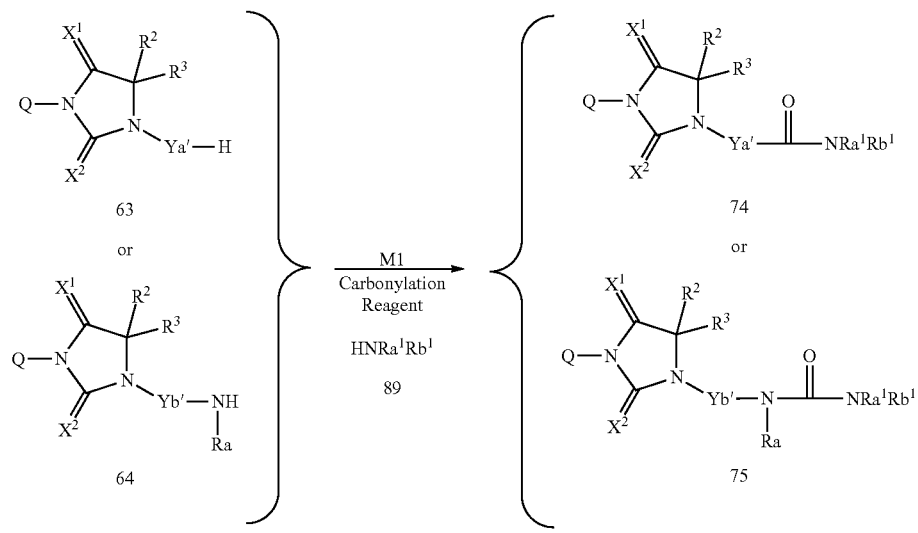

wherein Ya', Yb', $R^2$, $R^3$, Ra, $Ra^1$, $Rb^1$, Q, $X^1$ and $X^2$ are the same as defined above.

In Step M1, Compound 74 or Compound 75 can be synthesized by reacting Compound 63 or Compound 64 and a carbonylation agent and further reacting with Compound 89 in an inert solvent in the presence of a base.

There are no particular restrictions on the inert solvent used, as long as the solvent does not participate in the reaction, but, for example, it is ether type solvents such as diethylether, tetrahydrofuran, dioxane, dimethoxyethane; halogen solvents such as dichloromethane, carbon tetrachloride, 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and it is preferably ether type solvents such as diethylether, tetrahydrofuran, dioxane, dimethoxyethane; halogen solvents such as dichloromethane, carbon tetrachloride, 1,2-dichloroethane; dimethylacetamide, dimethylformamide, N-methylpyrrolidon, etc. and more preferably dioxane, tetrahydrofuran, dichloromethane, etc.

The base used is, for example, amines such as triethylamine, diisopropylethylamine, 1,8-diazabicyclo[5.4.0]-7-undecene, pyridine, dimethylaminopyridine, pyrazine and it is preferably triethylamine, pyridine, dimethylaminopyridine, etc.

The carbonylation agent used is, for example, phosgene, diphosgene, triphosgene, carbonyldiimidazole, phenyl chloroformate or p-nitrophenyl chloroformate, etc. and it is preferably triphosgene, phenyl chloroformate or p-nitrophenyl chloroformate, etc. The reaction temperature varies depending on the type of solvent and the like, but it is ordinarily both reaction, −30° C. to 80° C., and preferably −10° C. to 30° C. The reaction time varies depending on the reaction temperature and the like, but it is ordinarily from 10 minutes to 24 hours, and preferably from 20 minutes to 15 hours for the both reaction.

Compound 60 which is an intermediate for synthesizing a compound of the present invention can be also produced by Method N shown below:

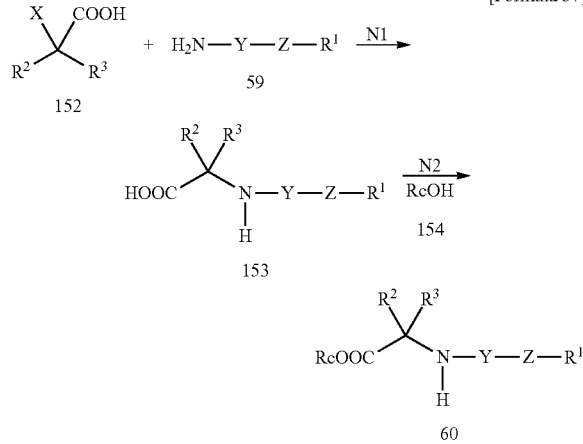

Method N

[Formula 37]

wherein X, Y, Z, $R^1$, $R^2$, $R^3$ and Rc are the same as defined above.

Step N1 is a step to produce Compound 153 and it is achieved by reacting Compound 152 and Compound 59 in an inert solvent in the presence of a base.

There are no particular restrictions on the inert solvent used, as long as the solvent does not participate in the reaction, but, for example, it is ether type solvents such as diethylether, tetrahydrofuran, dioxane, dimethoxyethane; halogen solvents such as dichloromethane, carbon tetrachloride, 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and it is preferably ether type solvents such as diethylether, tetrahydrofuran, dioxane; dimethoxyethane; dimethylacetamide; dimethylformamide; N-methylpyrrolidon, etc. and more preferably dioxane, tetrahydrofuran, etc.

The base used is, for example, amines such as triethylamine, diisopropylethylamine, 1,8-diazabicyclo[5.4.0]-7-undecene, pyridine, dimethylaminopyridine, pyrazine and it is preferably triethylamine, diisopropylethylamine, pyridine, dimethylaminopyridine, etc.

The reaction temperature varies depending on the type of solvent and the like, but it is ordinarily 0° C. to 100° C., and preferably 10° C. to 70° C. The reaction time varies depending on the reaction temperature and the like, but it is ordinarily from 10 minutes to 24 hours, and preferably from 20 minutes to 15 hours.

Step N2 is a step to produce Compound 60 and is achieved by reacting Compound 153 or the reactive derivative thereof (acid halide, mixed acid anhydride or active ester) and Compound 154 in an inert solvent or alternatively it is achieved by reacting Compound 153 and a diazoalkane compound.

This reaction is performed, for example, by an acid halide method, mixed anhydride method, active ester method or condensation method. The acid halide method is achieved by reacting Compound 153 with a halogenating agent (for example, thionyl chloride, oxalyl chloride, phosphorous pentachloride, etc.) in an inert solvent to produce an acid halide, and reacting the acid halide and Compound 154 in an inert solvent (or using Compound 154 itself as a solvent).

There are no particular restrictions on the inert solvent used, as long as the solvent does not participate in the reaction. Examples of the solvent which can be used include hydrocarbon solvents such as hexane, cyclohexane, benzene, toluene, xylene; halogen solvents such as dichloromethane, 1,2-dichloroethane and carbon tetrachloride; ether type solvents such as ether, tetrahydrofuran, dioxane; ketone solvents such as acetone; amide solvents such as N,N-dimethylacetamide, N,N-dimethylformamide, N-methyl-2-pyrrolidone; sulfoxide solvents such as dimethylsulfoxide, and it is preferably a hydrocarbon solvent, a halogen solvent or an ether type solvent and more preferably an ether type solvent (particularly preferably, tetrahydrofuran).

The reaction temperature may vary depending on the type of solvent and the like, but it is ordinarily −20° C. to 150° C. and preferably 0° C. to 100° C. both for the reaction of a halogenating agent with Compound 153 and the reaction of an acid halide with Compound 154. The reaction time varies depending on the reaction temperature and the like, but it is ordinarily from 15 minutes to 100 hours (preferably, from 30 minutes to 80 hours).

The mixed anhydride method is achieved by reacting a $C_{1-6}$ alkyl halogenoformate (here, the $C_{1-6}$ alkyl means a linear or branched alkyl group containing 1 to 6 carbon atoms), a di($C_{1-6}$ alkyl)cyanophosphoric acid or a diarylphosphoryl azide and Compound 153 to produce a mixed acid anhydride and reacting the mixed acid anhydride and Compound 154. The reaction to produce a mixed acid anhydride is performed by reacting a $C_{1-6}$ alkyl halogenoformate such as methyl chloroformate, ethyl chloroformate, isobutyl chloroformate, hexyl chloroformate (preferably, ethyl chloroformate or isobutyl chloroformate) and Compound 153 and it is preferably performed in an inert solvent in the presence of a base.

The base and inert solvent used are similar to those used by the acid halide method of the present process. The reaction temperature varies depending on the type of solvent and the like, but it is ordinarily $-20°$ C. to $50°$ C. (preferably, $0°$ C. to $30°$ C.). The reaction time varies depending on the reaction temperature and the like, but it is ordinarily from 15 minutes to 24 hours (preferably, from 30 minutes to 15 hours).

The reaction between the mixed acid anhydride and Compound 154 is performed in an inert solvent in the presence or in the absence of a base (preferably, in the presence a base) and the base and inert solvent used are similar to those used by the acid halide method mentioned above. The reaction temperature varies depending on the type of solvent and the like, but it is ordinarily $-20°$ C. to $50°$ C. (preferably, $0°$ C. to $30°$ C.). The reaction time varies depending on the reaction temperature and the like, but it is ordinarily from 15 minutes to 24 hours (preferably, from 30 minutes to 15 hours).

The active esterification method is achieved by reacting Compound 153 with active esterification agent (for example, N-hydroxy compounds such as N-hydroxysuccinimide, N-hydroxybenzotriazole) in the presence of condensing agent (for example, dicyclohexylcarbodiimide, carbonyldiimidazole) to produce an active ester, and reacting this active ester with Compound 154. The reaction to produce active ester is preferably performed in an inert solvent, and the inert solvent used can be, for example, an ether type solvent such as ether, tetrahydrofuran, dioxane, dimethoxyethane, a halogen solvent such as carbon tetrachloride, dichloromethane, dimethylformamide, ethyl acetate, acetonitrile, etc. and it is preferably dichloromethane, acetonitrile, ethyl acetate, etc. The reaction temperature varies depending on the type of solvent, but it is ordinarily $-20°$ C. to $50°$ C. (preferably, $-10°$ C. to $30°$ C.) in the active esterification reaction, and $-20°$ C. to $50°$ C. (preferably, $-10°$ C. to $30°$ C.) in the reaction between the active ester compound and Compound 154. The reaction time varies depending on the reaction temperature, but it is ordinarily from 15 minutes to 24 hours (preferably, from 30 minutes to 15 hours) for the both reaction.

The condensation method is performed by reacting Compound 153 and Compound 154 directly in the presence of a condensing agent [for example, dicyclohexylcarbodiimide, carbonyldiimidazole, 1-(N,N-dimethylaminopropyl)-3-ethyl carbodiimide hydrochloride]. This reaction is performed similarly as the reaction to produce the above active ester There are no particular restrictions on the inert solvent used in the reaction of Compound 153 and a diazoalkane compound, as long as the solvent does not participate in the reaction, but, for example, it is ether type solvents such as diethylether, tetrahydrofuran, dioxane, dimethoxyethane; halogen solvents such as dichloromethane, carbon tetrachloride, 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and it is preferably ether type solvents such as diethylether, tetrahydrofuran, dioxane, dimethoxyethane; halogen solvents such as dichloromethane, carbon tetrachloride, 1,2-dichloroethane, etc. and more preferably diethylether, dichloromethane, etc.

The reaction temperature varies depending on the type of solvent and the like, but it is ordinarily $0°$ C. to $100°$ C., and preferably $10°$ C. to $70°$ C. The reaction time varies depending on the reaction temperature and the like, but it is ordinarily from 5 minutes to 24 hours, and preferably from 10 minutes to 15 hours.

Method O is a method to produce Compound 73 in the following formula among the compounds expressed in a general formula (I):

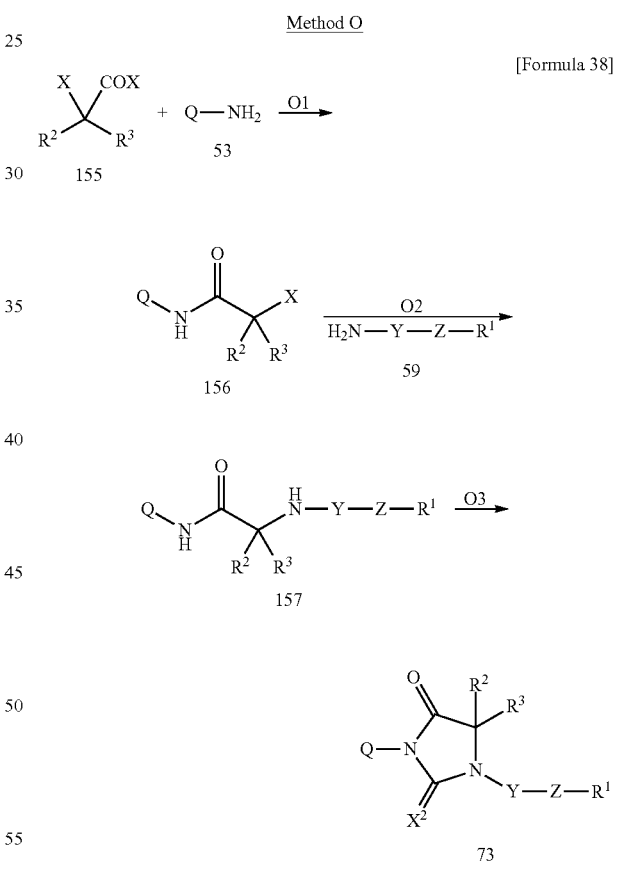

wherein Q, X, Y, Z, $R^1$, $R^2$ and $R^3$ are the same as defined above.

Step O1 is a step to produce Compound 156 and is achieved by reacting Compound 155 and Compound 53 in an inert solvent in the presence of a base.

There are no particular restrictions on the inert solvent used, as long as the solvent does not participate in the reaction, but, for example, it is ether type solvents such as diethylether, tetrahydrofuran, dioxane, dimethoxyethane; halogen solvents such as dichloromethane, carbon tetrachloride, 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and it is preferably ether type solvents such as diethylether, tetrahydrofuran, dioxane, dimethoxyethane; halogen solvents such as dichloromethane, carbon tetrachloride, 1,2-dichloroethane, etc. and more preferably diethylether, dichloromethane, etc.

Examples of the base used include metal alkoxides such as sodium alkoxide, potassium t-butoxide; metal hydrides such as sodium hydride, potassium hydride, calcium hydride; alkyllithium such as methyllithium, ethyllithium, n-butyllithium, t-butyllithium; metal hydroxides such as lithium hydroxide, sodium hydroxide, potassium hydroxide, calcium hydroxide, barium hydroxide, cesium hydroxide; metal amides such as sodium amide, potassium bistrimethylsilylamide, sodium bistrimethylsilylamide, lithium diisopropylamide, carbonates such as potassium carbonate, sodium carbonate, amines such as triethylamine, diisopropylethylamine, 1,8-diazabicyclo[5.4.0]-7-undecene, pyridine, dimethylaminopyridine, pyrazine, etc. and it is preferably carbonates such as potassium carbonate, sodium carbonate, amines such as triethylamine, diisopropylethylamine, 1,8-diazabicyclo[5.4.0]-7-undecene, pyridine, dimethylaminopyridine, pyrazine, etc. and more preferably potassium carbonate, diisopropylethylamine, etc.

The reaction temperature varies depending on the type of solvent and the like, but it is ordinarily 0° C. to 100° C., and preferably 10° C. to 70° C. The reaction time varies depending on the reaction temperature and the like, but it is ordinarily from 5 minutes to 24 hours, and preferably from 10 minutes to 18 hours.

Step O2 is a step to produce Compound 157 and is achieved by reacting Compound 156 and Compound 59 in an inert solvent in the presence of a base.

There are no particular restrictions on the inert solvent used, as long as the solvent does not participate in the reaction, but, for example, it is ether type solvents such as diethylether, tetrahydrofuran, dioxane, dimethoxyethane; halogen solvents such, as dichloromethane, carbon tetrachloride, 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and it is preferably ether type solvents such as diethylether, tetrahydrofuran, dioxane, dimethoxyethane; halogen solvents such as dichloromethane, carbon tetrachloride, 1,2-dichloroethane, etc. and more preferably tetrahydrofuran, etc.

Examples of the base used include metal alkoxides such as sodium alkoxide, potassium t-butoxide; metal hydrides such as sodium hydride, potassium hydride, calcium hydride; metal hydroxides such as lithium hydroxide, sodium hydroxide, potassium hydroxide, calcium hydroxide, barium hydroxide, cesium hydroxide; metal amides such as sodium amide, potassium bistrimethylsilylamide, sodium bistrimethylsilylamide, lithium diisopropylamide, carbonates such as potassium carbonate, sodium carbonate, amines such as triethylamine, diisopropylethylamine, 1,8-diazabicyclo[5.4.0]-7-undecene, pyridine, dimethylaminopyridine, pyrazine, etc. and it is preferably metal alkoxides such as sodium alkoxide, potassium t-butoxide, metal hydrides such as sodium hydride, potassium hydride, calcium hydride, etc. and more preferably sodium hydride, etc.

The reaction temperature varies depending on the type of solvent and the like, but it is ordinarily 0° C. to 100° C., and preferably 10° C. to 70° C. The reaction time varies depending on the reaction temperature and the like, but it is ordinarily from 5 minutes to 24 hours, and preferably from 10 minutes to 10 hours.

Step O3 is a step to produce Compound 73 and is achieved by reacting Compound 157 and thiocarbonylation agent in an inert solvent in the presence of a base.

There are no particular restrictions on the inert solvent used, as long as the solvent does not participate in the reaction, but, for example, it is ether type solvents such as diethylether, tetrahydrofuran, dioxane, dimethoxyethane; halogen solvents such as dichloromethane, carbon tetrachloride, 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and it is preferably ether type solvents such as diethylether, tetrahydrofuran, dioxane, dimethoxyethane; halogen solvents such as dichloromethane, carbon tetrachloride, 1,2-dichloroethane, etc. and more preferably tetrahydrofuran, etc.

Examples of the base used include metal alkoxides such as sodium alkoxide, potassium t-butoxide; metal hydrides such as sodium hydride, potassium hydride, calcium hydride; metal hydroxides such as lithium hydroxide, sodium hydroxide, potassium hydroxide, calcium hydroxide, barium hydroxide, cesium hydroxide; metal amides such as sodium amide, potassium bistrimethylsilylamide, sodium bistrimethylsilylamide, lithium diisopropylamide, carbonates such as potassium carbonate, sodium carbonate, amines such as triethylamine, diisopropylethylamine, 1,8-diazabicyclo[5.4.0]-7-undecene, pyridine, dimethylaminopyridine, pyrazine, etc. and it is preferably metal alkoxides such as sodium alkoxide, potassium t-butoxide, metal hydrides such as sodium hydride, potassium hydride, calcium hydride, etc. and more preferably sodium hydride, etc.

The carbonylation agent used is, for example, phenyl chloroformate, phosgene, diphosgene, triphosgene, carbonyldiimidazole, etc.

The thiocarbonylation agent used is, for example, phenyl chlorothionoformate, thiophosgene, thiocarbonyldiimidazole, etc. and it is preferably phenyl chlorothionoformate.

The reaction temperature varies depending on the type of solvent and the like, but it is ordinarily 0° C. to 100° C., and preferably 10° C. to 70° C. The reaction time varies depending on the reaction temperature and the like, but it is ordinarily from 5 minutes to 24 hours, and preferably from 10 minutes to 10 hours.

Method P is a method to produce Compound 161 or Compound 162 in the following formula among the compounds expressed in a general formula (I):

Method P

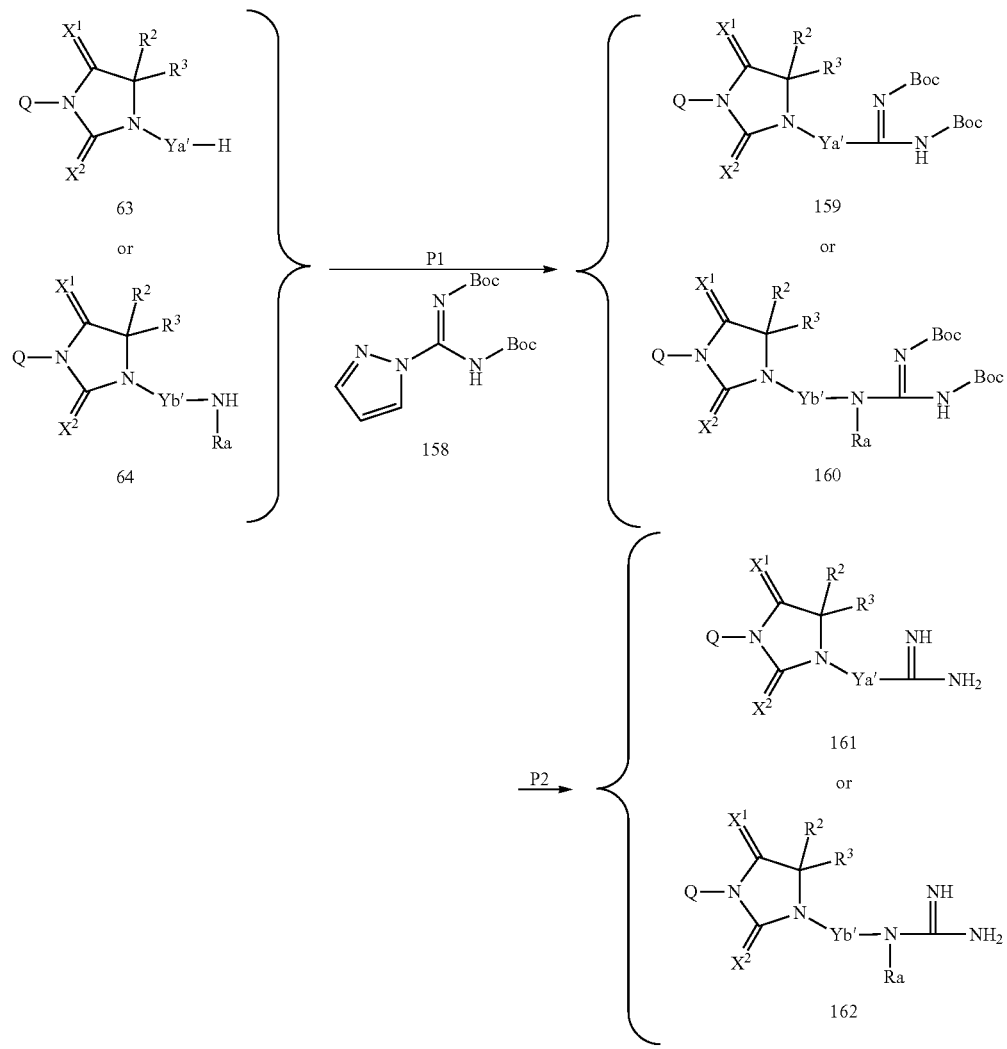

[Formula 39]

wherein Ya', Yb', $R^2$, $R^3$, Ra, Q, $X^1$ and $X^2$ are the same as defined above.

Step P1 is a step to produce Compound 159 or Compound 160 and is achieved by reacting Compound 63 or Compound 64 and Compound 158 in an inert solvent in the presence of acid.

There are no particular restrictions on the inert solvent used, as long as the solvent does not participate in the reaction, but, for example, it is ether type solvents such as diethylether, tetrahydrofuran, dioxane, dimethoxyethane; halogen solvents such as dichloromethane, chloroform, carbon tetrachloride, 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and it is preferably ether type solvents such as diethylether, tetrahydrofuran, dioxane, dimethoxyethane; halogen solvents such as dichloromethane, chloroform, carbon tetrachloride, 1,2-dichloroethane; dimethylacetamide, etc. and more preferably dimethylacetamide, etc.

Examples of the acid used include mineral acids such as hydrochloric acid, hydrobromic acid, hydroiodic acid, sulfuric acid, phosphoric acid, organic acids such as formic acid, acetic acid, oxalic acid, maleic acid, fumaric acid, methanesulfonic acid, trifluoromethane sulfonic acid, benzenesulfonic acid, p-toluenesulfonic acid, succinic acid, malonic acid, citric acid, gluconic acid, mandelic acid, benzoic acid, salicylic acid, trifluoroacetic acid, tartaric acid, propionic acid, a glutaric acid, and it is preferably acetic acid, trifluoroacetic acid, etc.

The reaction temperature varies depending on the type of solvent and the like, but it is ordinarily 0° C. to 100° C., and preferably 10° C. to 70° C. The reaction time varies depending on the reaction temperature and the like, but it is ordinarily from 5 minutes to 24 hours, and preferably from 10 minutes to 10 hours.

Step P2 is a step to remove t-butoxycarbonyl group which is a protecting group for deprotection and to produce Compound 161 or Compound 162, and it can be performed by methods well-known by those skilled in the art, for example, referring to "Protective Groups in Organic Synthesis 2nd edition", Theodora W. Green, John Wiley & Sons, Inc., 1991, etc.

Method Q is a method to produce Compound 164 or Compound 165 in the following formula among the compounds expressed in a general formula (I):

Method Q

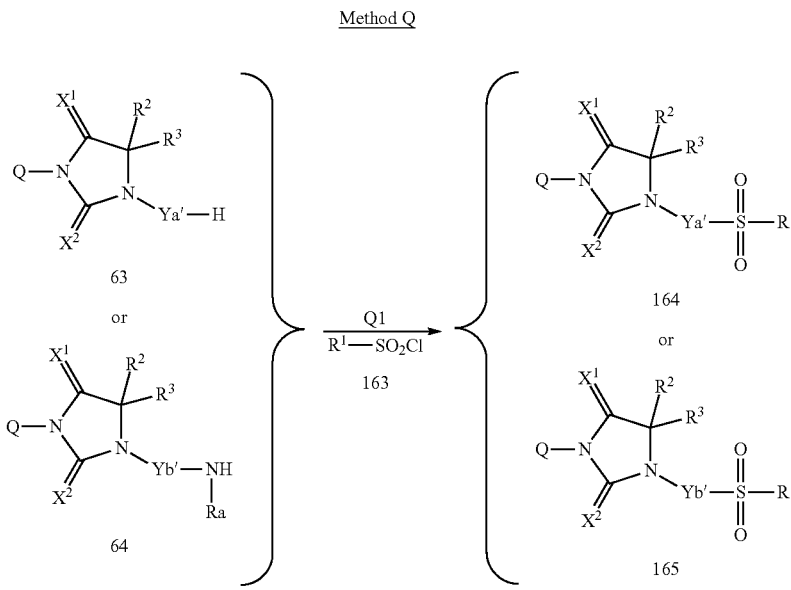

[Formula 40]

wherein Ya', Yb', $R^1$, $R^2$, $R^3$, Q, $X^1$ and $X^2$ are the same as defined above provided that $R^1$ here not a hydrogen atom nor a hydroxyl group and may have a protecting group when $R^1$ contains a substituent selected from B.

Step Q1 is a step to produce Compound 164 or Compound 165 and is achieved by reacting Compound 63 or Compound 64 and Compound 163 in an inert solvent in the presence of a base.

There are no particular restrictions on the inert solvent used, as long as the solvent does not participate in the reaction, but, for example, it is ether type solvents such as diethylether, tetrahydrofuran, dioxane, dimethoxyethane; halogen solvents such as dichloromethane, carbon tetrachloride, 1,2-dichloroethane; aromatic solvents such as benzene, toluene, xylene, quinoline, chlorobenzene; cyclohexane; dimethylsulfoxide; dimethylacetamide; dimethylimidazolidinone; dimethylformamide; N-methylpyrrolidon; acetonitrile, etc. and it is preferably halogen solvents such as dichloromethane, carbon tetrachloride, 1,2-dichloroethane; ether type solvents such as diethylether, tetrahydrofuran, dioxane, dimethoxyethane; dimethylacetamide; dimethylformamide; N-methylpyrrolidon, etc. and more preferably dichloromethane, tetrahydrofuran, etc.

The base used is, for example, amines such as triethylamine, diisopropylethylamine, 1,8-diazabicyclo[5.4.0]-7-undecene, pyridine, dimethylaminopyridine, pyrazine and it is preferably triethylamine, pyridine, dimethylaminopyridine, etc. The reaction temperature varies depending on the type of solvent and the like, but it is ordinarily −30° C. to 100° C., and preferably −10° C. to 50° C. The reaction time varies depending on the reaction temperature and the like, but it is ordinarily from 10 minutes to 48 hours, and preferably from 30 minutes to 24 hours.

When there are groups necessary for protection and deprotection in each step of above Method A to Method Q, protection and deprotection can be performed for each group by methods well-known in the art. For example, "Protective Groups in Organic Synthesis 2nd edition", Theodora W. Green, John Wiley & Sons, Inc., 1991, etc. can be referred to for peroming protection and deprotection.

The production process of the compounds of the present invention is not limited to the processes mentioned above. For example, the compounds of the present invention can be synthesized by appropriately combining steps contained in Method A to Method Q.

EXAMPLES

Preferred examples of the present invention will be described in detail below. However, the present invention is not limited to these examples.

NMR was measured using a nuclear magnetic resonance apparatus Mercury300 (manufactured by varian), ECP-400 (manufactured by JEOL) or EX 270 (manufactured by JEOL). Further, mass analysis was performed using a mass analysis apparatus LCQ Classic (manufactured by Thermo Electron), ZQ2000 (manufactured by Waters), QP5050A (manufactured by Shimadzu Corporation). Further, Rf values in thin-layer chromatography were measured using a silica gel plate Silica gel 60 $F_{254}$ (manufactured by Merck) or NH plate (manufactured by Fuji Silysia Chemical). In addition, as for LC/MS, measurement of retention time (hereinbelow also abbreviated as RT) and mass spectrometry were performed by the following device and analysis conditions. Measurement was performed in condition A for Examples 1 to 82 and 84 to 95, and in condition B for Example 83.

Condition A
System: LC/PDA/MS[HP1100 (manufactured by AgilentTechnologies)/TSP UV6000 (manufactured by ThermoElectron)/LCQClassic]
Column: CadenzaCD-C18 3.0×30 mm (manufactured by Imtakt)

Column temperature: 35° C.
Flow rate: 1 mL/min
Mobile phase A: $H_2O$ (0.05% TFA)
Mobile phase B: MeCN (0.05% TFA)
Gradient method: % B; 5-100 (for 9.5 min)-100 (for 2.5 min)
PDA range: 210-400 nm
Amount of injection: 5 μL
Condition B
System: LC/PDA[Alliance2690 (manufactured by Waters)/2, 996(manufactured by Waters)]
Column: Inertsil ODS-3 4.6×150 mm (manufactured by GLScience)
Column temperature: Room temperature
Flow rate: 1 mL/min
Mobile phase A: $H_2O$ (10 mM $AcONH_4$)
Mobile phase B: MeOH
Gradient method: % B; 5-5 (1 minute)-100 (19 minutes)-100 (5 minutes)
PDA range: 230-400 nm
Amount of injection: 10 μL Example 1

[Formula 41]

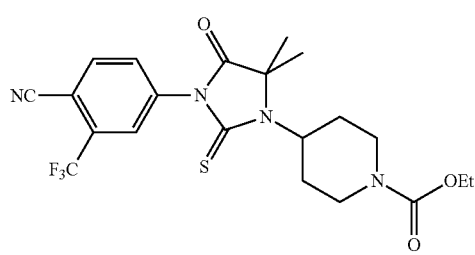

5

(Step 1)

[Formula 42]

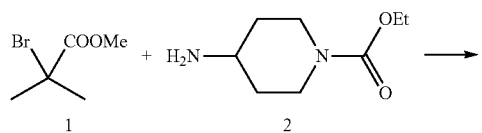

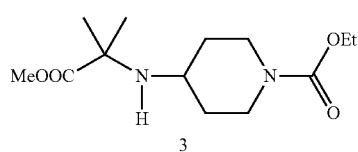

Compound 2 (5.0 g) was dissolved in methanol (20 mL), and added with Compound 1 (10.5 g) and sodium hydrogen carbonate (4.9 g) and the mixture was stirred at 100° C. under Ar atmosphere in a sealed tube for 36 hours. After standing to cool, the reaction solution was filtered and the filtrate was concentrated under reduced pressure and was purified by silica gel column chromatography (eluent, ethyl acetate) to obtain 2.2 g (yield 28%) of the target compound (Compound 3).

$^1$H-NMR (270 MHz, $CDCl_3$) δ: 1.25 (3H, t, J=7.1 Hz), 1.31 (6H, s), 1.60-1.80 (4H, m), 2.45-2.60 (1H, m), 2.70-2.88 (2H, m), 3.70 (3H, s), 3.95-4.20 (3H, m), 4.11 (2H, q, J=7.1 Hz).

Rf value (silica gel plate, eluent; Ethyl acetate): 0.37.

(Step 2)

[Formula 43]

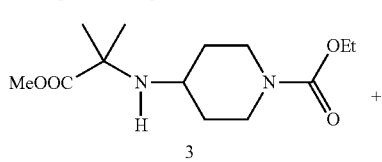

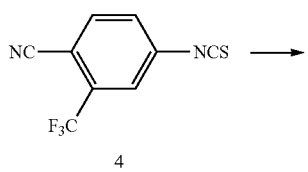

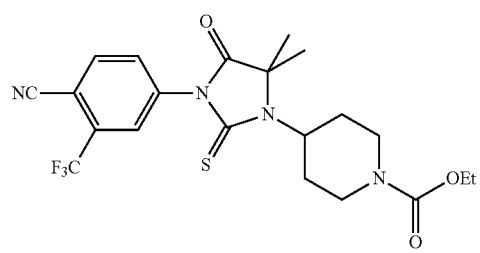

5

Compound 3 (2.2 g) was dissolved in 1,2-dichloroethane (81 mL), added with Compound 4 (2.1 g) and dimethylaminopyridine (1.48 g) and the mixture was stirred under nitrogen atmosphere at 100° C. for one hour. After standing to cool, the reaction solution was diluted with dichloromethane, washed with 10% citric acid aqueous solution and brine, dried over magnesium sulphate, filtered, concentrated under reduced pressure and purified by silica gel column chromatography (eluent, hexane:ethyl acetate=1:2) to obtain 3.47 g (yield 91%) of the target compound (Compound 5).

$^1$H-NMR (270 MHz, $CDCl_3$) δ: 1.28 (3H, t, J=7.1 Hz), 1.64 (6H, s), 1.78-1.90 (2H, m), 2.55-2.90 (4H, m), 4.10-4.45 (5H, m), 7.72 (1H, dd, J=1.7, 8.2 Hz), 7.84 (1H, s), 7.95 (1H, d, J=8.2 Hz).

MS(ESI)m/z: 468.9 ($[M+H]^+$).

Rf value (silica gel plate, eluent; hexane:ethyl acetate=1:2): 0.38.

The following compounds were synthesized by a method similar to that in Example 1.

TABLE 1

| Example No. | Structure | Data |
|---|---|---|
| 2 | 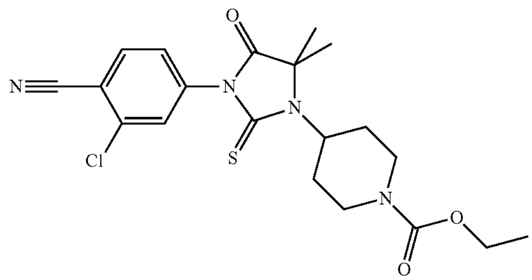 | MS(ESI) m/z: 435.0 ([M + H]⁺) RT: 5.99 min |
| 3 | 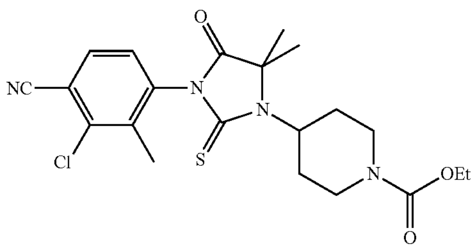 [SMILES: CCOC(=O)N1CCC(N2C(=S)N(c3ccc(C#N)c(Cl)c3C)C(=O)C2(C)C)CC1] | MS(ESI) m/z: 449.1 ([M + H]⁺) RT: 6.17 min |

Example 4

[Formula 44]

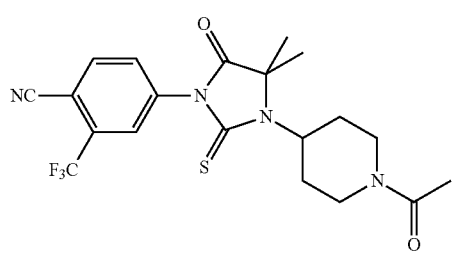

(Step 1)

[Formula 45]

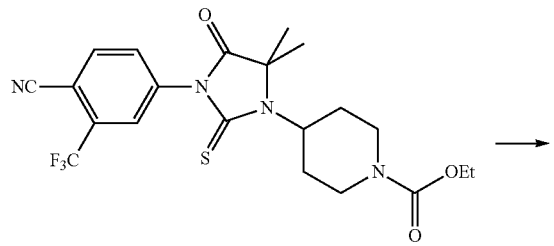

Compound 5 (3.47 g) was dissolved in dioxane (100 mL), added with 10 N hydrochloric acid (200 mL) and heated to reflux overnight. After standing to cool, the reaction solution was added with 10N aqueous sodium hydroxide while ice-cooled to make the pH of the reaction solution to about 10. Extracted with ethyl acetate, the organic layer was washed with brine, dried over magnesium sulphate, filtered and concentrated under reduced pressure, and purified by silica gel column chromatography (eluent, chloroform:methanol:aqueous ammonia=10:1:0.1) to obtain 2.2 g (yield 75%) of the target compound (Compound 6).

$^1$H-NMR (270 MHz, CDCl$_3$) δ: 1.64 (6H, s), 1.75-1.90 (2H, m), 2.60-2.80 (4H, m), 3.18-3.32 (2H, m), 4.00-4.18 (1H, m), 7.73 (1H, dd, J=1.7, 8.2 Hz), 7.84 (1H, s), 7.94 (1H, d, J=8.2 Hz).

MS(ESI)m/z: 397.1 ([M+H]⁺).

Rf value (an NH plate, eluent; chloroform:methanol=30:1): 0.52.

(Step 2)

[Formula 46]

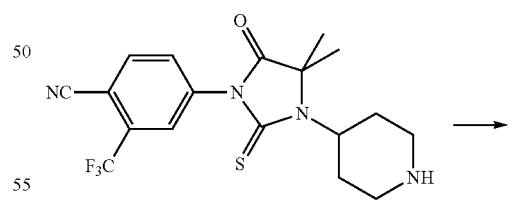

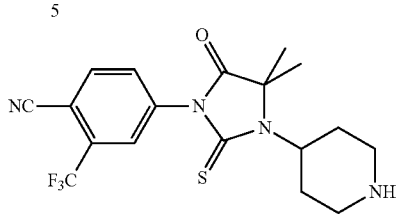

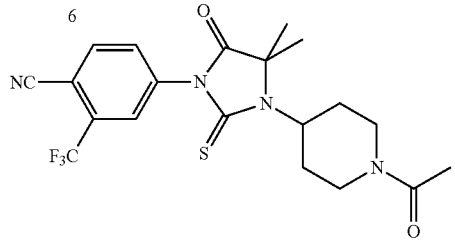

Compound 6 (36 mg) was dissolved in dichloromethane (1 mL) and added with acetyl chloride (0.0077 mL) and triethylamine (0.015 mL) under nitrogen atmosphere and the mixture was stirred for one hour. The reaction solution was concentrated under reduced pressure, and the obtained residual substance was add with ethyl acetate, washed with 10% citric acid aqueous solution, a saturated sodium hydrogen carbonate aqueous solution and brine, dried with anhydrous magnesium sulphate, filtered, concentrated under reduced pressure, and purified by thin layer chromatography (silica gel plate, eluent; chloroform:methanol=20:1) to obtain 30 mg (yield 76%) of the target compound (Compound 7).

Rf value (silica gel plate, eluent; chloroform:methanol=20:1): 0.32.

$^1$H-NMR (270 MHz, CDCl$_3$) δ: 1.64 (6H, s), 1.82-1.98 (2H, m), 2.14 (3H, s), 2.52-2.88 (3H, m), 3.09-3.21 (1H, m), 3.92-4.02 (1H, m), 4.08-4.25 (1H, m), 4.80-4.90 (1H, m), 7.72 (1H, dd, J=1.7, 8.1 Hz), 7.84 (1H, split s), 7.95 (1H, d, J=8.1 Hz).

MS(ESI)m/z: 439.1 ([M+H]$^+$).

The following compounds were synthesized by a method similar to that in Example 4.

TABLE 2

| Example No. | Structure | Data |
| --- | --- | --- |
| 5 | 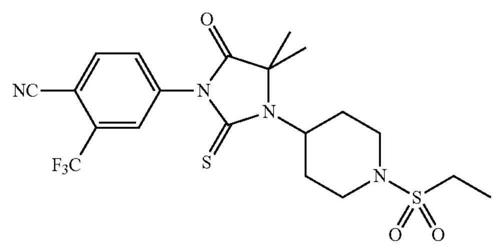 [SMILES: CCS(=O)(=O)N1CCC(N2C(=S)N(c3ccc(C#N)c(C(F)(F)F)c3)C(=O)C2(C)C)CC1] | Rf value (silica gel plate, eluent; hexane:ethyl acetate = 1:2): 0.3<br>MS(ESI) m/z: 489.0 ([M + H]$^+$) |
| 6 | 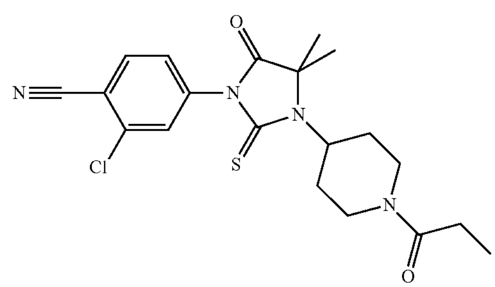 | MS(ESI) m/z: 405.1 ([M + H]$^+$)<br>RT: 4.79 min |
| 7 | 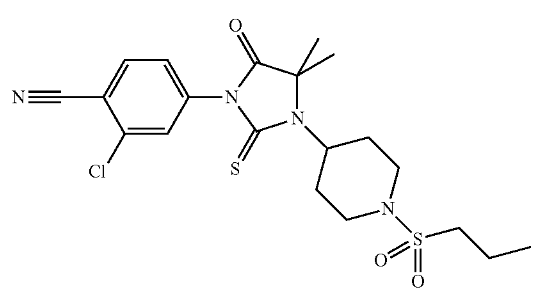 | MS(ESI) m/z: 419.1 ([M + H]$^+$)<br>RT: 5.19 min |
| 8 | 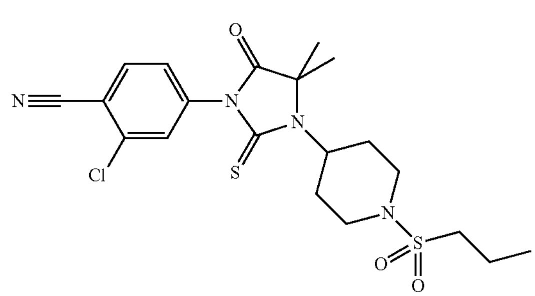 [SMILES: CCCS(=O)(=O)N1CCC(N2C(=S)N(c3ccc(C#N)c(Cl)c3)C(=O)C2(C)C)CC1] | MS(ESI) m/z: 469.2 ([M + H]$^+$)<br>RT: 6.00 min |

TABLE 2-continued

| Example No. | Structure | Data |
|---|---|---|
| 9 | (structure) | MS(ESI) m/z: 455.1 ([M + H]⁺) RT: 5.64 min |

The following compounds were synthesized from Compound 5 by a method similar to Step 1 of Example 23 and Example 4.

TABLE 3

| Example No. | Structure | Data |
|---|---|---|
| 10 | (structure) | MS(ESI) m/z: 487.1 ([M + H]⁺) RT: 5.52 min |
| 11 | (structure) | MS(ESI) m/z: 467.2 ([M + H]⁺) RT: 5.59 min |
| 12 | (structure) | MS(ESI) m/z: 417.2 ([M + H]⁺) RT: 4.72 min |

The following compounds were synthesized by a method similar to Step 2 of Example 4 from Compound 33.

TABLE 4

| Example No. | Structure | Data |
|---|---|---|
| 13 | 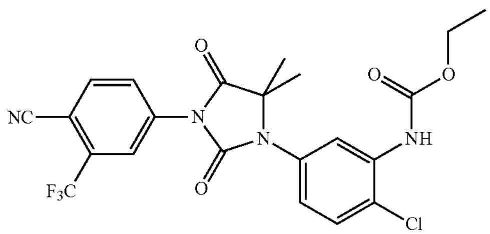 [SMILES: CCOC(=O)Nc1cc(N2C(=O)N(c3ccc(C#N)c(C(F)(F)F)c3)C(=O)C2(C)C)ccc1Cl] | mp: 155-157° C.<br>Rf value (silica gel plate, eluent; chloroform:methanol = 100:1): 0.35<br>$^1$H NMR (CDCl$_3$) δ: 1.35 (3H, t, J= 7 Hz), 1.61 (6H, s), 4.25 (2H, q, J = 7 Hz), 6.97 (1H, dd, J = 8, 2 Hz), 7.23 (1H, s), 7.47 (1H, d, J = 8 Hz), 7.94 (1H, d, J = 8 Hz), 8.03 (1H, d, J = 8 Hz), 8.18 (1H, s), 8.29 (1H, s)<br>MS(ESI) m/z: 495 ([M + H]$^+$) |

Example 14

[Formula 47]

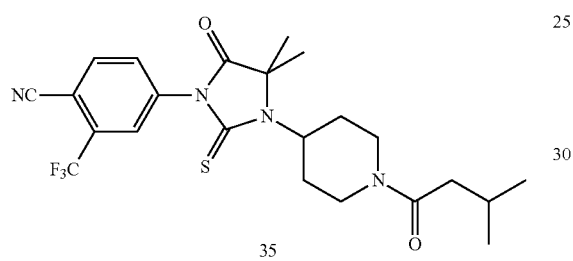

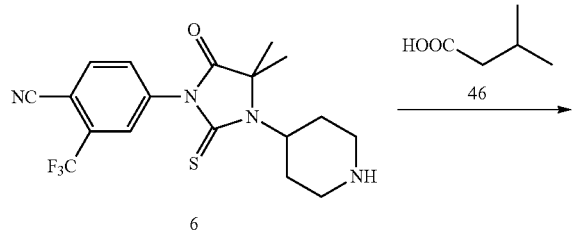

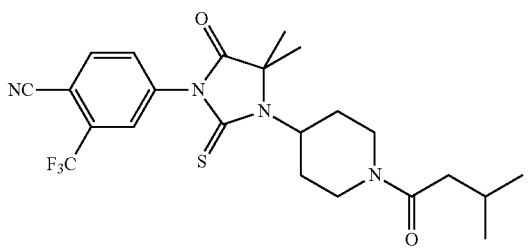

Compound 6 (20 mg) was dissolved in dimethylformamide (1 mL) and added with Compound 46 (0.0066 mL), 1-hydroxybenzotriazole monohydrate (9.3 mg) and 1-ethyl-3-(3-dimethylaminopropyl)carbodiimide hydrochloride (11.7 mg) at 0° C. and the mixture was stirred for 10 minutes at 0° C. and for four hours at room temperature. The reaction solution was added with 10% citric acid aqueous solution, and the mixture was extracted with chloroform, and the organic layer was washed with 10% citric acid aqueous solution, a saturated sodium hydrogen carbonate aqueous solution and brine, dried with sodium sulphate, filtered, concentrated under reduced pressure, and purified by thin layer chromatography (silica gel plate, eluent; chloroform:methanol=100:1) to obtain 4.6 mg (yield 19%) of the target compound (Compound 35).

$^1$H-NMR (270 MHz, CDCl$_3$) δ: 0.99 (6H, d, J=6.4 Hz), 1.63 (6H, s), 1.80-1.95 (2H, m), 2.07-2.28 (3H, m), 2.50-2.85 (3H, m), 3.03-3.15 (1H, m), 3.99-4.25 (2H, m), 4.80-4.93 (1H, m), 7.71 (1H, split d, J=8.3 Hz), 7.83 (1H, split s), 7.95 (1H, d, J=8.3 Hz).

MS(ESI)m/z: 481.0 ([M+H]$^+$).

Example 15

[Formula 48]

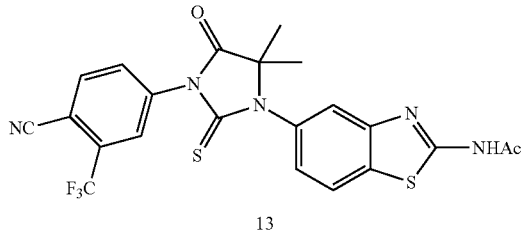

(Step 1)

[Formula 49]

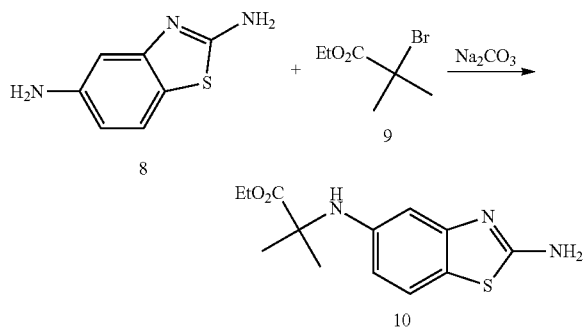

A mixture of Compound 8 (28.1 g), Compound 9 (76 mL) and sodium carbonate (54 g) in N,N-dimethylacetamide (200 mL) was heated to reflux under nitrogen atmosphere at 120° C. for 17 hours. It was cooled to room temperature, added with ethyl acetate and filtered and the solvent was concentrated under reduced pressure. Furthermore, it was added with water, extracted with ethyl acetate and dried with anhydrous magnesium sulphate. The residue obtained by concentrating under reduced pressure was purified by silica gel column chromatography (ethyl acetate: n-hexane=1:1-1:0) to obtain 47.5 g (yield 100%) of the target compound (Compound 10).

$^{1}$H-NMR (DMSO-d$_{6}$) δ: 7.30 (1H, d), 7.26 (1H, s), 6.81 (1H, d), 6.47 (1H, q), 5.22 (2H, s), 4.20-4.08 (2H, m), 1.59 (6H, s), 1.28-1.21 (3H, m).

(Step 2)

[Formula 50]

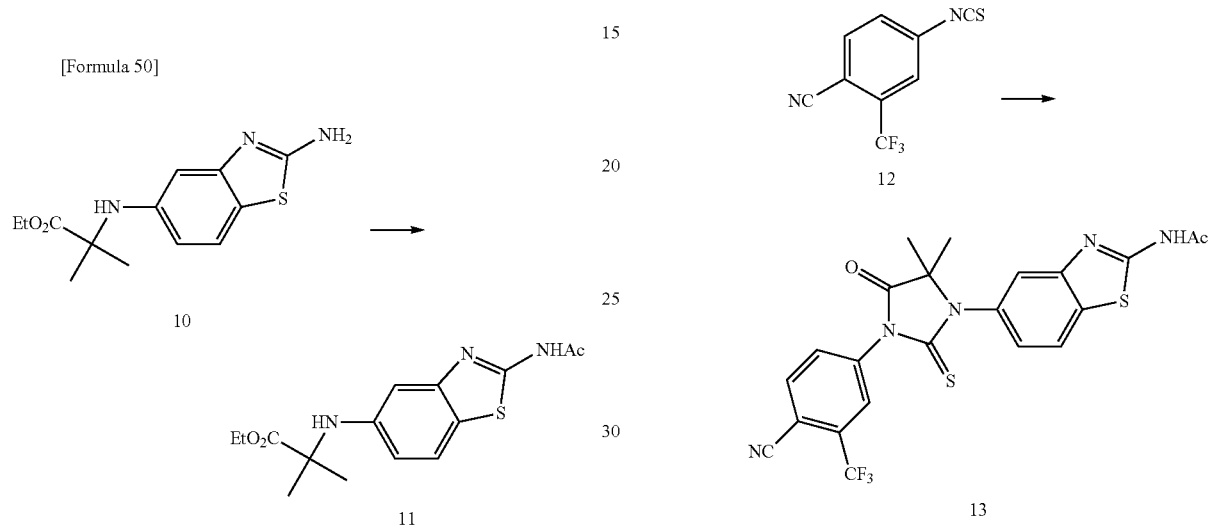

Compound 10 (45.7 g) and pyridine (27 g) were dissolved in dichloromethane (438 mL) under nitrogen atmosphere and the mixture was cooled to −10° C., slowly added with acetyl chloride (20.0 g) and the mixture was stirred at 0° C. for one hour. It was added with a saturated sodium hydrogen carbonate aqueous solution and the mixture was extracted with dichloromethane, washed with brine and concentrated under reduced pressure after drying with anhydrous magnesium sulphate. The obtained residue was recrystallized in diethyl ether to obtain 37 g (yield 68%) of the target compound (Compound 11).

$^{1}$H-NMR (DMSO-d$_{6}$) δ: 12.12 (1H, s), 7.56 (1H, d), 6.65 (1H, d), 6.59 (1H, q), 6.05 (1H, s), 4.16 (2H, q), 2.16 (3H, s), 1.47 (6H, s), 1.19 (3H, t).

(Step 3)

[Formula 51]

Compound 11 (29.97 g), Compound 12 (27.66 g) and dimethylaminopyridine (17.09 g) were dissolved in toluene (341 mL) under nitrogen atmosphere and the mixture was heated to reflux at 100° C. for 12 hours. It was cooled to room temperature, added with ethyl acetate and washed with 10% citric acid aqueous solution. The organic layer was washed with a saturated sodium hydrogen carbonate aqueous solution and brine and concentrated under reduced pressure after drying with anhydrous magnesium sulphate. The obtained residue was recrystallized using ethyl acetate-diethylether to obtain 32.74 g (yield 70%) of the target compound (Compound 13).

$^{1}$H-NMR (DMSO-d$_{6}$) δ: 12.48 (1H, s), 8.39 (1H, d), 8.31 (1H, d), 8.16-8.06 (2H, m), 7.30 (1H, q), 2.23 (3H, s), 1.60 (6H, s).

The following compounds were synthesized by a method similar to that in Example 15.

TABLE 5

| Example No. | Structure | Data |
|---|---|---|
| 16 | 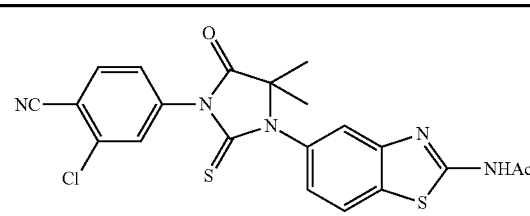 | MS(ESI) m/z: 469.9 ([M + H]$^{+}$) RT: 5.60 min |

TABLE 5-continued

| Example No. | Structure | Data |
|---|---|---|
| 17 | 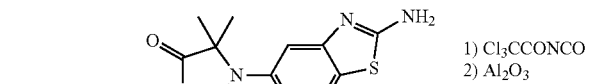 | MS(ESI) m/z: 465.9 ([M + H]+) RT: 5.27 min |

Example 18

[Formula 52]

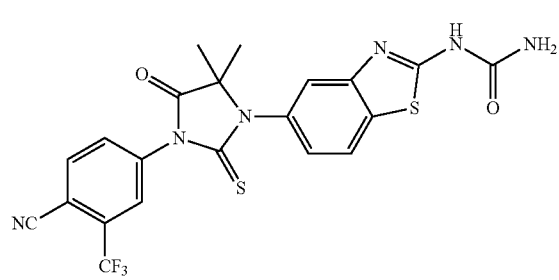

(Step 1)

[Formula 53]

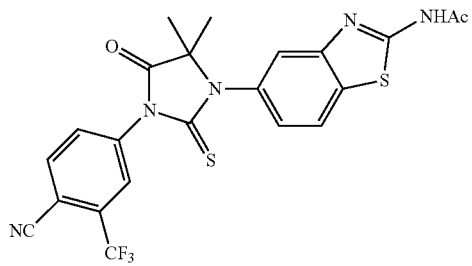
13

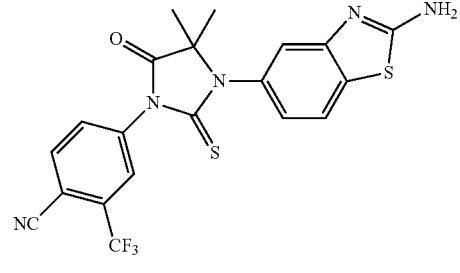
14

Compound 13 (38.85 g) was dissolved in dioxane (777 mL), and added with conc.HCl (233.1 mL) and the mixture was heated to reflux at 100° C. for two hours. After cooled to room temperature, it was added with water and then 2 N aqueous sodium hydroxide aqueous solution to adjust the pH to 10 and the mixture was extracted with ethyl acetate and concentrated under reduced pressure after drying with anhydrous magnesium sulphate. The obtained residue was recrystallized using ethyl acetate-diethylether to obtain 29.29 g (yield 82%) of the target compound (Compound 14).

$^1$H-NMR (DMSO-d$_6$) δ: 8.39 (1H, d), 8.31 (1H, d), 8.10 (1H, q), 7.81 (1H, d), 7.68 (2H, s), 7.30 (1H, d), 6.99 (1H, q), 1.53 (6H, s).
MS(ESI)m/z: 462.1 ([M+H]+).
(Step 2)

[Formula 54]

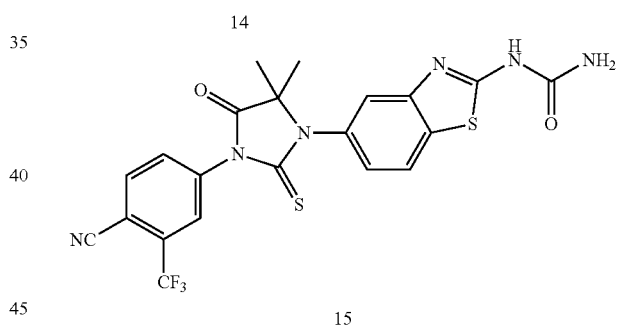

Compound 14 (29.26 g) was dissolved in a mixed solvent of acetonitrile (308 mL) and toluene (920 mL) and cooled to 0° C. and added with trichloroacetyl isocyanate (15.74 mL) and the mixture was stirred under nitrogen, atmosphere at room temperature for 30 minutes. It was concentrated under reduced pressure and added with Al$_2$O$_3$ (977 g) and ethyl acetate (500 mL) and the mixture was stirred at 40° C. for two hours. Furthermore, a mixture (100 mL) of chloroform:methanol=1:5 was added and the mixture was stirred at 40° C. for two hours. The reaction mixture was celite filtered and washed with 4 L of methanol, and the residual substance obtained by evaporating the solvent under reduced pressure was purified by silica gel column chromatography (eluent, ethyl acetate: n-hexane, 1:3-1:0) and was recrystallized with ethyl acetate-diethylether to obtain 24.73 g (yield 77%) of the target compound (Compound 15).

$^1$H-NMR (DMSO-d$_6$) δ: 10.87 (1H, s), 8.40 (1H, d), 8.32 (1H, s), 8.12-8.03 (2H, m), 7.62 (1H, d), 7.19 (1H, q), 6.73 (2H, brs), 1.55 (6H, s).
MS(ESI)m/z: 505.1 ([M+H]+).

The following compounds were synthesized by the method similar to that in Example 18.

TABLE 6

| Example No. | Structure | Data |
|---|---|---|
| 19 | 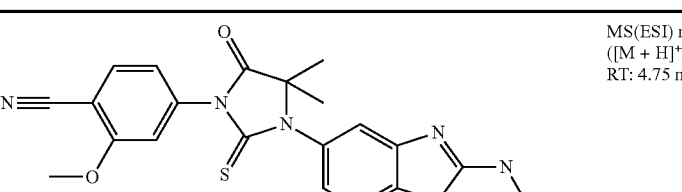 | MS(ESI) m/z: 467.0 ([M + H]⁺) RT: 4.75 min |
| 20 | 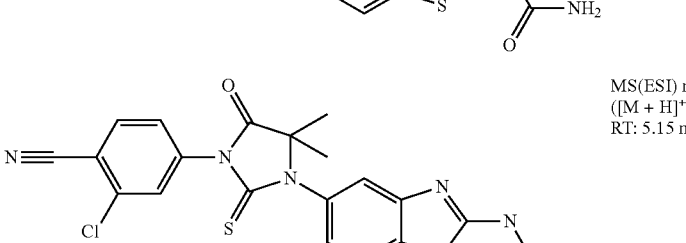 | MS(ESI) m/z: 471.0 ([M + H]⁺) RT: 5.15 min |

Example 21 (Step 1)

[Formula 55]

[Formula 57]

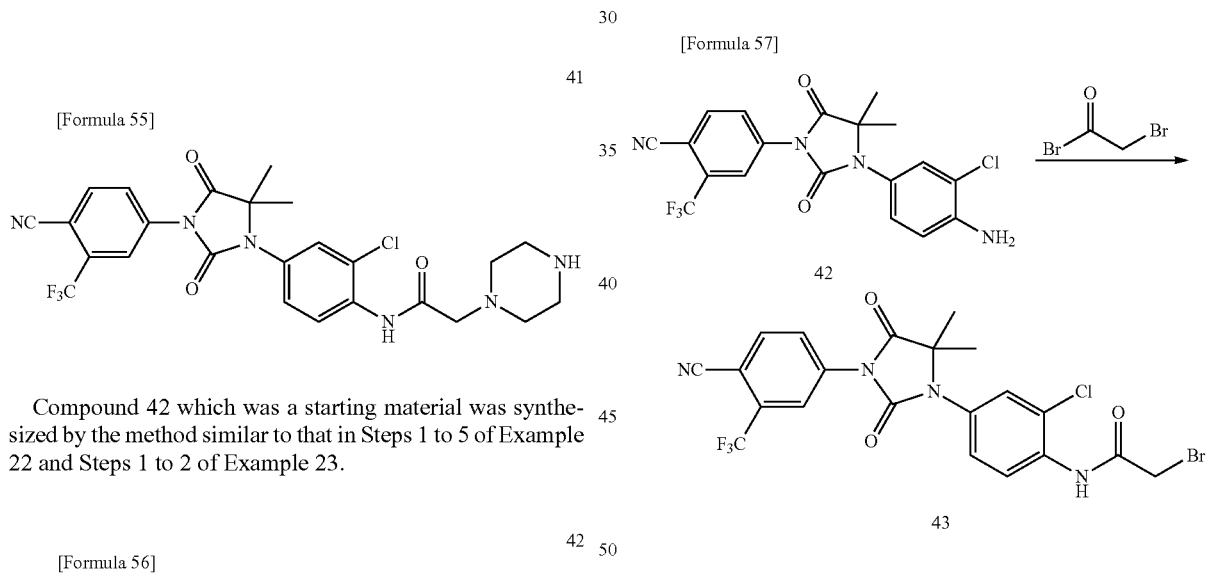

Compound 42 which was a starting material was synthesized by the method similar to that in Steps 1 to 5 of Example 22 and Steps 1 to 2 of Example 23.

[Formula 56]

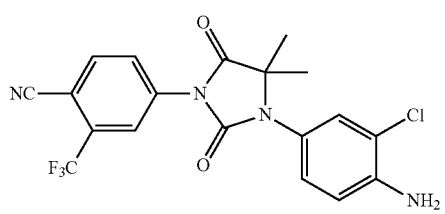

Rf value (silica gel plate, eluent; hexane:ethyl acetate=2:1): 0.22.

$^1$H-NMR (400 MHz, CDCl$_3$) δ: 1.54 (6H, s), 4.27 (2H, br), 6.83 (1H, d, J=8.4 Hz), 6.99 (1H, dd, J=2.2, 8.4 Hz), 7.19 (1H, d, J=2.2 Hz), 7.94 (1H, d, J=8.4 Hz), 8.04 (1H, d, J=8.4 Hz), 8.19 (1H, s).

Compound 42 (400 mg) was dissolved in dichloromethane (5 mL) and added with bromoacetyl bromide (0.123 mL) and triethylamine (0.198 mL) under nitrogen atmosphere at 0° C. and the mixture was stirred at room temperature for one hour. The reaction solution was diluted with chloroform, washed with 10% citric acid aqueous solution and brine, dried with anhydrous magnesium sulphate, filtered, concentrated under reduced pressure, and purified by flash chromatography (eluent, hexane to hexane:ethyl acetate=1:1) to obtain 456 mg (yield 88%) of the target compound (Compound 43).

Rf value (silica gel plate, eluent; hexane:ethyl acetate=2:1): 0.24.

$^1$H-NMR (400 MHz, CDCl$_3$) δ: 1.59 (6H, s), 4.12 (2H, s), 7.27 (1H, dd, J=1.8, 8.8 Hz), 7.41 (1H, d, J=1.8 Hz), 7.95 (1H, d, J=8.4 Hz), 8.03 (1H, d, J=8.4 Hz), 8.17 (1H, s), 8.54 (1H, d, J=8.8 Hz), 8.90 (1H, s).

(Step 2)

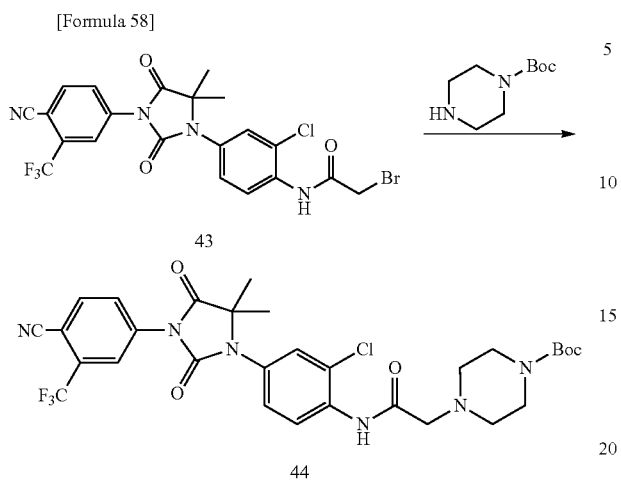

Compound 43 (150 mg) was dissolved in dichloromethane (3 mL) and added with 1-(t-butoxycarbonyl)piperazine (154 mg) and triethylamine (0.115 mL) at 0° C. and the mixture was stirred at room temperature for one hour. The reaction solution was diluted with chloroform, washed with a saturated sodium hydrogen carbonate aqueous solution and brine, dried with anhydrous magnesium sulphate, filtered, concentrated under reduced pressure, and purified by flash chromatography (eluent, hexane to hexane:ethyl acetate=2:3) to obtain 166 mg (yield 93%) of the target compound (Compound 44).

Rf value (silica gel plate, eluent; hexane:ethyl acetate=1:1): 0.28.

$^{1}$H-NMR (400 MHz, CDCl$_3$) δ: 1.48 (9H, s), 1.58 (6H, s), 2.63 (4H, br), 3.24 (2H, s), 3.55 (4H, br), 7.23 (1H, dd, J=2.2, 8.8 Hz), 7.38 (1H, d, J=2.2 Hz), 7.95 (1H, d, J=8.4 Hz), 8.03 (1H, d, J=8.1 Hz), 8.17 (1H, s), 8.65 (1H, d, J=8.8 Hz), 10.07 (1H, s).

(Step 3)

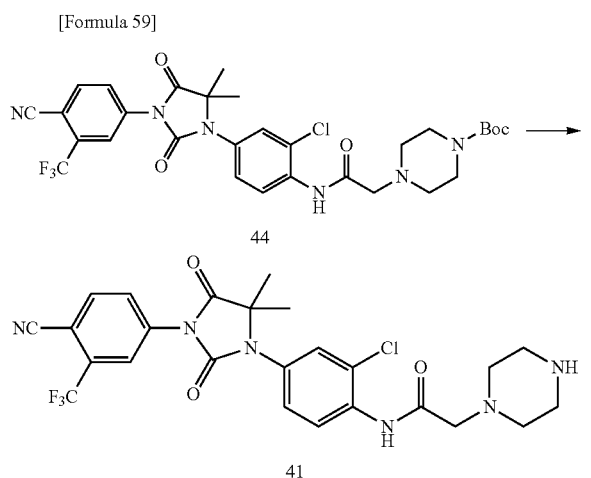

Compound 44 (166 mg) was dissolved in dichloromethane (3 mL) and added with trifluoroacetic acid (3 mL) and the mixture was stirred under nitrogen atmosphere at room temperature for one hour. The reaction solution was concentrated under reduced pressure, added with chloroform, washed with a saturated sodium hydrogen carbonate aqueous solution and brine, dried with anhydrous magnesium sulphate, filtered, concentrated under reduced pressure, and purified by thin layer chromatography (silica gel plate, eluent; chloroform:methanol: 1% aqueous ammonia=10:1:0.1) to obtain 32 mg of the target compound (Compound 41).

Rf value (silica gel plate, eluent; chloroform:methanol: 1% aqueous ammonia=10:1: 0.1): 0.31.

$^{1}$H-NMR (400 MHz, CDCl$_3$) δ: 1.58 (6H, s), 2.63 (4H, br), 2.96-3.04 (4H, m), 3.20 (2H, s), 7.24 (1H, dd, J=1.8, 8.8 Hz), 7.37 (1H, d, J=1.8 Hz), 7.95 (1H, d, J=8.4 Hz), 8.02 (1H, d, J=8.4 Hz), 8.18 (1H, s), 8.66 (1H, d, J=8.8 Hz), 10.19 (1H, s).

MS(ESI)m/z: 549.20 ([M+H]$^+$).

Example 22

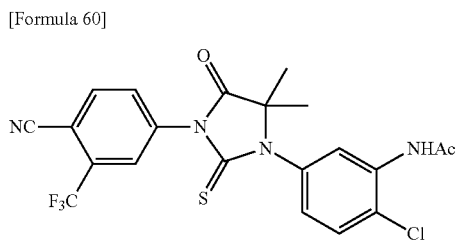

(Step 1)

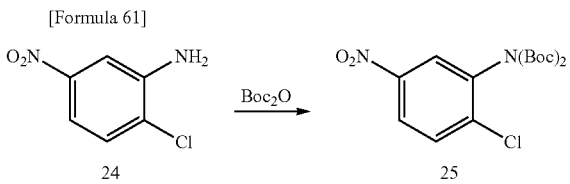

Compound 24 (34.5 g) was dissolved in dioxane (400 mL) and added with di-t-butyl dicarbonate (109 g) and dimethylaminopyridine (4.9 g) and was heated to reflux for 45 minutes. After standing to cool, the residual substance obtained by vacuum concentration was added with ethyl acetate and washed with 10% citric acid aqueous solution, a saturated sodium hydrogen carbonate aqueous solution and brine, dried with anhydrous magnesium sulphate, filtered, concentrated under reduced pressure and recrystallized from ethyl acetate-hexane to obtain 54.2 g (yield 73%) of the target compound (Compound 25).

$^{1}$H-NMR (300 MHz, CDCl$_3$) δ: 1.42 (18H, s), 7.62 (1H, d, J=8.5 Hz), 8.12-8.18 (2H, m).

(Step 2)

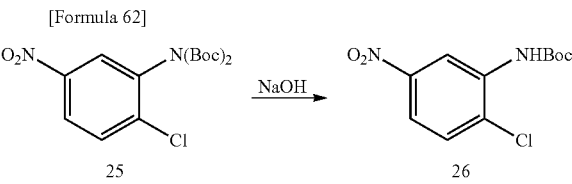

Compound 25 (54.2 g) was dissolved in a mixed solvent of tetrahydrofuran (240 mL) and methanol (480 mL), added with sodium hydroxide (5.82 g) and the mixture was stirred at room temperature for one hour. The reaction solution was concentrated under reduced pressure, added with ethyl acetate, washed with water and brine, dried with anhydrous magnesium sulphate, filtered, concentrated under reduced pressure, and recrystallized from ethyl acetate-hexane to obtain 54.2 g (yield 75%) of the target compound (Compound 26).

$^{1}$H-NMR (300 MHz, CDCl$_3$) δ: 1.55 (9H, s), 7.12 (1H, brs), 7.49 (1H, d, J=8.8 Hz), 7.82 (1H, dd, J=2.7, 8.8 Hz), 9.12 (1H, d, J=2.7 Hz).

(Step 3)

[Formula 63]

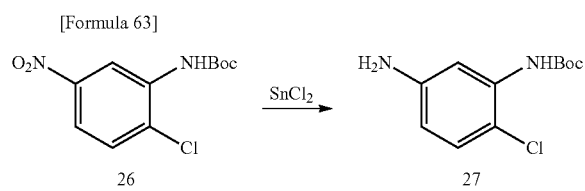

Compound 26 (29.6 g) was dissolved in ethanol (1,100 mL) and added with tin (II) chloride (103 g) and the mixture was heated to reflux for one hour. After standing to cool, it was added with iced water, adjusted to about pH 8 with 1 N aqueous sodium hydroxide and a saturated sodium hydrogen carbonate aqueous solution, and cerite filtered and the insoluble matters were washed with ethyl acetate. The aqueous layer was extracted with ethyl acetate, and the organic layer was washed with brine, dried with anhydrous magnesium sulphate, filtered, concentrated under reduced pressure, and purified by silica gel column chromatography (hexane:ethyl acetate=2:1) to obtain 21.7 g (yield 82%) of the target compound (Compound 27).

$^{1}$H-NMR (300 MHz, CDCl$_3$) δ: 1.52 (9H, s), 2.60-3.60 (2H, br), 6.28 (1H, dd, J=2.7, 8.5 Hz), 6.95 (1H, brs), 7.06 (1H, d, J=8.5 Hz), 7.59 (1H, d, J=2.7 Hz).

(Step 4)

[Formula 64]

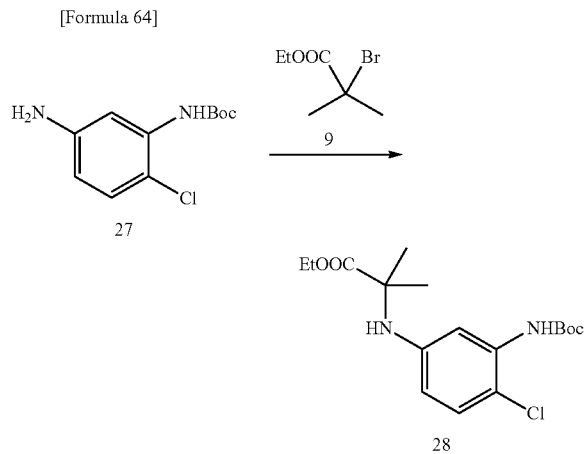

Compound 27 (21.7 g) was dissolved in ethanol (15 mL), and added with sodium carbonate (28 g) and Compound 9 (40 mL), and the mixture was heated to reflux for three days. After standing to cool, it was celite filtered, and the filtrate was concentrated under reduced pressure and purified by silica gel column chromatography (hexane:ethyl acetate=9:1-7:3) to obtain 10.0 g (yield 31%) of the target compound (Compound 28).

$^{1}$H-NMR (300 MHz, CDCl$_3$) δ: 1.21 (3H, t, J=7.1 Hz), 1.51 (9H, s), 1.54 (6H, s), 4.17 (2H, q, J=7.1 Hz), 6.14 (1H, dd, J=2.7, 8.8 Hz), 6.91 (1H, brs), 7.04 (1H, d, J=8.8 Hz), 7.53 (1H, d, J=2.7 Hz).

(Step 5)

[Formula 65]

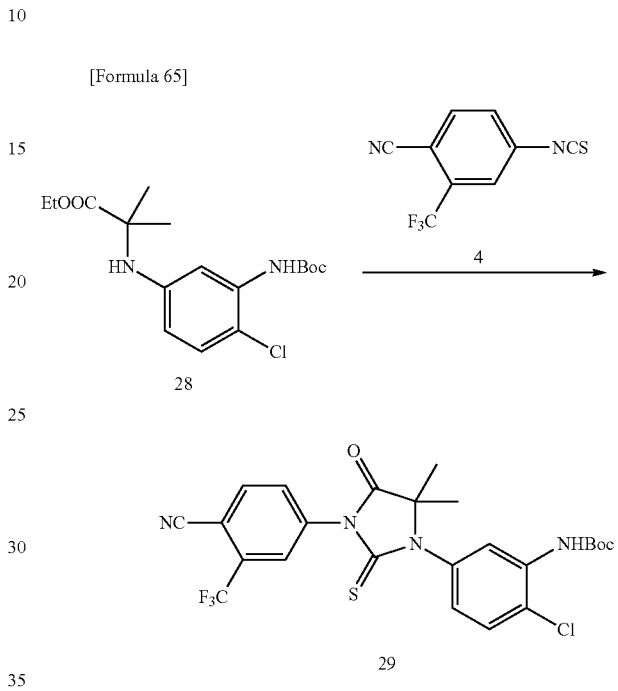

Compound 28 (10.0 g) was dissolved in 1,2-dichloroethane (150 mL) and added with Compound 4 (6.4 g) and dimethylaminopyridine (5.31 g) and the mixture was stirred at 100° C. for 15 hours. After standing to cool, it was concentrated under reduced pressure and added with water and the mixture was extracted with ethyl acetate. The organic layer was washed with brine, dried with anhydrous magnesium sulphate, filtered, concentrated under reduced pressure, and purified by silica gel column chromatography (hexane:ethyl acetate=9:1) to obtain 5.84 g (yield 39%) of the target compound (Compound 29).

$^{1}$H-NMR (300 MHz, CDCl$_3$) δ: 1.52 (9H, s), 1.61 (6H, 6.91 (1H, dd, J=2.5, 8.5 Hz), 7.01 (1H, brs), 7.48 (1H, d, J=8.5 Hz), 7.81 (1H, dd, J=2.5, 8.2 Hz), 7.94-7.98 (2H, m), 8.25 (1H, d, J=2.5 Hz).

(Step 6)

[Formula 66]

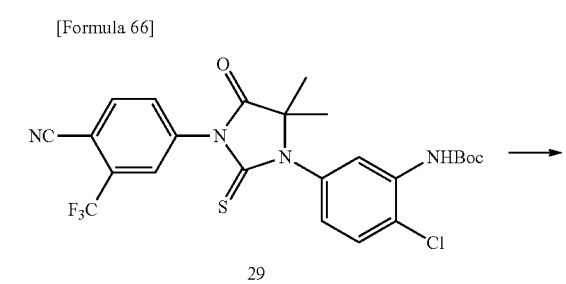

-continued

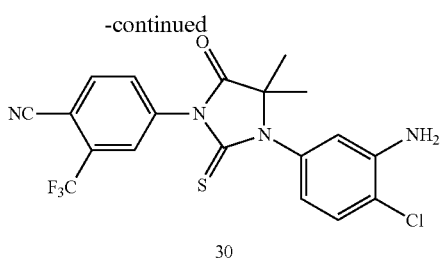

30

5.84 g of Compound 29 was dissolved in dichloromethane (50 mL) and added dropwise with trifluoroacetic acid (25 mL) at 0° C. for 15 minutes, and then stirred at room temperature for 30 minutes. The reaction solution was added with ethyl acetate, washed with water, a saturated sodium hydrogen carbonate aqueous solution and brine, and the organic layer was dried with anhydrous magnesium sulphate, filtered, concentrated under reduced pressure, and purified by silica gel column chromatography (hexane:ethyl acetate=4:1) to obtain 4.68 g (yield 99%) of the target compound (Compound 30).

$^1$H-NMR (300 MHz, CDCl$_3$) δ: 1.58 (6H, s), 6.61 (1H, dd, J=2.2, 8.2 Hz), 6.67 (1H, d, J=2.2 Hz), 7.39 (1H, d, J=8.2 Hz), 7.81 (1H, dd, J=2.2, 8.2 Hz), 7.93-7.98 (2H, m).

(Step 7)

[Formula 67]

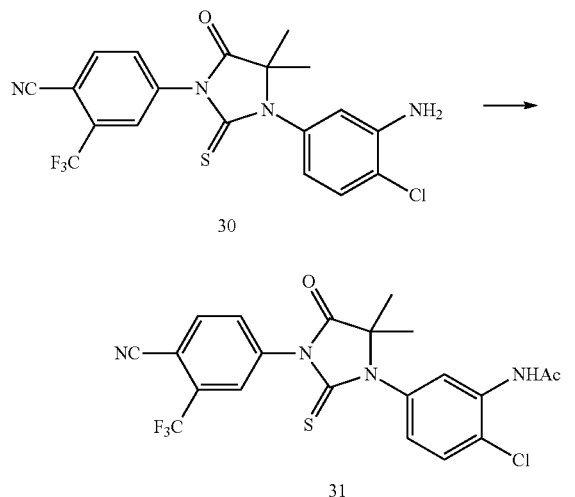

Compound 30 (2.5 g) was dissolved in dichloromethane (60 mL) and added dropwise with pyridine (1.4 mL) and acetyl chloride (0.81 mL) at 0° C. and the mixture was stirred for one hour. It was added with water and the mixture was extracted with dichloromethane. The organic layer was washed with 10% citric acid aqueous solution and brine, dried with anhydrous magnesium sulphate, filtered, concentrated under reduced pressure, and purified by silica gel column chromatography (hexane:ethyl acetate=7:3) to obtain 2.5 g (yield 91%) of the target compound (Compound 31).

Rf value (silica gel plate, eluent; hexane:ethyl acetate=2:1):0.1

$^1$H-NMR (270 MHz, CDCl$_3$) δ: 1.62 (6H, s), 2.28 (3H, s), 7.02 (1H, dd, J=2.5, 8.5 Hz), 7.54 (1H, d, J=8.5 Hz), 7.71 (1H, brs), 7.83 (1H, dd, J=1.9, 8.3 Hz), 7.96-8.00 (2H, m), 8.49 (1H, d, J=1.9 Hz).

MS(ESI$^-$)m/z: 479([M–H]$^-$).

Example 23

34

[Formula 68]

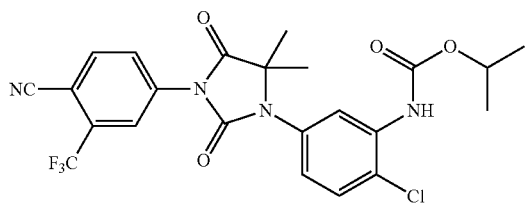

(Step 1)

[Formula 69]

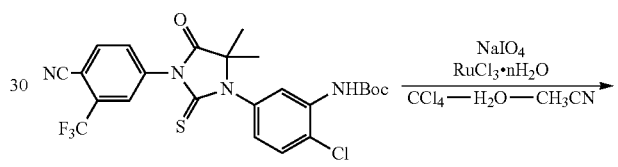

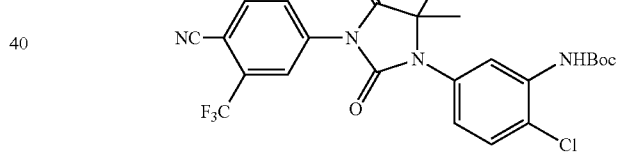

32

Compound 29 (3.3 g) was dissolved in a mixed solvent of carbon tetrachloride (60 mL) and acetonitrile (60 mL), added with water (120 mL) and added with sodium metaperiodate (5.2 g) and ruthenium chloride n-hydrate (63.5 mg) while stirring at 0° C. and the mixture was then stirred at 0° C. for 1 hour and 45 minutes. The reaction solution was added with a saturated sodium hydrogen carbonate aqueous solution and the mixture was extracted with chloroform, and the organic layer was washed with brine, dried with sodium sulphate, filtered, concentrated under reduced pressure, and purified by silica gel column chromatography (eluent, chloroform) to obtain 2.76 g (yield 86%) of the target compound (Compound 32).

Rf value (silica gel plate, eluent; hexane:chloroform=1:9, three times development): 0.38.

$^1$H-NMR (400 MHz, CDCl$_3$) δ: 1.53 (9H, s), 1.61 (6H, s), 6.92 (1H, dd, J=2.6, 8.4 Hz), 7.10 (1H, s), 7.45 (1H, d, J=8.4 Hz), 7.95 (1H, d, J=8.8 Hz), 8.03 (1H, d, J=8.1 Hz), 8.18 (1H, s), 8.28 (1H, split s).

(Step 2)

[Formula 70]

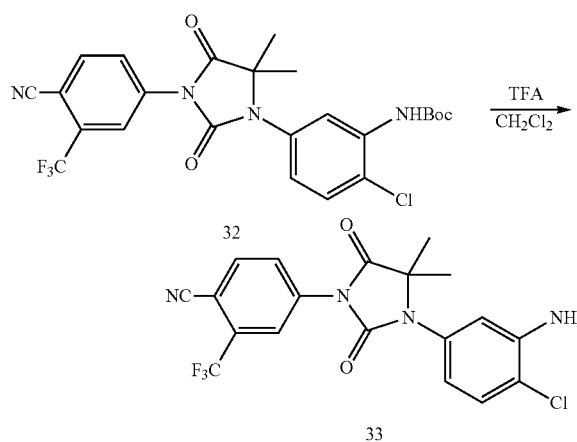

1.87 g (yield 84%) of the target compound (Compound 33) was obtained from Compound 32 (2.76 g) by the reaction similar to that in Step 6 of Example 22.

$^1$H-NMR (400 MHz, CDCl$_3$) δ: 4.22 (2H, s), 6.61 (1H, dd, J=2.2, 8.4 Hz), 6.69 (1H, d, J=2, 2 Hz), 7.35 (1H, d, J=8.4 Hz), 7.94 (1H, d, J=8.4 Hz), 8.03 (1H, d, J=8.4 Hz), 8.18 (1H, s).
MS(ESI)m/z: 423.1 ([M+H]$^+$).

(Step 3).

[Formula 71]

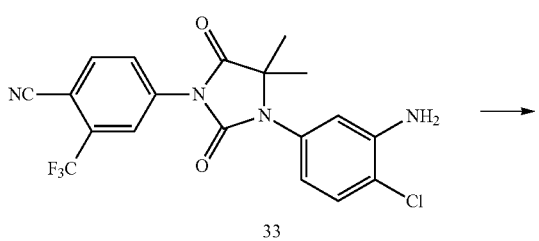

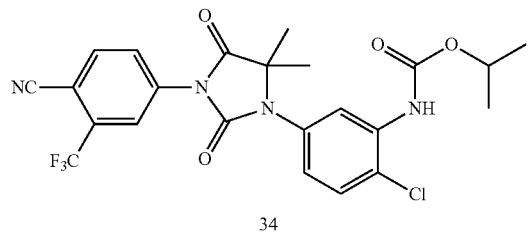

Compound 33 (40 mg) was dissolved in dioxane (1 mL) and added with triphosgene (20 mg), and the mixture was stirred for 30 minutes, and then added with isopropanol (0.2 mL). The reaction solution was cooled to 0° C. and added with triethylamine (0.086 mL) and the mixture was stirred at room temperature for two hours. It was added with a saturated sodium hydrogen carbonate aqueous solution, the mixture was extracted with chloroform, and the organic layer was dried, concentrated under reduced pressure, and purified by thin layer chromatography (silica gel plate, eluent; hexane: ethyl acetate=2:1) to obtain 40.5 mg (yield 83%) of the target compound (Compound 34).

Rf value (silica gel plate, eluent; hexane:ethyl acetate=2:1 or two times development): 0.41.

$^1$H-NMR (400 MHz, CDCl$_3$) δ: 1.33 (6H, d, J=6.2 Hz), 1.61 (6H, s), 5.00-5.06 (1H, m), 6.96 (1H, dd, J=2.2, 8.4 Hz), 7.18 (1H, s), 7.46 (1H, d, J=8.4 Hz), 7.95 (1H, d, J=8.4 Hz), 8.04 (1H, dd, J=1.8, 8.4 Hz), 8.18 (1H, s), 8.30 (1H, split s).
MS(ESI)m/z: 509.1 ([M+H]$^+$).

The following compounds were synthesized by a method similar to that in Example 23.

TABLE 7-1

| Example No. | Structure | Data |
|---|---|---|
| 24 | 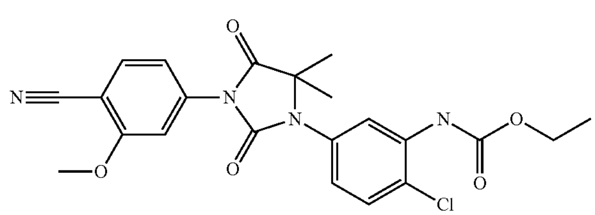 [SMILES: CCOC(=O)Nc1cc(N2C(=O)N(c3ccc(C#N)c(OC)c3)C(=O)C2(C)C)ccc1Cl] | $^1$H-NMR (400 MHz, CDCl$_3$) δ: 1.35 (3H, t), 1.60 (6H, s), 3.96 (3H, s), 4.26 (2H, q), 7.00 (1H, dd), 7.22-7.31 (3H, m), 7.46 (1H, d), 7.65 (1H, d), 8.29 (1H, s). RT: 5.97 min |
| 25 | 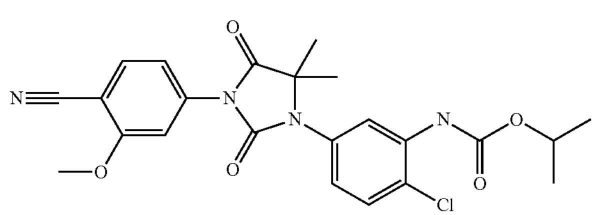 [SMILES: COc1cc(N2C(=O)N(c3ccc(Cl)c(NC(=O)OC(C)C)c3)C(C)(C)C2=O)ccc1C#N] | MS(ESI) m/z: 471.0 ([M + H]$^+$) RT: 6.47 min |

TABLE 7-1-continued

| Example No. | Structure | Data |
|---|---|---|
| 26 | 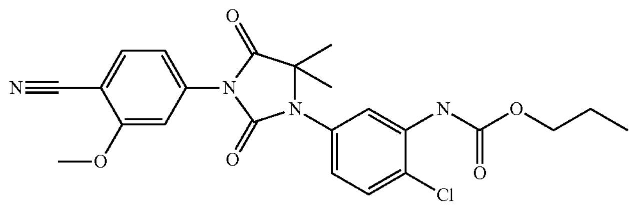 [SMILES: CCCOC(=O)Nc1cc(N2C(=O)N(c3ccc(C#N)c(OC)c3)C(=O)C2(C)C)ccc1Cl] | MS(ESI) m/z: 471.0 ([M + H]+)<br>RT: 6.50 min |
| 27 | 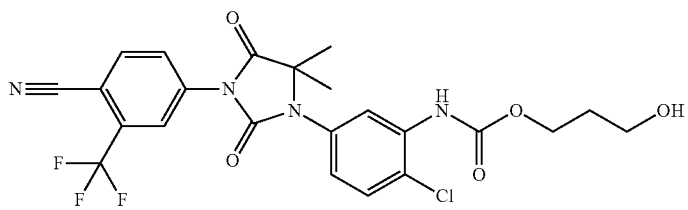 [SMILES: CC1(C)C(=O)N(c2ccc(C#N)c(C(F)(F)F)c2)C(=O)N1c1ccc(Cl)c(NC(=O)OCCCO)c1] | MS(ESI) m/z: 547.1 ([M + Na]+)<br>RT: 5.70 min |
| 28 | 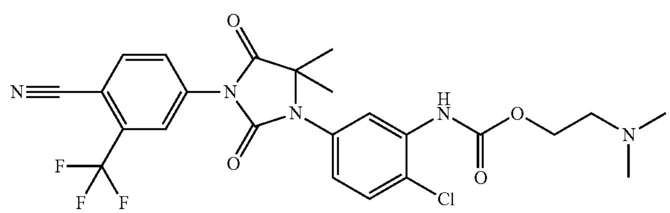 [SMILES: CN(C)CCOC(=O)Nc1cc(N2C(=O)N(c3ccc(C#N)c(C(F)(F)F)c3)C(=O)C2(C)C)ccc1Cl] | MS(ESI) m/z: 538.2 ([M + H]+)<br>RT: 4.70 min |
| 29 | 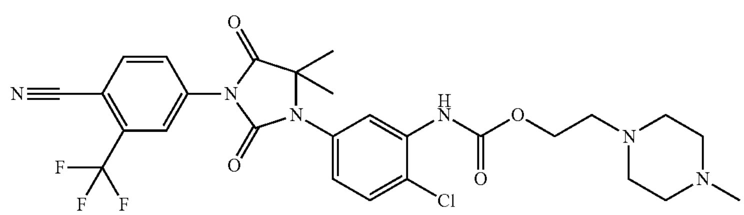 [SMILES: CN1CCN(CCOC(=O)Nc2cc(N3C(=O)N(c4ccc(C#N)c(C(F)(F)F)c4)C(=O)C3(C)C)ccc2Cl)CC1] | MS(ESI) m/z: 593.3 ([M + H]+)<br>RT: 4.45 min |
| 30 | 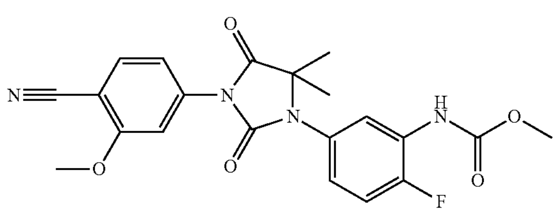 [SMILES: COC(=O)Nc1cc(N2C(=O)N(c3ccc(C#N)c(OC)c3)C(=O)C2(C)C)ccc1F] | MS(ESI) m/z: 427.1 ([M + H]+)<br>RT: 5.12 min |
| 31 | 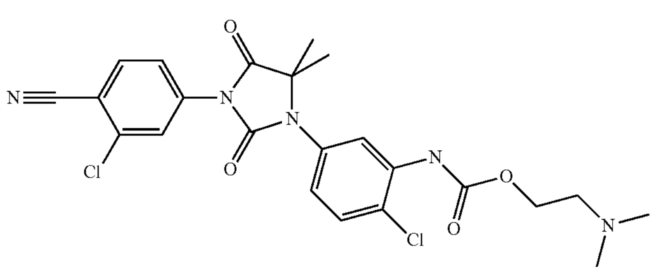 [SMILES: CN(C)CCOC(=O)Nc1cc(N2C(=O)N(c3ccc(C#N)c(Cl)c3)C(=O)C2(C)C)ccc1Cl] | MS(ESI) m/z: 504.2 ([M + H]+)<br>RT: 4.40 min |

TABLE 7-1-continued

| Example No. | Structure | Data |
|---|---|---|
| 32 | 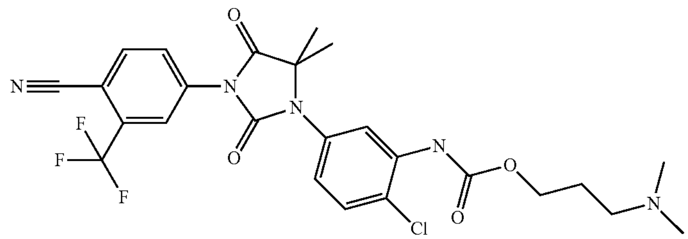 [SMILES: CN(C)CCCOC(=O)Nc1cc(N2C(=O)N(c3ccc(C#N)c(C(F)(F)F)c3)C(=O)C2(C)C)ccc1Cl] | MS(ESI) m/z: 552.2 ([M + H]+)<br>RT: 4.79 min |
| 33 | 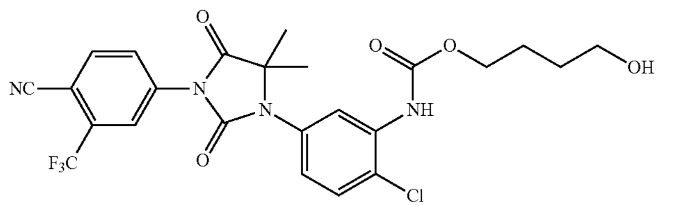 [SMILES: CC1(C)C(=O)N(c2ccc(C#N)c(C(F)(F)F)c2)C(=O)N1c1ccc(Cl)c(NC(=O)OCCCCO)c1] | MS(ESI) m/z: 561.1 ([M + Na]+)<br>RT: 5.82 min |

TABLE 7-2

| | | |
|---|---|---|
| 34 | | MS(ESI) m/z: 632.0 ([M + Na]+)<br>RT: 6.80 min |

The following compounds were synthesized from Compound 6 by the method similar to that in Step 3 of Example 23.

TABLE 8

| Example No. | Structure | Data |
|---|---|---|
| 35 | 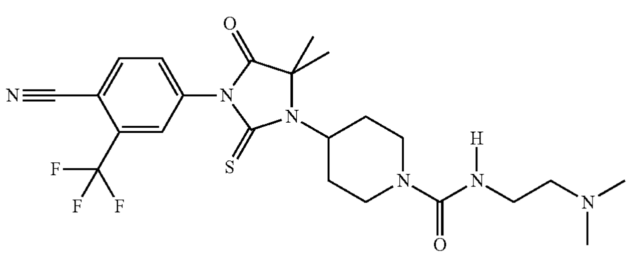 [SMILES: CN(C)CCNC(=O)N1CCC(N2C(=S)N(c3ccc(C#N)c(C(F)(F)F)c3)C(=O)C2(C)C)CC1] | MS(ESI) m/z: 511.2 ([M + H]+)<br>RT: 4.29 min |
| 36 | 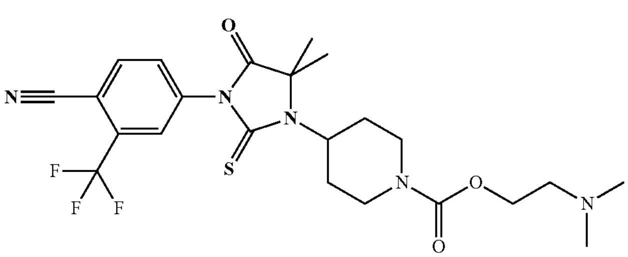 [SMILES: CN(C)CCOC(=O)N1CCC(N2C(=S)N(c3ccc(C#N)c(C(F)(F)F)c3)C(=O)C2(C)C)CC1] | MS(ESI) m/z: 512.2 ([M + H]+)<br>RT: 4.49 min |

Example 37

[Formula 72]

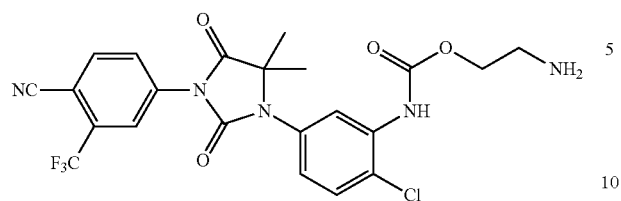

The target compound was obtained from the compound of Example 34 (65.1 mg) by the method similar to that in Step 6 of Example 22.

MS(ESI)m/z: 532.1 ([M+Na]$^+$).
RT: 4.57 min.

Example 38

[Formula 73]

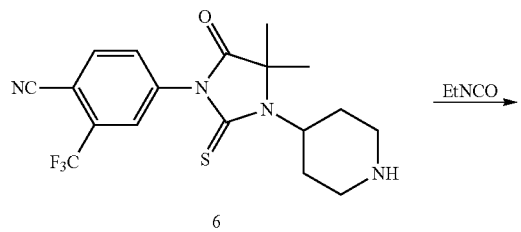

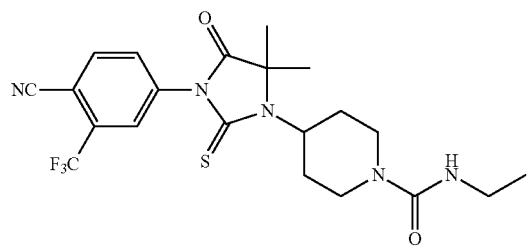

Compound 6 (50.0 mg) was dissolved in acetonitrile (1 mL) and added with ethyl isocyanate (0.0197 mL) and the mixture was stirred at room temperature for three hours. The reaction solution was concentrated under reduced pressure and purified by flash chromatography (eluent, dichloromethane to dichloromethane: methanol=9:1) to obtain 50.9 mg (yield 86%) of the target compound (Compound 45).

MS(ESI)m/z: 468.1 ([M+H]$^+$).
RT: 5.27 min.

The following compounds were synthesized by the method similar to that in Example 38.

TABLE 9

| Example No. | Structure | Data |
|---|---|---|
| 39 | 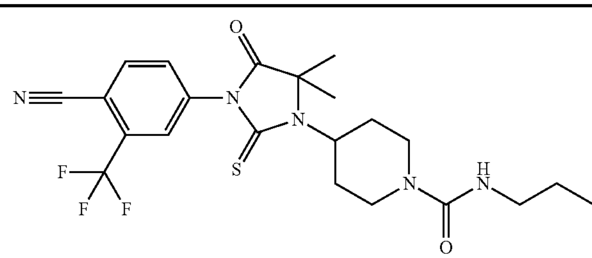 | MS(ESI) m/z: 482.0 ([M + H]$^+$) RT: 5.57 min |
| 40 | 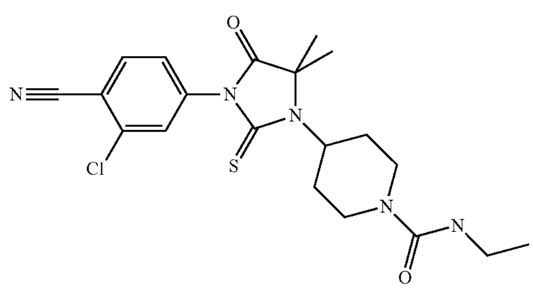 | MS(ESI) m/z: 434.0 ([M + H]$^+$) RT: 4.94 min |
| 41 | 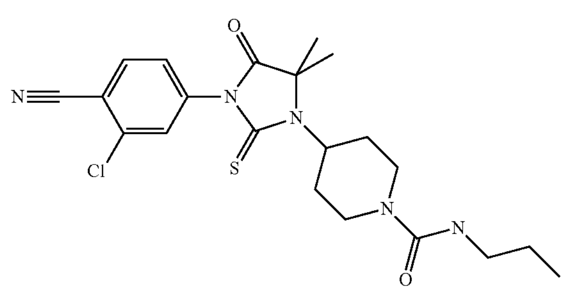 [SMILES: CCCNC(=O)N1CCC(N2C(=S)N(c3ccc(C#N)c(Cl)c3)C(=O)C2(C)C)CC1] | MS(ESI) m/z: 448.1 ([M + H]$^+$) RT: 5.27 min |

Example 42

[Formula 74]

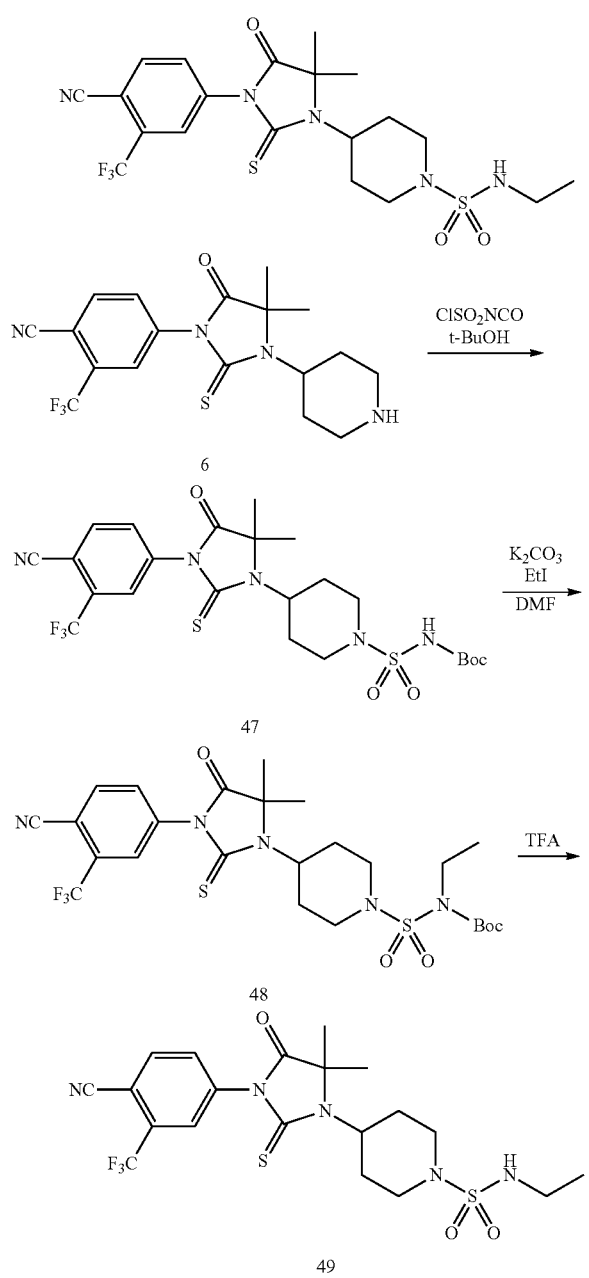

Chlorosulfonyl isocyanate (0.0326 mL) was dissolved in dichloromethane (1 mL) and added with t-butanol (0.0346 mL) and triethylamine (0.105 mL) at 0° C. and the mixture was stirred for 20 minutes. This was added with a solution in which Compound 6 (100 mg) was dissolved in dichloromethane (1 mL) and the mixture was stirred at room temperature for 15 minutes. The reaction solution was added with water and the mixture was extracted with chloroform. The organic layer was washed with brine, dried with anhydrous magnesium sulphate, filtered, concentrated under reduced pressure, and purified by flash column chromatography to obtain Compound 47 (94.0 mg, yield 65%).

Compound 47 (51.0 mg) was dissolved in dimethylformamide and added with potassium carbonate and ethyl iodide and the mixture was stirred at room temperature overnight. The reaction solution was added with water and the mixture was extracted with ethyl acetate. The organic layer was washed with brine, dried with anhydrous magnesium sulphate, filtered, concentrated under reduced pressure, and purified by flash column chromatography to obtain Compound 48 (42.3 mg, yield 79%). Compound 48 (42.3 mg) was dissolved in dichloromethane (1 mL) and added with trifluoroacetic acid (0.5 mL) and the mixture was stirred at room temperature for one hour. The reaction solution was concentrated under reduced pressure and purified by thin-layer chromatography (silica gel plate, eluent; dichloromethane:methanol=10:1) to obtain 30.8 mg (yield 87%) of the target compound (Compound 49).

$^1$H-NMR (270 MHz, CDCl$_3$) δ: 1.23 (3H, t, J=7.3 Hz), 1.65 (6H, s), 1.88-1.97 (2H, m), 2.79-2.95 (3H, m), 3.11-3.21 (2H, m), 3.83-4.03 (3H, m), 4.06-4.25 (1H, m), 7.72 (1H, split d, J=8.2 Hz), 7.84 (1H, split s), 7.95 (1H, d, J=8.2 Hz).

RT: 5.97 min.

Example 43

[Formula 75]

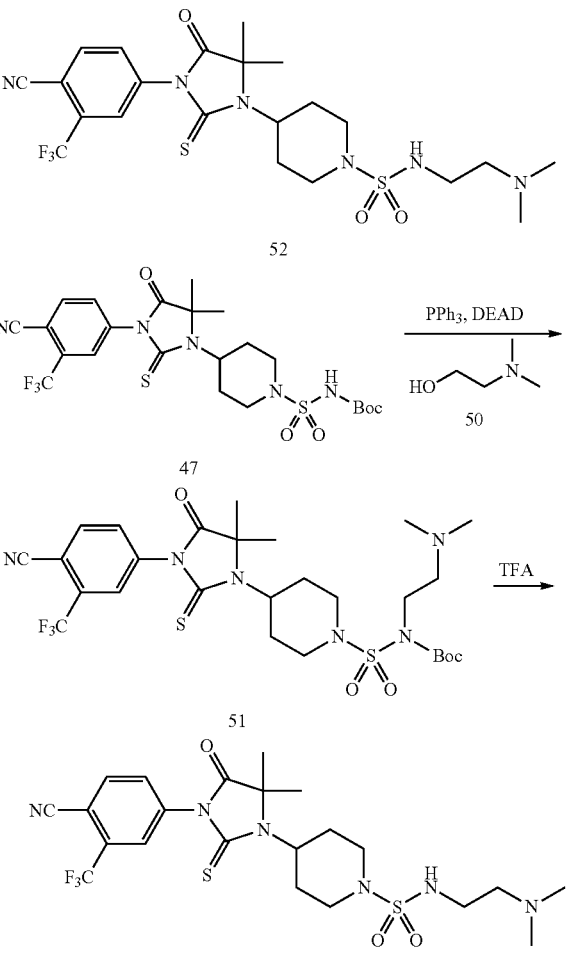

Compound 47 (40.0 mg) was dissolved in tetrahydrofuran (2 mL) and added with triphenylphosphine (27.2 mg), Compound 50 (0.0105 mL) and diethyl azo dicarboxylate (0.0472 mL) under nitrogen atmosphere at 0° C. and the mixture was stirred overnight. The reaction solution was added with water and the mixture was extracted with chloroform. The organic layer was washed with brine, dried with anhydrous magnesium sulphate, filtered, concentrated under reduced pressure, and purified by flash column chromatography to obtain Compound 51 (31.2 mg). This was dissolved in dichloromethane (1 mL) and added with trifluoroacetic acid (0.5 mL) and the mixture was stirred at room temperature for one hour. The reaction solution was concentrated under reduced pressure and added with a saturated sodium hydrogen carbonate aqueous solution at 0° C. and the mixture was extracted with dichloromethane. The organic layer was washed with brine, dried with anhydrous magnesium sulphate, filtered, concentrated under reduced pressure, and purified by thin layer chromatography (silica gel plate, eluent; dichloromethane: methanol=10:1) to obtain 7.0 mg (yield 18%) of the target compound (Compound 52).

MS(ESI)m/z: 547.1 ([M+H]$^+$).
RT: 4.55 min.

Example 44

[Formula 76]

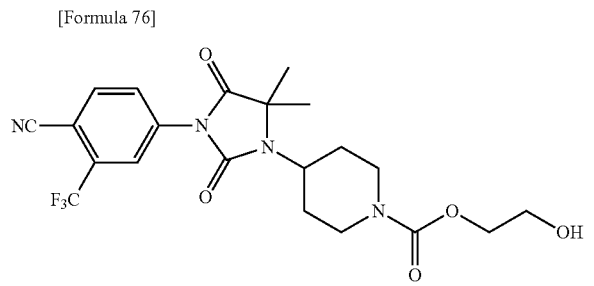

(Step 1)

[Formula 77]

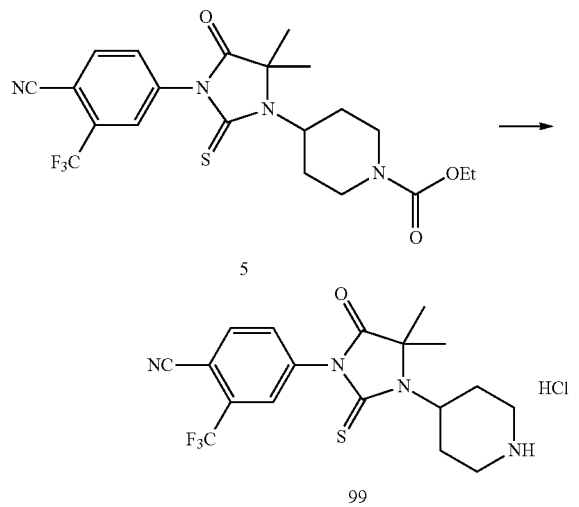

Compound 5 (6.9 g) was dissolved in dioxane (150 mL) and added with concentrated hydrochloric acid (150 mL) and the mixture was stirred at 100° C. overnight. The reaction solution was cooled to room temperature and added with 5 N NaOH to adjust the pH to about pH 10. The mixture was extracted with ethyl acetate, and the organic layer was washed with brine, dried with anhydrous magnesium sulphate, filtered, and concentrated under reduced pressure. The obtained residue was dissolved in ethyl acetate (150 mL) and added with 4 N HCl dioxane solution (5 mL) at 0° C. The precipitate was separated by filtration and vacuum-dried to obtain 5.8 g (yield 91%) of the target compound (Compound 99).

$^1$H-NMR (400 MHz, DMSO-d$_6$) δ: 1.58 (6H, s), 1.83-1.86 (2H, br m), 3.03-3.13 (4H, m), 3.36-3.39 (2H, br m), 3.47-3.49 (1H, m), 3.65-3.73 (1H, m), 4.16-4.19 (1H, br m), 7.99 (1H, dd, J=8.1, 1.5 Hz), 8.21 (1H, d, J=1.5 Hz), 8.36 (1H, d, J=8.1 Hz).

MS(ESI)m/z: 397.1 ([M+H]$^+$).

(Step 2)

[Formula 78]

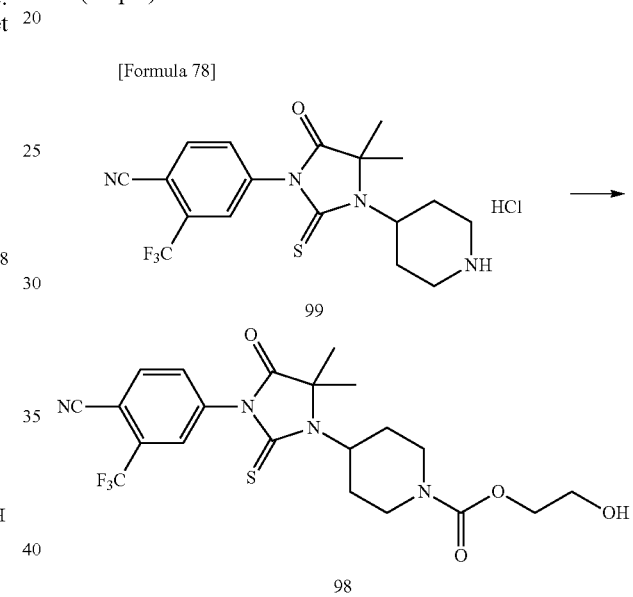

Compound 99 (100 mg) was suspended in dioxane (4 mL) and added with triphosgene (48 mg) under nitrogen atmosphere at 0° C. and the mixture was stirred at room temperature for 30 minutes. It was added with acetic acid 2-hydroxyethyl ester (72 mg), triethylamine (140 mg) and dimethylaminopyridine (28 mg) and the mixture was stirred for 30 minutes. The reaction solution was added with water and the mixture was extracted with chloroform. The organic layer was washed with a saturated sodium hydrogen carbonate aqueous solution, 1 N HCl and brine, dried, and concentrated under reduced pressure. The obtained residue was dissolved in tetrahydrofuran (2 mL) and added with 1 N NaOH (2 mL) and the mixture was stirred for one hour. The reaction solution was neutralized with 2 N HCl and the mixture was extracted with chloroform. The organic layer was washed with brine, dried and concentrated under reduced pressure, and purified by thin layer chromatography (eluent, chloroform:methanol=20:1) to obtain 67 mg (yield 60%) of the target compound (Compound 98).

$^1$H-NMR (400 MHz, CDCl$_3$) δ: 1.64 (6H, s), 1.86 (2H, d, J=11.4 Hz), 2.41 (1H, t, J=5.9 Hz), 2.74-2.87 (3H, br m), 3.86 (2H, dd, J=4.6, 2.3 Hz), 4.21-4.33 (5H, m), 7.73 (1H, d, J=8.3 Hz), 7.84 (1H, s), 7.96 (1H, d, J=8.3 Hz).

MS(ESI)m/z: 585.0 ([M+H]$^+$).

Example 45

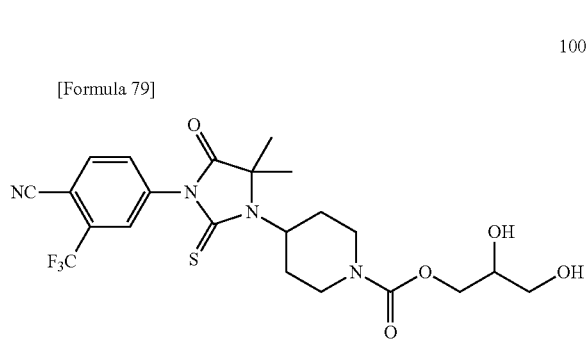 [SMILES: CC1(C)C(=O)N(c2ccc(C#N)c(C(F)(F)F)c2)C(=S)N1C1CCN(C(=O)OCC(O)CO)CC1]

(Step 1)

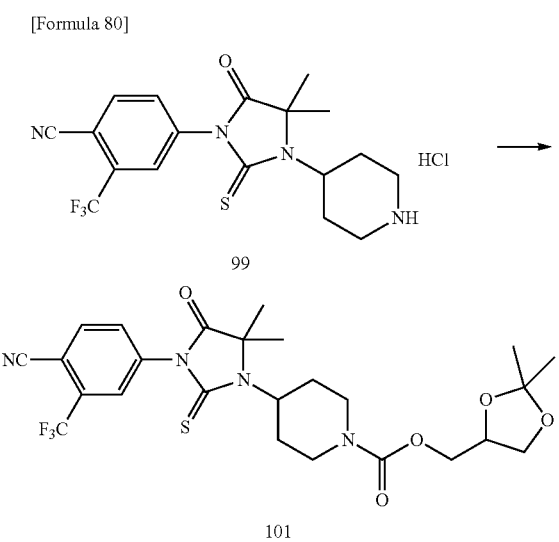

Compound 99 (150 mg) was suspended in dioxane (6 mL) and added with triphosgene (72 mg) under nitrogen atmosphere at 0° C. and the mixture was stirred at room temperature for 30 minutes. It was added with 2,2-dimethyl-1,3-dioxolan-4-ylmethanol (231 mg), triethylamine (212 mg) and dimethylaminopyridine (43 mg) and the mixture was stirred for 30 minutes. The reaction solution was added with water and the mixture was extracted with chloroform. The organic layer was washed with a saturated sodium hydrogen carbonate aqueous solution, 1 N HCl and brine, dried, concentrated under reduced pressure, and purified by flash column chromatography (eluent, hexane:ethyl acetate=1:0-1:3) to obtain 52 mg (yield 27%) of the target compound (Compound 101).

Rf value (silica gel plate, eluent; hexane:ethyl acetate=1:3): 0.33.

$^1$H-NMR (400 MHz, CDCl$_3$) δ: 1.37 (3H, s), 1.44 (3H, s), 1.64 (6H, s), 1.85 (2H, d, J=9.5 Hz), 2.73-2.85 (4H, m), 3.78 (1H, t, J=7.1 Hz), 4.07-4.20 (4H, m), 4.34-4.35 (3H, m), 7.73 (1H, d, J=8.3 Hz), 7.84 (1H, s), 7.95 (1H, d, J=8.3 Hz).

MS(ESI−)m/z: 613.2 ([M+AcONH$_4$]$^−$)

(Step 2)

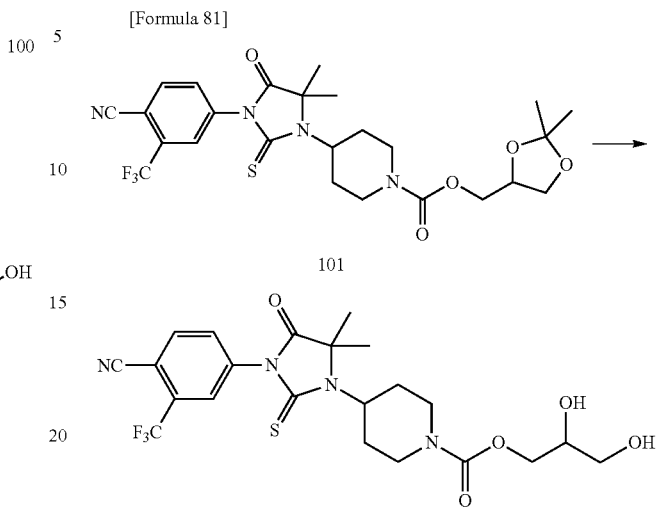

Compound 101 (52 mg) was dissolved in tetrahydrofuran (2.5 mL) and added with 6 N HCl (2.5 mL) and the mixture was stirred at a under nitrogen atmosphere at room temperature for one hour. It was neutralized with 2 N NaOH and the mixture was extracted with ethyl acetate. The organic layer was dried with anhydrous magnesium sulphate, filtered, concentrated under reduced pressure, and purified by thin layer chromatography (eluent, chloroform:methanol=15:1) to obtain 32 mg (yield 66%) of the target compound (Compound 100). Rf value (silica gel plate, eluent; chloroform:methanol=15:1): 0.41.

$^1$H-NMR (400 MHz, CDCl$_3$) δ: 1.64 (6H, s), 1.86 (2H, d, J=9.5 Hz), 2.32 (1H, s), 2.81-2.95 (5H, br m), 3.59-3.71 (2H, m), 3.91-3.92 (1H, m), 4.18-4.32 (5H, br m), 7.72 (1H, d, J=8.3 Hz), 7.84 (1H, s), 7.96 (1H, d, J=8.3 Hz).

MS(ESI)m/z: 515.1 ([M+H]$^+$).

Example 46

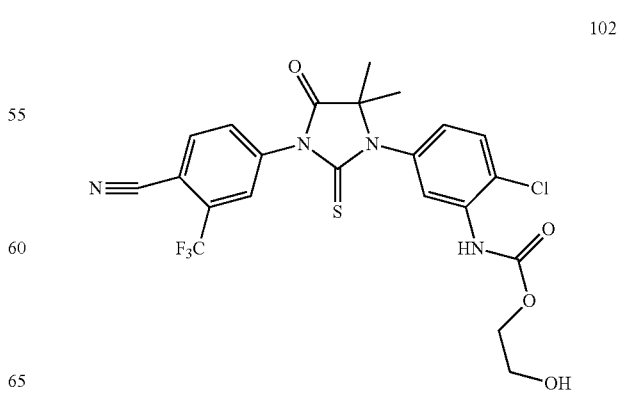

(Step 1)

[Formula 83]

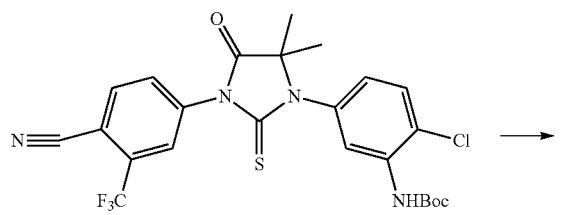
29

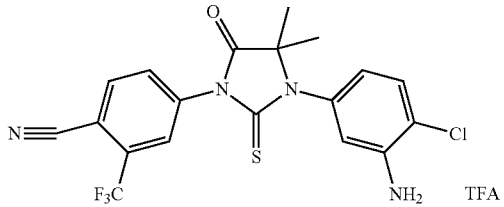
103

Compound 29 (277 mg) was dissolved in dichloromethane (1 mL) and added with trifluoroacetic acid (0.5 mL) and the mixture was stirred at room temperature for 1.5 hours. Furthermore, it was added with trifluoroacetic acid (0.5 mL) and the mixture was stirred at room temperature for 1.5 hours. The reaction solution was concentrated under reduced pressure to obtain 236 mg (yield 88%) of the target compound (Compound 103).

$^1$H-NMR (400 MHz, CDCl$_3$) δ: 1.59 (6H, s), 6.61 (1H, d, J=8.4 Hz), 6.68 (1H, s), 7.40 (1H, d, J=8.4 Hz), 7.83 (1H, d, J=8.3 Hz), 7.95 (1H, s), 7.98 (1H, d, J=8.3 Hz).

MS(ESI)m/z: 439.1 ([M+H]$^+$).

(Step 2).

[Formula 84]

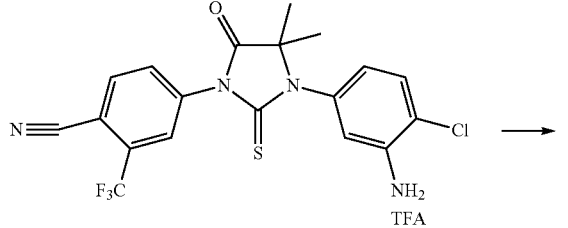
103

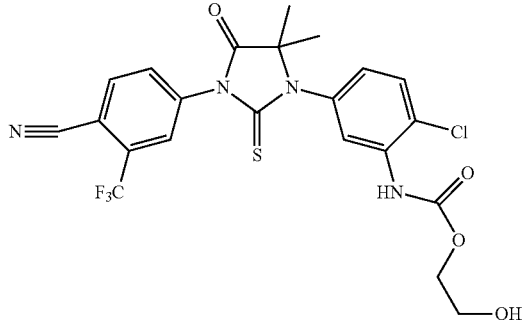
102

Compound 103 (97 mg) was suspended in dioxane (0.23 mL) and added with triphosgene (80 mg) at 0° C. and the mixture was stirred at room temperature for 10 minutes. The reaction solution was cooled to 0° C. again and added with acetic acid 2-hydroxyethyl ester (0.15 mL), triethylamine (0.08 mL) and the mixture was stirred at 0° C. for 10 minutes and at room temperature for 30 minutes. The reaction solution was added with water and adjusted to pH 8-10 with a saturated sodium hydrogen carbonate aqueous solution, and the mixture was extracted with ethyl acetate. The organic layer was dried with sodium sulfate, filtered, and concentrated under reduced pressure. The obtained residue was dissolved in tetrahydrofuran (1 mL) and added with 1 N NaOH (2 mL) and the mixture was stirred at 0° C. to room temperature for one hour. The reaction solution was adjusted to about pH 4 by adding hydrochloric acid, extracted with ethyl acetate, and the organic layer was dried with sodium sulphate, filtered, and concentrated under reduced pressure. The obtained residue was purified by flash column chromatography (eluent, hexane:ethyl acetate=1:0-2:3) to obtain 61.2 mg (yield 62%) of the target compound (Compound 102).

Rf value (silica gel plate, eluent; hexane:ethyl acetate=1:1): 0.31.

MS(ESI)m/z: 527.0 ([M+H]$^+$).

$^1$H-NMR (300 MHz, CDCl$_3$) δ: 1.62 (6H, s), 3.90-3.92 (2H, m), 4.33-4.36 (2H, m), 6.97 (1H, dd, J=8.5, 2.5 Hz), 7.34 (1H, s), 7.52 (1H, d, J=8.5 Hz), 7.82 (1H, dd, J=8.3, 2.0 Hz), 7.94 (1H, d, J=2.0 Hz), 7.97 (1H, d, J=8.3 Hz), 8.23 (1H, d, J=2.5 Hz).

Example 47

[Formula 85]

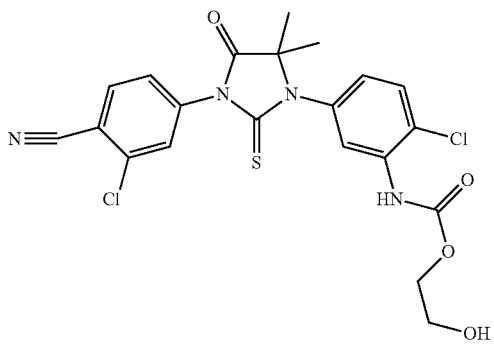
104

Compound 105 which was a starting material was synthesized by a method similar to that in Steps 1 to 5 of Example 22 and Step 1 of Example 46.

[Formula 86]

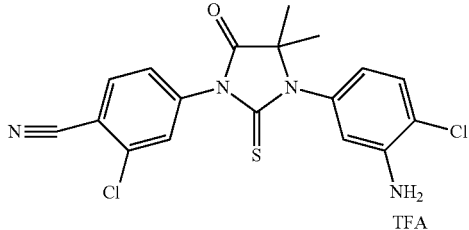
105

¹H-NMR (400 MHz, CDCl₃) δ: 1.57 (6H, s), 6.61 (1H, d, J=8.1 Hz), 6.68 (1H, s), 7.40 (1H, d, J=8.4 Hz), 7.51 (1H, d, J=8.4 Hz), 7.67 (1H, s), 7.81 (1H, d, J=8.1 Hz).

MS(ESI)m/z: 405.1 ([M+H]⁺).

[Formula 87]

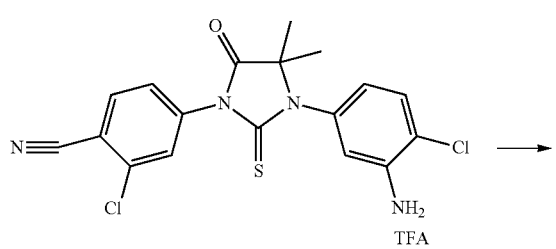

105

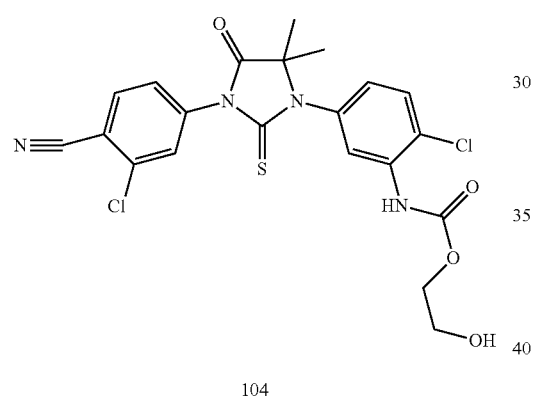

104

Compound 105 (90 mg) was suspended in dioxane (0.16 mL) and added with triethylamine (0.02 mL). The reaction solution was cooled to 0° C. and added with triphosgene (73 mg) and the mixture was stirred at room temperature for 15 minutes. It was added with ethylene glycol (0.2 mL) at 0° C. and added with triethylamine (0.2 mL) at room temperature and the mixture was stirred at room temperature for two hours. It was added with water and a saturated sodium hydrogen carbonate aqueous solution, the mixture was extracted with ethyl acetate, and the organic layer was dried with sodium sulphate, filtered, concentrated under reduced pressure, and purified by flash column chromatography (eluent, hexane:ethyl acetate=1:0-2:3) and thin-layer chromatography (eluent, chloroform:methanol=35:1) to obtain 41.4 mg (yield 54%) of the target compound (Compound 104).

¹H-NMR (400 MHz, CDCl₃) δ: 1.58 (6H, s), 2.07 (1H, s), 3.92 (2H, s), 4.35 (2H, s), 6.98 (1H, d, J=8.4 Hz), 7.36 (1H, s), 7.51-7.53 (2H, m), 7.68 (1H, s), 7.81 (1H, d, J=8.4 Hz), 8.24 (1H, s).

MS(ESI)m/z: 493.0 ([M+H]⁺).

Example 48

[Formula 88]

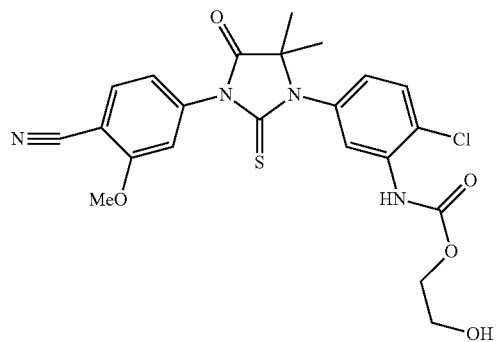

106

This compound was synthesized by a method similar to that in Example 47.

¹H-NMR (400 MHz, CDCl₃) δ: 1.60 (6H, s), 1.97 (1H, t, J=5.5 Hz), 3.92-3.93 (2H, m), 3.98 (3H, s), 4.35 (2H, t, J=3.8 Hz), 6.99 (1H, d, J=7.7 Hz), 7.08-7.10 (2H, m), 7.35 (1H, s), 7.53 (1H, d, J=8.4 Hz), 7.70 (1H, d, J=7.7 Hz), 8.25 (1H, s).

MS(ESI)m/z: 489.1 ([M+H]⁺).

Example 49

[Formula 89]

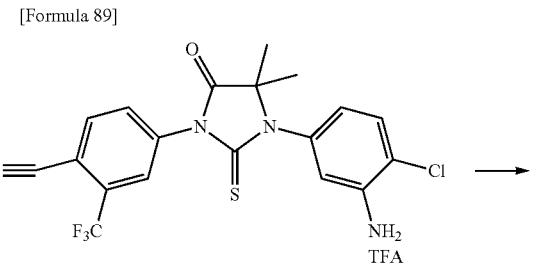

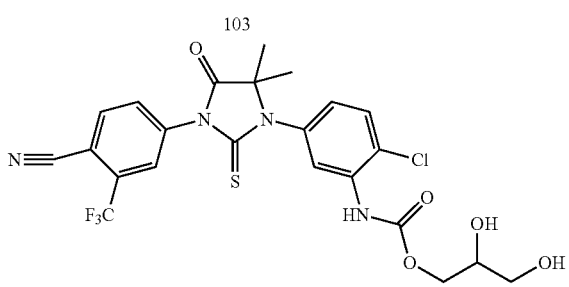

107

103.4 mg (yield 70%) of the target compound (Compound 107) was obtained from Compound 103 (139 mg) by the method similar to that in Example 45.

Rf value (silica gel plate, eluent; Ethyl acetate): 0.52.

MS(ESI)m/z: 557.1 ([M+H]⁺).

Example 50

[Formula 90]

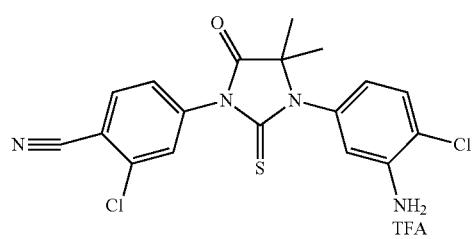

105

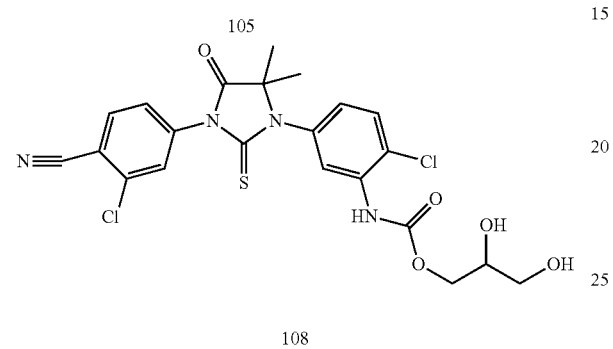

108

47.3 mg (yield 47%) of the target compound (Compound 108) was obtained from Compound 105 (100 mg) by the method similar to that in Example 45.

$^1$H-NMR (300 MHz, CDCl$_3$) δ: 1.59 (6H, s), 2.09 (1H, brs), 2.63 (1H, d, J=5.2 Hz), 3.60-3.80 (2H, m), 3.95-4.05 (1H, m), 4.24-4.36 (2H, m), 6.97 (1H, dd, J=8.3, 2.2 Hz), 7.34 (1H, s), 7.48-7.52 (2H, m), 7.67 (1H, d, J=3.4 Hz), 7.80 (1H, d, J=8.5 Hz), 8.20 (1H, d, J=2.2 Hz).

MS(ESI)m/z: 523.0 ([M+H]$^+$).

Example 51

[Formula 91]

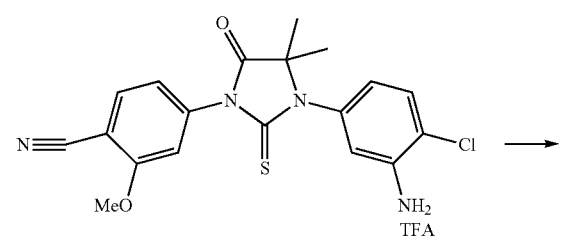

109

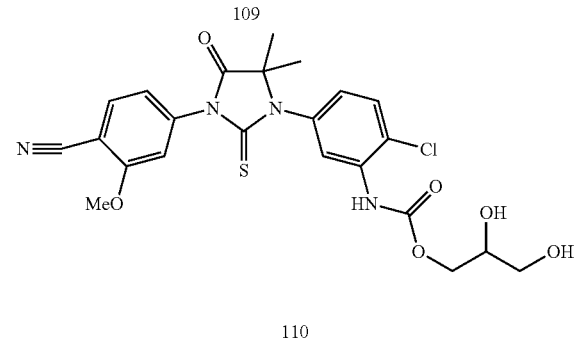

110

48.6 mg (yield 49%) of the target compound (Compound 110) was obtained from Compound 109 (98 mg) by the method similar to that in Example 45.

$^1$H-NMR (300 MHz, CDCl$_3$) δ: 1.60 (6H, s), 2.07 (1H, t, J=5.8 Hz), 2.60 (1H, d, J=5.2 Hz), 3.62-3.77 (2H, m), 3.95-4.02 (1H, m), 3.97 (3H, s), 4.24-4.36 (2H, m), 6.99 (1H, dd, J=8.5, 2.5 Hz), 7.00-7.09 (2H, m), 7.34 (1H, s), 7.51 (1H, d, J=8.2 Hz), 7.68 (1H, d, J=8.2 Hz), 8.21 (1H, d, J=2.5 Hz).

MS(ESI)m/z: 519.1 ([M+H]$^+$).

Example 52

[Formula 92]

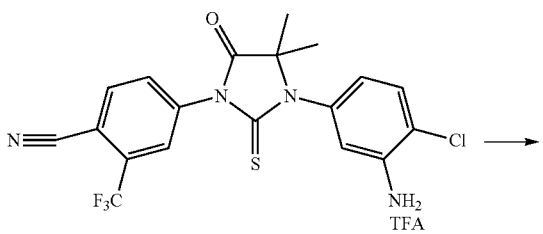

103

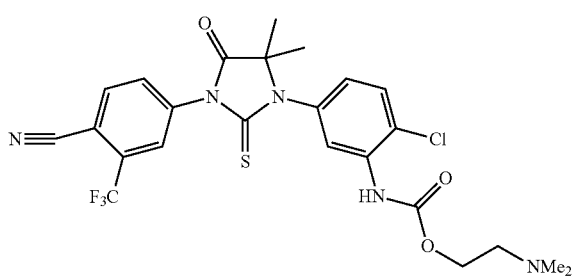

111

Compound 103 (120 mg) was dissolved in dichloromethane (0.23 mL) and added with triphosgene (120 mg) and N,N-dimethylaminoethanol (0.46 mL) and the mixture was stirred at room temperature for two hours. The reaction solution was diluted with dichloromethane and washed with water and a saturated sodium hydrogen carbonate aqueous solution, and the organic layer was dried with sodium sulphate, filtered, concentrated under reduced pressure, and purified by flash column chromatography and thin layer chromatography to obtain 70.5 mg (yield 55%) of the target compound (Compound 111).

$^1$H-NMR (300 MHz, CDCl$_3$) δ: 1.61 (6H, s), 2.32 (6H, s), 2.63 (2H, t, J=5.5 Hz), 4.29 (2H, t, J=5.5 Hz), 6.95 (1H, dd, J=10.4, 1.3 Hz), 7.37 (1H, s), 7.49 (1H, d, J=10.4 Hz), 7.83 (1H, dd, J=10.4, 1.3 Hz), 7.92-7.99 (2H, m), 8.26 (1H, d, J=1.3 Hz).

MS(ESI)m/z: 554.0 ([M+H]$^+$).

Example 53

[Formula 93]

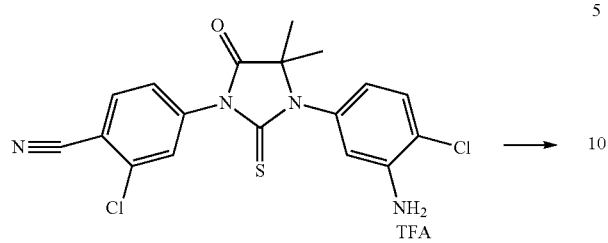

59.1 mg (yield 53%) of the target compound (Compound 112) was obtained from Compound 105 (130 mg) by the method similar to that in Example 52.

$^1$H-NMR (300 MHz, CDCl$_3$) δ: 1.59 (6H, s), 2.31 (6H, s), 2.63 (2H, t, J=5.5 Hz), 4.29 (2H, t, J=5.5 Hz), 6.94 (1H, dd, J=8.5, 2.5 Hz), 7.36 (1H, s), 7.48-7.51 (2H, m), 7.65 (1H, d, J=1.8 Hz), 7.79 (1H, d, J=8.2 Hz), 8.24 (1H, d, J=2.5 Hz).

MS(ESI)m/z: 520.1 ([M+H]$^+$).

Example 54

[Formula 94]

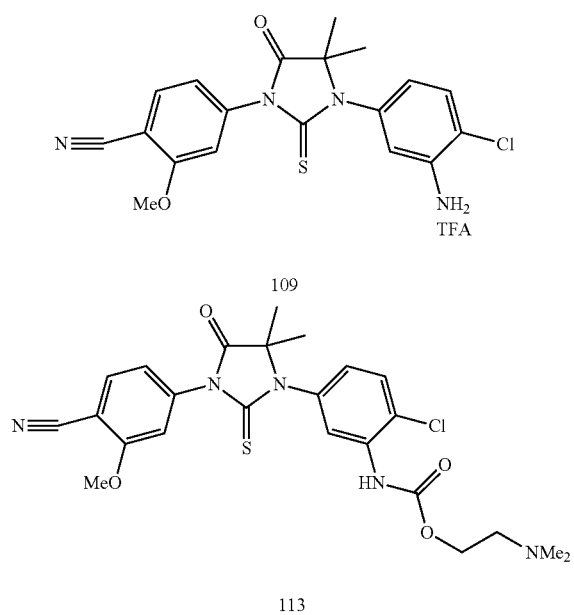

80.8 mg (yield 66%) of the target compound (Compound 113) was obtained from Compound 109 (122 mg) by the method similar to that in Example 52.

$^1$H-NMR (300 MHz, CDCl$_3$) δ: 1.60 (6H, s), 2.31 (6H, s), 2.63 (2H, t, J=5.5 Hz), 3.97 (3H, s), 4.29 (2H, t, J=5.5 Hz), 6.95 (1H, dd, J=8.5, 2.5 Hz), 7.06-7.09 (2H, m), 7.36 (1H, s), 7.49 (1H, d, J=8.2 Hz), 7.69 (1H, d, J=8.2 Hz), 8.25 (1H, d, J=2.5 Hz).

MS(ESI)m/z: 516.2 ([M+H]$^+$).

Example 55

[Formula 95]

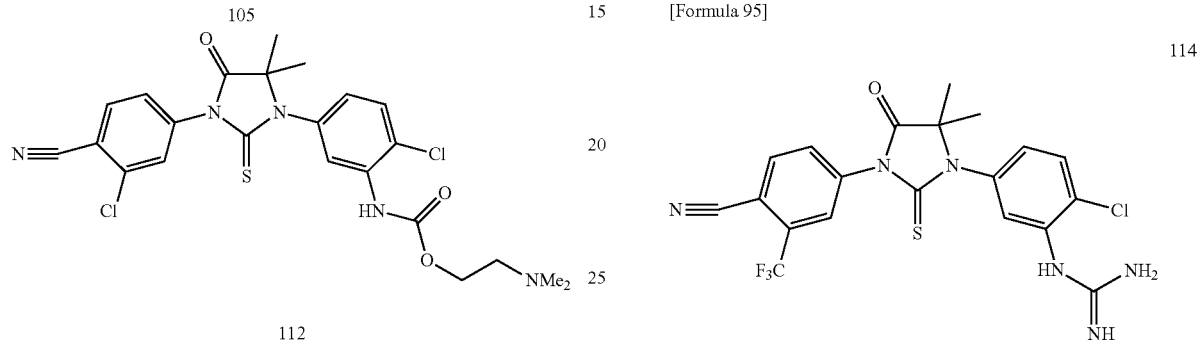

(Step 1)

[Formula 96]

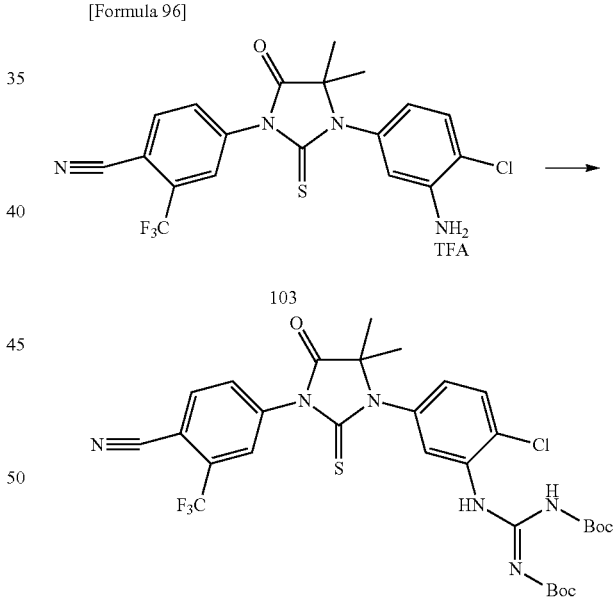

Compound 103 (50 mg) was dissolved in N,N-dimethylacetamide (0.1 mL) and added with triethylamine (0.04 mL) and N,N'-bis-Boc-guanylpyrazole (46 mg) and the mixture was stirred for two hours. It was added with triethylamine (0.04 mL) and the mixture was stirred for three hours. It was added with trifluoroacetic acid (0.046 mL) and the mixture was stirred for one hour. It was added with N,N'-bis-Boc-guanylpyrazole (46 mg) and the mixture was stirred overnight. The reaction solution was diluted with dichloromethane and washed with water, and the organic layer was dried with sodium sulfate, filtered, concentrated under reduced pressure, and purified by flash column chromatography (eluent, hexane:ethyl acetate=1:0-7:3) and thin-layer chromatography (eluent, hexane:ethyl acetate=3:1) to obtain 51.5 mg (yield 79%) of the target compound (Compound 115).

Rf value (silica gel plate, eluent; hexane:ethyl acetate=3: Two): 0.7.

MS(ESI)m/z: 702.9 ([M+Na]$^+$).

(Step 2)

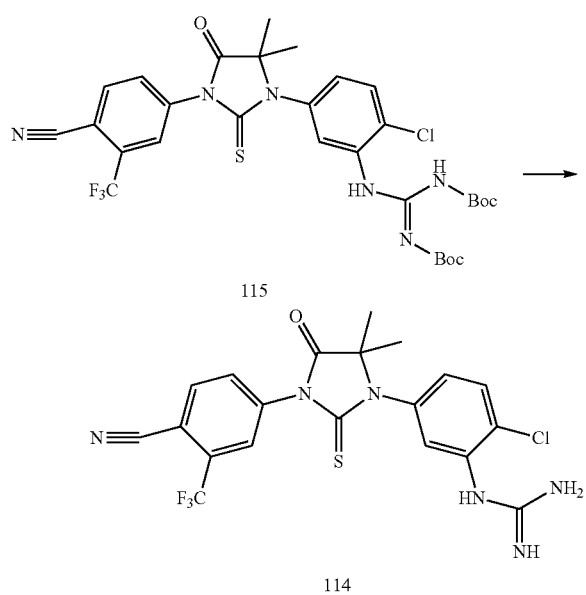

Compound 115 (51.5 mg) was dissolved in dichloromethane (0.15 mL) and added with trifluoroacetic acid (0.15 mL) at 0° C. and the mixture was stirred at room temperature for 2.5 hours. It was added with trifluoroacetic acid (0.05 mL) and the mixture was stirred for 30 minutes. The reaction solution was concentrated under reduced pressure and purified by flash column chromatography to obtain 35.7 mg (yield 98%) of the target compound (Compound 114).

$^1$H-NMR (300 MHz, CDCl$_3$) δ: 1.60 (6H, s), 6.40 (1H, s), 6.85 (1H, dd, J=8.4, 2.5 Hz), 6.97 (1H, d, J=2.5 Hz), 7.52 (1H, d, J=8.4 Hz), 7.60 (1H, s), 7.81 (1H, d, J=8.2 Hz), 7.95-7.97 (2H, m), 8.27 (1H, s).

MS(ESI)m/z: 481.2 ([M+H]$^+$).

Example 56

[Formula 98]

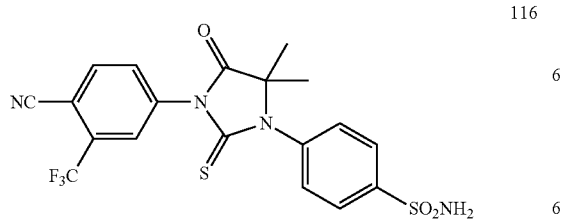

(Step 1)

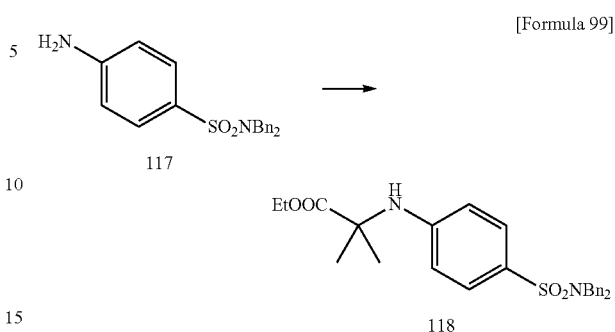

Compound 117 (6.41 g) was dissolved in dioxane (38.5 mL) and added with diisopropylethylamine (12.7 mL). A dioxane (38.5 mL) solution of 2-bromo-2-methylpropionic acid (6.08 g) was added dropwise under nitrogen atmosphere at 60° C. and the mixture was stirred at 60° C. for two hours. The reaction solution was ice-cooled and added with 5 N NaOH (90 mL) and the mixture was stirred at 60° C. for two hours. After standing to cool, extracted with toluene, the aqueous layer was ice-cooled and adjusted to pH 6 with 5 N HCl and the mixture was extracted with ethyl acetate. The organic layer was dried with anhydrous magnesium sulphate, filtered, and concentrated under reduced pressure. The obtained residue was dissolved in ethanol (25 mL) and added dropwise with thionyl chloride (1.35 mL) at 0° C. and the mixture was heated to reflux for 66 hours. After standing to cool, the mixture was concentrated under reduced pressure and added with toluene, the mixture was washed with a sodium carbonate aqueous solution, and the organic layer was dried with anhydrous magnesium sulphate, filtered, concentrated under reduced pressure, and purified by flash column chromatography (hexane-ethyl acetate) to obtain 7.33 g (yield 85%) of the target compound (Compound 118).

Rf value (silica gel plate, eluent; hexane:ethyl acetate=1: 1): 0.69.

$^1$H-NMR (400 MHz, CDCl$_3$) δ: 1.21 (3H, t, J=7.0 Hz), 1.61 (6H, s), 4.20 (2H, q, J=7.0 Hz), 4.27 (4H, s), 4.61 (1H, s), 6.55 (2H, d, J=8.3 Hz), 7.03 (4H, br s), 7.21 (6H, s), 7.62 (2H, d, J=8.3 Hz).

MS(ESI)m/z: 467.1 ([M+H]$^+$).

(Step 2)

[Formula 100]

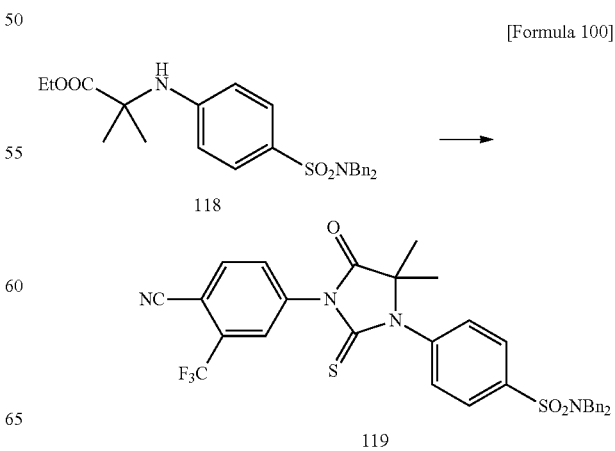

Compound 118 (1.0 g) was dissolved in N,N-dimethylformamide (2.28 mL) and added with 2-trifluoromethyl-4-isothiocyanate-benzonitrile (624 mg) and diisopropylethylamine (0.0794 mL) and the mixture was stirred at 100° C. for four hours. After standing to cool, it was added with water, the mixture was extracted with ethyl acetate, and the organic layer was washed with water and brine, dried with anhydrous magnesium sulphate, filtered, and concentrated under reduced pressure, and purified by flash column chromatography (hexane-ethyl acetate) to obtain 442 mg (yield 30%) of the target compound (Compound 119).

$^1$H-NMR (400 MHz, CDCl$_3$) δ: 1.62 (6H, s), 4.42 (4H, s), 7.04-7.06 (4H, m), 7.25-7.26 (6H, m), 7.43 (2H, d, J=8.8 Hz), 7.85 (1H, dd, J=8.2, 2.0 Hz), 7.96-8.02 (4H, m).

MS(ESI)m/z: 649.1 ([M+H]$^+$).

(Step 3)

[Formula 101]

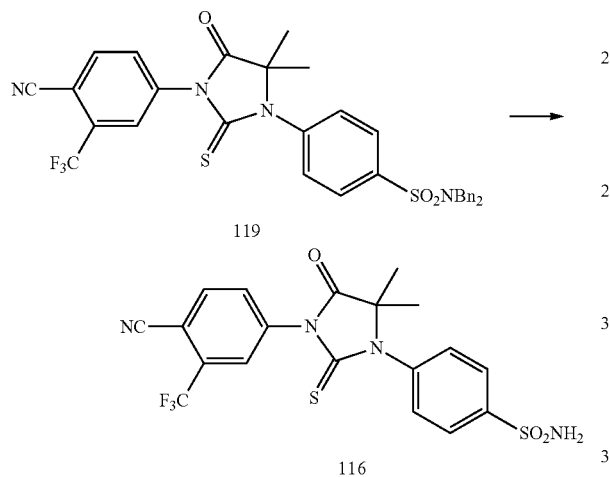

Compound 119 (442 mg) was added with conc. sulfuric acid (13 mL) and the mixture was stirred at room temperature for 15 minutes. It was added with water and extracted with ethyl acetate, and the organic layer was washed with water and brine, dried with anhydrous magnesium sulphate, filtered and concentrated under reduced pressure, and purified by flash column chromatography (hexane-ethyl acetate) to obtain 197 mg (yield 62%) of the target compound (Compound 116).

$^1$H-NMR (400 MHz, DMSO-d$_6$) δ: 1.54 (6H, s), 7.53 (2H, s), 7.61 (2H, d, J=8.4 Hz), 8.01 (2H, d, J=8.4 Hz), 8.10 (1H, d, J=8.3 Hz), 8.31 (1H, s), 8.41 (1H, d, J=8.3 Hz).

MS(ESI)m/z: 469.1 ([M+H]$^+$).

Example 57

[Formula 102]

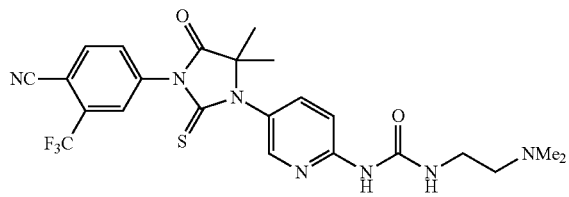

Compound 121 which was a starting material was synthesized by a method similar to that in Steps 1 to 2 of Example 56 and Step 6 of Example 22

[Formula 103]

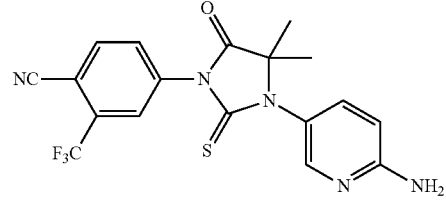

$^1$H-NMR (400 MHz, CDCl$_3$) δ: 1.58 (6H, s), 4.73 (2H, s), 6.62 (1H, d, J=8.4 Hz), 7.35 (1H, dd, J=8.4, 2.6 Hz), 7.83 (1H, dd, J=8.2, 2.0 Hz), 7.93-8.01 (3H, m).

MS(ESI)m/z: 406.2 ([M+H]$^+$).

[Formula 104]

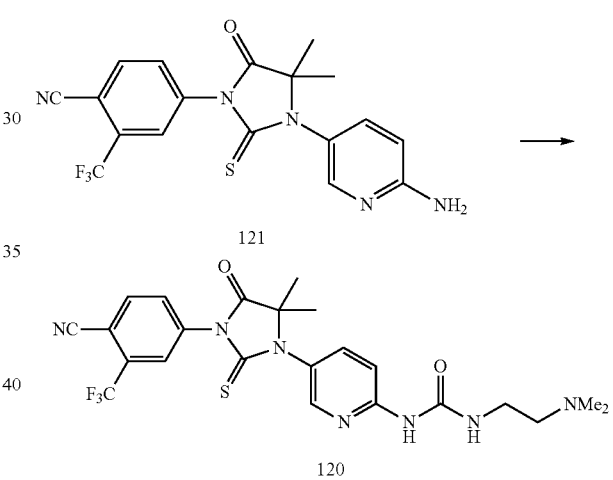

Compound 121 (150 mg) was dissolved in dioxane (3.7 mL) and added with triethylamine (0.515 mL). It was cooled to 0° C. and added with triphosgene (110 mg) and the mixture was stirred at 0° C. for 10 minutes. It was added with N,N-dimethylethylenediamine (0.406 mL) and the reaction solution was resumed to room temperature while stirring. It was added with water and the mixture was extracted with dichloromethane. The organic layer was dried with anhydrous magnesium sulphate, filtered, concentrated, under reduced pressure, and purified by flash column chromatography (dichloromethane-methanol) to obtain 29 mg (yield 15%) of the target compound (Compound 120).

$^1$H-NMR (400 MHz, CDCl$_3$) δ: 1.60 (6H, s), 2.30 (6H, s), 2.53 (2H, t, J=6.2 Hz), 3.46-3.48 (2H, m), 7.02 (1H, br s), 7.53 (1H, dd, J=8.8, 2.6 Hz), 7.83 (1H, dd, J=8.2, 1.7 Hz), 7.95 (1H, d, J=1.7 Hz), 7.99 (1H, d, J=8.2 Hz), 8.15 (1H, d, J=2.6 Hz).

Here, a peak for 1H overlaps the peak of chloroform at or around δ 7.26.

MS(ESI)m/z: 520.1 ([M+H]$^+$).

Example 58

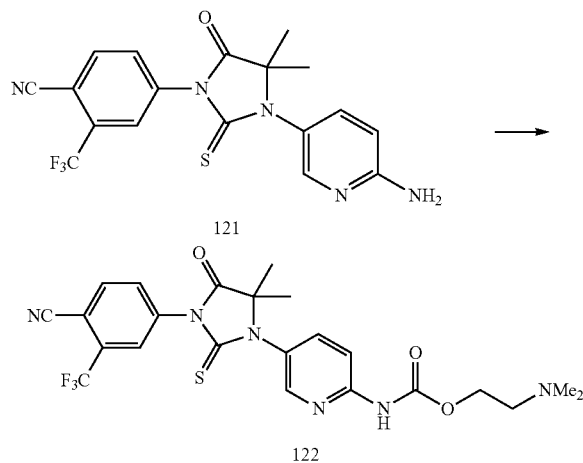

[Formula 105]

51 mg (yield 26%) of the target compound (Compound 122) was obtained from Compound 121 (150 mg) by the method similar to that in Example 57.

¹H-NMR (400 MHz, CDCl₃) δ: 1.60 (6H, s), 2.32 (6H, s), 2.64 (2H, t, J=5.5 Hz), 4.32 (2H, t, J=5.5 Hz), 7.63 (1H, dd, J=8.8, 2.6 Hz), 7.69 (1H, s), 7.84 (1H, dd, J=8.2, 1.6 Hz), 7.95 (1H, d, J=1.6 Hz), 7.99 (1H, d, J=8.2 Hz), 8.17 (1H, d, J=8.8 Hz), 8.20 (1H, d, J=2.6 Hz).
MS(ESI)m/z: 520.9 ([M+H]⁺).

Example 59

[Formula 106]

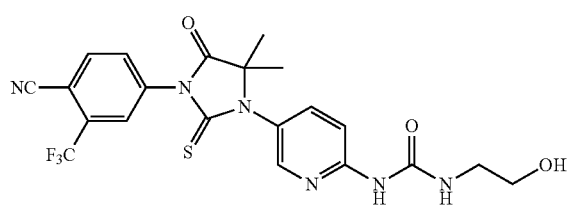

(Step 1)

[Formula 107]

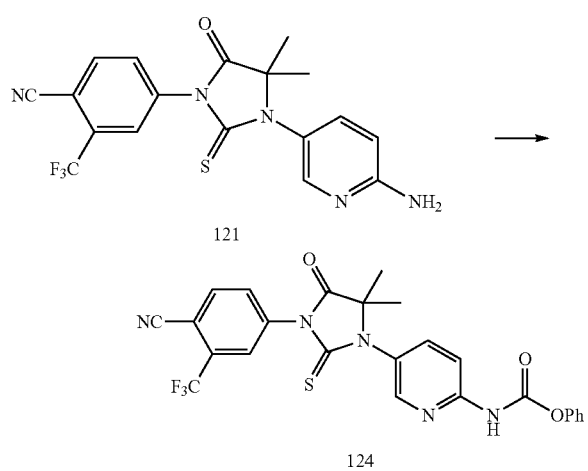

Compound 121 (150 mg) was dissolved in tetrahydrofuran (1.85 mL) and added with pyridine (0.039 mL) and phenyl chloroformate (0.06 mL) at 0° C. and the mixture was stirred at room temperature for two hours. The reaction solution was added with ethyl acetate, washed with a saturated sodium hydrogen carbonate aqueous solution, 1 N HCl and brine, dried with anhydrous magnesium sulphate, filtered, concentrated under reduced pressure, and purified by flash column chromatography (hexane-ethyl acetate) to obtain 201.6 mg (yield 77%) of the target compound (Compound 124). Rf value (silica gel plate, eluent; hexane:ethyl acetate=2:3): 0.78.

¹H-NMR (400 MHz, CDCl₃) δ: 1.59 (6H, s), 7.21 (2H, d, J=7.7 Hz), 7.29-7.30 (1H, m), 7.43-7.45 (2H, m), 7.68 (1H, dd, J=8.8, 2.6 Hz), 7.83 (1H, dd, J=8.1, 1.8 Hz), 7.95 (1H, d, J=1.8 Hz), 7.99 (1H, d, J=8.1 Hz), 8.22 (1H, d, J=8.8 Hz), 8.29 (1H, d, J=2.6 Hz), 8.40 (1H, s).
MS(ESI)m/z: 526.1 ([M+H]⁺).

(Step 2)

[Formula 108]

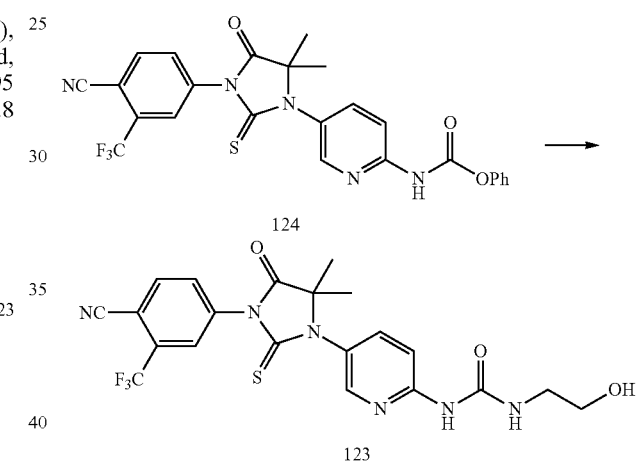

Compound 124 (20 mg) was dissolved in dichloromethane (0.6 mL) and added with ethanolamine (0.0046 mL) and triethylamine (0.0106 mL) and the mixture was stirred at room temperature overnight. Separately from this, Compound 124 (60 mg) was dissolved in dichloromethane (1.8 mL) and added with ethanolamine (0.0413 mL) and triethylamine (0.095 mL) and the mixture was stirred at room temperature for two hours. These two reaction solutions are combined added with water and the mixture was extracted with dichloromethane. The organic layer was washed with 0.5 N HCl and a saturated sodium hydrogen carbonate aqueous solution, dried with anhydrous magnesium sulphate, filtered, concentrated under reduced pressure, and purified by flash column chromatography (hexane-ethyl acetate) to obtain 54.8 mg (yield 73%) of the target compound (Compound 123).

Rf value (silica gel plate, eluent; Ethyl acetate): 0.32.

¹H-NMR (CDCl₃) δ: 1.60 (6H, s), 2.80 (1H, s), 3.59 (2H, dd, J=5.1, 10.2 Hz), 3.85 (2H, dd, J=4.9, 9.8 Hz), 6.97 (1H, d, J=8.8 Hz), 7.56 (1H, dd, J=8.8, 2.6 Hz), 7.84 (1H, d, J=8.1 Hz), 7.96 (1H, s), 7.99 (1H, d, J=8.1 Hz), 8.16 (1H, d, J=2.6 Hz), 8.36 (1H, s), 9.41 (1H, s).
MS(ESI)m/z: 493.1 ([M+H]⁺).

Example 60

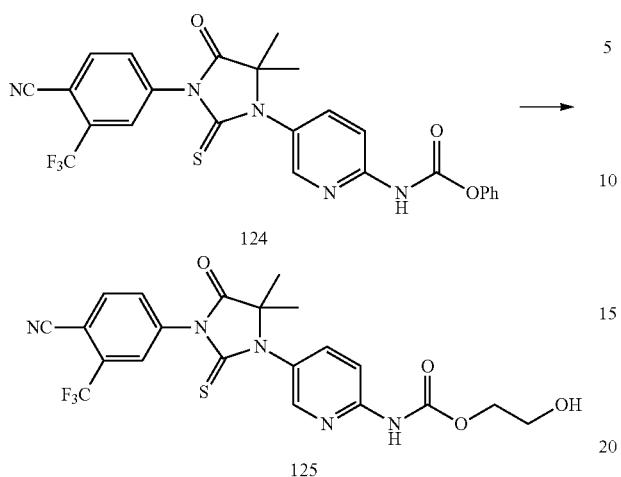

43 mg (yield 65%) of the target compound (Compound 125) was obtained from Compound 124 (70 mg) by the method similar to that in Step 2 of Example 59.

Rf value (silica gel plate, eluent; Ethyl acetate): 0.49.
MS(ESI)m/z: 494.1 ([M+H]$^+$).

Example 61

[Formula 110]

126

[Formula 111]

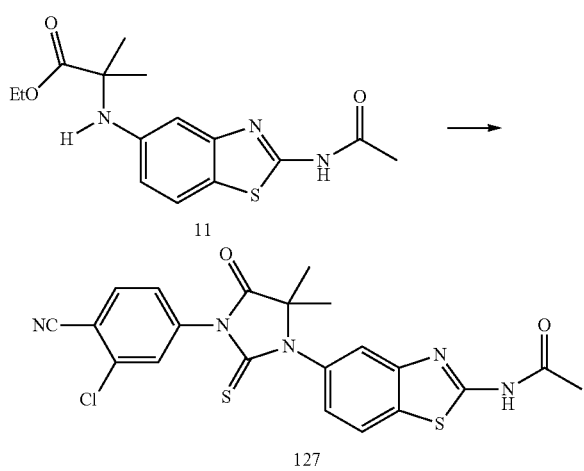

Compound 11 (1.5 g) and 2-chloro-4-isothiocyanate-benzonitrile (1.9 g) were dissolved in N,N-dimethylacetamide (5 mL) and the mixture was stirred at 160° C. in a microwave reaction apparatus for five minutes. After standing to cool, it was added with water and the mixture was extracted with dichloromethane. The organic layer was concentrated under reduced pressure and purified by flash column chromatography (eluent; hexane:ethyl acetate=1:0-2:3) and the precipitate was separated by filtration, washed with dichloromethane, and vacuum-dried to obtain 1.12 g (yield 51%) of the target compound (Compound 127).

Rf value (silica gel plate, eluent; hexane:ethyl acetate=1:1): 0.21.

MS(ESI)m/z: 470.0 ([M+H]$^+$).

(Step 2)

[Formula 112]

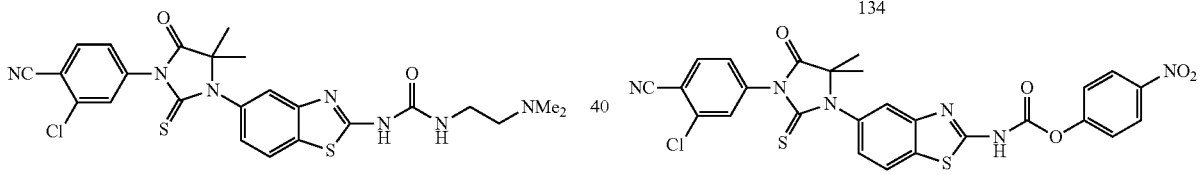

Compound 127 (1.12 g) was suspended in dioxane (10 mL) and added with concentrated hydrochloric acid (3 mL) and the mixture was stirred at 100° C. for two hours. The reaction solution was cooled to 0° C., adjusted to pH about 10 with 2 N NaOH and the mixture was extracted with ethyl acetate. The organic layer was concentrated and added with hexane. The precipitate was separated by filtration to obtain 655.5 mg of crude product of Compound 134. Furthermore, the filtrate was concentrated and added with hexane, and the precipitate was separated by filtration to obtain 320.6 mg of crude product of Compound 134. 320.6 mg of this crude product was dissolved in toluene and added with 4-nitrophenyl chloroformate (250 mg) and the mixture was stirred at 110° C. for 4.5 hours. After standing to cool, it was concentrated and added with ethyl acetate, and the precipitate was separated by filtration to obtain 326.4 mg of the target compound (Compound 128).

Rf value (silica gel plate, eluent; dichloromethane: methanol=10:1): 0.41.

MS(ESI)m/z: 593.1 ([M+H]$^+$).

(Step 3)

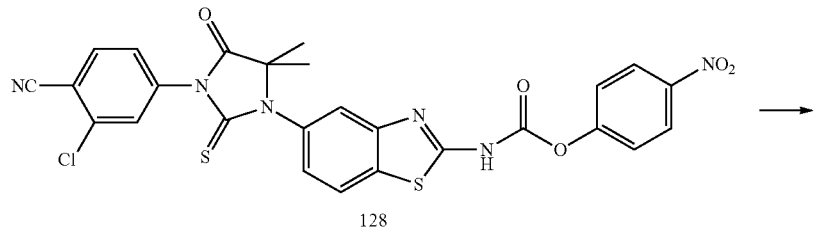

[Formula 113]

Compound 128 (97 mg) was suspended in dichloromethane (0.17 mL) added with N,N-dimethylethylenediamine (0.36 mL) and the mixture was stirred at room temperature for four hours. The reaction solution was diluted with dichloromethane and washed with water and the organic layer was dried with sodium sulphate, filtered, concentrated under reduced pressure, and purified by flash column chromatography and thin layer chromatography to obtain 31.3 mg (yield 43%) of the target compound (Compound 126).

Rf value (silica gel plate, dichloromethane:methanol=10: 1): 0.22.

$^1$H-NMR (300 MHz, CDCl$_3$) δ: 1.60 (6H, s), 2.38 (6H, s), 2.61 (2H, s), 3.46 (2H, s), 7.12 (1H, dd, J=8.2, 1.9 Hz), 7.53 (1H, dd, J=8.4, 2.1 Hz), 7.59 (1H, d, J=1.6 Hz), 7.70 (1H, d, J=1.9 Hz), 7.79 (1H, d, J=8.5 Hz), 7.83 (1H, d, J=8.5 Hz).

MS(ESI)m/z: 542.0 ([M+H]$^+$).

Example 62

Compound 128 (102.7 mg) was suspended in dichloromethane (0.17 mL) and added dropwise with 2,2-dimethyl-1,3-dioxolan-4-ylmethyl amine (0.448 mL) and the mixture was stirred at room temperature for 2.5 hours. It was added with water and the organic layer was extracted with dichloromethane, dried with sodium sulfate, filtered, and concentrated under reduced pressure. The obtained residue was dissolved in tetrahydrofuran (0.2 mL) and added with 6 N HCl (0.4 mL) and the mixture was stirred at room temperature for 2.5 hours. It was added with a saturated sodium hydrogen carbonate aqueous solution and the mixture was extracted with dichloromethane, and the organic layer was dried with sodium sulphate, filtered, concentrated under reduced pressure, and purified by flash column chromatography (eluent; dichloromethane:methanol=1:0-4:1) to obtain 51 mg (yield 54%) of the target compound (Compound 129).

Rf value (silica gel plate, dichloromethane:methanol=10: 1): 0.32.

MS(ESI)m/z: 545.0 ([M+H]$^+$).

[Formula 114]

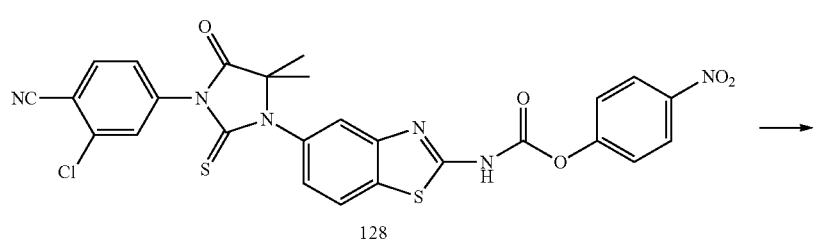

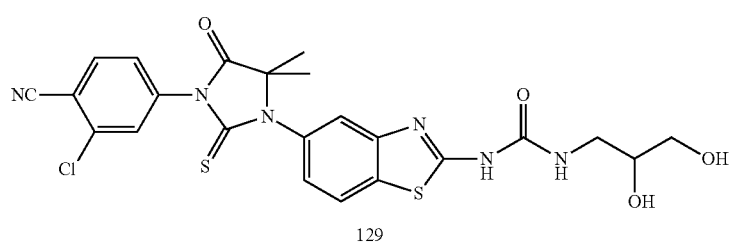

Example 63

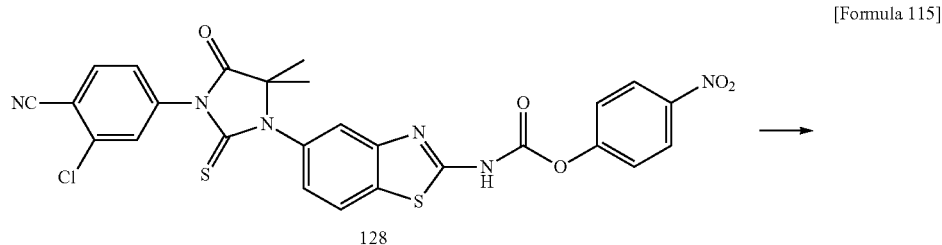

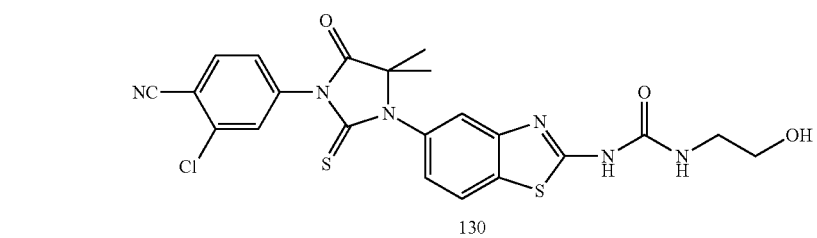

35.3 mg (yield 42%) of the target compound (Compound 130) was obtained from Compound 128 (97 mg) by the method similar to that in Step 3 of Example 61.

Rf value (silica gel plate, dichloromethane:methanol=10:1): 0.35.

MS(ESI)m/z: 515.1 ([M+H]$^+$).

Example 64

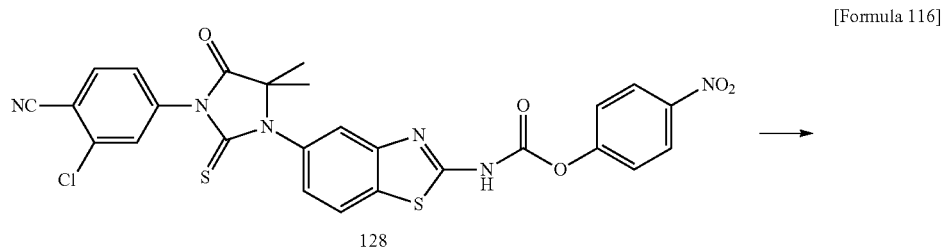

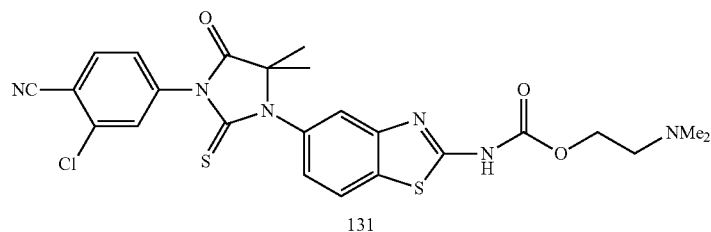

55.4 mg (yield 62%) of the target compound (Compound 131) was obtained from Compound 128 (97 mg) by the method similar to that in Step 3 of Example 61.

Rf value (silica gel plate, dichloromethane:methanol= 10:1): 0.31.

$^1$H-NMR (300 MHz, CDCl$_3$) δ: 1.60 (6H, s), 2.36 (6H, s), 2.71 (2H, t, J=5.5 Hz), 4.43 (2H, t, J=5.5 Hz), 7.12 (1H, dd, J=8.3, 1.9 Hz), 7.53 (1H, dd, J=8.3, 1.9 Hz), 7.66 (1H, d, J=1.9 Hz), 7.71 (1H, d, J=1.9 Hz), 7.80 (2H, d, J=8.3 Hz).

MS(ESI)m/z: 543.0 ([M+H]$^+$).

Example 65

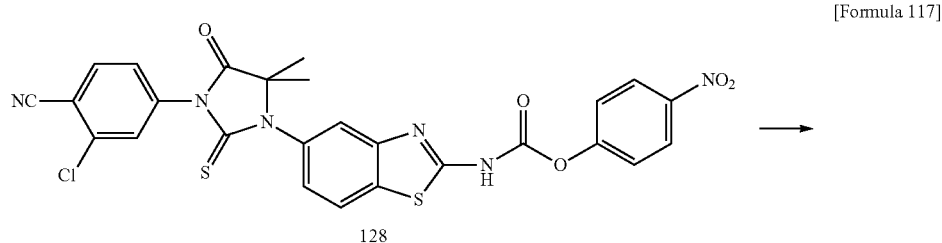

[Formula 117]

128

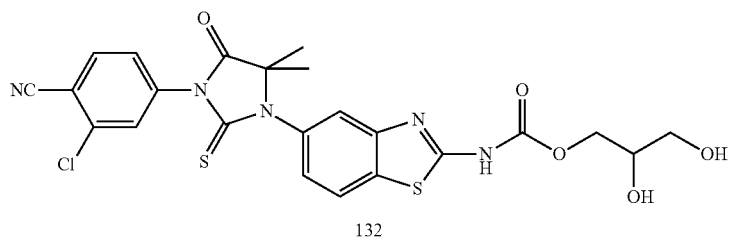

132

Compound 128 (102 mg) was suspended in dichloromethane (0.17 mL) and added dropwise with 2,2-dimethyl-1,3-dioxolan-4-ylmethanol (0.45 mL) and triethylamine (0.048 mL) and the mixture was stirred at room temperature for 1.5 hours. It was added with water and the mixture was extracted with dichloromethane and the organic layer was dried with sodium sulfate, filtered, and concentrated under reduced pressure. The obtained residue was dissolved in tetrahydrofuran (0.2 mL) and added with 6 N HCl (0.6 mL) and the mixture was stirred at room temperature for 1.5 hours. It was added with 2 N NaOH, extracted with dichloromethane, and the organic layer was dried with sodium sulfate, filtered, and concentrated under reduced pressure, purified by flash column chromatography (eluent; dichloromethane:methanol=1:0-9:1) to obtain 55.3 mg (yield 59%) of the target compound (Compound 132).

Rf value (silica gel plate, dichloromethane:methanol=10:1): 0.22.

MS(ESI)m/z: 546.2 ([M+H]$^+$).

Example 66

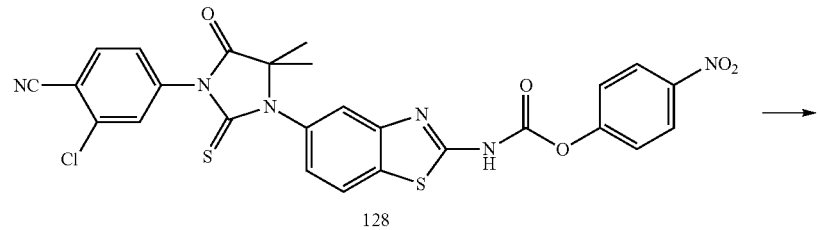

[Formula 118]

128

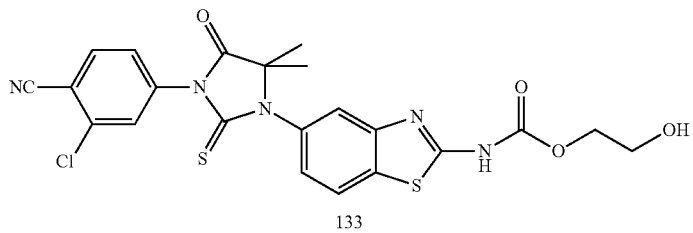

133

Compound 128 (100 mg) was suspended in dichloromethane (0.17 mL) and added dropwise with ethyleneglycol (0.189 mL) and triethylamine (0.047 mL) and the mixture was stirred at room temperature for 30 minutes. It was added with water and the mixture was extracted with dichloromethane, and the organic layer was dried with sodium sulfate, filtered, and concentrated under reduced pressure and purified by flash column chromatography (eluent; dichloromethane:methanol=1:0-9:1) to obtain 56.6 mg (yield 71%) of the target compound (Compound 133).

$^1$H-NMR (300 MHz, CDCl$_3$) δ: 1.62 (6H, s), 1.96 (1H, s), 3.92-3.99 (2H, br m), 4.45-4.50 (2H, m), 7.21 (1H, dd, J=8.2, 1.9 Hz), 7.53 (1H, dd, J=8.2, 1.9 Hz), 7.70 (1H, d, J=1.9 Hz), 7.81 (1H, d, J=8.2 Hz), 7.87 (1H, s), 7.94 (1H, d, J=8.2 Hz), 10.65 (1H, brs).

Example 67

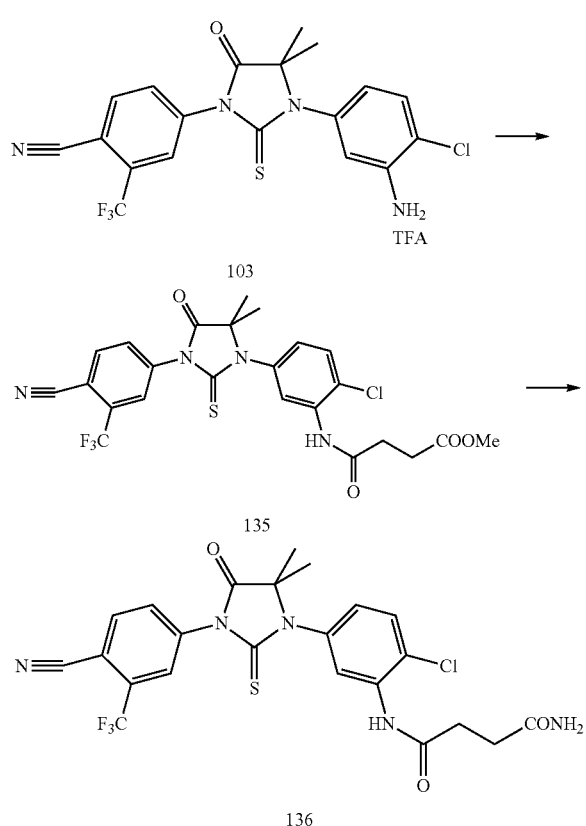

[Formula 118-1]

Compound 103 (50 mg) was dissolved in dichloromethane and added with triethylamine (0.04 mL) and methyl 4-chloro-4-oxobutyrate (0.018 mL) and the mixture was stirred at room temperature for two hours. It was added with triethylamine (0.04 mL) and the mixture was stirred for two hours. It was added with methyl 4-chloro-4-oxobutyrate (0.018 mL) and the mixture was stirred at room temperature for one hour. It was added with water, and the mixture was extracted with dichloromethane, and the organic layer was dried with sodium sulfate, filtered, and concentrated under reduced pressure to obtain 68.8 mg of crude product of Compound 135. 65 mg of this crude product was added with 7 N ammonia/methanol (2 mL) at 0° C. and the mixture was stirred at 50° C. for four hours. After standing to cool, it was concentrated under reduced pressure and purified by flash column chromatography and thin layer chromatography to obtain 32.3 mg of the target compound (Compound 136).

Rf value (silica gel plate, dichloromethane:methanol=10:1): 0.24.
MS(ESI)m/z: 538.0 ([M+H]$^+$).

Example 68

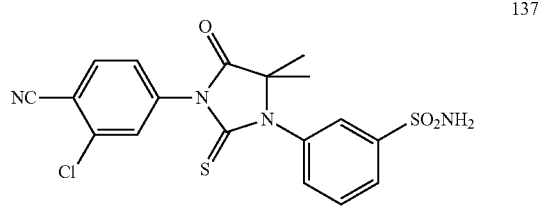

[Formula 119]

(Step 1)

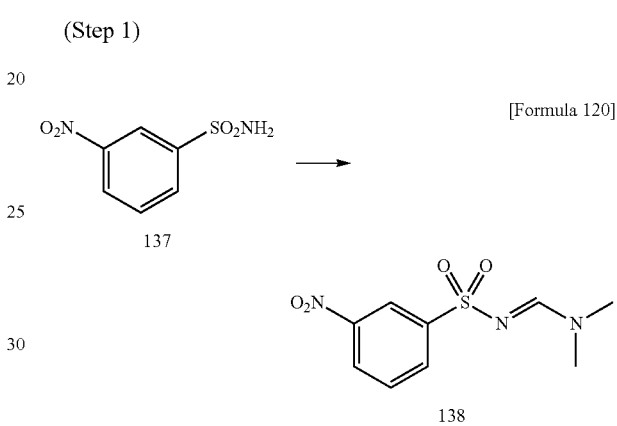

[Formula 120]

Compound 137 (2.03 g) was dissolved in ethyl acetate (10 mL) and N,N-dimethylformamide (2 mL) and added dropwise with N,N-dimethylformamide dimethylacetal (1.47 mL) and the mixture was stirred at room temperature overnight. The reaction solution was added with hexane (20 mL) and allowed to stand still overnight. The precipitate was separated by filtration and vacuum-dried to obtain 2.37 g (yield 92%) of the target compound (Compound 138).

Rf value (silica gel plate, hexane:ethyl acetate=1:2): 0.29.
$^1$H-NMR (400 MHz, CDCl$_3$) δ: 3.04 (3H, s), 3.21 (3H, s), 7.68 (1H, t, J=8.1 Hz), 8.18 (1H, s), 8.26 (1H, d, J=8.1 Hz), 8.37 (1H, d, J=8.1 Hz), 8.71 (1H, s).
MS(ESI)m/z: 258.1 ([M+H]$^+$).
(Step 2)

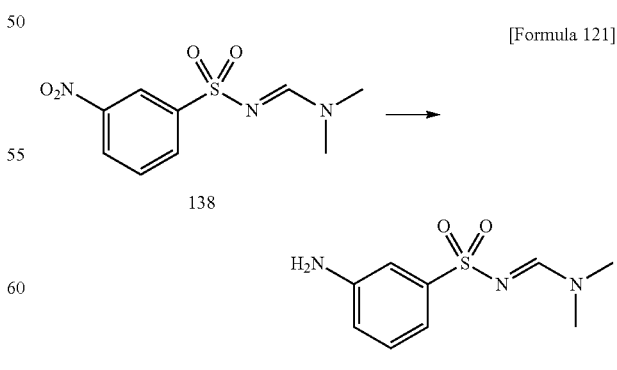

[Formula 121]

Compound 138 (1.18 g) was dissolved in methanol (50 mL) and tetrahydrofuran (15 mL) and added with 10% Pd/C (108 mg) and the mixture was stirred under hydrogen atmosphere at room temperature overnight. The reaction solution was filtered, concentrated under reduced pressure, and vacuum-dried to obtain 1.02 g (yield 98%) of the target compound (Compound 139).

Rf value (silica gel plate, hexane:ethyl acetate=1:2): 0.097.

$^1$H-NMR (400 MHz, CDCl$_3$) δ: 3.03 (3H, d, J=2.2 Hz), 3.13 (3H, d, J=2.6 Hz), 3.86 (2H, s), 6.77-6.80 (1H, m), 7.22-7.26 (3H, m), 8.11 (1H, s).

(Step 3)

[Formula 122]

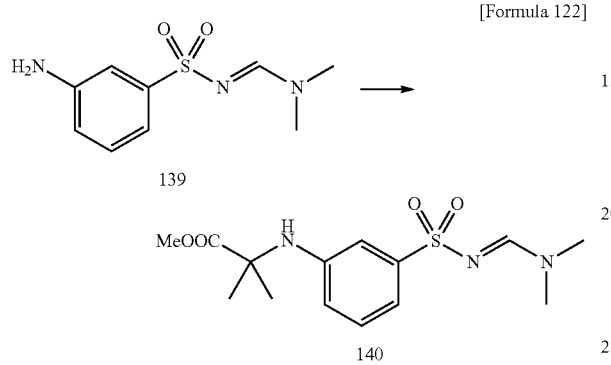

Compound 139 (250 mg) and 2-bromo-2-methylpropionic acid (185 mg) were dissolved in dioxane (1.1 mL) and added with diisopropylethylamine (0.385 mL) and the mixture was stirred at 70° C. for two hours. After standing to cool, it was added with 6 N HCl and the mixture was extracted with ethyl acetate. The organic layer was dried with sodium sulfate, filtered and concentrated under reduced pressure. The obtained residue was dissolved in dichloromethane, and added with an etherl solution of diazomethane (which was prepared by dissolving N-methyl-N'-nitro-N-nitrosoguanidine in 40% KOH aqueous solution and the mixture was extracted with ether) while stirring at room temperature till yellow color of the reaction solution disappeared. The reaction solution was concentrated under reduced pressure and purified by flash column chromatography to obtain 275.5 mg (yield 77%) of the target compound (Compound 140).

Rf value (silica gel plate, hexane:ethyl acetate=1:1): 0.079.
MS(ESI)m/z: 328.0 ([M+H]$^+$).

(Step 4)

[Formula 123]

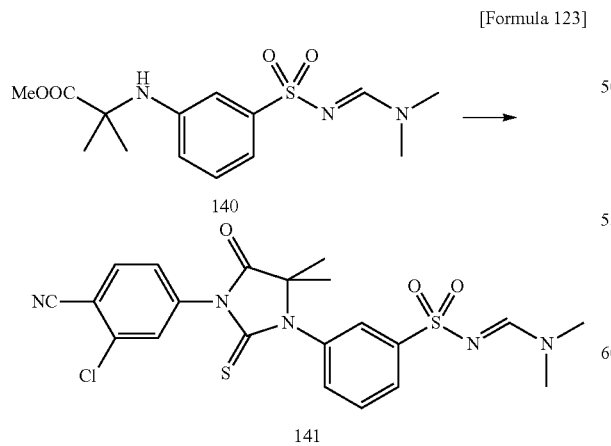

322.3 mg (yield 80%) of the target compound (Compound 141) was obtained from Compound 140 (327 mg) by the method similar to that in Step 3 of Example 15.

Rf value (silica gel plate, hexane:ethyl acetate=1:1): 0.24.
MS(ESI)m/z: 490.1 ([M+H]$^+$).

(Step 5)

[Formula 124]

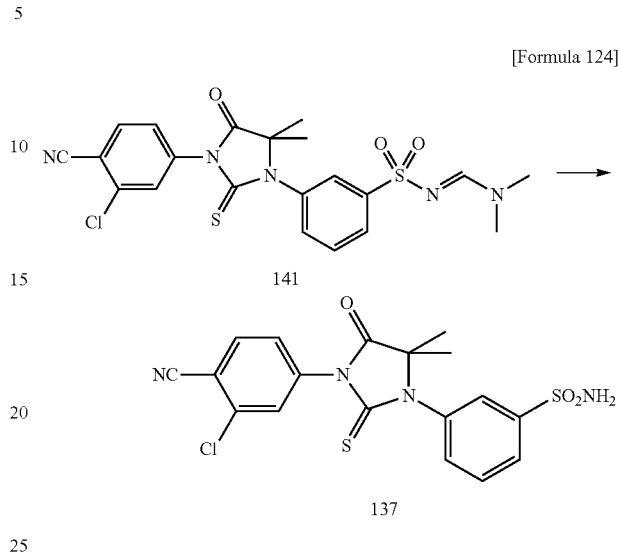

Compound 141 (222.3 mg) was dissolved in ethanol (0.3 mL) and added with 4 N sulfuric acid (0.3 mL) and the mixture was stirred at 90° C. for five hours. After standing to cool, it was added with aqueous sodium hydroxide, the mixture was extracted with dichloromethane and the organic layer was concentrated under reduced pressure. The obtained residue was dissolved in ethanol (0.2 mL) and added with 4.5 N sulfuric acid (0.2 mL) and the mixture was stirred at 90° C. for 1.5 hours. After standing to cool, it was added with aqueous sodium hydroxide and the mixture was extracted with dichloromethane, and the organic layer was concentrated under reduced pressure and purified by flash column chromatography and thin layer chromatography to obtain 78 mg (yield 39%) of the target compound (Compound 137).

$^1$H-NMR (300 MHz, CDCl$_3$) δ: 1.60 (6H, s), 4.92 (2H, s), 7.48-7.54 (2H, m), 7.67 (1H, d, J=1.9 Hz), 7.71 (1H, t, J=7.9 Hz), 7.81 (1H, d, J=8.2 Hz), 7.89 (1H, t, J=1.9 Hz), 8.06 (1H, dt, J=7.9, 1.9 Hz).

MS(ESI)m/z: 435.0 ([M+H]$^+$).

Example 69

[Formula 125]

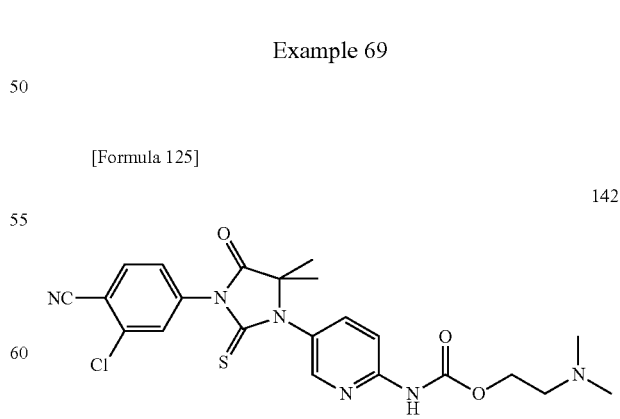

Compound 143 which was a starting material was synthesized by the method similar to that in Steps 1 to 2 of Example 56 and Step 6 of Example 22.

Example 70

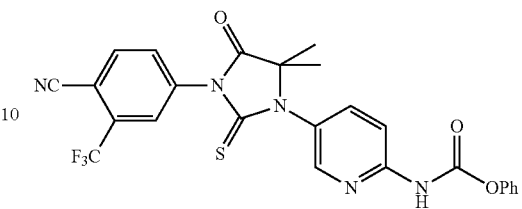

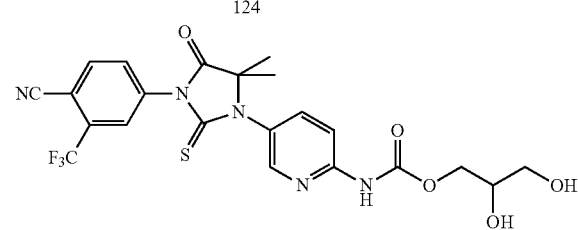

Compound 124 (75 mg) and 2,2-dimethyl-1,3-dioxolan-4-ylmethanol (0.106 mL) were dissolved in dichloromethane (1.5 mL) and added with triethylamine (0.12 mL) and the mixture was stirred at room temperature overnight. The reaction solution was added with water, the mixture was extracted with dichloromethane and the organic layer was dried with anhydrous magnesium sulphate, filtered, and concentrated under reduced pressure. The obtained residue was dissolved in tetrahydrofuran (2 mL) and added with 6 N HCl (1 mL) and the mixture was stirred at room temperature for one hour. The reaction solution was added with a saturated sodium hydrogen carbonate aqueous solution and the mixture was extracted with ethyl acetate, and the organic layer was washed with brine, dried with anhydrous magnesium sulphate, filtered, concentrated under reduced pressure, and purified by flash column chromatography (hexane-ethyl acetate) to obtain 40 mg (yield 53%) of the target compound (Compound 144).

$^1$H-NMR (400 MHz, CDCl$_3$) δ: 1.60 (6H, s), 2.14 (1H, s), 2.65 (1H, d, J=4.4 Hz), 3.65-3.79 (2H, m), 4.01-4.04 (1H, m), 4.34 (2H, ddd, J=21.7, 11.6, 5.2 Hz), 7.66 (1H, dd, J=8.9, 2.3 Hz), 7.85 (1H, dd, J=8.1, 1.8 Hz), 7.96 (1H, d, J=1.8 Hz), 7.99 (1H, d, J=8.1 Hz), 8.12 (1H, s), 8.17 (1H, d, J=8.9 Hz), 8.26 (1H, d, J=2.3 Hz).

MS(ESI)m/z: 524.0 ([M+H]$^+$).

Example 71

[Formula 129]

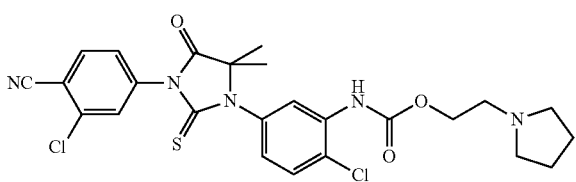

[Formula 126]

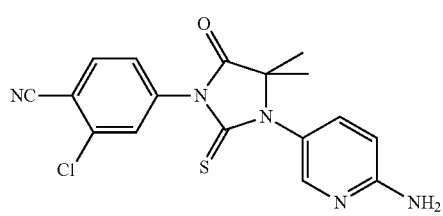

$^1$H-NMR (400 MHz, DMSO-d$_6$) δ: 1.50 (6H, s), 6.37 (2H, s), 6.58 (1H, d, J=8.8 Hz), 7.37 (1H, dd, J=8.8, 2.6 Hz), 7.75 (1H, dd, J=8.2, 1.8 Hz), 7.88 (1H, d, J=2.6 Hz), 8.05 (1H, d, J=1.8 Hz), 8.21 (1H, d, J=8.2 Hz).

MS(ESI)m/z: 372.1 ([M+H]$^+$).

[Formula 127]

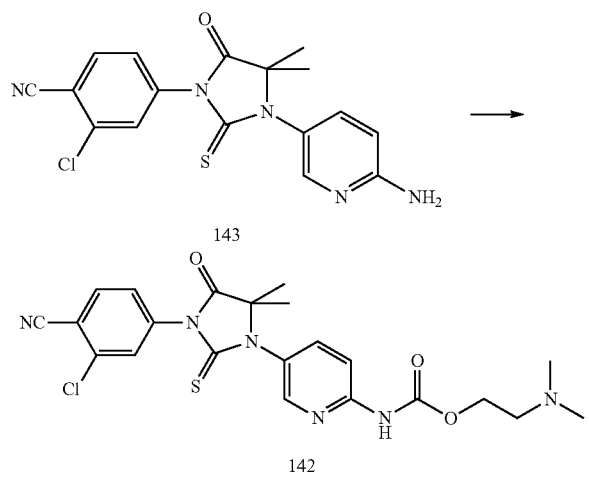

Compound 143 (150 mg) was dissolved in dioxane (15 mL) and added with triethylamine (0.558 mL) and the mixture was cooled to 0° C. under nitrogen atmosphere. It was added with triphosgene (119 mg) and the mixture was stirred for 10 minutes and then added with dimethylaminoethanol (0.801 mL) and the mixture was stirred at room temperature for 10 minutes. It was added with a saturated sodium hydrogen carbonate aqueous solution and the mixture was extracted with ethyl acetate, and the organic layer was dried with anhydrous magnesium sulphate, filtered, concentrated under reduced pressure, and purified by flash column chromatography (NH silica gel, eluent; hexane:ethyl acetate=1:0-0:1) and thin-layer chromatography (eluent; dichloromethane:methanol=15:1) to obtain 50 mg (yield 26%) of the target compound (Compound 142).

$^1$H-NMR (400 MHz, DMSO-d$_6$) δ: 1.51 (6H, s), 2.20 (6H, s), 2.52 (2H, t, J=5.9 Hz), 4.22 (2H, t, J=5.9 Hz), 7.73 (1H, dd, J=8.4, 1.8 Hz), 7.80 (1H, dd, J=9.0, 2.6 Hz), 8.00 (1H, d, J=9.0 Hz), 8.03 (1H, d, J=1.8 Hz), 8.19 (1H, d, J=8.4 Hz), 8.26 (1H, d, J=2.6 Hz), 10.48 (1H, s).

MS(ESI)m/z: 487.1 ([M+H]$^+$).

(Step 1)

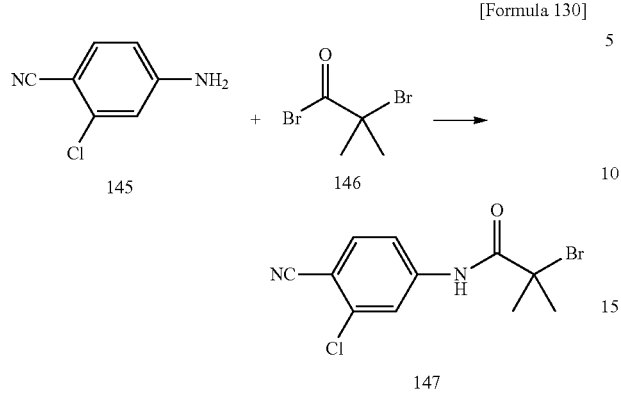

Compound 145 (3.08 g) was dissolved in dichloromethane (90 mL) and added with water (100 mL) and potassium carbonate (3.08 g) and added dropwise with Compound 146 (2.48 mL) at 0° C. and the mixture was stirred at room temperature overnight. The organic layer was washed with brine, dried with anhydrous magnesium sulphate, filtered, concentrated under reduced pressure, and purified by flash column chromatography (eluent, hexane:ethyl acetate=1:0-3:1) to obtain 5.31 g (yield 87%) of the target compound (Compound 147).

Rf value (silica gel plate, hexane:ethyl acetate=2:1): 0.55.
$^1$H-NMR (400 MHz, CDCl$_3$) δ: 2.05 (6H, s), 7.51 (1H, dd, J=8.5, 1.9 Hz), 7.64 (1H, d, J=8.5 Hz), 7.92 (1H, d, J=1.9 Hz), 8.61 (1H, s).

(Step 2)

[Formula 131]

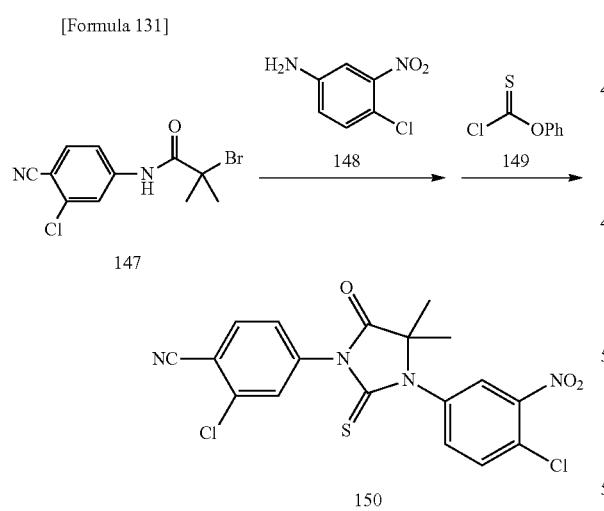

Compound 147 (10.0 g), Compound 148 (5.72 g) and sodium hydride (60% in oil, 1.59 g) were dissolved in tetrahydrofuran (67 mL) and the mixture was stirred under nitrogen atmosphere at 45° C. for one hour. The reaction solution was cooled to 0° C. and added with sodium hydride (60% in oil, 7.96 g) and added dropwise with Compound 149 (13.76 mL). It was stirred at 0° C. for 10 minutes and at room temperature for 30 minutes. The reaction solution was diluted with t-butyl methyl ether and poured into a saturated ammonium chloride aqueous solution cooled to 0° C. The organic layer was washed with brine and dried with anhydrous magnesium sulphate, filtered, concentrated under reduced pressure, and purified by flash column chromatography (hexane-ethyl acetate). The precipitate was separated by filtration from a hexane-ethyl acetate mixed solvent and vacuum-dried to obtain 3.22 g (yield 22%) of the target compound (Compound 150).

Rf value (silica gel plate, hexane:ethyl acetate=2:1): 0.39.
$^1$H-NMR (400 MHz, CDCl$_3$) δ: 1.62 (6H, s), 7.48-7.53 (2H, s), m), 7.66 (1H, s), 7.75 (1H, d, J=8.4 Hz), 7.83 (1H, d, J=8.4 Hz), 7.90 (1H, d, J=1.1 Hz).

(Step 3)

[Formula 132]

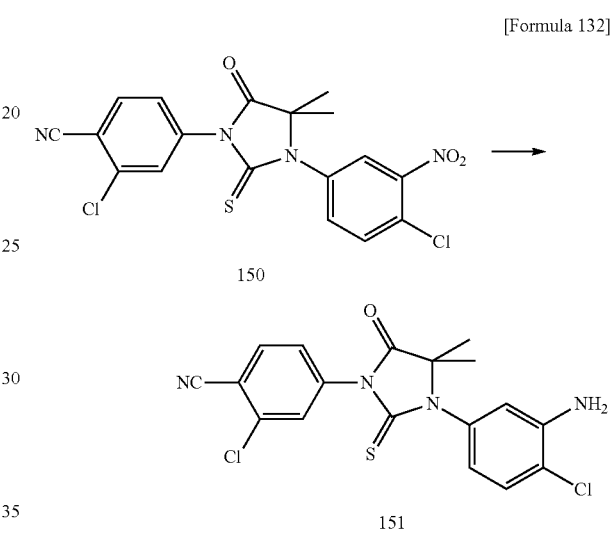

Compound 150 (3.22 g) was dissolved in ethanol (60 mL) and added with iron powder (4.13 g) and the mixture was concentrated hydrochloric acid (0.3 mL) and heated to reflux for 90 minutes. The reaction solution was filtered and the residue was washed with ethyl acetate, and concentrated under reduced pressure and purified by flash column chromatography (NH silica, hexane-ethyl acetate) to obtain 2.34 g (yield 78%) of the target compound (Compound 151).

Rf value (silica gel plate, hexane:ethyl acetate=1:1): 0.55.
$^1$H-NMR (400 MHz, CDCl$_3$) δ: 1.57 (6H, s), 4.24 (2H, s), 6.60 (1H, dd, J=8.3, 2.3 Hz), 6.67 (1H, d, J=2.3 Hz), 7.39 (1H, d, J=8.3 Hz), 7.51 (1H, dd, J=8.2, 1.9 Hz), 7.67 (1H, d, J=1.9 Hz), 7.80 (1H, d, J=8.2 Hz).

(Step 4)

[Formula 133]

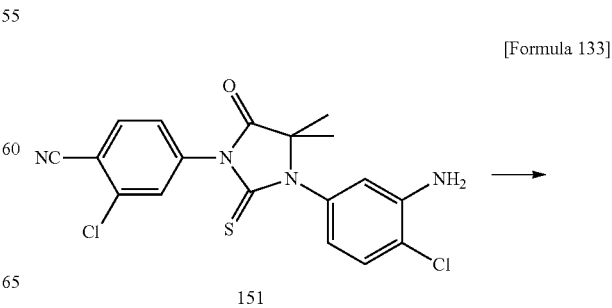

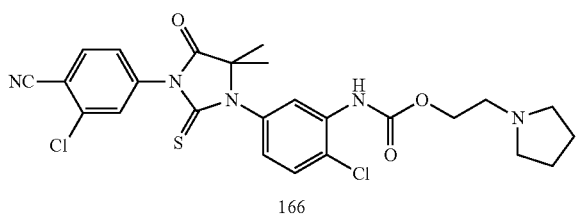

166

Triphosgene (194 mg) was dissolved in dichloromethane (2 mL) and added with diisopropylethylamine (0.086 mL) and a dichloromethane solution of Compound 151 (80 mg) at 0° C. and the mixture was stirred at room temperature at 0° C. for 20 minutes for five minutes. The reaction solution was cooled to 0° C. and added with 1-(2-hydroxyethyl)pyrrolidine (0.648 mL) and the mixture was stirred at room temperature for one hour. It was added with water, the mixture was extracted with dichloromethane, and the organic layer was washed with a saturated sodium hydrogen carbonate, and dried with anhydrous magnesium sulphate, filtered, concentrated under reduced pressure, and purified by flash column chromatography and thin layer chromatography to obtain 52 mg (yield 48%) of the target compound (Compound 166).

Rf value (silica gel plate, dichloromethane:methanol=20:1): 0.28.

$^1$H-NMR (400 MHz, CDCl$_3$) δ: 1.60 (6H, s), 1.83 (4H, br s), 2.60 (4H, br s), 2.82 (2H, t, J=5.6 Hz), 4.33 (2H, t, J=5.6 Hz), 6.95 (1H, dd, J=8.6, 2.4 Hz), 7.39 (1H, s), 7.51 (2H, d, J=8.4 Hz), 7.68 (1H, d, J=1.8 Hz), 7.81 (1H, d, J=8.4 Hz), 8.26 (1H, d, J=1.8 Hz).

MS(ESI)m/z: 546.1 ([M+H]$^+$).

Example 72

[Formula 134]

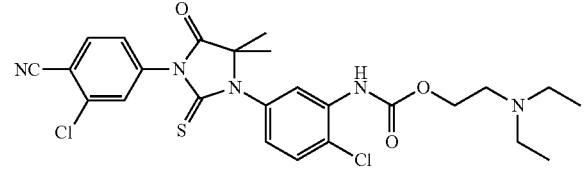

167

This compound was synthesized by a method similar to that in Example 71.

Rf value (silica gel plate, dichloromethane:methanol=20:1): 0.27.

$^1$H-NMR (400 MHz, CDCl$_3$) δ: 1.06 (6H, t, J=7.1 Hz), 1.60 (6H, s), 2.62 (4H, q, J=7.1 Hz), 2.76 (2H, t, J=5.9 Hz), 4.27 (2H, t, J=5.9 Hz), 6.95 (1H, dd, J=8.4, 2.2 Hz), 7.33 (1H, s), 7.49-7.53 (2H, m), 7.68 (1H, d, J=1.8 Hz), 7.81 (1H, d, J=8.4 Hz), 8.26 (1H, d, J=1.8 Hz).

MS(ESI)m/z: 548.0 ([M+H]$^+$).

Example 73

[Formula 135]

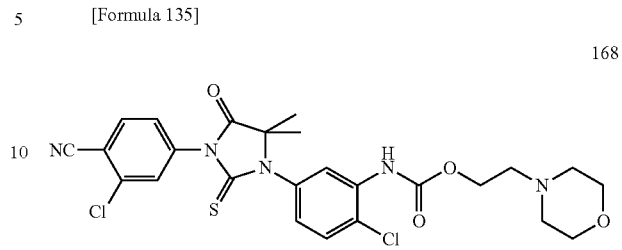

168

This compound was synthesized by a method similar to that in Example 71.

Rf value (silica gel plate, hexane:ethyl acetate=2:3): 0.14.

$^1$H-NMR (400 MHz, CDCl$_3$) δ: 1.60 (6H, s), 2.52-2.54 (4H, br m), 2.70 (2H, t, J=5.6 Hz), 3.74 (4H, t, J=4.8 Hz), 4.33 (2H, t, J=5.6 Hz), 6.97 (1H, dd, J=8.0, 2.1 Hz), 7.33 (1H, s), 7.49-7.54 (2H, m), 7.68 (1H, d, J=1.8 Hz), 7.81 (1H, d, J=8.1 Hz), 8.25 (1H, s).

MS(ESI)m/z: 562.1 ([M+H]$^+$).

Example 74

[Formula 136]

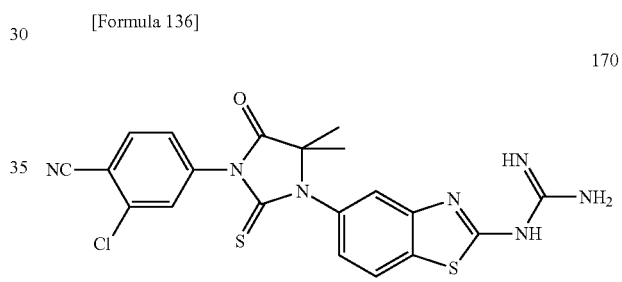

170

(Step 1)

[Formula 137]

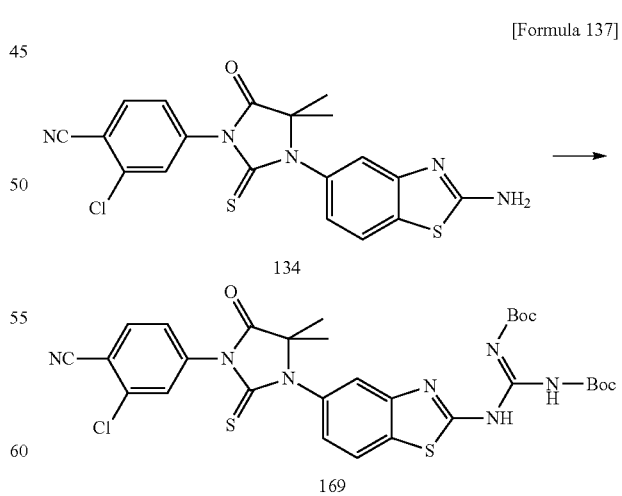

Compound 134 (100 mg) was dissolved in N,N-dimethylacetamide (0.234 mL) and added with N,N'-bis-Boc-guanylpyrazole (225 mg) and trifluoroacetic acid (0.054 mL) and the mixture was stirred at room temperature for 19 hours.

Furthermore, it was added with trifluoroacetic acid (0.054 mL) and the mixture was stirred at 50° C. at room temperature for 19 hours for five hours. It was added with water, and the mixture was extracted with dichloromethane, and the organic layer was dried, concentrated under reduced pressure, and purified by flash column chromatography (eluent; hexane: ethyl acetate=1:0-2:1) to obtain 34 mg (yield 22%) of the target compound (Compound 169).

Rf value (silica gel plate, chloroform:methanol=19:1): 0.91.

MS(ESI)m/z: 670.2 ([M+H]$^+$).

(Step 2)

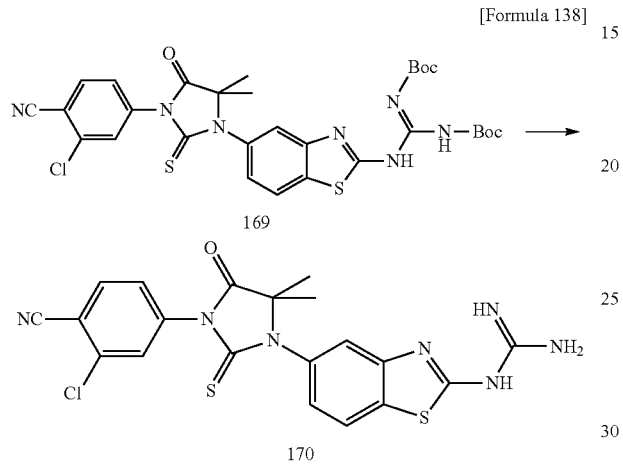

[Formula 138]

Compound 170 was synthesized by the method similar to that in Step 2 of Example 55.

Rf value (silica gel plate, hexane:ethyl acetate=1:1): 0.11.
MS(ESI)m/z: 470.0 ([M+H]$^+$).

Example 75

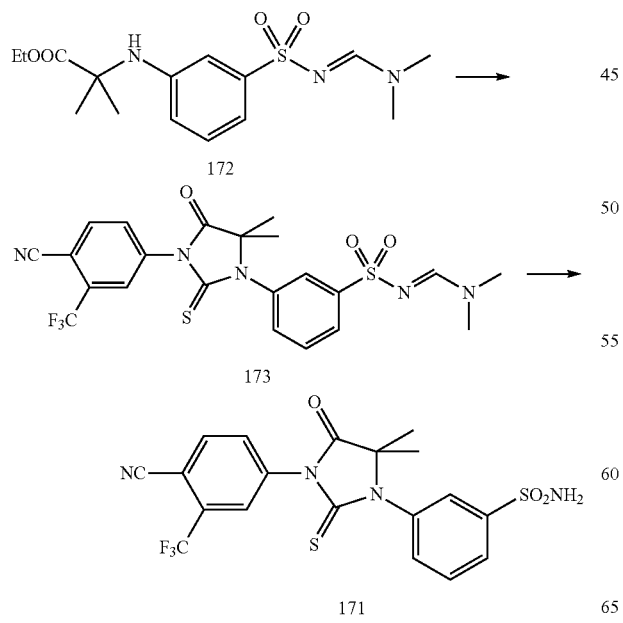

[Formula 139]

The target compound (Compound 171) was synthesized by the method similar to that in Steps 4 and 5 of Example 68, except that diisopropylamine was used as a base and dimethylformamide was used as a solvent in the step to produce Compound 173 and that 6 N hydrochloric acid was used as an acid and dioxane was used as a solvent in the step to produce Compound 171.

Rf value (silica gel plate, dichloromethane:methanol=20:1): 0.38.

MS(ESI)m/z: 469.1 ([M+H]$^+$).

Example 76

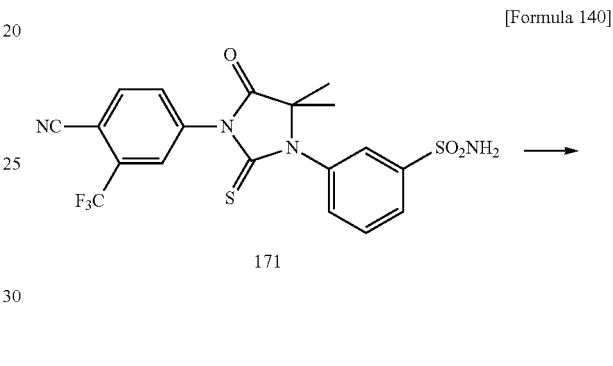

[Formula 140]

Compound 171 (80 mg) was dissolved in dichloromethane (3.5 mL) and added with acetic anhydride (0.0484 mL) and triethylamine (0.0714 mL) and the mixture was stirred at room temperature for 16 hours. It was added with water and the mixture was extracted with dichloromethane, and the organic layer was dried with anhydrous magnesium sulphate, filtered, concentrated under reduced pressure, and purified by flash column chromatography (dichloromethane-methanol) to obtain 67.3 mg (yield 77%) of the target compound (Compound 174).

Rf value (silica gel plate, dichloromethane:methanol=20:1): 0.33.

$^1$H-NMR (400 MHz, CDCl$_3$) δ: 1.64 (6H, s), 2.09 (3H, s), 7.63 (1H, d, J=8.1 Hz), 7.75 (1H, t, J=8.1 Hz), 7.84 (1H, d, J=8.1 Hz), 7.96-8.01 (3H, m), 8.12 (1H, s), 8.18 (1H, d, J=8.1 Hz).

MS(ESI)m/z: 511.1 ([M+H]$^+$).

Example 77

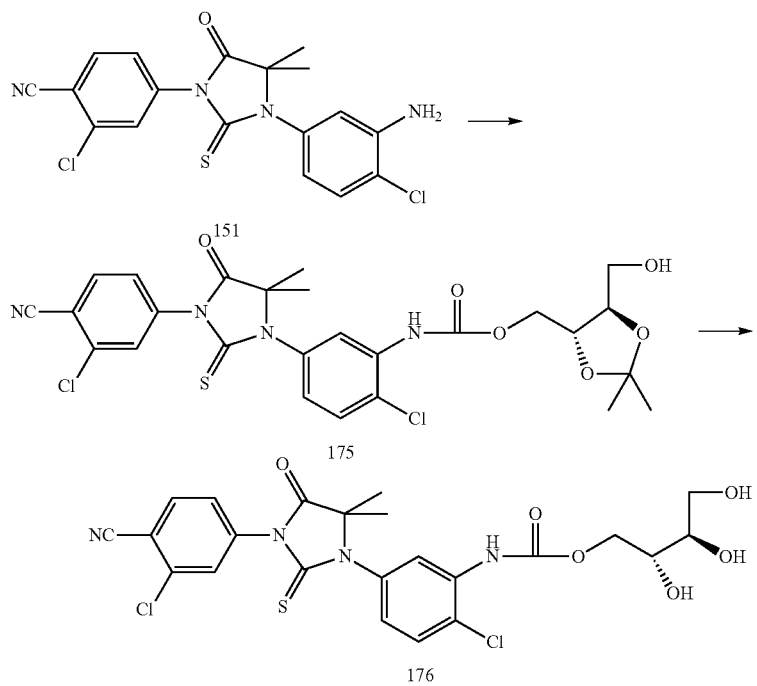

Triphosgene (240 mg) was dissolved in dichloromethane (1 mL) and added with diisopropylethylamine (0.09 mL) and a dichloromethane (1.5 mL) solution of Compound 151 (80 mg) at 0° C. and the mixture was stirred at room temperature for 20 minutes. The reaction solution was cooled to 0° C. and added with (−)-2,3-O-isopropylidene-D-threitol (990 mg) and triethylamine (0.68 mL) and the mixture was stirred at room temperature for one hour. It was added with water, and the mixture was extracted with dichloromethane, and the organic layer was dried with sodium sulfate, filtered, and concentrated under reduced pressure, and purified by flash column chromatography (eluent; Hexane ethyl acetate=7:3-1:1) to obtain Compound 175. This was dissolved in tetrahydrofuran (0.2 mL) and added with 6 N hydrochloric acid (0.4 mL) and the mixture was stirred at room temperature for one hour. It was added with water, extracted with ethyl acetate and the organic layer was dried with sodium sulphate, filtered, concentrated under reduced pressure, and purified by thin layer chromatography to obtain 44.4 mg (yield 33%) of the target compound (Compound 176).

Rf value (silica gel plate, dichloromethane:methanol=10:1): 0.35.

MS(ESI)m/z: 552.9 ([M+H]$^+$).

Example 78

[Formula 142]

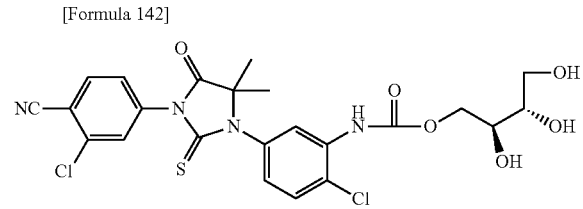

This compound was synthesized by a method similar to that in Example 77.

Rf value (silica gel plate, dichloromethane:methanol=10:1): 0.35.

MS(ESI)m/z: 575.0 ([M+Na]$^+$).

Example 79

[Formula 143]

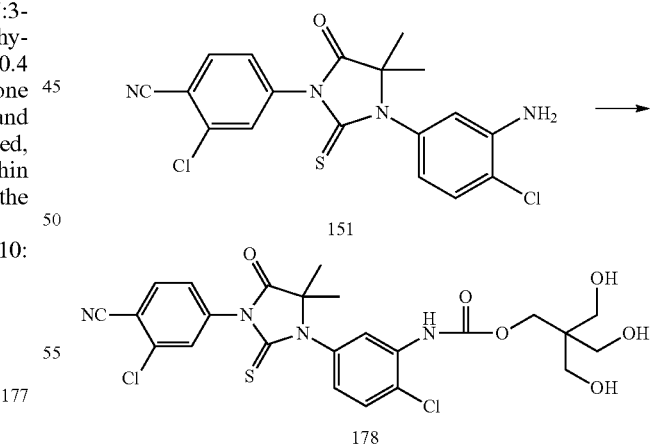

Triphosgene (240 mg) was dissolved in dichloromethane (0.5 mL) and added with diisopropylethylamine (0.09 mL) and a dichloromethane (1 mL) solution of Compound 151 (100 mg) at 0° C. and the mixture was stirred at room temperature for 30 minutes. The reaction solution was cooled to 0° C. and added with pentaerythritol (673 mg) and dichloromethane (1 mL) solution of diisopropylethylamine (0.86 mL) and the mixture was stirred at room temperature overnight. It was added with water and the mixture was extracted with dichloromethane, the organic layer was washed with a saturated sodium hydrogen carbonate, dried with anhydrous magnesium sulphate, filtered, concentrated under reduced pressure, and purified by flash column chromatography and thin layer chromatography to obtain 25.7 mg (yield 18%) of the target compound (Compound 178).

Rf value (silica gel plate, dichloromethane:methanol=10:1): 0.18.

MS(ESI)m/z: 567.0 ([M+H]$^+$).

Example 80

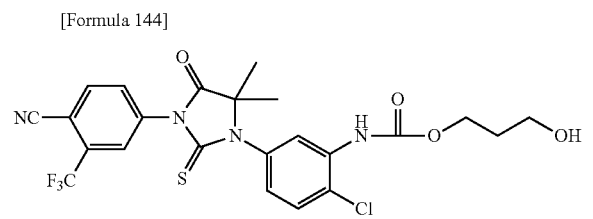

[Formula 144]

179

This compound was synthesized by a method similar to that in Example 79.

Rf value (silica gel plate, chloroform:methanol=20:1): 0.22.

$^1$H-NMR (400 MHz, CDCl$_3$) δ: 1.62 (6H, s), 1.81 (1H, t, J=5.7 Hz), 1.92-1.98 (2H, m), 3.75-3.79 (2H, m), 4.38 (2H, t, J=6.0 Hz), 6.98 (1H, dd, J=8.5, 2.4 Hz), 7.28 (1H, s), 7.53 (1H, d, J=8.5 Hz), 7.84 (1H, dd, J=8.4, 1.7 Hz), 7.96 (1H, d, J=1.7 Hz), 7.99 (1H, d, J=8.4 Hz), 8.25 (1H, s).

MS(ESI)m/z: 541.1 ([M+H]$^+$).

Example 81

[Formula 145]

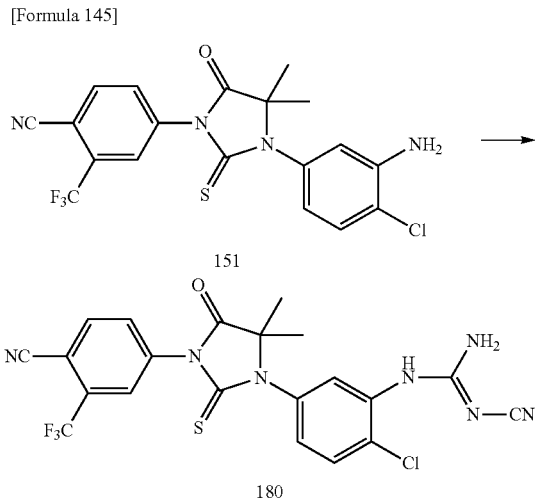

Compound 151 (200 mg) was dissolved in dimethylformamide (5 mL) and added with 4 N hydrochloric acid (0.123 mL) and sodium dicyanide (89 mg) and the mixture was stirred under nitrogen atmosphere 40° C. for two hours. After standing to cool, it was added with 4 N hydrochloric acid (0.246 mL) and sodium dicyanide (89 mg) and the mixture was stirred under nitrogen atmosphere 40° C. for two hours. After standing to cool, it was added with 4 N hydrochloric acid (0.246 mL) and sodium dicyanide (89 mg) and the mixture was stirred under nitrogen atmosphere 40° C. overnight. After standing to cool, it was added with 4 N hydrochloric acid (0.246 mL) and sodium dicyanide (89 mg) and the mixture was stirred under nitrogen atmosphere 40° C. for two hours. The reaction solution was added with water and extracted with ethyl acetate, and the organic layer was washed with brine, dried with anhydrous magnesium sulphate, filtered, concentrated under reduced pressure, and purified by flash column chromatography (eluent; hexane:ethyl acetate=1:0-1:3) and thin-layer chromatography (eluent; hexane:ethyl acetate=1:3) to obtain 50 mg (yield 22%) of the target compound (Compound 180).

Rf value (silica gel plate, hexane:ethyl acetate=1:2): 0.23.

MS(ESI)m/z: 471.9 ([M+H]$^+$).

Example 82

[Formula 146]

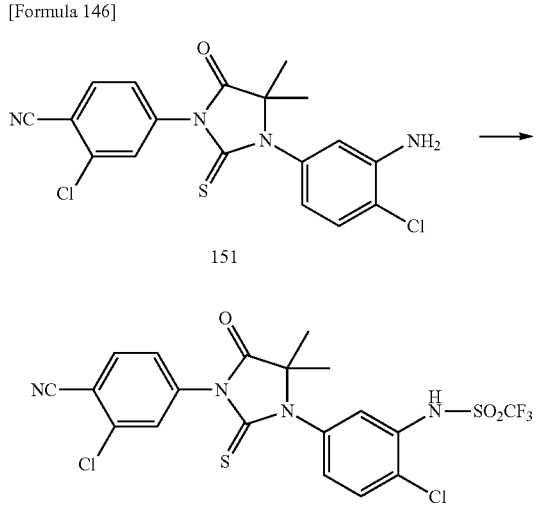

Compound 151 (20 mg) was dissolved in dichloromethane (0.04 mL) and added with triethylamine (0.0057 mL). The reaction solution was cooled to 0° C. and added dropwise with anhydrous trifluoromethane sulfonic acid (0.016 mL) while stirring for 10 minutes. The reaction solution was added with 0.1 N NaOH and the mixture was extracted with dichloromethane, and the organic layer was dried with sodium sulfate, filtered, concentrated under reduced pressure, and purified by thin layer chromatography (dichloromethane:methanol=10:1) to obtain 7.4 mg of the salt with triethylamine of the target compound (Compound 181).

$^1$H-NMR (400 MHz, CDCl$_3$) δ: 1.62 (6H, s), 1.81 (1H, t, J=5.7 Hz), 1.92-1.98 (2H, m), 3.75-3.79 (2H, m), 4.38 (2H, t, J=6.0 Hz), 6.98 (1H, dd, J=8.5, 2.4 Hz), 7.28 (1H, s), 7.53 (1H, d, J=8.5 Hz), 7.84 (1H, dd, J=8.4, 1.7 Hz), 7.96 (1H, d, J=1.7 Hz), 7.99 (1H, d, J=8.4 Hz), 8.25 (1H, s).

MS(ESI)m/z: 537.0 ([M+H]$^+$).

Example 83

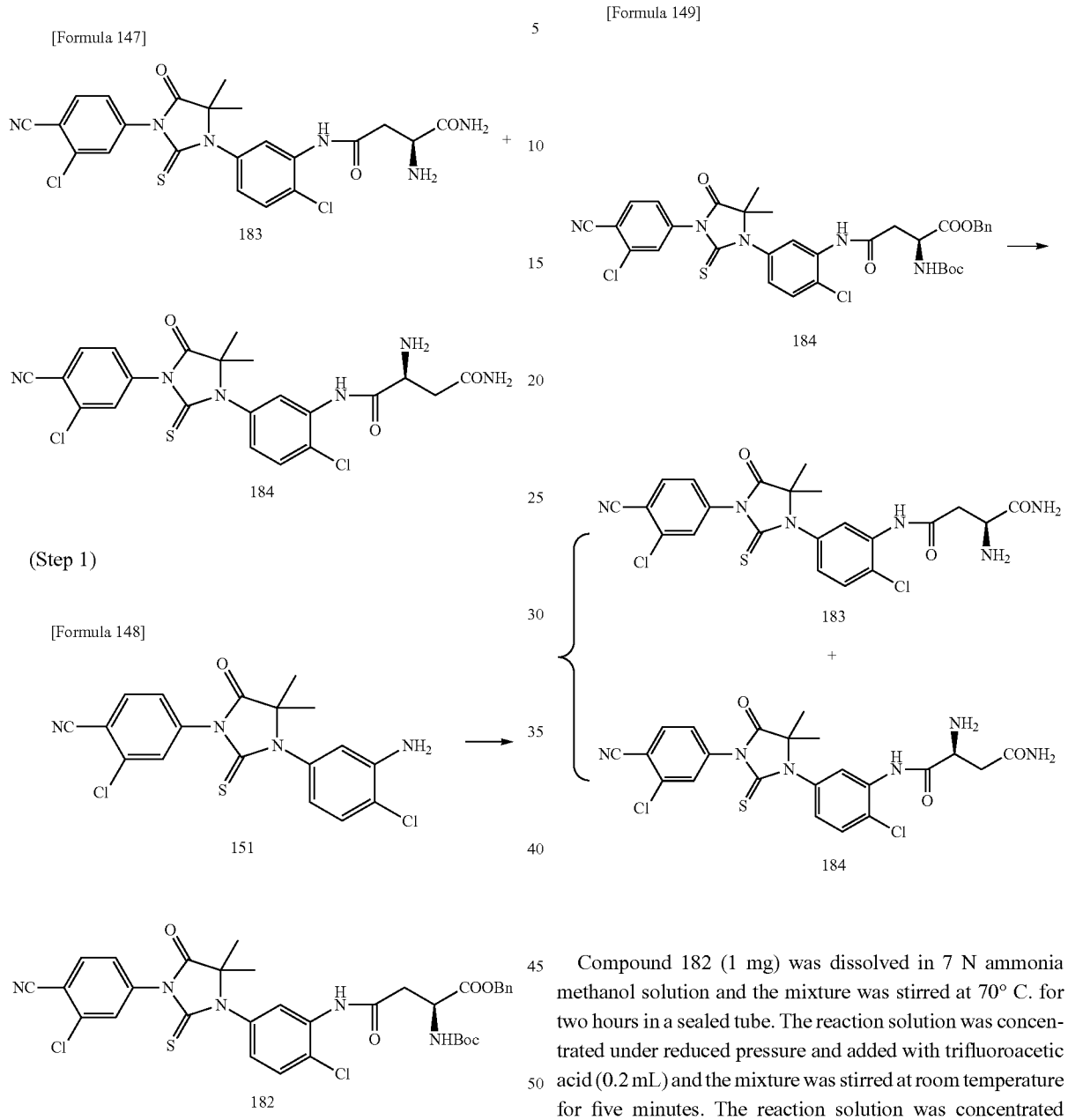

[Formula 147]

183

184

(Step 1)

[Formula 148]

151

182

Boc-Asp-OBzl (180 mg) was dissolved in dichloromethane (1 mL) and added with diisopropylethylamine (0.193 mL). It was cooled to 0° C. and added dropwise with thionyl chloride (0.0365 mL) and the mixture was stirred at 0° C. for five minutes. It was added with Compound 151 (150 mg) and the mixture was stirred at 0° C. for 10 minutes. It was added with dimethylaminopyridine (48.8 mg) and the mixture was stirred at room temperature overnight. The reaction solution was concentrated under reduced pressure and purified by flash column chromatography to obtain 70.1 mg (yield 27%) of the target compound (Compound 182).

Rf value (silica gel plate, hexane:ethyl acetate=1:1): 0.60.

MS(ESI)m/z: 732.0 ([M+Na]$^+$).

(Step 2)

[Formula 149]

184

183

184

Compound 182 (1 mg) was dissolved in 7 N ammonia methanol solution and the mixture was stirred at 70° C. for two hours in a sealed tube. The reaction solution was concentrated under reduced pressure and added with trifluoroacetic acid (0.2 mL) and the mixture was stirred at room temperature for five minutes. The reaction solution was concentrated under reduced pressure and purified by flash column chromatography to obtain 0.9 mg of the target compound (a mixture of Compound 183 and Compound 184).

Compound A,

RT: 16.838 min.

MS(ESI)m/z: 519.1 ([M+H]$^+$).

Compound B,

RT: 17.278 min.

MS(ESI)m/z: 519.1 ([M+H]$^+$).

(Among the above compounds A and B, either one is Compound 183 and the other is Compound 184.)

Example 84

[Formula 150]

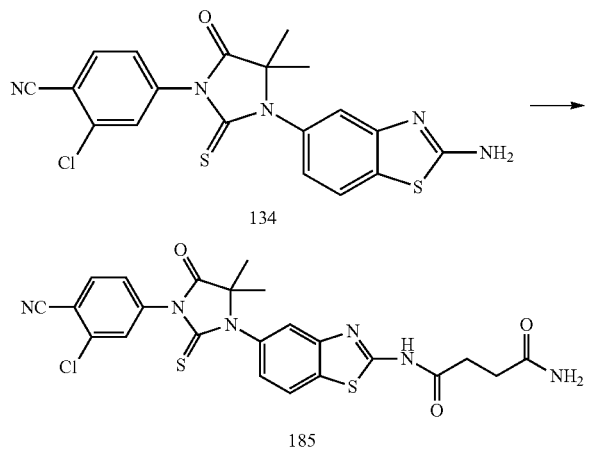

Compound 134 (50 mg) was dissolved in acetonitrile (0.2 mL) and added with succinic anhydride (15 mg) and dimethylaminopyridine (18.3 mg) and the mixture was stirred at 80° C. for 30 minutes. It was added with phthalic anhydride (30 mg) and dimethylaminopyridine (36.6 mg) and the mixture was stirred at 80° C. for 30 minutes. The reaction solution was cooled to 0° C. and added with 7 N ammonia methanol solution (2 mL) and the mixture was stirred at room temperature for 30 minutes.

The reaction solution was concentrated under reduced pressure and purified by flash column chromatography to obtain 9.5 mg (yield 15%) of the target compound (Compound 185).

Rf value (silica gel plate, dichloromethane:methanol=10:1): 0.30.

MS(ESI)m/z: 527.0 ([M+H]$^+$).

Example 85

[Formula 151]

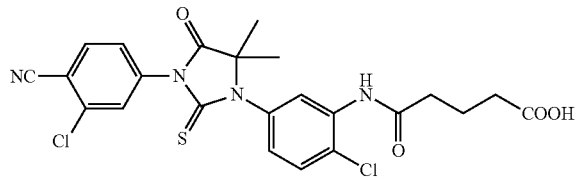

(Step 1)

[Formula 152]

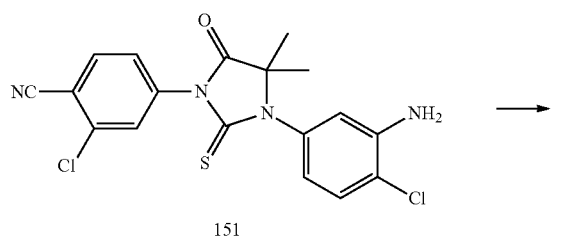

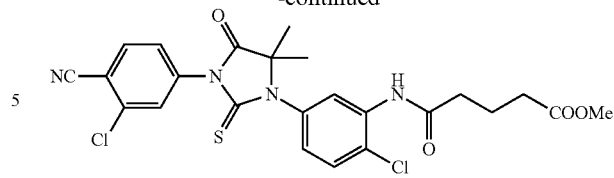

Compound 151 (41 mg) was dissolved in dichloromethane (3 mL) and added with triethylamine (0.021 mL) and methyl 4-(chloroformyl)butyrate (0.021 mL) and the mixture was stirred at room temperature for two hours. Furthermore, it was added with triethylamine (0.021 mL) and methyl 4-(chloroformyl)butyrate (0.021 mL) and the mixture was stirred at room temperature for one hour. It was added with water and the mixture was extracted with dichloromethane, and the organic layer was dried and concentrated under reduced pressure and purified by flash column chromatography (hexane:ethyl acetate=1:0-65:35) to obtain 45 mg (yield 84%) of the target compound (Compound 186).

Rf value (silica gel plate, hexane:ethyl acetate=1:1): 0.44.

MS(ESI)m/z: 532.9 ([M+H]$^+$).

(Step 2)

[Formula 153]

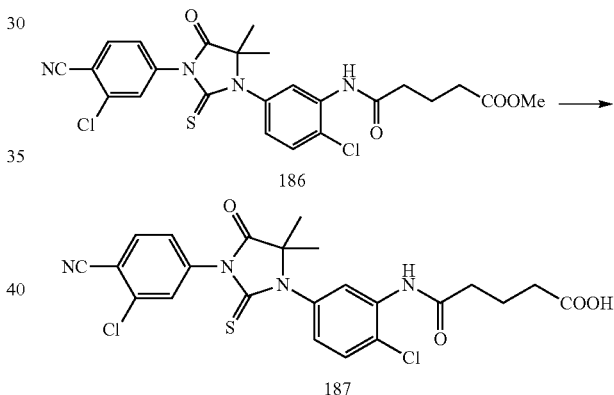

Compound 186 (34 mg) was dissolved in methanol (1 g) and added with 5% NaOH (0.3 g) and the mixture was stirred at 30° C. for 2.5 hours. It was neutralized with diluted hydrochloric acid, concentrated under reduced pressure, and purified by thin-layer chromatography to obtain 23 mg (yield 69%) of the target compound (Compound 187).

Rf value (silica gel plate, chloroform:methanol=10:1): 0.48.

MS(ESI)m/z: 518.9 ([M+H]$^+$)

Example 86

[Formula 154]

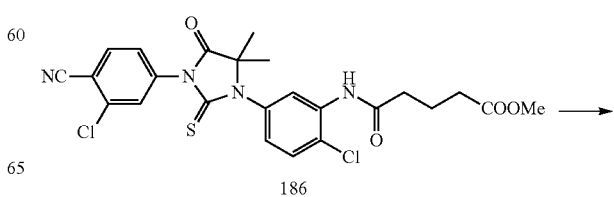

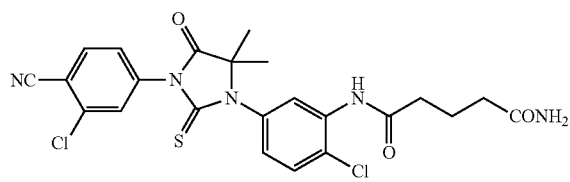

188

Compound 186 (25 mg) was dissolved in 7 N ammonia methanol solution (3 mL) and the mixture was stirred at 70° C. for 24 hours. The reaction solution was concentrated under reduced pressure and purified by thin-layer chromatography (chloroform:methanol=10:1) to obtain 5 mg (yield 21%) of the target compound (Compound 188).

Rf value (silica gel plate, chloroform:methanol=10:1): 0.28.

MS(ESI)m/z: 517.8 ([M+H]⁺).

Example 87

[Formula 155]

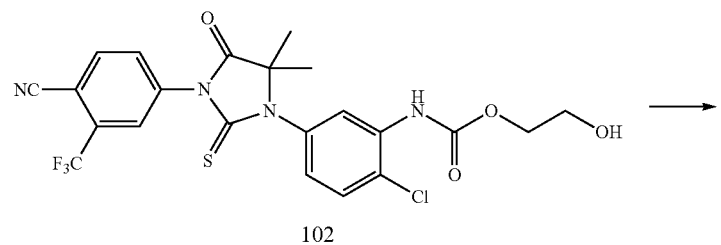

189

Compound 189 was obtained by the method similar to that in Example 85.

Rf value (silica gel plate, chloroform:methanol=10:1): 0.31.

MS(ESI)m/z: 505.0 ([M+H]⁺).

Example 88

[Formula 156]

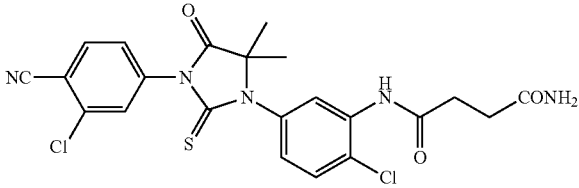

190

Compound 190 was obtained by the method similar to that in Example 86.

Rf value (silica gel plate, dichloromethane:methanol=20:1): 0.21.

$^1$H-NMR (270 MHz, CD$_3$OD) δ: 1.55 (6H, s), 2.60 (2H, t, J=6.7 Hz), 2.76 (2H, t, J=6.7 Hz), 7.17 (1H, dd, J=8.6, 2.4 Hz), 7.57 (1H, d, J=8.6 Hz), 7.62 (1H, dd, J=8.4, 2.0 Hz), 7.85 (1H, d, J=2.0 Hz), 7.93 (1H, d, J=8.4 Hz), 7.99 (1H, d, J=2.4 Hz).

MS(ESI)m/z: 503.9 ([M+H]⁺).

Example 89

[Formula 157]

102

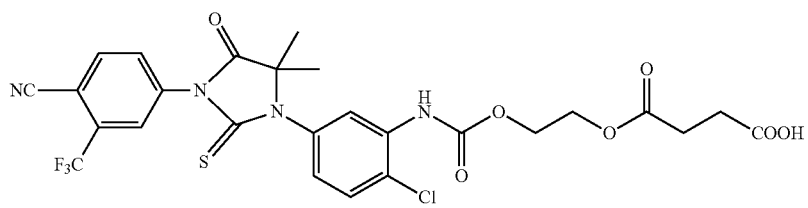

191

Compound 102 (100 mg) and succinic anhydride (24.7 mg) were dissolved in dichloromethane (1 mL) and added with diisopropylethylamine (0.043 mL) at 0° C. and the mixture was stirred at room temperature for two hours. It was added with water and 0.5 N hydrochloric acid, and the mixture was extracted with dichloromethane, and the organic layer was washed with water and brine, dried with anhydrous magnesium sulphate, filtered, concentrated under reduced pressure, and purified by flash column chromatography (dichloromethane/methanol) to obtain 102.9 mg (yield 86%) of the target compound (Compound 191).

Rf value (silica gel plate, dichloromethane:methanol=10:1): 0.44.

MS(ESI)m/z: 626.9 ([M+H]$^+$).

Example 90

[Formula 158]

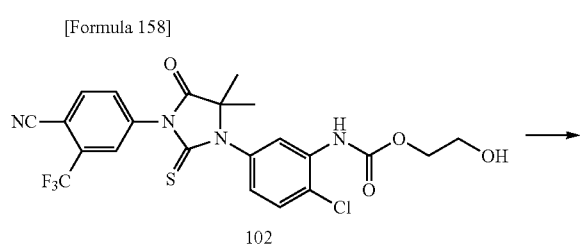

Compound 102 (100 mg) and N,N-dimethylglycine (39 mg) were dissolved in dichloromethane (1.9 mL) and added with 1-(N,N-dimethylaminopropyl)-3-ethyl carbodiimide hydrochloride (73 mg) and dimethylaminopyridine (23 mg) and the mixture was stirred at room temperature for 4.5 hours. It was added with 1-(N,N-dimethylaminopropyl)-3-ethyl carbodiimide hydrochloride (36.5 mg) and dimethylaminopyridine (11.5 mg) and the mixture was stirred at room temperature for 2.5 hours. The reaction solution was added with water and the mixture was extracted with dichloromethane and the organic layer was washed with water and a saturated sodium hydrogen carbonate, dried with anhydrous magnesium sulphate, filtered, concentrated under reduced pressure, and purified by flash column chromatography to obtain 68 mg (yield 58%) of the target compound (Compound 192).

Rf value (silica gel plate, hexane:ethyl acetate=1:1): 0.25.

MS(ESI)m/z: 612.0 ([M+H]$^+$).

Example 91

[Formula 159]

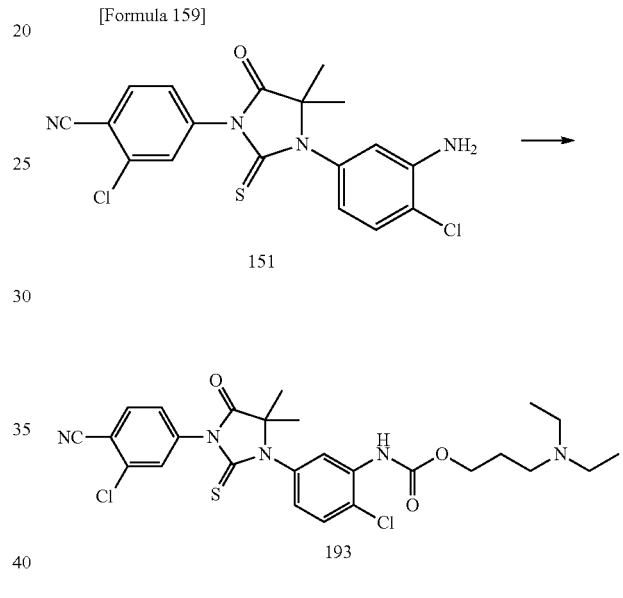

Compound 193 was obtained by the method similar to that in Example 71.

Rf value (silica gel plate, dichloromethane:methanol=20:1): 0.18.

MS(ESI)m/z: 562.2 ([M+H]$^+$).

Example 92

[Formula 160]

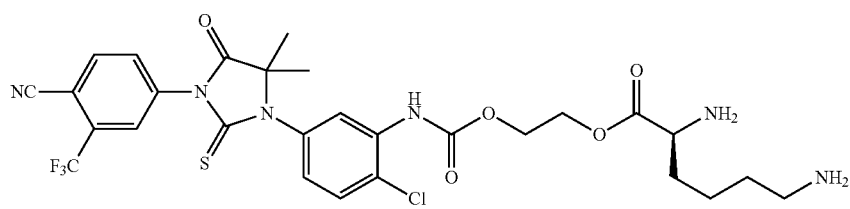

(Step 1)

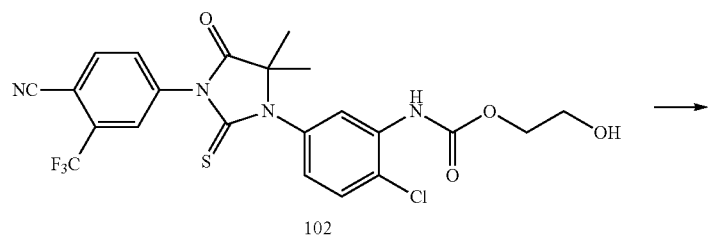

[Formula 161]

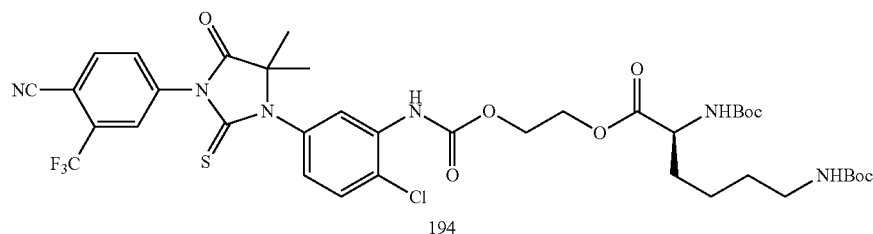

Compound 102 (200 mg) was dissolved in dichloromethane (5 mL) and added with Boc-Lys (Boc)-OH (263 mg) and added with 1-(N,N-dimethylaminopropyl)-3-ethyl carbodiimide hydrochloride (146 mg) and dimethylaminopyridine (46 mg) under nitrogen atmosphere at 0° C. and the mixture was stirred at room temperature for two hours. The reaction solution was added with water, and the mixture was extracted with dichloromethane, and the organic layer was washed with a saturated sodium hydrogen carbonate aqueous solution, 10% citric acid aqueous solution and brine, dried, concentrated under reduced pressure, and purified by flash column chromatography to obtain 290 mg (yield 89%) of the target compound (Compound 194).

Rf value (silica gel plate, hexane:ethyl acetate=1:1): 0.48.
MS(ESI)m/z: 877.1 ([M+Na]$^+$).

(Step 2)

[Formula 162]

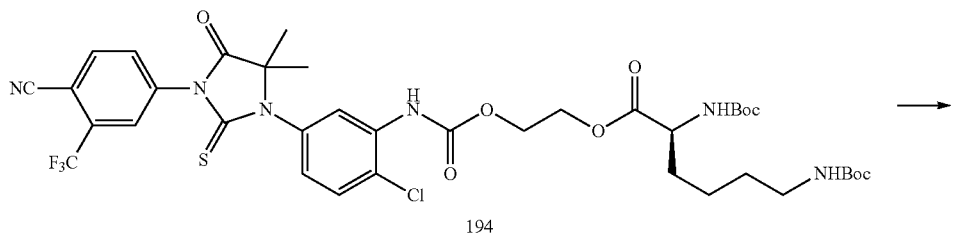

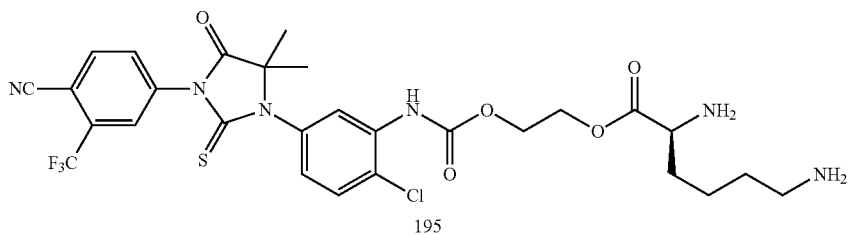

Compound 194 (290 mg) was dissolved in dichloromethane (5 mL) and added with trifluoroacetic acid (5 mL) and the mixture was stirred at a under nitrogen atmosphere at room temperature for 30 minutes. The reaction solution was concentrated under reduced pressure, and 400 mg of the target compound (Compound 195) was obtained as trifluoroacetate.

Rf value (an NH plate, dichloromethane:methanol=20:1): 0.41.

MS(ESI)m/z: 655.2 ([M+H]$^+$).

Example 93

[Formula 163]

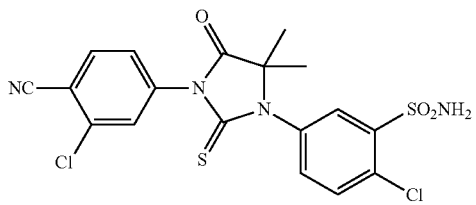

(Step 1)

[Formula 164]

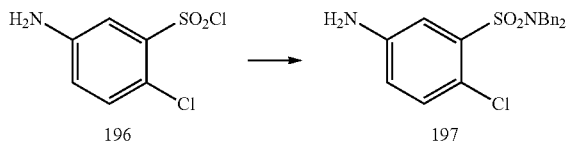

Compound 196 (880.9 mg) was suspended in dichloromethane (16 mL), and added dropwise with dibenzylamine (2.25 mL) at 0° C. and the mixture was stirred at room temperature overnight. The reaction solution was added with water, extracted with ethyl acetate and the organic layer was washed with brine, dried with anhydrous magnesium sulphate, filtered, and concentrated under reduced pressure. The obtained residue was added with ethyl acetate and hexane and the deposits were separated by filtration and vacuum-dried to obtain 583.0 mg (yield 39%) of the target compound (Compound 197).

Rf value (silica gel plate, hexane:ethyl acetate=2:1): 0.32.

MS(ESI)m/z: 387.0 ([M+H]$^+$).

(Step 2)

[Formula 165]

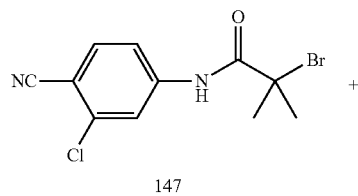

-continued

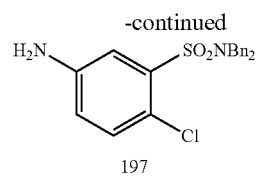

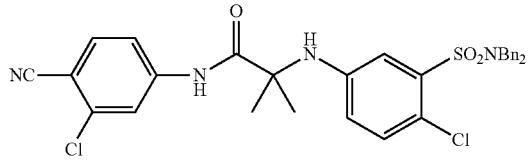

Compound 147 (301.7 mg) and Compound 197 (386.9 mg) were dissolved in tetrahydrofuran (5 mL) and added with potassium t-butoxide (116.1 mg) under nitrogen atmosphere at 0° C. and the mixture was stirred at room temperature overnight. The reaction solution was added with a saturated ammonium chloride aqueous solution, extracted with ethyl acetate, and the organic layer was washed with brine, dried with anhydrous magnesium sulphate, filtered, concentrated under reduced pressure, and purified by flash column chromatography to obtain 287.5 mg (yield 47%) of the target compound (Compound 198).

Rf value (silica gel plate, hexane:ethyl acetate=2:1): 0.16.

MS(ESI)m/z: 607.0 ([M+H]$^+$).

(Step 3)

[Formula 166]

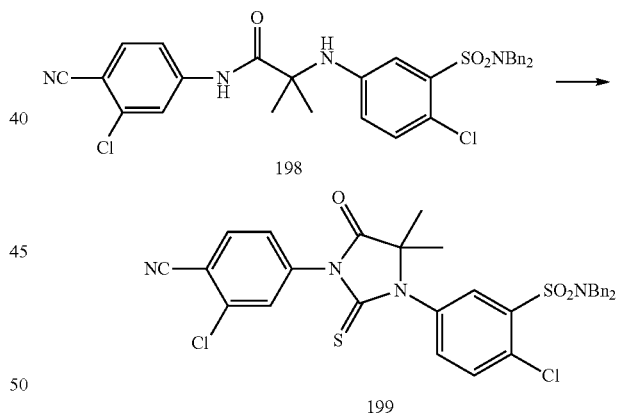

Compound 198 (271.2 mg) was dissolved in tetrahydrofuran (3 mL) and added with sodium hydride (120 mg) and Compound 149 (0.2 mL) under nitrogen atmosphere at 0° C. and the mixture was stirred at room temperature for 30 minutes. The reaction solution was added with water at 0° C., and extracted with ethyl acetate, and the organic layer was washed with brine, dried with anhydrous magnesium sulphate, filtered, concentrated under reduced pressure, and purified by flash column chromatography (eluent; hexane ethyl acetate=1:0-3:2) to obtain 141.9 mg (yield 49%) of the target compound (Compound 199).

Rf value (silica gel plate, hexane:ethyl acetate=1:1): 0.62.

MS(ESI)m/z: 649.1 ([M+H]$^+$).

(Step 4)

[Formula 167]

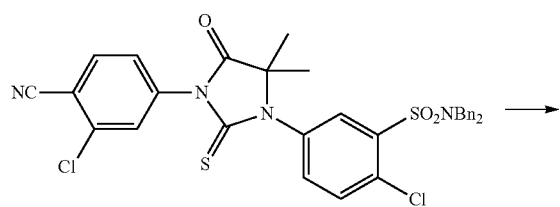

Compound 199 (109.9 mg) was added with trifluoromethane sulfonic acid (1 mL) at 0° C. and the mixture was stirred at room temperature for five minutes. The reaction solution was added in an ice-cooled water and the mixture was extracted with ethyl acetate. The organic layer was washed with a saturated sodium hydrogen carbonate aqueous solution and brine, dried with anhydrous magnesium sulphate, filtered, concentrated under reduced pressure, and purified by flash column chromatography to obtain an object (Compound 200).

Rf value (silica gel plate, hexane:ethyl acetate=1:3): 0.53. MS(ESI)m/z: 469.0 ([M+H]$^+$).

Example 94

[Formula 168]

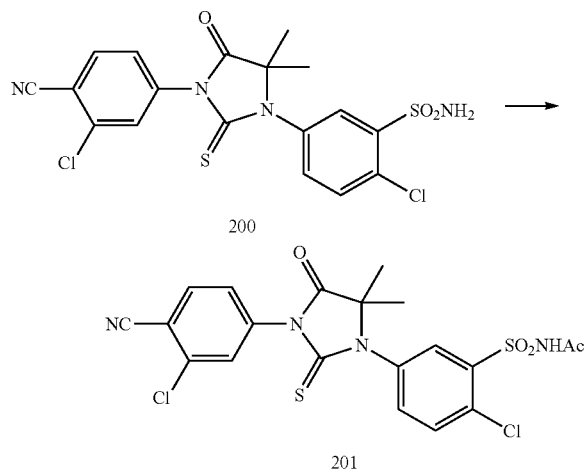

Compound 200 (38.4 mg) was dissolved in dichloromethane (1.6 mL) and added with acetic anhydride (0.023 mL) and triethylamine (0.034 mL) and the mixture was stirred at room temperature for three hours. The reaction solution was added with water, and the mixture was extracted with dichloromethane, and the organic layer was dried and concentrated under reduced pressure to obtain the target compound (Compound 201).

Rf value (silica gel plate, hexane:ethyl acetate=1:3): 0.25. MS(ESI)m/z: 511.0 ([M+H]$^+$).

Example 95

[Formula 169]

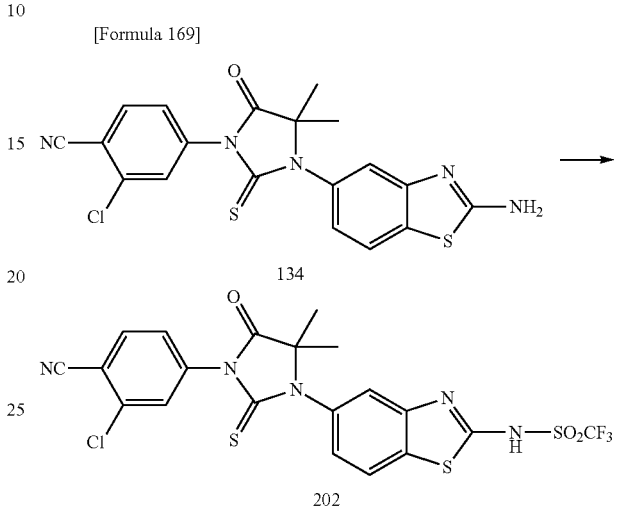

Compound 134 (21.3 mg) and 2-[N,N-bis(trifluoromethanesulfonyl)amino]pyridine (53.5 mg) were dissolved in tetrahydrofuran (0.2 mL) and added dropwise with 1 M sodium hexamethyldisilazide tetrahydrofuran solution (0.2 mL) at 0° C. and the mixture was stirred for 30 minutes. The reaction solution was added with methanol (1 mL) and was purified by thin-layer chromatography (dichloromethane/methanol) to obtain 12.7 mg (yield 46%) of the target compound (Compound 202).

Rf value (an NH plate, dichloromethane:methanol=10:1): 0.25.

MS(ESI)m/z: 560.0 ([M+H]$^+$).

[Bilogical Evaluation Test]

Preparation of 11A11B2 Cell

HeLa cells (purchased from Dai-Nippon Seiyaku K. K.) were cultured overnight in Dulbecco's Modified Eagle Medium containing no phenol red, but containing 3% charcoal-treated fetal bovine serum (hereafter referred to as DCC-FBS) (this medium is hereafter referred to as phenol-red-free DMEM). An MMTV-Luc-Hyg vector (reporter plasmid with mouse mammary tumor virus long terminal repeat, containing an androgen response element and a hygromycin resistance gene: a vector obtained by substituting a chloramphenicol acetyl transferease gene of a GM-CAT vector (A.T.C.C No. 67282) purchased from the A.T.C.C. with the firefly luciferase gene, and inserting a hygromycin resistance gene as a drug resistant gene), and pSG5-hAR-neo (human androgen receptor expression vector: a vector having an androgen receptor gene under the control of the SV40 promoter, and having a neomycin resistance gene inserted as a drug resistance gene) were transfected into the HeLa cells using an FuGENE™ 6 Transfection Reagent (obtained from Roche).

A clone in which transcription activity was elevated in a dose-dependent manner by dihydrotestosterone (DHT) was obtained by culturing the transfected cells in DMEM containing 500 μg/mL neomycin, 300 μg/mL hygromycin and 10% fetal bovine serum (FBS, hereinbelow). The clone cells thus obtained (11A11B2 cells) were maintained and propagated using DMEM containing 400 μg/mL neomycin, 200 μg/mL hygromycin and 10% FBS, and were propagated using phenol-red-free DMEM containing 10% DCC-FBS three to four days prior to the performance of an androgen receptor reporter gene assay.

Test Example 1

Measurement of Agonist Effect on Androgen Receptor

The 11A11B2 cells were inoculated in a white clear-bottomed 96-well microplate (COSTAR) so that the cell concentration was $1.0\times10^4$/well, and were cultured overnight using phenol-red-free DMEM containing 3% DCC-FBS (hereafter referred to as the assay medium). Samples of the assay medium containing the compounds of the Examples and compounds of the Comparative Examples were added so that the final concentrations of the compounds of the Examples and compounds of the Comparative Examples were 1, 10, 100, 1,000 and 10,000 nmol/L), and the cells were cultured for 48 hours, after which the transcription activity value was measured. The transcription activity was measured using a Bright-Glo™ Luciferase Assay System (Promega).

The transcription activity rates of the compounds of the Examples were calculated from the transcription activity measured by the abovementioned method, with the transcription activity value obtained at 0.1 nmol/L DHT taken as 100%, and the transcription activity value in the case of the assay medium alone taken as 0%. The compound concentration showing a transcription activity of 5% (EC5 value) was calculated from a linear equation for two points on either side of 5%.

Test Example 2

Investigation of Antagonist Effect on Androgen Receptor

The 11A11B2 cells were inoculated in a white clear-bottomed 96-well microplate (COSTAR) so that the cell concentration was $1.0\times10^4$/well, and were cultured overnight. The assay medium containing DHT was added so that the final concentration of DHT was 0.1 nmol/L, and samples of the assay medium containing the compounds of the Examples or compounds of the Comparative Examples were added so that the final concentrations of the compounds of the Examples or compounds of the Comparative Examples were 1, 10, 100, 1,000 and 10,000 nmol/L, respectively. After culturing for 48 hours, the transcription activity values were measured. The transcription activity was measured using a Bright-Glo™ Luciferase Assay System (Promega).

The transcription activity rates of the compounds of the Examples were calculated from the transcription activity measured by the abovementioned method, with the transcription activity value obtained at 0.1 nmol/L DHT taken as 100%, and the transcription activity value in the case of the assay, medium alone taken as 0%.

In the present test system (Test Example 2), there were cases in which the transcription activity dropped to 50% in compounds showing both antagonist activity and agonist activity. Accordingly, the value obtained by subtracting the transcription activity rate of Test Example 1 (Investigation of Agonist Activity) from the transcription activity rate of Test Example 2 (Investigation of Antagonist Activity) was used to calculate the compound concentration at which a transcription activity of 50% was shown (IC50 value). The IC50 value was calculated from a linear equation for two points on either side of 50%.

The results of Test Examples 1 and 2 are shown in Table 1.

TABLE 1

| Compound | EC5 (nM) | IC50 (nM) | EC5/IC50 |
|---|---|---|---|
| 4-[3-(1-ethoxycarbonylpiperidin-4-yl)-4,4-dimethyl-5-oxo-2-thioxoimidazolidin-1-yl]-2-chlorobenzonitrile (compound of Example 2) | 8000 | 80 | 100 |
| 4-[3-(1-acetylpiperidin-4-yl)-4,4-dimethyl-5-oxo-2-thioxoimidazolidin-1-yl]-2-trifluoromethylbenzonitrile (compound of Example 4) | >10000 | 300 | >33 |
| 4-[3-(1-ethanesulfonylpiperidin-4-yl)-4,4-dimethyl-5-oxo-2-thioxoimidazolidin-1-yl]-2-trifluoromethylbenzonitrile (compound of Example 5) | >10000 | 300 | >33 |
| 4-[3-(1-acetylpiperidin-4-yl)-4,4-dimethyl-5-oxo-2-thioxoimidazolidin-1-yl]-2-chlorobenzonitrile (compound of Example 6) | >10000 | 200 | >50 |
| 4-[3-(1-propionylpiperidin-4-yl)-4,4-dimethyl-5-oxo-2-thioxoimidazolidin-1-yl]-2-chlorobenzonitrile (compound of Example 7) | >10000 | 300 | >33 |
| 4-[3-(1-propanesulfonylpiperidin-4-yl)-4,4-dimethyl-5-oxo-2-thioxoimidazolidin-1-yl]-2-chlorobenzonitrile (compound of Example 8) | >10000 | 300 | >33 |
| 4-[3-(1-ethanesulfonylpiperidin-4-yl)-4,4-dimethyl-5-oxo-2-thioxoimidazolidin-1-yl]-2-chlorobenzonitrile (compound of Example 9) | >10000 | 300 | >33 |
| 4-[3-(1-ethanesulfonylpiperidin-4-yl)-4,4-dimethyl-2,5-dioxoimidazolidin-1-yl]-2-trifluoromethyl-3-methylbenzonitrile (compound of Example 10) | >10000 | 600 | >16 |
| 4-[3-(1-propanesulfonylpiperidin-4-yl)-4,4-dimethyl-2,5-dioxoimidazolidin-1-yl]-2-chloro-3-methylbenzonitrile (compound of Example 11) | >10000 | 300 | >33 |
| 4-[3-(1-propionylpiperidin-4-yl)-4,4-dimethyl-2,5-dioxoimidazolidin-1-yl]-2-chloro-3-methylbenzonitrile (compound of Example 12) | >10000 | 700 | >14 |
| {2-chloro-5-[3-(4-cyano-3-trifluoromethylphenyl)-5,5-dimethyl-2,4-dioxoimidazolidin-1-yl]phenyl}carbamic acid ethyl ester (compound of Example 13) | >10000 | 200 | >50 |
| 4-{4,4-dimethyl-3-[1-(3-methylbutyryl)-piperidin-4-yl]-5-oxo-2-thioxoimidazolidin-1-yl}-2-trifluoromethylbenzonitrile (compound of Example 14) | >10000 | 200 | >50 |
| 4-[3-(2-acetylaminobenzothiazol-5-yl)-4,4-dimethyl-5-oxo-2-thioxoimidazolidin-1-yl]-2-chlorobenzonitrile (compound of Example 16) | 3000 | 40 | 75 |
| {5-[3-(4-cyano-3-trifluoromethylphenyl)-5,5-dimethyl-4-oxo-2-thioxoimidazolidin-1-yl]-benzothiazol-2-yl}urea (compound of Example 18) | >10000 | 100 | >100 |
| {5-[3-(4-cyano-3-methoxyphenyl)-5,5-dimethyl-4-oxo-2-thioxoimidazolidin-1-yl]-benzothiazol-2-yl}urea (compound of Example 19) | >10000 | 200 | >50 |

TABLE 1-continued

| Compound | EC5 (nM) | IC50 (nM) | EC5/IC50 |
|---|---|---|---|
| {5-[3-(4-cyano-3-chlorophenyl)-5,5-dimethyl-4-oxo-2-thioxoimidazolidin-1-yl]-benzothiazol-2-yl}urea (compound of Example 20) | >10000 | 100 | >100 |
| N-{2-chloro-4-[3-(4-cyano-3-trifluoromethylphenyl)-5,5-dimethyl-2,4-dioxoimidazolidin-1-yl]-phenyl}-2-piperazin-1-ylacetamide (compound of Example 21) | >10000 | 500 | >20 |
| 4-[3-(3-acetylamino-4-chlorophenyl)-4,4-dimethyl-5-oxo-2-thioxoimidazolidin-1-yl]-2-trifluoromethylbenzonitrile (compound of Example 22) | >10000 | 200 | >50 |
| 4-[3-(3-isopropoxycarbonylamino-4-chlorophenyl)-4,4-dimethyl-2,5-dioxoimidazolidin-1-yl]-2-trifluoromethylbenzonitrile (compound of Example 23) | >10000 | 500 | >20 |
| 4-[3-(3-ethoxycarbonylamino-4-chlorophenyl)-4,4-dimethyl-2,5-dioxoimidazolidin-1-yl]-2-methoxybenzonitrile (compound of Example 24) | >10000 | 200 | >50 |
| 4-[3-(3-isopropoxycarbonylamino-4-chlorophenyl)-4,4-dimethyl-2,5-dioxoimidazolidin-1-yl]-2-methoxybenzonitrile (compound of Example 25) | >10000 | 400 | >25 |
| 4-[3-(3-n-propoxycarbonylamino-4-chlorophenyl)-4,4-dimethyl-2,5-dioxoimidazolidin-1-yl]-2-methoxybenzonitrile (compound of Example 26) | >10000 | 200 | >50 |
| {2-chloro-5-[3-(4-cyano-3-trifluoromethylphenyl)-5,5-dimethyl-2,4-dioxoimidazolidin-1-yl]phenyl}-carbamic acid 3-hydroxypropyl ester (compound of Example 27) | >10000 | 400 | >25 |
| {2-chloro-5-[3-(4-cyano-3-trifluoromethylphenyl)-5,5-dimethyl-2,4-dioxoimidazolidin-1-yl]phenyl}-carbamic acid 2-dimethylamino ethyl ester (compound of Example 28) | >10000 | 500 | >20 |
| {2-chloro-5-[3-(4-cyano-3-trifluoromethylphenyl)-5,5-dimethyl-2,4-dioxoimidazolidin-1-yl]phenyl}-carbamic acid 2-(4-methylpiperazin-1-yl)ethyl ester (compound of Example 29) | >10000 | 500 | >20 |
| {2-chloro-5-[3-(4-cyano-3-methoxyphenyl)-5,5-dimethyl-2,4-dioxoimidazolidin-1-yl]phenyl}-carbamic acid methyl ester (compound of Example 30) | >10000 | 500 | >20 |
| {2-chloro-5-[3-(4-cyano-3-chlorophenyl)-5,5-dimethyl-2,4-dioxoimidazolidin-1-yl]phenyl}-carbamic acid 2-dimethylaminoethyl ester (compound of Example 31) | >10000 | 600 | >16 |
| {2-chloro-5-[3-(4-cyano-3-trifluoromethylphenyl)-5,5-dimethyl-2,4-dioxoimidazolidin-1-yl]phenyl}-carbamic acid 3-dimethylaminopropyl ester (compound of Example 32) | >10000 | 500 | >20 |
| {2-chloro-5-[3-(4-cyano-3-trifluoromethylphenyl)-5,5-dimethyl-2,4-dioxoimidazolidin-1-yl]phenyl}-carbamic acid 4-hydroxybutyl ester (compound of Example 33) | >10000 | 300 | >33 |
| 4-[3-(4-cyano-3-trifluoromethylphenyl)-5,5-dimethyl-4-oxo-2-thioxoimidazolidin-1-yl]piperidine-1-carbamic acid 2-dimethylaminoethyl ester (compound of Example 36) | >10000 | 500 | >20 |
| {2-chloro-5-[3-(4-cyano-3-trifluoromethylphenyl)-5,5-dimethyl-2,4-dioxoimidazolidin-1-yl]phenyl}-carbamic acid 2-aminoethyl ester (compound of Example 37) | >10000 | 700 | >14 |
| 4-[3-(1-ethylaminocarbonylpiperidin-4-yl)-4,4-dimethyl-5-oxo-2-thioxoimidazolidin-1-yl]-2-trifluoromethylbenzonitrile (compound of Example 38) | >10000 | 1000 | >10 |
| 4-[3-(1-n-propylaminocarbonylpiperidin-4-yl)-4,4-dimethyl-5-oxo-2-thioxoimidazolidin-1-yl]-2-trifluoromethylbenzonitrile (compound of Example 39) | >10000 | 900 | >11 |
| 4-[3-(1-ethylaminocarbonylpiperidin-4-yl)-4,4-dimethyl-5-oxo-2-thioxoimidazolidin-1-yl]-2-chlorobenzonitrile (compound of Example 40) | >10000 | 1000 | >10 |
| 4-[3-(1-n-propylaminocarbonylpiperidin-4-yl)-4,4-dimethyl-5-oxo-2-thioxoimidazolidin-1-yl]-2-chlorobenzonitrile (compound of Example 41) | >10000 | 500 | >20 |
| 4-[3-(1-ethylaminosulfonylpiperidin-4-yl)-4,4-dimethyl-5-oxo-2-thioxoimidazolidin-1-yl]-2-trifluoromethylbenzonitrile (compound of Example 42) | >10000 | 700 | >14 |
| 4-[3-(4-cyano-3-trifluoromethylphenyl)-5,5-dimethyl-4-oxo-2-thioxoimidazolidin-1-yl]piperidine-1-carboxylic acid 2-hydroxyethyl ester (compound of Example 44) | >10000 | 600 | >16 |
| 4-[3-(4-cyano-3-trifluoromethylphenyl)-5,5-dimethyl-4-oxo-2-thioxoimidazolidin-1-yl]piperidine-1-carboxylic acid 2,3-dihydroxypropyl ester (compound of Example 45) | >10000 | 1000 | >10 |
| {2-chloro-5-[3-(4-cyano-3-trifluoromethylphenyl)-5,5-dimethyl-4-oxo-2-thioxoimidazolidin-1-yl]phenyl}-carbamic acid 2-hydroxyethyl ester (compound of Example 46) | >10000 | 300 | >33 |
| {2-chloro-5-[3-{4-cyano-3-chlorophenyl)-5,5-dimethyl-4-oxo-2-thioxoimidazolidin-1-yl]phenyl}-carbamic acid 2-hydroxyethyl ester (compound of Example 47) | >10000 | 300 | >33 |
| {2-chloro-5-[3-(4-cyano-3-methoxyphenyl)-5,5-dimethyl-4-oxo-2-thioxoimidazolidin-1-yl]phenyl}-carbamic acid 2-hydroxyethyl ester (compound of Example 48) | >10000 | 500 | >20 |
| {2-chloro-5-[3-(4-cyano-3-trifluoromethylphenyl)-5,5-dimethyl-4-oxo-2-thioxoimidazolidin-1-yl]phenyl}-carbamic acid 2,3-dihydroxypropyl ester (compound of Example 49) | >10000 | 300 | >33 |

TABLE 1-continued

| Compound | EC5 (nM) | IC50 (nM) | EC5/IC50 |
|---|---|---|---|
| {2-chloro-5-[3-(4-cyano-3-chlorophenyl)-5,5-dimethyl-4-oxo-2-thioxoimidazolidin-1-yl]phenyl}-carbamic acid 2,3-dihydroxypropyl ester (compound of Example 50) | >10000 | 300 | >33 |
| {2-chloro-5-[3-(4-cyano-3-methoxyphenyl)-5,5-dimethyl-4-oxo-2-thioxoimidazolidin-1-yl]phenyl}-carbamic acid 2,3-dihydroxypropyl ester (compound of Example 51) | >10000 | 1000 | >10 |
| {2-chloro-5-[3-(4-cyano-3-trifluoromethylphenyl)-5,5-dimethyl-4-oxo-2-thioxoimidazolidin-1-yl]phenyl}-carbamic acid 2-dimethylaminoethyl ester (compound of Example 52) | >10000 | 300 | >33 |
| {2-chloro-5-[3-(4-cyano-3-chlorophenyl)-5,5-dimethyl-4-oxo-2-thioxoimidazolidin-1-yl]phenyl}-carbamic acid 2-dimethylaminoethyl ester (compound of Example 53) | >10000 | 300 | >33 |
| {2-chloro-5-[3-(4-cyano-3-methoxyphenyl)-5,5-dimethyl-4-oxo-2-thioxoimidazolidin-1-yl]phenyl}-carbamic acid 2-dimethylaminoethyl ester (compound of Example 54) | >10000 | 500 | >20 |
| N-{2-chloro-5-[3-(4-cyano-3-trifluoromethylphenyl)-5,5-dimethyl-4-oxo-2-thioxoimidazolidin-1-yl]phenyl}guanidine (compound of Example 55) | >10000 | 700 | >14 |
| 4-[3-(4-cyano-3-trifluoromethylphenyl)-5,5-dimethyl-4-oxo-2-thioxoimidazolidin-1-yl]benzenesulfonamide (compound of Example 56) | >10000 | 400 | >25 |
| {5-[3-(4-cyano-3-trifluoromethylphenyl)-5,5-dimethyl-4-oxo-2-thioxoimidazolidin-1-yl]pyridin-2-yl}carbamic acid 2-dimethylaminoethyl ester (compound of Example 58) | >10000 | 500 | >20 |
| {5-[3-(4-cyano-3-trifluoromethylphenyl)-5,5-dimethyl-4-oxo-2-thioxoimidazolidin-1-yl]pyridin-2-yl}carbamic acid 2-hydroxyethyl ester (compound of Example 60) | >10000 | 300 | >33 |
| 1-{5-[3-(3-chloro-4-cyanophenyl)-5,5-dimethyl-4-oxo-2-thioxoimidazolidin-1-yl]benzothiazol-2-yl}-3-(2-dimethylaminoethyl)urea (compound of Example 61) | >10000 | 300 | >33 |
| 1-{5-[3-(3-chloro-4-cyanophenyl)-5,5-dimethyl-4-oxo-2-thioxoimidazolidin-1-yl]benzothiazol-2-yl}-3-(2,3-dihydroxypropyl)urea (compound of Example 62) | >10000 | 1000 | >10 |
| 1-{5-[3-(3-chloro-4-cyanophenyl)-5,5-dimethyl-4-oxo-2-thioxoimidazolidin-1-yl]benzdthiazol-2-yl}-3-(2-hydroxyethyl)urea (compound of Example 63) | >10000 | 300 | >33 |
| {5-[3-(3-chloro-4-cyanophenyl)-5,5-dimethyl-4-oxo-2-thioxoimidazolidin-1-yl]benzothiazol-2-yl}carbamic acid 2-dimethylaminoethyl ester (compound of Example 64) | >10000 | 200 | >50 |
| {5-[3-(3-chloro-4-cyanophenyl)-5,5-dimethyl-4-oxo-2-thioxoimidazolidin-1-yl]benzothiazol-2-yl}carbamic acid 2,3-dihydroxypropyl ester (compound of Example 65) | >10000 | 200 | >50 |
| {5-[3-(3-chloro-4-cyanophenyl)-5,5-dimethyl-4-oxo-2-thioxoimidazolidin-1-yl]benzothiazol-2-yl}carbamic acid 2-hydroxyethyl ester (compound of Example 66) | 6000 | 100 | 60 |
| N-{2-chloro-5-[3-(4-cyano-3-trifluoromethylphenyl)-5,5-dimethyl-4-oxo-2-thioxoimidazolidin-1-yl]phenyl}-succinamide (compound of Example 67) | >10000 | 1000 | >10 |
| 3-[3-(3-chloro-4-cyanophenyl)-5,5-dimethyl-4-oxo-2-thioxoimidazolidin-1-yl]benzenesulfonamide (compound of Example 68) | >10000 | 400 | >25 |
| {5-[3-(3-chloro-4-cyanophenyl)-5,5-dimethyl-4-oxo-2-thioxoimidazolidin-1-yl]pyridin-2-yl}-carbamic acid 2-dimethylaminoethyl ester (compound of Example 69) | >10000 | 500 | >20 |
| {5-[3-(4-cyano-3-trifluoromethylphenyl)-5,5-dimethyl-4-oxo-2-thioxoimidazolidin-1-yl]pyridin-2-yl}-carbamic acid 2,3-dihydroxypropyl ester (compound of Example 70) | >10000 | 500 | >20 |
| Comparative Example 1 | 0.08 | 1 | 0.080 |
| Comparative Example 2 (BP-139) | 3000 | 800 | 3.8 |
| Comparative Example 3 (bicalutamide) | 20 | 300 | 0.067 |
| Comparative Example 4 (hydroxyflutamide) | 10 | 100 | 0.1 |

Comparative Example 1

Compound of Example 12 in Japanese Patent Application Laid-Open No. 4-308579 (4-(5-oxo-2-thioxo-3,4,4-trimethyl-1-imidazolidinyl)-2-trifluoromethyl-benzonitrile)

Comparative Example 2

Compound of Example 15 in Japanese Patent Publication No. 10-510845 ((4-[3'-(2"-N-acetylaminoethyl)-4',4'-dimethyl-5'-oxo-2'-thioxo-1'-imidazolidinyl]-2-trifluoromethylbenzonitrile)

Comparative Examples 3 and 4 are commonly known compounds, and can be prepared by commonly known methods.

The effect as an anti-androgen agent with reduced agonist activity can be judged by comparing the EC5/IC50 values. Specifically, compounds that have a high EC5/IC50 value are compounds that have a more desirable effect. In concrete terms, it is desirable that the EC5/IC50 value be 5 or greater, preferably 10 or greater, and even more preferably 20 or greater.

In Test Examples 1 and 2, it was confirmed that the compounds represented by formula (I) of the present invention have EC5/IC50 values that are clearly higher than those of the compounds of the Comparative Examples.

INDUSTRIAL APPLICABILITY

It is expected that the compounds of the present invention represented by formula (I) will act as anti-androgen agents which are not associated with androgen resistance due to long-term administration, and/or side effects such as liver toxicity or the like. Furthermore, it is expected that these compounds will be useful for drug compositions, e.g., therapeutic agents for diseases such as prostate cancer, benign prostatic hypertrophy, male pattern baldness, sexual precociousness, acnevulgaris, seborrhea, hypertrichosis and the like. Furthermore, it is expected that the compounds of the present invention expressed by general formula (I) will prevent or delay the onset of diseases such as prostate cancer, benign prostatic hypertrophy, male pattern baldness, sexual precociousness, acnevulgaris, seborrhea, hypertrichosis and the like, if these compounds are administered in advance. Accordingly, it is expected that these compounds will act as prophylactic agents for such diseases.

The invention claimed is:
1. A compound represented by formula (I):

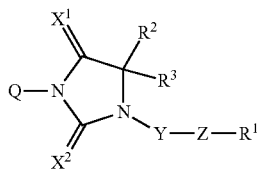

wherein Q is

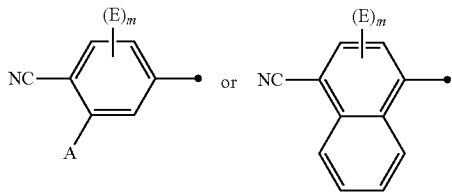

wherein
A is a hydrogen atom, a halogen atom, —ORa or a $C_{1-4}$ alkyl group which may be substituted by one or more halogen atoms;
E is independently selected from a $C_{1-6}$ alkyl group;
m is selected from integers from 0 to 3;
$R^2$ and $R^3$ are independently selected from a $C_{1-6}$ alkyl group;
$X^1$ and $X^2$ are independently selected from O and S,
Y is selected from an arylene group and a divalent 5- or 6-membered monocyclic or 8- to 10-membered condensed heterocyclic group, wherein the arylene group and the heterocyclic group may be substituted by 1 to 3 substituents independently selected from $E^1$,
$E^1$ is independently selected from a hydroxyl group, a halogen atom, a $C_{1-4}$ alkyl group, a cyano group, a $C_{1-4}$ alkoxy group, a carbamoyl group, a $C_{1-4}$ alkylcarbamoyl group, a di($C_{1-4}$ alkyl)carbamoyl group, an amino group, a $C_{1-4}$ alkylamino group, a di($C_{1-4}$ alkyl)amino group, a sulfamoyl group, a $C_{1-4}$ alkylsulfamoyl group and a di($C_{1-4}$ alkyl)sulfamoyl group;
Z is —CON(—Ra)—, —CO—, —C(=NH)—, —SO$_2$—, —SO$_2$N(—Ra)—, —SO$_2$N(—R$^1$)—, —N(—Ra)CO—, —N(—Ra)CON(—Rb)—, —N(—COR$^1$)CO—, —N(—Ra)SO$_2$—, —N(SO$_2$R$^1$)SO$_2$—, —N(—Ra)— or —N(—Ra)SO$_2$N(—Rb)—;

$R^1$ is a hydrogen atom, a hydroxyl group, a $C_{1-6}$ alkyl group which may be substituted by one or more substituents selected from B, a heterocyclic group which may be substituted by one or more substituents selected from B, an aryl group which may be substituted by one or more substituents selected from B, or a $C_{3-8}$ cycloalkyl group which may be substituted by one or more substituents selected from B;
B is independently selected from a $C_{1-4}$ alkyl group (except in the case where $R^1$ is a $C_{1-6}$ alkyl group), a halogen atom, a hydroxyl group, a cyano group, —CONRa$^1$Rb$^1$, —N(—Ra)CORb, —NRa$^1$Rb$^1$, —N(—Ra)SO$_2$Rb, —SO$_2$NRa$^1$Rb$^1$, —SO$_2$Ra, —COORa, —ORa, an aryl group, a heterocyclic group, and a $C_{3-8}$ cycloalkyl group (wherein the aryl group, the heterocyclic group, the heteroaryl group, and the cycloalkyl group may be substituted by one or more substituents selected from a $C_{1-4}$ alkyl group or a $Cl_{1-4}$ alkoxy group, a halogen atom, and a hydroxyl group);
Ra and Rb are independently selected from a hydrogen atom, and a $C_{1-6}$ alkyl group wherein the alkyl group may be substituted by one or more substituents selected from a hydroxyl group, a $C_{1-6}$ alkoxy group, a halogen atom, an aryl group and a heterocyclic group;
Ra$^1$ and Rb$^1$ are independently selected from a hydrogen atom and a $C_{1-6}$ alkyl group wherein the alkyl group may be substituted by one or more substituents selected from a hydroxyl group, a $C_{1-6}$ alkoxy group, a halogen atom, an aryl group and a heterocyclic group; or Ra$^1$ and Rb$^1$ together with a nitrogen atom to which they bind may form a nitrogen-containing heterocyclic group;
provided that when Y is a heterocyclic group and $X^1$ and $X^2$ are O, m is not 0;
and that when Y is an arylene group,
Z is not —CON(—Ra)— or —CO—; and
—Z—R$^1$ is not an arylsulphonyl group, an amino group, a $C_{1-6}$ alkylamino group or a di($C_{1-6}$ alkyl)amino group, or a salt, or prodrug thereof.

2. The compound or a salt, or prodrug thereof according to claim 1, wherein, in formula (I), —Y—Z— is selected from the following YZ$^1$ to YZ$^7$:

[Formula 3]

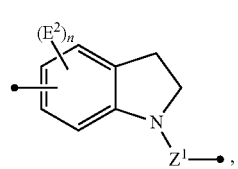

YZ$^1$

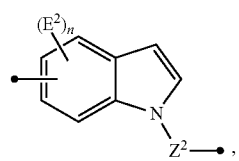

YZ$^2$

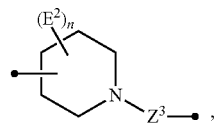

YZ$^3$

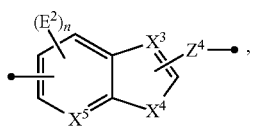
YZ⁴

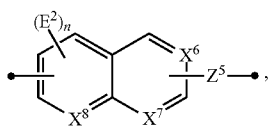
YZ⁵

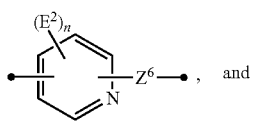
YZ⁶ , and

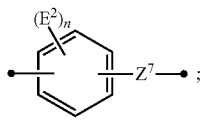
YZ⁷ ;

wherein n is selected from integers from 0 to 3;

$E^2$ is independently selected from a hydroxyl group, a halogen atom, a $C_{1-4}$ alkyl group, a cyano group, a $C_{1-4}$ alkoxy group, a carbamoyl group, a $C_{1-4}$ alkylcarbamoyl group, a di($C_{1-4}$ alkyl)carbamoyl group, an amino group, a $C_{1-4}$ alkylamino group, a di($C_{1-4}$ alkyl)amino group, a sulfamoyl group, a $C_{1-4}$ alkylsulfamoyl group and a di($C_{1-4}$ alkyl)sulfamoyl group;

$X^3$, $X^5$, $X^6$, $X^7$ and $X^8$ are independently selected from CH and N, provided that $X^6$, $X^7$ and $X^8$ are not CH at the same time;

$X^4$ is —CH₂—, —S—, —O— or —N(—W)—, provided that $X^4$ is not —CH₂— when both $X^3$ and $X^5$ are CH;

W is a hydrogen atom, a $C_{1-6}$ alkyl group, a $C_{1-6}$ alkoxy group, —SO₂Ra, —SO₂NRa¹Rb¹ or —CORa;

$Z^1$, $Z^2$, $Z^3$, $Z^4$, $Z^5$, $Z^6$ and $Z^7$ are —CON(—Ra)—, —CO—, —C(=NH)—, —SO₂—, —SO₂N(—Ra)—, —SO₂N(—R¹)—, —N(—Ra)CO—, —N(—Ra)CON(—Rb)—, —N(—COR¹)CO—, —N(—Ra)SO₂—, —N(—SO₂R¹)SO₂—, —N(—Ra)— or —N(—Ra)SO₂N(—Rb)—;

provided that m is not 0 when both of $X^1$ and $X^2$ above are O and —Y—Z— is any of YZ¹ to YZ⁶.

3. The compound or a pharmaceutically acceptable salt, or prodrug thereof according to claim 2, wherein, in formula (I), —Y—Z— is selected from YZa¹, YZb¹, YZa² and YZa³ of the following formulas:

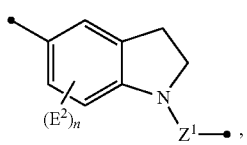
YZa¹

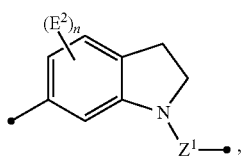
YZb¹

YZa²

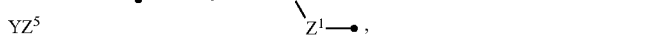
YZa³ wherein $Z^1$, $Z^2$, $Z^3$, $E^2$ and n are as defined in claim 2.

4. The compound or a pharmaceutically acceptable salt, or prodrug thereof according to claim 2, wherein, in formula (I), —Y—Z— is selected from YZa⁶, YZb⁶ and YZc⁶ of the following formulas:

YZa⁶

YZb⁶

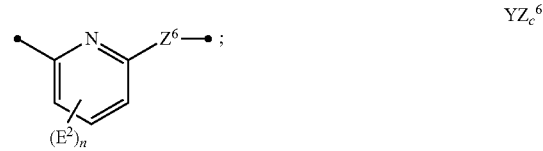
YZc⁶ wherein $Z^6$, $E^2$ and n are as defined in claim 2.

5. The compound or a pharmaceutically acceptable salt, or prodrug thereof according to claim 2, wherein, in formula (I), —Y—Z— is selected from YZa⁷ or YZb⁷ of the following formulas:

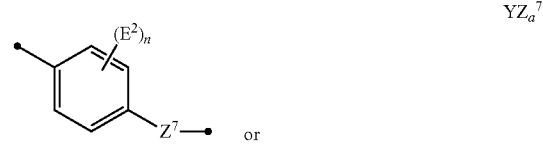
YZa⁷ or

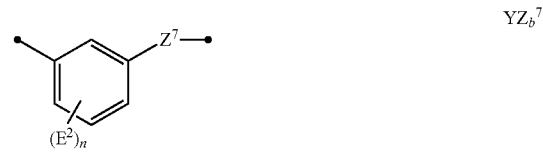
YZb⁷ wherein $Z^7$, $E^2$ and n are as defined in claim 2.

6. The compound or a pharmaceutically acceptable salt, or prodrug thereof according to claim 2, wherein $Z^1$, $Z^2$ and $Z^3$ are selected from —CONH—, —SO₂— and —SO₂NH—.

7. The compound or a pharmaceutically acceptable salt, or prodrug thereof according to claim 2, wherein $E^2$ is selected from a hydroxyl group, a chlorine atom, a fluorine atom, a methyl group, an ethyl group, a methoxy group, an ethoxy group and a carbamoyl group.

8. A compound according to claim 2 represented by formula (VIII):

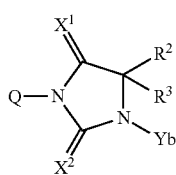

(VIII)

wherein Yb is selected from the following formulas:

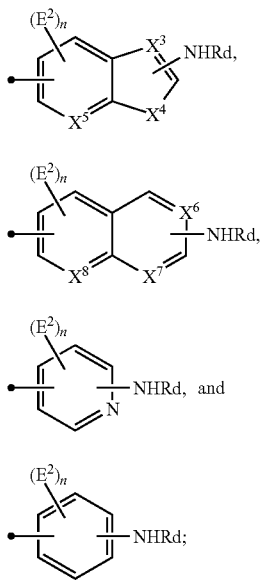

and Rd is a hydrogen atom or a $C_{1-6}$ alkyl group.

9. The compound or a pharmaceutically acceptable salt, or prodrug thereof according to claim 2,
wherein $Z^6$ is selected from the group consisting of —N(—Ra)SO$_2$—, —N(—Ra)CON(—Rb)—, —N(—Ra)CO—, —SO$_2$N(—Ra)—, —SO$_2$N(—R$^1$)—, —N(Ra)SO$_2$—, —N(SO$_2$R$^1$)SO$_2$—, and —N(—Ra)—.

10. The compound or a pharmaceutically acceptable salt, or prodrug thereof according to claim 2,
wherein —Y—Z— is YZ$^4$, YZ$^5$, YZ$^6$ or YZ$_7$;
$Z^4$ and $Z^5$ are —NHCO—, —NHCONH—, —N(COR$^1$)CO—, —NHSO$_2$— or —SO$_2$—;
$Z^6$ and $Z^7$ are —NHCO—, —NHCONH—, —SO$_2$—, —SO$_2$NH— or —NHSO$_2$—;
$R^1$ is a hydrogen atom, a $C_{1-6}$ alkyl group substituted by a heterocyclic group, a $C_{1-6}$ alkyl group substituted by a heterocyclic group which is itself substituted by a $C_{1-4}$ alkyl group, a hydroxyl $C_{1-4}$ alkyl group, an amino $C_{1-4}$ alkyl group, a $C_{1-4}$ alkylamino $C_{1-4}$ alkyl group, a di($C_{1-4}$ alkyl)amino $C_{1-4}$ alkyl group, a hydroxyl $C_{1-4}$ alkyl group, a phenyl group, a hydroxyl group or a $C_{1-4}$ alkyl group.

11. The compound or a pharmaceutically acceptable salt or prodrug thereof according to claim 2, wherein $Z^4$ and $Z^5$ are selected from —N(—Ra)CO—, —N(—Ra)CON(—Rb)—, —SO$_2$—, —SO$_2$N(—Ra)— and —SO$_2$N(—R$^1$)—.

12. The compound or a pharmaceutically acceptable salt or prodrug thereof according to claim 2, wherein $Z^6$ and $Z^7$ are selected from —N(—Ra)CO—, —N(—Ra)CON(—Rb)—, —SO$_2$—, —SO$_2$N(—Ra)—, —SO$_2$N(—R$^1$)— and —N(—Ra)SO$_2$—.

13. The compound or a pharmaceutically acceptable salt, or prodrug thereof according to claim 1, wherein A is a hydrogen atom, a trifluoromethyl group, a methyl group, an ethyl group, a chlorine atom or a methoxy group.

14. The compound or a pharmaceutically acceptable salt, or prodrug thereof according to claim 1, wherein $X^1$ is O and $X^2$ is O or S.

15. The compound or a pharmaceutically acceptable salt, or prodrug thereof according to claim 14, wherein $X^1$ is O and $X^2$ is S.

16. The compound or a pharmaceutically acceptable salt, or prodrug thereof according to claim 14, wherein $X^1$ is O and $X^2$ is O.

17. The compound or a pharmaceutically acceptable salt, or prodrug thereof according to claim 1, wherein B is independently selected from a halogen atom, a carbamoyl group, a $C_{1-4}$ alkylcarbamoyl group, a di($C_{1-4}$ alkyl)carbamoyl group, a $C_{1-4}$ alkylcarbonylamino group, an amino group, a $C_{1-4}$ alkylamino group, a di($C_{1-4}$ alkyl)amino group, a $C_{1-4}$ alkylsulfonylamino group, a sulfamoyl group, a $C_{1-4}$ alkylsulfamoyl group, a di($C_{1-4}$ alkyl)sulfamoyl group, a $C_{1-4}$ alkylsulfonyl, a carboxyl group, a $C_{1-4}$ alkoxycarbonyl group, a hydroxy group, a $C_{1-4}$ alkoxy group, a piperazinyl group, a piperidyl group, a pyridyl group, an imidazolyl group, a morpholinyl group, and a thienyl group (wherein the pyridyl group and the morpholinyl group may be substituted by a $C_{1-4}$ alkyl group.

18. The compound or a pharmaceutically acceptable salt, or prodrug thereof according to claim 1, wherein B is independently selected from a hydroxyl group, a methyl group, an ethyl group, an n-propyl group, an i-propyl group, a methoxy group, an ethoxy group, an n-propoxy group, an i-propoxy group, an amino group, a methylamino group, a dimethylamino group, an ethylamino group, a diethylamino group, a fluorine atom, a chlorine atom, a bromine atom, an iodine atom, a carbamoyl group, a methylcarbamoyl group, a dimethylcarbamoyl group, a carboxyl group, a formamide group, an acetamide group, a methylsulfonylamino group, a sulfamoyl group, a methylsulfamoyl group, a dimethylsulfamoyl group, a methylsulfonyl group, a methoxycarbonyl group, an ethoxycarbonyl group, a piperazinyl group, a piperidyl group, a pyrrolidinyl group, a pyridyl group, an imidazolyl group, a morpholinyl group, a thienyl group or a thiazolyl group (wherein the piperazinyl group, the piperidyl group, the pyrrolidinyl group, the pyridyl group, the imidazolyl group, the morpholinyl group, the thienyl group, the thiazolyl group may be substituted by one or more substituents selected from a hydroxyl group, a methyl group, and an ethyl group).

19. The compound or a pharmaceutically acceptable salt, or prodrug thereof according to claim 1, wherein $R^1$ is selected from a hydrogen atom, a $C_{1-4}$ alkyl group, a hydroxy $C_{1-4}$ alkyl group, a $C_{1-4}$ alkoxy $C_{1-4}$ alkyl group, a piperazinyl group, a piperazinyl $C_{1-4}$ alkyl group, a $C_{1-4}$ alkylpiperazinyl group, a ($C_{1-4}$ alkylpiperazinyl) $C_{1-4}$ alkyl group, a piperidyl group, a $C_{1-4}$ alkylpiperidyl group, a ($C_{1-4}$ alkylpiperidyl) $C_{1-4}$ alkyl group, an amino $C_{1-4}$ alkyl group, a $C_{1-4}$ alkylamino $C_{1-4}$ alkyl group, a di($C_{1-4}$ alkyl)amino $C_{1-4}$ alkyl group, a thienyl group, an imidazolyl group, a morpholinyl group, a morpholinyl $C_{1-4}$ alkyl group, a thienyl $C_{1-4}$ alkyl group, a phenyl group, a phenyl $C_{1-4}$ alkyl group.

20. The compound or a pharmaceutically acceptable salt, or prodrug thereof according to claim 1, wherein both $R^2$ and $R^3$ are a methyl group.

21. A compound represented by formula (I):

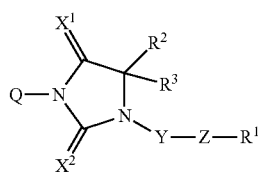
(I)

wherein Q is

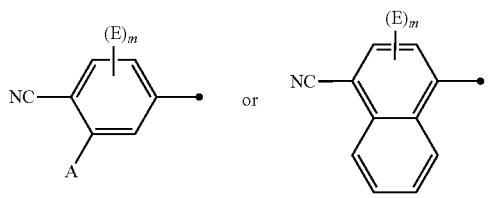

wherein
- A is a hydrogen atom, a halogen atom, —ORa or a $C_{1-4}$ alkyl group which may be substituted by one or more halogen atoms;
- E is independently selected from a $C_{1-6}$ alkyl group;
- m is selected from integers from 0 to 3;
- $R^2$ and $R^3$ are independently selected from a $C_{1-6}$ alkyl group;
- $X^1$ and $X^2$ are independently selected from O and S;
- $R^1$ is a hydrogen atom, a hydroxyl group, a $C_{1-6}$ alkyl group which may be substituted by one or more substituents selected from B, a heterocyclic group which may be substituted by one or more substituents selected from B, an aryl group which may be substituted by one or more substituents selected from B, or a $C_{3-8}$ cycloalkyl group which may be substituted by one or more substituents selected from B;
- B is independently selected from a $C_{1-4}$ alkyl group (except in the case where $R^1$ is a $C_{1-6}$ alkyl group), a halogen atom, a hydroxyl group, a cyano group, —CONRa$^1$Rb$^1$, —N(—Ra)CORb, —NRa$^1$Rb$^1$, —N(—Ra)SO$_2$Rb, —SO$_2$NRa$^1$Rb$^1$, —SO$_2$Ra, —COORa, —ORa, an aryl group, a heterocyclic group, and a $C_{3-8}$ cycloalkyl group (wherein the aryl group, the heterocyclic group, the heteroaryl group, and the cycloalkyl group may be substituted by one or more substituents selected from a $C_{1-4}$ alkyl group or a $C_{1-4}$ alkoxy group, a halogen atom, and a hydroxyl group);
- Ra and Rb are independently selected from a hydrogen atom, and a $C_{1-6}$ alkyl group wherein the alkyl group may be substituted by one or more substituents selected from a hydroxyl group, a $C_{1-6}$ alkoxy group, a halogen atom, an aryl group and a heterocyclic group;
- Ra$^1$ and Rb$^1$ are independently selected from a hydrogen atom and a $C_{1-6}$ alkyl group wherein the alkyl group may be substituted by one or more substituents selected from a hydroxyl group, a $C_{1-6}$ alkoxy group, a halogen atom, an aryl group and a heterocyclic group; or Ra$^1$ and Rb$^1$ together with a nitrogen atom to which they bind may form a nitrogen-containing heterocyclic group;

provided that when $X^1$ and $X^2$ are O, m is not 0; and —Z—$R^1$ is not an arylsulphonyl group, an amino group, a $C_{1-6}$ alkylamino group or a di($C_{1-6}$ alkyl)amino group, or a pharmaceutically acceptable salt, or prodrug thereof, wherein, in formula (I), —Y—Z— is selected from YZa$^4$, YZb$^4$, YZc$^4$, YZd$^4$, YZe$^4$, YZf$^4$, YZa$^5$, YZb$^5$ and YZc$^5$ of the following formulas:

[Formula 5]

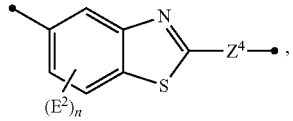
YZ$_a^4$

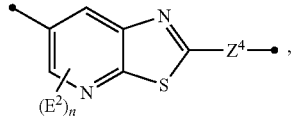
YZ$_b^4$

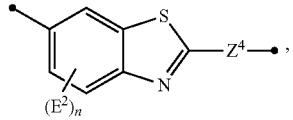
YZ$_c^4$

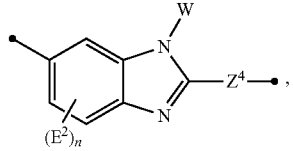
YZ$_d^4$

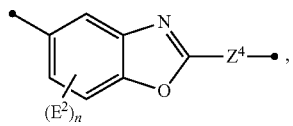
YZ$_e^4$

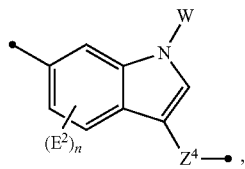
YZ$_f^4$

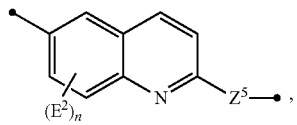
YZ$_a^5$

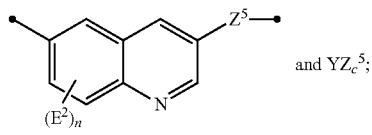
YZ$_b^5$ and YZ$_c^5$;

-continued

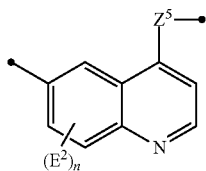

wherein:

n is selected from integers from 0 to 3;

$E^2$ is independently selected from a hydroxyl group, a halogen atom, a $C_{1-4}$ alkyl group, a cyano group, a $C_{1-4}$ alkoxy group, a carbamoyl group, a $C_{1-4}$ alkylcarbamoyl group, a di($C_{1-4}$ alkyl)carbamoyl group, an amino group, a $C_{1-4}$ alkylamino group, a di($C_{1-4}$ alkyl)amino group, a sulfamoyl group, a $C_{1-4}$ alkylsulfamoyl group and a di($C_{1-4}$ alkyl)sulfamoyl group;

W is a hydrogen atom, a $C_{1-6}$ alkyl group, a $C_{1-6}$ alkoxy group, —$SO_2Ra$, —$SO_2NRa^1Rb^1$ or —CORa;

$Z^4$ and $Z^5$ are —CON(—Ra)—, —CO—, —C(=NH)—, —$SO_2$—, $SO_2N$(—Ra)—, —$SO_2N$(—$R^1$)—, —N(—Ra)CO—, —N(—Ra)CON(—Rb)—, —N(—$COR^1$)CO—, —N(—Ra)$SO_2$—, —N(—$SO_2R^1$)$SO_2$—, —N(—Ra)— or —N(—Ra)$SO_2N$(—Rb)—;

provided that m is not 0 when both of $X^1$ and $X^2$ above are O.

22. A compound represented by formula (VII):

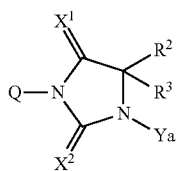

(VII)

wherein Q is

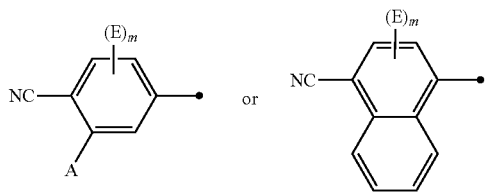

wherein

A is a hydrogen atom, a halogen atom, —ORa or a $C_{1-4}$ alkyl group which may be substituted by one or more halogen atoms;

E is independently selected from a $C_{1-6}$ alkyl group;

m is selected from integers from 0 to 3;

$R^2$ and $R^3$ are independently selected from a $C_{1-6}$ alkyl group;

$X^1$ and $X^2$ are independently selected from O and S,

Ya is selected from the following formulas:

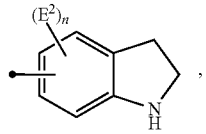

Ya¹

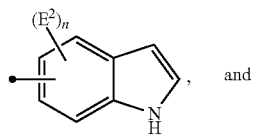

and

Ya²

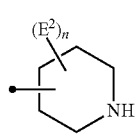

Ya³ n is selected from integers from 0 to 3;

$E^2$ is independently selected from a hydroxyl group, a halogen atom, a $C_{1-4}$ alkyl group, a cyano group, a $C_{1-4}$ alkoxy group, a carbamoyl group, a $C_{1-4}$ alkylcarbamoyl group, a di($C_{1-4}$ alkyl)carbamoyl group, an amino group, a $C_{1-4}$ alkylamino group, a di($C_{1-4}$ alkyl)amino group, a sulfamoyl group, a $C_{1-4}$ alkylsulfamoyl group and a di($C_{2-4}$ alkyl)sulfamoyl group Ra is selected from a hydrogen atom, and a $C_{1-6}$ alkyl group, wherein the alkyl group may be substituted by one or more substituents selected from a hydroxyl group, a $C_{1-6}$ alkoxy group, a halogen atom, an aryl group and a heterocyclic group.

23. A compound represented by formula (I'):

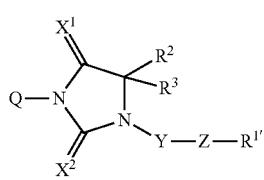

(I')

wherein: Q is

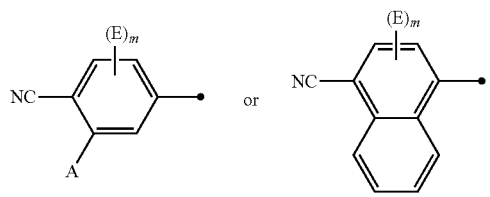

wherein

A is a hydrogen atom, a halogen atom, —ORa or a $C_{1-4}$ alkyl group which may be substituted by one or more halogen atoms;

E is independently selected from a $C_{1-6}$ alkyl group;

m is selected from integers from 0 to 3;

$R^2$ and $R^3$ are independently selected from a $C_{1-6}$ alkyl group;

$X^1$ and $X^2$ are independently selected from O and S,

Y is selected from an arylene group and a divalent 5- or 6-membered monocyclic or 8- to 10-membered condensed heterocyclic group, wherein the arylene group and the heterocyclic group may be substituted by 1 to 3 substituents independently selected from $E^1$, $E^1$ is independently selected from a hydroxyl group, halogen atom, a $C_{1-4}$ alkyl group, a cyano group, a $C_{1-4}$ alkoxy group, a carbamoyl group, a $C_{1-4}$ alkylcarbamoyl group, a di($C_{1-4}$ alkyl)carbamoyl group, an amino group, a $C_{1-4}$ alkylamino group, a di($C_{1-4}$ alkyl)amino group, a sulfamoyl group, a $C_{1-4}$ alkylsulfamoyl group and a di($C_{1-4}$ alkyl)sulfamoyl group;

Z is —CON(—Ra)—, —CO—, —C(=NH)—, —SO$_2$—, —SO$_2$N(—Ra)—, —SO$_2$N(—R$^1$)—, —N(—Ra)CO—, —N(—Ra)CON(—Rb)—, —N(—COR$^1$)CO—, —N(—Ra)SO$_2$—, —N(SO$_2$R$^1$)SO$_2$—, —N(—Ra)— or —N(—Ra)SO$_2$N(—Rb)—;

$R^1$ is a hydrogen atom, a hydroxyl group, a $C_{1-6}$ alkyl group which may be substituted by one or more substituents selected from B, a heterocyclic group which may be substituted by one or more substituents selected from B, an aryl group which may be substituted by one or more substituents selected from B, or a $C_{3-8}$ cycloalkyl group which may be substituted by one or more substituents selected from B;

B is independently selected from a $C_{1-4}$ alkyl group (except in the case where $R^1$ is a $C_{1-6}$ alkyl group), a halogen atom, a hydroxyl group, a cyano group, —CONRa$^1$Rb$^1$, —N(—Ra)CORb, —NRa$^1$Rb$^1$, —N(—Ra)SO$_2$Rb, —SO$_2$NRa$^1$Rb$^1$, —SO$_2$Ra, —COORa, —ORa, an aryl group, a heterocyclic group, and a $C_{3-8}$ cycloalkyl group (wherein the aryl group, the heterocyclic group, the heteroaryl group, and the cycloalkyl group may be substituted by one or more substituents selected from a $C_{1-4}$ alkyl group or a $C_{1-4}$ alkoxy group, a halogen atom, and a hydroxyl group);

Ra and Rb are independently selected from a hydrogen atom, and a $C_{1-6}$ alkyl group wherein the alkyl group may be substituted by one or more substituents selected from a hydroxyl group, a $C_{1-6}$ alkoxy group, a halogen atom, an aryl group and a heterocyclic group;

Ra$^1$ and Rb$^1$ are independently selected from a hydrogen atom and a $C_{1-6}$ alkyl group wherein the alkyl group may be substituted by one or more substituents selected from a hydroxyl group, a $C_{1-6}$ alkoxy group, a halogen atom, an aryl group and a heterocyclic group; or Ra$^1$ and Rb$^1$ together with a nitrogen atom to which they bind may form a nitrogen-containing heterocyclic group;

provided that when Y is a heterocyclic group and $X^1$ and $X^2$ are O, m is not 0;

and that when Y is an arylene group,

Z is not —CON(—Ra)— or —CO—; and

—Z—R$^1$ is not an arylsulphonyl group, an amino group, a $C_{1-6}$ alkylamino group or a di($C_{1-6}$ alkyl)amino group, or a salt, or prodrug thereof and R$^{1'}$ is the same as $R^1$, and when R$^{1'}$ contains a hydroxyl group, an amino group or a $C_{1-4}$ alkylamino group, these groups may be protected by a protecting group.

24. A compound selected from the group consisting of:

4-[3-(1-ethoxycarbonylpiperidin-4-yl)-4,4-dimethyl-5-oxo-2-thioxoimidazolidin-1-yl]-2-trifluoromethylbenzonitrile;

4-[3-(1-ethoxycarbonylpiperidin-4-yl)-4,4-dimethyl-5-oxo-2-thioxoimidazolidin-1-yl]-2-chlorobenzonitrile;

4-[3-(1-ethoxycarbonylpiperidin-4-yl)-4,4-dimethyl-5-oxo-2-thioxoimidazolidin-1-yl]-2-chloro-3-methylbenzonitrile;

4-[3-(1-acetylpiperidin-4-yl)-4,4-dimethyl-5-oxo-2-thioxoimidazolidin-1-yl]-2-trifluoromethylbenzonitrile;

4-[3-(1-ethanesulfonylpiperidin-4-yl)-4,4-dimethyl-5-oxo-2-thioxoimidazolidin-1-yl]-2-trifluoromethylbenzonitrile;

4-[3-(1-acetylpiperidin-4-yl)-4,4-dimethyl-5-oxo-2-thioxoimidazolidin-1-yl]-2-chlorobenzonitrile;

4-[3-(1-propionylpiperidin-4-yl)-4,4-dimethyl-5-oxo-2-thioxoimidazolidin-1-yl]-2-chlorobenzonitrile;

4-[3-(1-propanesulfonylpiperidin-4-yl)-4,4-dimethyl-5-oxo-2-thioxoimidazolidin-1-yl]-2-chlorobenzonitrile;

4-[3-(1-ethanesulfonylpiperidin-4-yl)-4,4-dimethyl-5-oxo-2-thioxoimidazolidin-1-yl]-2-chlorobenzonitrile;

4-[3-(1-ethanesulfonylpiperidin-4-yl)-4,4-dimethyl-2,5-dioxoimidazolidin-1-yl]-2-trifluoromethyl-3-methylbenzonitrile;

4-[3-(1-propanesulfonylpiperidin-4-yl)-4,4-dimethyl-2,5-dioxoimidazolidin-1-yl]-2-chloro-3-methylbenzonitrile;

4-[3-(1-propionylpiperidin-4-yl)-4,4-dimethyl-2,5-dioxoimidazolidin-1-yl]-2-chloro-3-methylbenzonitrile;

{2-chloro-5-[3-(4-cyano-3-trifluoromethylphenyl)-5,5-dimethyl-2,4-dioxoimidazolidin-1-yl]phenyl}carbamic acid ethyl ester;

4-{4,4-dimethyl-3-[1-(3-methylbutyryl)-piperidin-4-yl]-5-oxo-2-thioxoimidazolidin-1-yl}-2-trifluoromethylbenzonitrile;

4-[3-(2-acetylaminobenzothiazol-5-yl)-4,4-dimethyl-5-oxo-2-thioxoimidazolidin-1-yl]-2-trifluoromethylbenzonitrile;

4-[3-(2-acetylaminobenzothiazol-5-yl)-4,4-dimethyl-5-oxo-2-thioxoimidazolidin-1-yl]-2-chlorobenzonitrile;

4-[3-(2-acetylaminobenzothiazol-5-yl)-4,4-dimethyl-5-oxo-2-thioxoimidazolidin-1-yl]-2-methoxybenzonitrile;

{5-[3-(4-cyano-3-trifluoromethylphenyl)-5,5-dimethyl-4-oxo-2-thioxoimidazolidin-1-yl]-benzothiazol-2-yl}urea;

{5-[3-(4-cyano-3-methoxyphenyl)-5,5-dimethyl-4-oxo-2-thioxoimidazolidin-1-yl]-benzothiazol-2-yl}urea;

{5-[3-(4-cyano-3-chlorophenyl)-5,5-dimethyl-4-oxo-2-thioxoimidazolidin-1-yl]-benzothiazol-2-yl}urea;

N-{2-chloro-4-[3-(4-cyano-3-trifluoromethylphenyl)-5,5-dimethyl-2,4-dioxoimidazolidin-1-yl]-phenyl}-2-piperazin-1-ylacetamide;

4-[3-(3-acetylamino-4-chlorophenyl)-4,4-dimethyl-5-oxo-2-thioxoimidazolidin-1-yl]-2-trifluoromethylbenzonitrile;

4-[3-(3-isopropoxycarbonylamino-4-chlorophenyl)-4,4-dimethyl-2,5-dioxoimidazolidin-1-yl]-2-trifluoromethylbenzonitrile;

4-[3-(3-ethoxycarbonylamino-4-chlorophenyl)-4,4-dimethyl-2,5-dioxoimidazolidin-1-yl]-2-methoxybenzonitrile;

4-[3-(3-isopropoxycarbonylamino-4-chlorophenyl)-4,4-dimethyl-2,5-dioxoimidazolidin-1-yl]-2-methoxybenzonitrile;

4-[3-(3-n-propoxycarbonylamino-4-chlorophenyl)-4,4-dimethyl-2,5-dioxoimidazolidin-1-yl]-2-methoxybenzonitrile;

{2-chloro-5-[3-(4-cyano-3-trifluoromethylphenyl)-5,5-dimethyl-2,4-dioxoimidazolidin-1-yl]phenyl}-carbamic acid 3-hydroxypropyl ester;

{2-chloro-5-[3-(4-cyano-3-trifluoromethylphenyl)-5,5-dimethyl-2,4-dioxoimidazolidin-1-yl]phenyl}-carbamic acid 2-dimethylaminoethyl ester;

{2-chloro-5-[3-(4-cyano-3-trifluoromethylphenyl)-5,5-dimethyl-2,4-dioxoimidazolidin-1-yl]phenyl}-carbamic acid 2-(4-methylpiperazin-1-yl)ethyl ester;

{2-chloro-5-[3-(4-cyano-3-methoxyphenyl)-5,5-dimethyl-2,4-dioxoimidazolidin-1-yl]phenyl}-carbamic acid methyl ester;

{2-chloro-5-[3-(4-cyano-3-chlorophenyl)-5,5-dimethyl-2,4-dioxoimidazolidin-1-yl]phenyl}-carbamic acid 2-dimethylaminoethyl ester;

{2-chloro-5-[3-(4-cyano-3-trifluoromethylphenyl)-5,5-dimethyl-2,4-dioxoimidazolidin-1-yl]phenyl}-carbamic acid 3-dimethylaminopropyl ester;

{2-chloro-5-[3-(4-cyano-3-trifluoromethylphenyl)-5,5-dimethyl-2,4-dioxoimidazolidin-1-yl]phenyl}-carbamic acid 4-hydroxybutyl ester;

{2-chloro-5-[3-(4-cyano-3-trifluoromethylphenyl)-5,5-dimethyl-2,4-dioxoimidazolidin-1-yl]phenyl}carbamic acid 2-tert-butoxycarbonylaminoethyl ester;

4-[3-(4-cyano-3-trifluoromethylphenyl)-5,5-dimethyl-4-oxo-2-thioxoimidazolidin-1-yl]piperidine-1-carbamic acid (2-dimethylaminoethyl)amide;

4-[3-(4-cyano-3-trifluoromethylphenyl)-5,5-dimethyl-4-oxo-2-thioxoimidazolidin-1-yl]piperidine-1-carbamic acid 2-dimethylaminoethyl ester;

{2-chloro-5-[3-(4-cyano-3-trifluoromethylphenyl)-5,5-dimethyl-2,4-dioxoimidazolidin-1-yl]phenyl}carbamic acid 2-aminoethyl ester;

4-[3-(1-ethylaminocarbonylpiperidin-4-yl)-4,4-dimethyl-5-oxo-2-thioxoimidazolidin-1-yl]-2-trifluoromethylbenzonitrile;

4-[3-(1-n-propylaminocarbonylpiperidin-4-yl)-4,4-dimethyl-5-oxo-2-thioxoimidazolidin-1-yl]-2-trifluoromethylbenzonitrile;

4-[3-(1-ethylaminocarbonylpiperidin-4-yl)-4,4-dimethyl-5-oxo-2-thioxoimidazolidin-1-yl]-2-chlorobenzonitrile;

4-[3-(1-n-propylaminocarbonylpiperidin-4-yl)-4,4-dimethyl-5-oxo-2-thioxoimidazolidin-1-yl]-2-chlorobenzonitrile;

4-[3-(1-ethylaminosulfonylpiperidin-4-yl)-4,4-dimethyl-5-oxo-2-thioxoimidazolidin-1-yl]-2-trifluoromethylbenzonitrile; and 4-{3-[1-(2-dimethylaminoethyl)aminosulfonylpiperidin-4-yl]-4,4-dimethyl-5-oxo-2-thioxoimidazolidin-1-yl}-2-trifluoromethylbenzonitrile or a pharmaceutically acceptable salt, or prodrug.

25. A process for preparing a compound represented by formula (I):

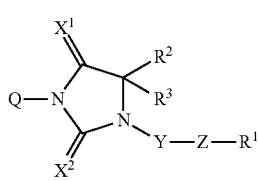

wherein Q, $X^1$, $X^2$, Y, Z, $R^1$, $R^2$ and $R^3$ are the same as defined in claim 1, which comprises a step of reacting a compound represented by formula (III):

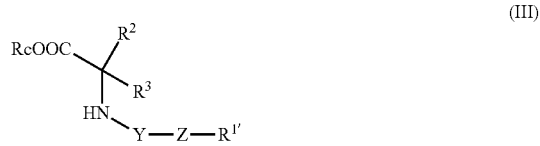

wherein Y, Z, $R^2$ and $R^3$ are the same as defined above;

$R^{1'}$ is defined as $R^1$ above, and when $R^{1'}$ contains a hydroxyl group, a carboxyl group, an amino group or a $C_{1-4}$ alkylamino group, these groups may be protected by a protecting group;

Rc is a hydrogen atom or a $C_{1-6}$ alkyl group, and the alkyl group may be substituted by one or more substituents selected from a halogen atom, an aryl group or a $C_{1-6}$ alkoxy group;

with a compound represented by the following formula (IX):

$$Q\text{-}N{=}C{=}X^2 \quad (IX)$$

wherein Q and $X^2$ are the same as defined above and which may further comprise a step of removing the protecting group.

26. A process for preparing a compound represented by formula (I):

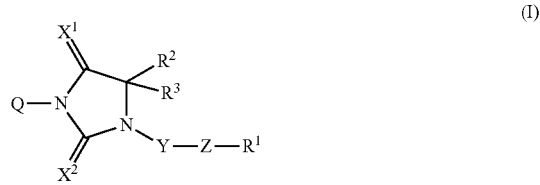

wherein Q, $X^2$, Y, Z, $R^1$, $R^2$ and $R^3$ are the same as defined in claim 1 and $X^1$ is O, which comprises a step of reacting a compound represented by formula (IV):

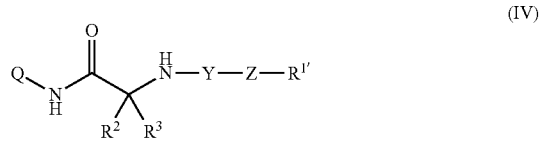

wherein Q, Y, Z, $R^2$ and $R^3$ are the same as defined above;

$R^1$ is defined the same as above $R^1$, and when $R^{1'}$ contains a hydroxyl group, a carboxyl group, an amino group or a $C_{1-4}$ alkylamino group, these groups may be protected by a protecting group with a carbonylating agent or a thiocarbonylating agent;

and which may further comprise a step of removing the protecting group.

27. A drug which comprises the compound or a pharmaceutically acceptable salt, or prodrug thereof according to claim 1 as an active ingredient, in a pharmaceutically acceptable dosage form.

28. A pharmaceutical composition which comprises the compound or a pharmaceutically acceptable salt, or prodrug thereof according to claim 1 as an active ingredient, together with a pharmaceutically acceptable carrier or excipient.

29. An anti-androgen agent which comprises the compound or a pharmaceutically acceptable salt, or prodrug thereof according to claim 1 as an active ingredient in an anti-androgen-effective amount.

* * * * *